US010618958B2

(12) United States Patent
Williams et al.

(10) Patent No.: US 10,618,958 B2
(45) Date of Patent: Apr. 14, 2020

(54) ANTI-TIGIT ANTIBODIES

(71) Applicant: Merck Sharp & Dohme Corp., Rahway, NJ (US)

(72) Inventors: Sybil M. G. Williams, Wayland, MA (US); Drake LaFace, Half Moon Bay, CA (US); Laurence Fayadat-Dilman, Sunnyvale, CA (US); Gopalan Raghunathan, San Diego, CA (US); Linda Liang, Mountain View, CA (US); Wolfgang Seghezzi, Mountain View, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/817,691

(22) Filed: Nov. 20, 2017

(65) Prior Publication Data
US 2018/0066055 A1 Mar. 8, 2018

Related U.S. Application Data

(63) Continuation of application No. 15/121,624, filed as application No. PCT/US2015/045447 on Aug. 17, 2015, now abandoned.

(60) Provisional application No. 62/126,733, filed on Mar. 2, 2015, provisional application No. 62/038,912, filed on Aug. 19, 2014.

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC ...... *C07K 16/2803* (2013.01); *A61K 39/3955* (2013.01); *A61K 45/06* (2013.01); *C07K 16/28* (2013.01); *C07K 16/2818* (2013.01); *A61K 2039/505* (2013.01); *A61K 2039/507* (2013.01); *C07K 2317/21* (2013.01); *C07K 2317/24* (2013.01); *C07K 2317/34* (2013.01); *C07K 2317/52* (2013.01); *C07K 2317/56* (2013.01); *C07K 2317/565* (2013.01); *C07K 2317/73* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,193,069 | B2 | 3/2007 | Isogai et al. |
| 7,368,527 | B2 | 5/2008 | Rosen et al. |
| 8,968,750 | B2 | 3/2015 | Mueller et al. |
| 2005/0064518 | A1 | 3/2005 | Albone et al. |
| 2005/0129690 | A1 | 6/2005 | Bowdish et al. |
| 2005/0265998 | A1 | 12/2005 | Elson |
| 2009/0017039 | A1 | 1/2009 | Mi et al. |
| 2009/0047213 | A1 | 2/2009 | Young et al. |
| 2009/0258013 | A1 | 10/2009 | Clark et al. |
| 2010/0150918 | A1 | 6/2010 | Kufer et al. |
| 2012/0177664 | A1 | 7/2012 | Yokoseki et al. |
| 2012/0195831 | A1 | 8/2012 | Zhang et al. |
| 2013/0064843 | A1 | 3/2013 | Brusic et al. |
| 2013/0142732 | A1 | 6/2013 | Lee et al. |
| 2013/0224210 | A1 | 8/2013 | Adamkewicz et al. |
| 2013/0280280 | A1 | 10/2013 | Algate et al. |
| 2014/0308276 | A1 | 10/2014 | Liu et al. |
| 2015/0086570 | A1 | 3/2015 | Violette et al. |
| 2015/0216970 | A1 | 8/2015 | Grogan et al. |
| 2016/0355589 | A1 | 12/2016 | Williams et al. |
| 2017/0198042 | A1 | 7/2017 | Williams et al. |

FOREIGN PATENT DOCUMENTS

| AU | 2015202123 A1 | 5/2015 |
| WO | WO2000058334 | 10/2000 |
| WO | WO2000058334 A1 | 10/2000 |
| WO | WO2003072035 | 9/2003 |
| WO | WO2004024068 A2 | 3/2004 |
| WO | WO2004024077 | 3/2004 |
| WO | WO2004024077 A2 | 3/2004 |
| WO | WO2006124667 A2 | 11/2006 |
| WO | WO2009126688 | 10/2009 |
| WO | WO2009126688 A2 | 10/2009 |
| WO | WO2011156356 A1 | 12/2011 |
| WO | WO2013151999 A1 | 10/2013 |
| WO | WO2013184912 A2 | 12/2013 |
| WO | WO2014089169 | 6/2014 |
| WO | WO2014089169 A2 | 6/2014 |
| WO | WO2014172591 A2 | 10/2014 |
| WO | WO2014089113 | 12/2014 |
| WO | WO2014089113 A1 | 12/2014 |
| WO | WO2015009856 | 1/2015 |
| WO | WO2015009856 A2 | 1/2015 |
| WO | WO2015127273 A1 | 8/2015 |

(Continued)

OTHER PUBLICATIONS

Beiboer (J. Mol. Biol. (2000) 296:833-849) (Year: 2000).*
Rudikoff et al. (Proc Natl Acad Sci USA 79: 1979-1983, 1982) (Year: 1982).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*

(Continued)

*Primary Examiner* — Michael Allen
(74) *Attorney, Agent, or Firm* — Teofilo Javier, Jr.; Anna L. Cocuzzo

(57) ABSTRACT

The present invention relates to anti-TIGIT antibodies, as well as use of these antibodies in the treatment of diseases such as cancer and infectious disease.

32 Claims, 22 Drawing Sheets
Specification includes a Sequence Listing.

(56) References Cited

FOREIGN PATENT DOCUMENTS

| WO | WO2016011264 | 1/2016 |
|---|---|---|
| WO | WO2016011264 A1 | 1/2016 |
| WO | WO2016028656 A1 | 2/2016 |
| WO | WO2016073282 | 5/2016 |
| WO | WO2016073282 A1 | 5/2016 |
| WO | WO2016081746 | 5/2016 |
| WO | WO2016081746 A2 | 5/2016 |
| WO | WO2016106302 | 6/2016 |
| WO | WO2016106302 A1 | 6/2016 |
| WO | 2016191643 A2 | 12/2016 |
| WO | 2017053748 A2 | 3/2017 |

OTHER PUBLICATIONS

Portolano (The Journal of Immunology, vol. 150, No. 3, p. 880-887, 1993) (Year: 1993).*
Klimka (British Journal of Cancer (2000) 83: 252-260) (Year: 2000).*
Allard Er al., Targeting CD73 Enhances the Antibumor Activity of Anti-PD-1 and Anti-CTLA-4 mAbs, Clinical Cancer Research, 2013, pp. 5626-5635, vol. 19 (20).
Bin Dhuban, Khalid et al., Coexpression of TIGIT and FCRL3 Identifies Helios+ Human memory Regulatory T Cells, J. Immunol., 2015, 3687-3696, 194(8).
Boles et al., A novel molecular interaction for the adhesion of follicular CD4 T cells to follicular DC, European Journal of Immunology, 2009, pp. 695-703, vol. 39.
Bottino et al., Natural killer cells and neuroblastoma: tumor recognition, escape mechanisms, and positive model immunotherapeutic approaches, Frontiers in Immunology, 2014, pp. 1-10, vol. 5, Article 56.
Broere et al., T cell subsets and T cell-mediated immunity, Principles of Immunopharmacology, 2011, pp. 15-27.
Carlsten, Mattias et al., DNAX Accessory Molecule-1 Mediated Recognition of Freshly Isolated Ovarian Carcinoma by Resting Natural Killer Cells, Cancer Res., 2007, 1317-1325, 67(3).
Chan et al., Receptors that interact with nectin and nectin-like proteins in the immunosurveillance and immunotherapy of cancer, Current Opinion in Immunology, 2012, pp. 1-6, vol. 24.
Chauvin et al., TIGIT and PD-1 impair tumor antigen-specific CD8 T cells in melanoma patients, Journal of Clinical Investigation, 2015, pp. 2046-2058, vol. 125(5).
D. M. Pardoll, The blockade of immune checkpoints in cancer immunotherapy, Nature Reviews/Cancer, 2012, pp. 252-264, vol. 12.
Dardalhon, Valerie et al., CD226 Is Specifically Expressed on the Surface of Th1 Cells and Regulates their Expansion and Effector Functions, J. Immunol., 2005, 1558-1565, 175.
Everds, Nancy et al., Unexpected Thrombocytopenia and Anemia in Cynomolgus Monkeys Induced by a Therapeutic human Nomoclonal Antibody, Toxicol. Pathol., 2013, 951-969, 41.
Finco, D. et al., Cytokine release assays: Current practices and future directions, Cytokine, 2014, 143-155, 66.
Findlay, Lucy et al., Improed in vitro methods to predict the in vivo toxicity in man of therapeutic monoclonal antibodies including TGN1412, J. Immunol. Methods, 2010, 1-12, 352.
Foks et al., Agonistic Anti-TIGIT Treatment Inhibits T Cell Responses in LDLr Deficient Mice without Affecting Atherosclerotic Lesion Development, PLOS ONE, 2013, pp. 1-7, vol. 8 (12).
Fourcade et al., CD8 T cells Specific for Tumor Antigens Can Be Rendered Dysfunctional by the Tumor Microenvironment through Upregulation of hte Inhibitory receptors BTLA and PD-1, Cancer Research, 2012, pp. 887-896 (Published OnineFirst Dec. 28, 2011), vol. 72.
Fuhrman et al., Divergent Phenotypes of Human Regulatory T Cells Expressing the Receptors TIGIT and CD226, The Journal of Immunology, 2015, pp. 145-155, vol. 195.

Goding et al., Restoring Immune Function of Tumor Specific CD4+ T Cells during recurrence of Melanoma, The Journal of Immunology, 2013, pp. 4899-4909, vol. 190.
Gray et al., Optimising anti-tumor CD8 T-cell responses using combinations of ummunnomodulatory antibodies, Eur. J. Immunol., 2008, pp. 2499-2511, vol. 38.
Grogan et al., TIGIT inhibits CD8+ T cell effector function during chronic viral infection and cancer, The Journal of Immunology, 2014, Supplement 203.15, vol. 192, No. 1.
Guillerey et al., Immunosurveillance and therapy of multiple myeloma are CD226 dependent, Journal of Clinical Investigation, 2015, pp. 2077-2089, vol. 125(5).
Haryadi, Ryan et al., Optimization of heavy Chain and Light chain Signal Peptides for High Level Expression of Therapeutic Antibodies in CHO Cells, PLOS ONE, 2015, 1, 10.
Hirota, Takeshi et al., Transcriptional activation of the mouse Necl-5/Tage4/PVR/CD155 gene by fibroblast growth factor or oncogenic Ras through the Raf-MEK-ERK-AP-1 pathway, Oncogene, 2005, 2229-2235, 24(13).
Iguchi-Manaka et al., Accelerated tumor growth in mice deficient in DNAM-1 receptor, The Journal of Experimental Medicince, 2008, pp. 2959-2964, vol. 205, No. 13.
International Search Report of PCT/US2015/045447 dated Oct. 8, 2015.
Johnston, et al., The Immunoreceptor TIGIT Regulates Antitumor and Antibiral CD8+ T Cell Effector Function, Cancer Cell, 2014, pp. 923-937, 26.
Joller et al., Cutting Edge: TIGIT has T Cell-Intrinic Inhibitory Functions, The Journal of Immunology, 2011, pp. 1338-1342, vol. 186.
Joller et al., Immune Checkpoints in CNS Autoimmunity, Immunol. Rev., 2012, pp. 122-139, vol. 248(1).
Joller et al., Treg cells expressing the co-inhibitory molecule TIGIT selectively inhibit pro-inflammatory Th1 and Th17 cell responses, Immunity, 2014, pp. 569-581, vol. 40(4).
Kocak et al., Combination Therapy with Anti-CTL Antigen-4 and Anti-4-1BB Antibodies Enhances Cancer Immunity and Reduces Autoimmunity, Cancer Research, 2006, pp. 7276-7284, vol. 66(1).
Kurtulus et al., Mechanisms of TIGIT-driven immune suppression in cancer, Journal for ImmunoTherapy of Cancer, 2014, pp. O13, Supplement 3.
Lemercier et al., Beyond CTLA-4 and PD-1, the generation X of negative checkpoint regulators, Frontiers in Immunology, 2015, pp. 1-15, vol. 6, Article 418.
Levin et al, Vstm3 is a member of the CD28 family and an important modulator for T-cell function, Eur. J. Immunol., 2011, pp. 902-915, vol. 41.
Li, Man et al., T-cell Immunoglobulin and ITIM Domain (TIG(T) Receptor/poliovirus Receptor (PVR) Ligand Engagement Suppresses Interferon-gamma Production of Natural Killer Cells via Beta-Arrestin 2-mediated Negative Signaling, J. Biol. Chem., 2014, 17647-17657, 289(25).
Liu, S. et al., Recruitment of Grb2 and SHIP1 by the ITT-like motif of TIGIT suppresses granule polarization and cytotoxicity of NK cells, Cell Death Differ, 2013, 456-464, 20(3).
Lozano et al., The TIGIT CD226 Axis Regulates Human T Cell Function, The Journal of Immunology, 2012, pp. 3869-3875, vol. 188.
Masson, D. et al., Overexpression of the CD155 gene in human colorectal carcinoma, Gut, 2001, 236-240, 49(2).
P. M. Watt, Engineered antibody fragments and alternative protein scaffolds, Biospectrum, 2008, pp. 12-14.
Pauken et al., Overcoming T cell exhaustion in infection and cancer, Trends in Immunology, 2015, pp. 265-276, vol. 36, No. 4.
Pauken et al., TIGIT and CD226: Tipping the Balance between Costimulatory and Coinhibitory Molecules to Augment the Cancer Immunotherapy Toolkit, Cancer Cells, 2014, pp. 785-787, vol. 26.
Perez-Garcia et al., Clinical development of combination strategies in immunotherapy: are we redy for more than one investigational product in an early trial?, Immunotherapy, 2009, pp. 845-853, vol. 1(5).

(56) References Cited

OTHER PUBLICATIONS

Ribas, Antoni et al., Association of response to programmed death receptor 1 (PD-1) blockade with pembrolizumab (MK-3475) with an interferon-inflammatory immune gene signature, J. Clin. Oncol., 2015, 1, 33.

Sakuishi et al., Targeting Tim-3 and PD-1 pathways to reverse T cell exhaustion and restore anti-tumor immunity, The Journal of Expeimental Medicine, 2010, pp. 2187-2194, vol. 207, No. 10.

Santostefano, Michael J. et al., Off-Target Platelet Activation in Macaques Unique to a Therapeutic Monoclonal Antibody, Toxicol., 2012, 899-917, 40.

Seiwert, T. et al., Antitumor activity and safety of pembrolizumba in patients (pts) with advanced squamous cell carcinoma of the head and neck (SCCHN): Preliminary results from KEYNOTE-012 expansion cohort, J. Clin. Oncol., 2015, 1, 33.

Soriani, A. et al., ATM-ATR-dependent up-regulation of DNAM-1 and NKG2D ligands on multiple myeloma cells by therapeutic agents results in enhanced NK-cell susceptibility and is associated with a senescent phenotype, Blood, 2009, 3503-3511, 113(15).

Stanietsky et al., Mouse TIGIT inhibits NK-cell cytotoxicity upon interaction with PVR, European Journal of Immunology, 2013, pp. 2138-2150, vol. 43.

Stanietsky et al., The Interaction of TIGIT with PVR and PVRL2 Inhibits Human NK Cell Cytotoxicity, PNAS, 2009, pp. 17856-17863, vol. 106.

Stebbings, Richard et al., "Cytokine Storm" in the Phase 1 Trial of Monoclonal Antibody TGN1412: Better Understanding the Causes to Improve PreClinical Testing of Immunotherapeutics, J. Immunol., 2007, 3325-3331, 179.

Stengel et al., Structure of TIGIT immunoreceptor bound to poliovirus receptor reveals a cell-cell adhesion and signaling mechanism that requires cis-trans receptor clustering, PNAS, 2012, pp. 5399-5404 (pnas. 1120606109), vol. 109, No. 14.

Takeda et al., Combination Therapy of Established Tumors by Antibodies Targeting Immune Activating and Suppressing Molecules, The Journal of Immunology, 2010, pp. 5493-5501, vol. 184.

Teng et al., Classifying Cancers Based on T-cell Infiltration and PD-L1, Cancer Research, 2015, pp. 2139-2145, vol. 75, No. 11.

Topalian et al., Immune Checkpoint Blockade: A Common Denominator Approach to Cancer Therapy, Cancer Cell, 2015, pp. 450-461, vol. 27.

Turnis et al., Inhibitory receptors as targets for cancer immunotherapy, European Journal of Immunology, 2015, pp. 1892-1905, vol. 45, Issue 7.

Uno et al., Eradication of established tumors in mice by a combination antibody-based therapy, Nature Medicine, 2006, pp. 693-698, vol. 12, No. 6.

Vanneman et al., Combining immunotherapy and targeted therapies in cancer treatment, Nature Reviews/Cancer, 2012, pp. 237-251, vol. 12.

Wainwright et al., Targeting Tregs in Malignant brain cancer: overcoming IDO, Frontiers in Immunology, 2013, Article 116—pp. 1-17, 4.

Wolchok et al., Nivolumab plus Ipilimumab in Advanced Melanoma, The New England Journal of Medicine, 2013, pp. 122-133, vol. 369(2).

Woo et al., Immune inhibitory molecules LAG-3 and PD-1 synergistically regulate T cell function to promote tumoral immune escape, Cancer Res., 2012, 917-927, 72(4).

Written Opinion of PCT/US2015/045447 dated Oct. 8, 2015.

Yu et al., The surface protein TIGIT suppresses T cell activation by promoting the generation of mature immunoregulatory dendritic cells, Nature Immunology, 2009, pp. 48-57, vol. 10(1).

Zhang et al., Increased Expression of TIGIT on CD4+ T Cells Ameliorates Immune Mediated Bone Marrow Failure of Aplastic Anemia, Journal of Cellular Biochemistry, 2014, pp. 1918-1927, 115.

Topalian, Suzanne, et al., Targeting the PD-1/B7-H1(PD-L1) pathway to activate anti-tumor immunity, Current Opinion in Immunology, 2012, pp. 207-212, vol. 24.

Fourcade, Julien, et al., Upregulation of Tim-3 and PD-1 expression is associated with tumor antigen-specific CD8+ T cell dysfunction in melanoma patients, J. Exp. Med, 2010, pp. 2175-2186, vol. 207.

Topalian, Suzanne et al., Safety, Activity, and Immune Correlates of Anti-Pd-1 Antibody in Cancer, The New England Journal of Medicine, 2012, pp. 2443-2454, vol. 366(26).

Inozume, T. et al., Development of a novel immunotherapy for melanoma which inhibits interaction betwen CD155 on relanoma cells and TIGIT on activated CTL, Journal of Investigative Dermatology, 2013, 1, 133.

Johnston et al., TIGIT inhibits CD8+ T cell effector function during chronic viral infection and cancer, presented at Immune Evolution in Cancer Meeting, Mar. 9-14, 2014, 1, poster X2 2003.

Peterson, Eric C. et al., Using Hapten Design to Discover Therapeutic Monoclonal Antibodies for Treating Methamphetamine Abuse, The Journal of Pharmacology and Experimental Therapeutics, 2007, 30-41, 322(1).

Portolano, Lack of Promiscuity in Autoantigen-Specific H and L Chain Combinations as Revealed by Human H and L Chain "Roulette", Journal of Immunology, 1993, pp. 880-887, 150.

Stengel, Katharina F. et al., Supporting Information, PNAS, Apr. 3, 2012, 1-8, 109 (14).

Thaventhiran, T. et al., T cell co-inhibitory receptors functions and signalling mechanisms, J. Clin. Cell Immunol., 2012, e1-12, 512.

Comps-Agrar, L et al., TIGIT mediated T cell exhaustion in cancer is dependent on TIGIT/CD226 interaction (TUM2P.907), The Journal of Immunology, 2014, 1-4, vol. 192, No. S1.

Evans, T.R.J. et al., Vaccine therapy for cancer—fact or fiction?, Q. J. Med., 1999, 299-0307, 92.

Hernandez-Ledesma, Blanca et al., Lunasin, a novel seed peptide for cancer prevention, Peptides, 2009, 425-430, 30.

Komenaka, Ian et al., Immunotherapy for Melanoma, Clinics in Dermatology, 2004, 251-255, 22.

Schiffman, Mark et al., The Promise of Global Cervical-Cancer Prevention, The New England Journal of Medicien, 2005, 2101-2104, 353(20).

\* cited by examiner

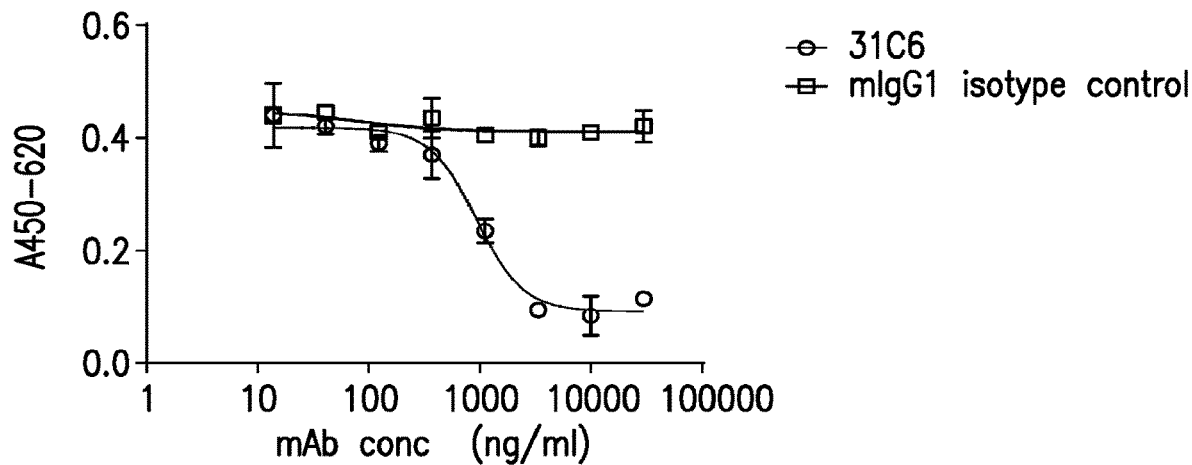
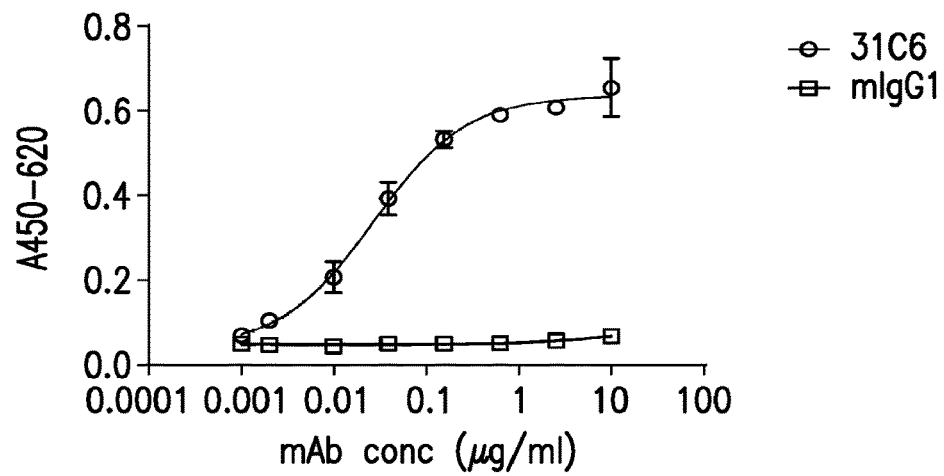
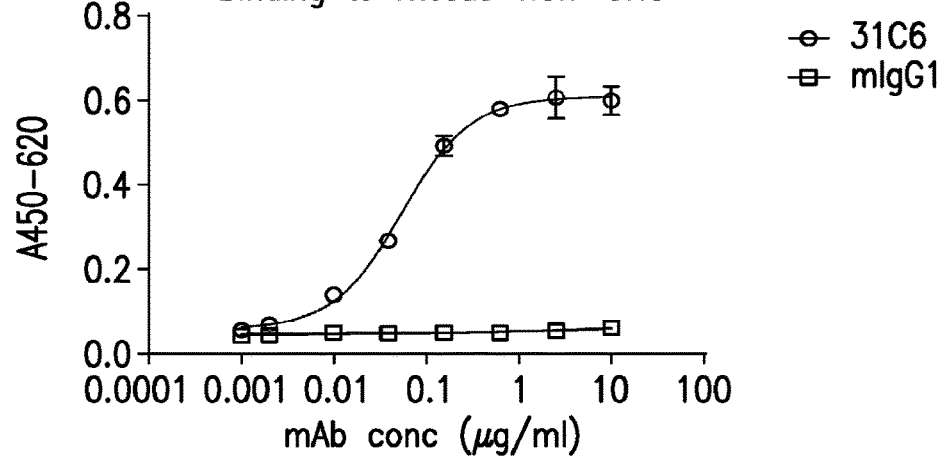
FIG. 4

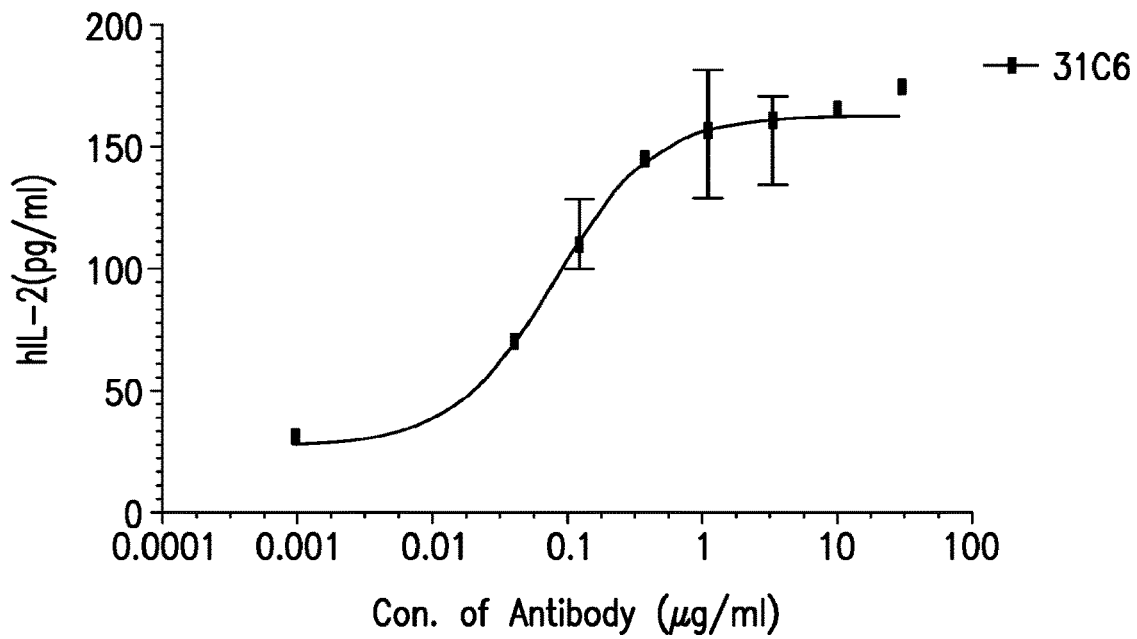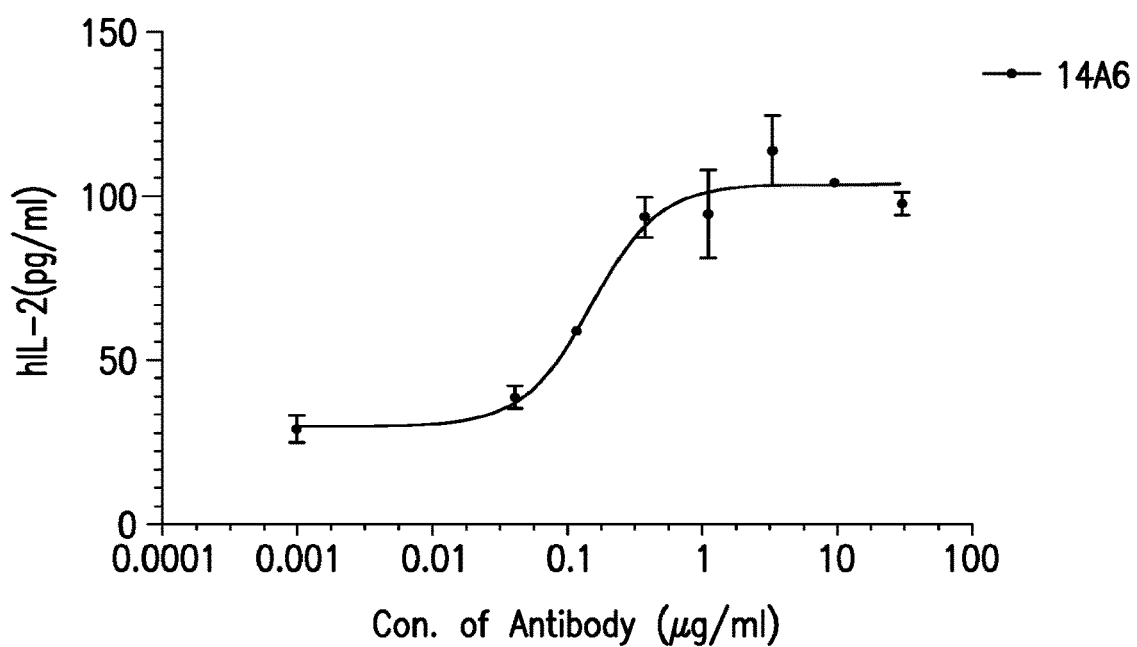
FIG.6

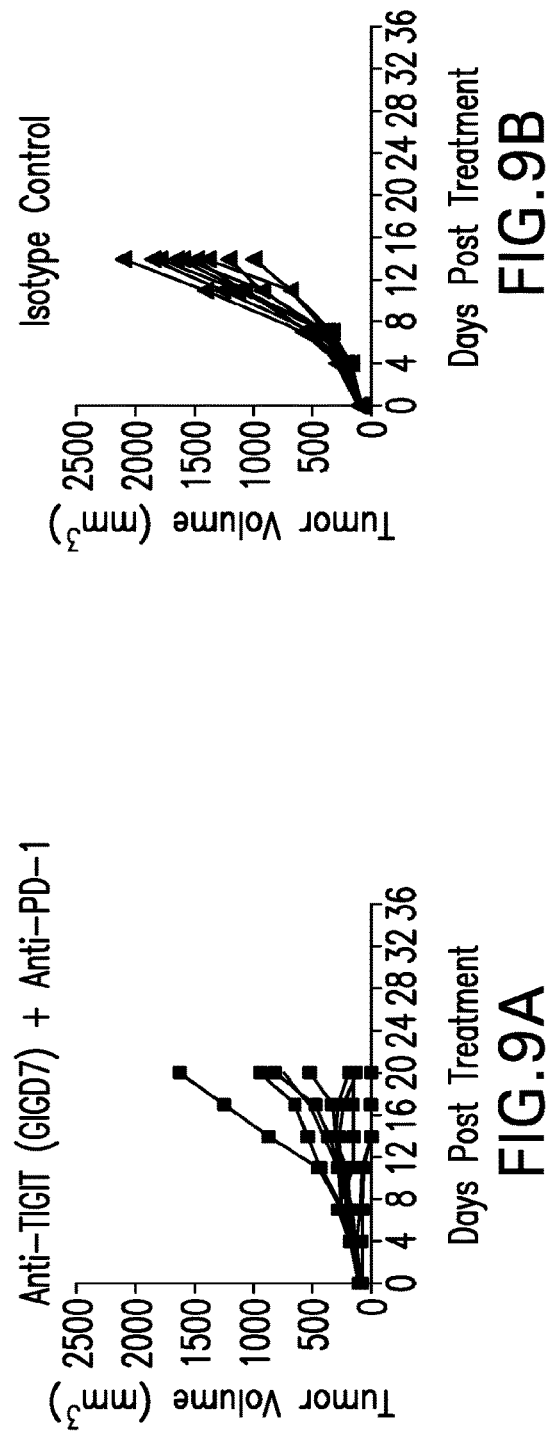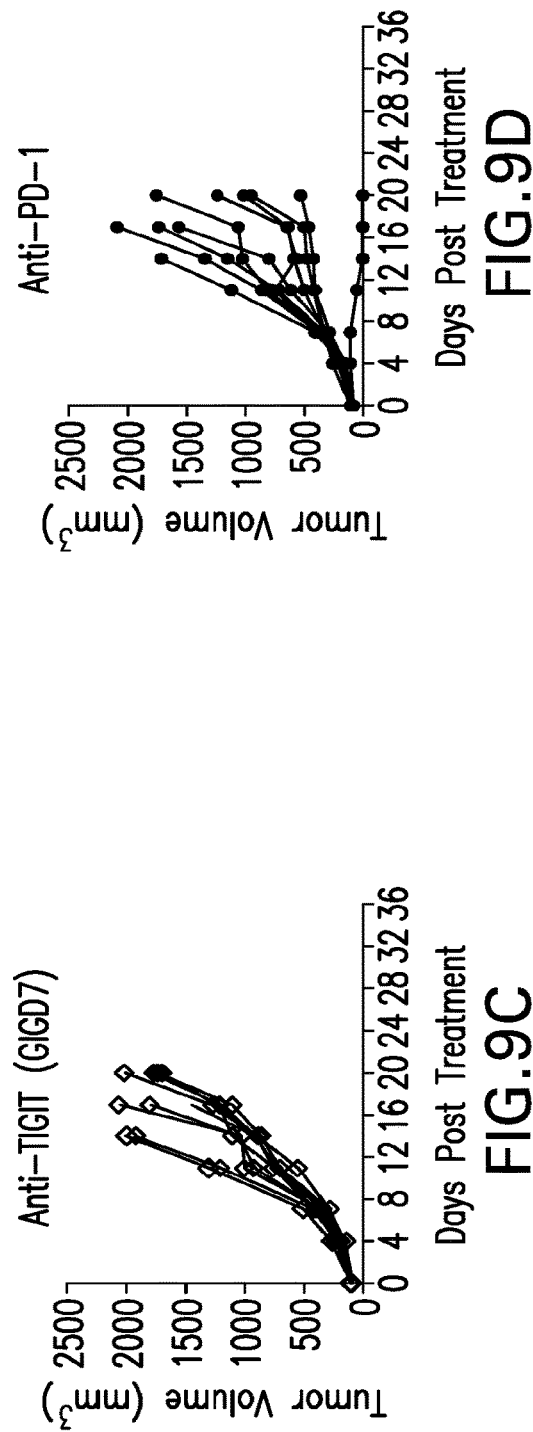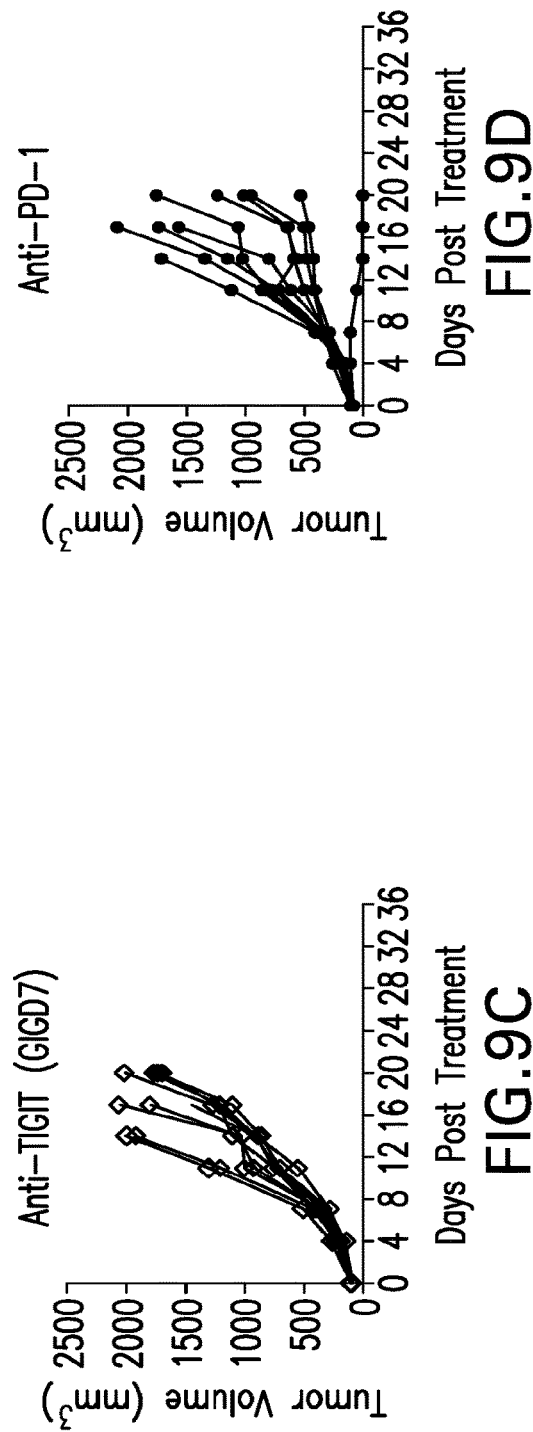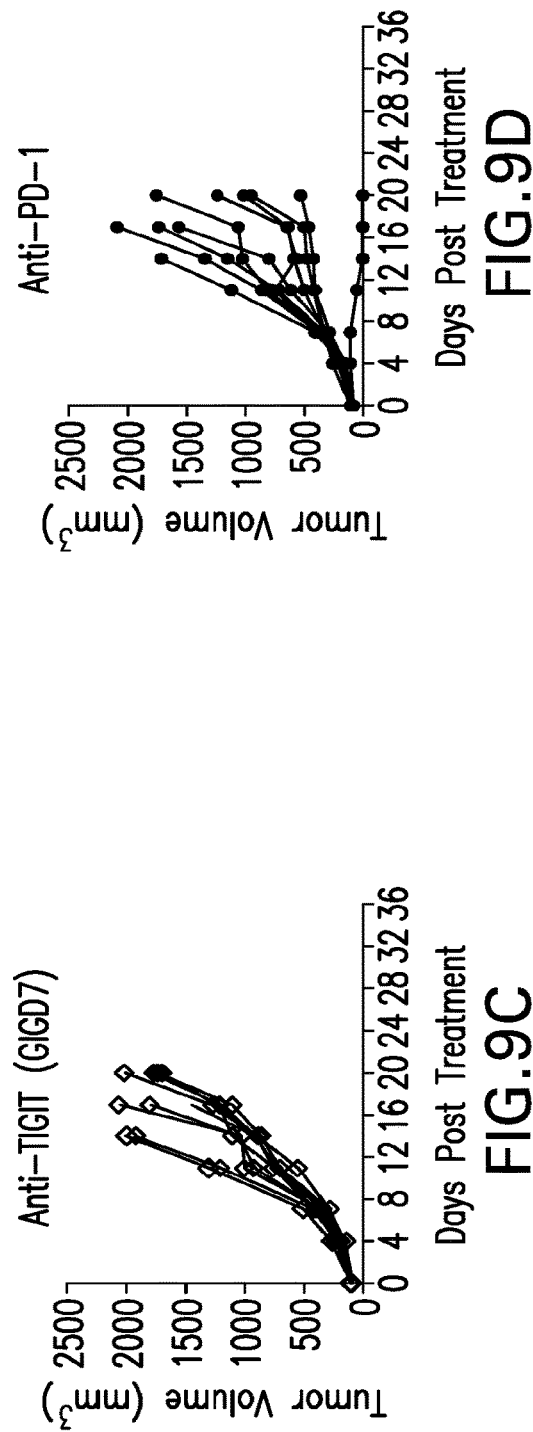

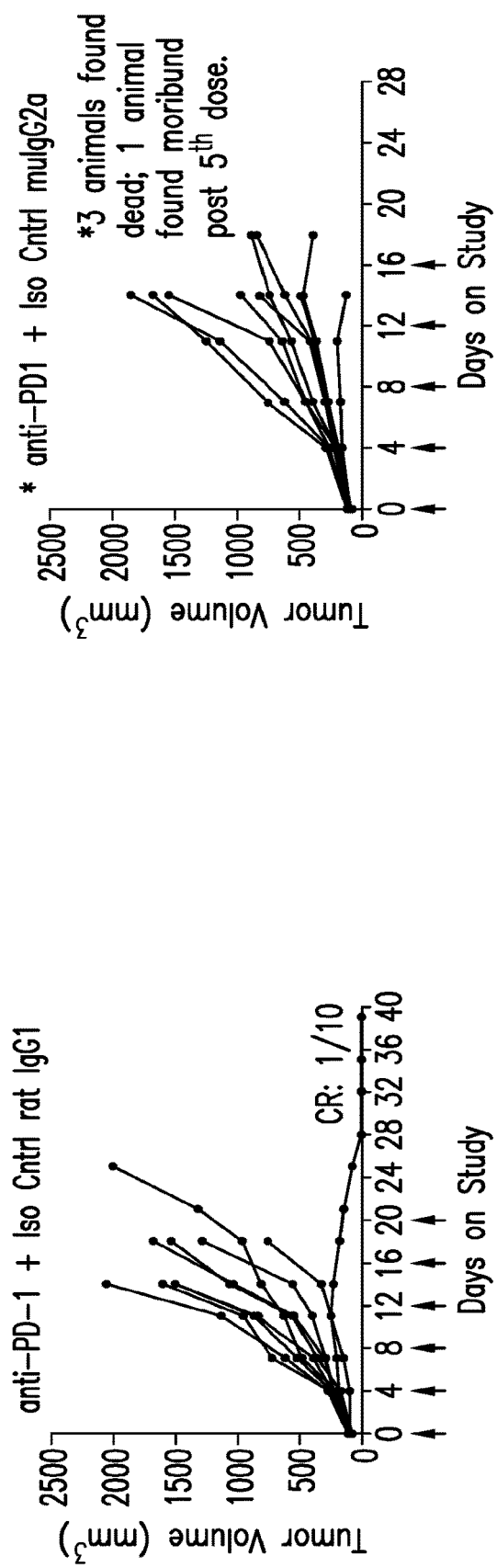
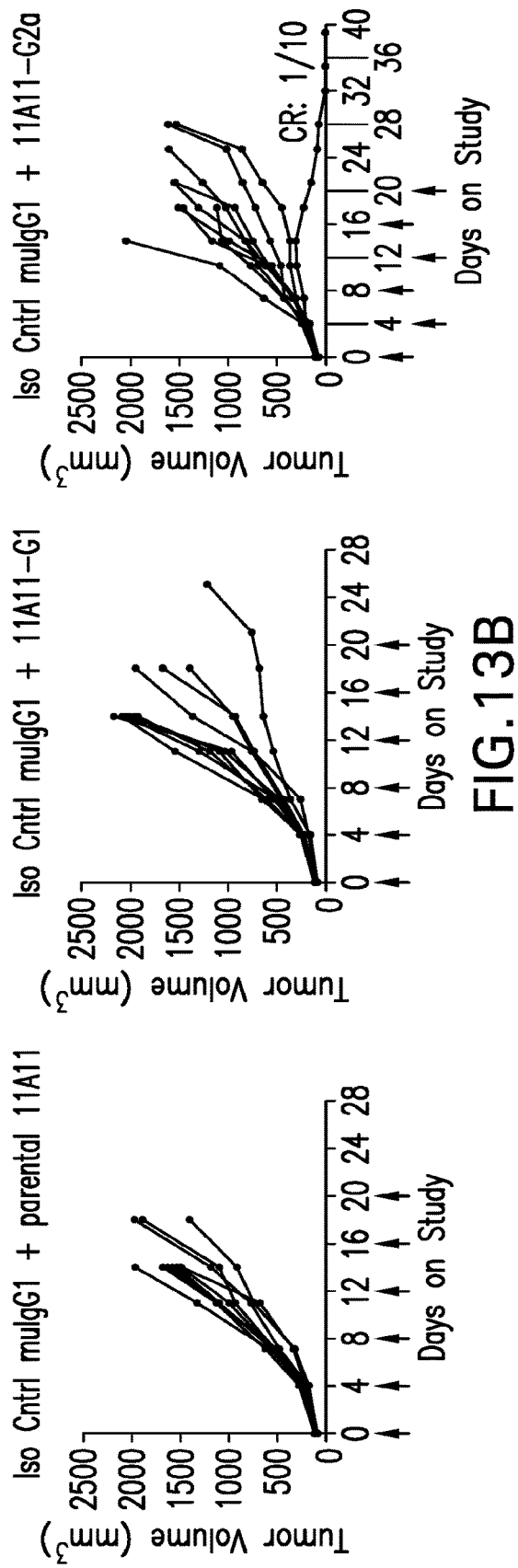
FIG. 13B

SEQUENCE LISTING

```
<160> NUMBER OF SEQ ID NOS: 167

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 1

Ser Asp Tyr Trp Gly
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 2

Phe Ile Thr Tyr Ser Gly Ser Thr Ser Tyr Asn Pro Ser Leu Lys Ser
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 3

Met Pro Ser Phe Ile Thr Leu Ala Ser Leu Ser Thr Trp Glu Gly Tyr
1               5                   10                  15

Phe Asp Phe

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 4

Lys Ala Ser Gln Ser Ile His Lys Asn Leu Ala
1               5                   10
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 5

Tyr Ala Asn Ser Leu Gln Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 6

Gln Gln Tyr Tyr Ser Gly Trp Thr
1               5

<210> SEQ ID NO 7
<211> LENGTH: 127
<212> TYPE: PRT
<213> ORGANISM: Rattus norvegicus

<400> SEQUENCE: 7

Glu Val Gln Leu Gln Glu Ser Gly Pro Gly Leu Val Lys Pro Ser Gln
1               5                   10                  15

Ser Leu Ser Leu Thr Cys Ser Val Thr Gly Ser Ser Ile Ala Ser Asp
            20                  25                  30

Tyr Trp Gly Trp Ile Arg Lys Phe Pro Gly Asn Lys Met Glu Trp Met
        35                  40                  45

Gly Phe Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu His Ser Val Thr Thr Asp Asp Thr Ala Thr Tyr Ser Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Pro Gly Thr Met Val Thr Val Ser Ser
        115                 120                 125

<210> SEQ ID NO 8
<211> LENGTH: 106
<212> TYPE: PRT
<213> ORGANISM: Rattus norvegicus

<400> SEQUENCE: 8

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Ser Ile His Lys Asn
            20                  25                  30

Leu Ala Trp Tyr Gln Gln Lys Leu Gly Glu Ala Pro Lys Phe Leu Ile
        35                  40                  45

Tyr Tyr Ala Asn Ser Leu Gln Thr Gly Ile Pro Ser Arg Phe Ser Gly
    50                  55                  60
```

Ser Gly Ser Gly Thr Asp Phe Thr Leu Thr Ile Ser Gly Leu Gln Pro
65                  70                  75                  80

Glu Asp Val Ala Thr Tyr Phe Cys Gln Gln Tyr Tyr Ser Gly Trp Thr
                85                  90                  95

Phe Gly Gly Gly Thr Lys Val Glu Leu Lys
            100                 105

<210> SEQ ID NO 9
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 9

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
                20                  25                  30

Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 10
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 10

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
                20                  25                  30

Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
        50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

```
<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 11
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

```
<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 12
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Ser Asp
            20                  25                  30

Tyr Trp Gly Trp Ile Arg Gln Pro Pro Gly Lys Gly Leu Glu Trp Met
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

```
<210> SEQ ID NO 13
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide
```

<400> SEQUENCE: 13

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu His Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 14
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 14

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu His Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 15
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 15

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Ser Asp
            20                  25                  30

Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
     50                  55                  60

Ser Arg Ile Thr Ile Ser Arg Asp Thr Ser Lys Asn Gln Phe Ser Leu
 65                  70                  75                  80

Lys Leu His Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
            115                 120                 125

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 16

Glu Val Gln Leu Gln Glu Ser Gly Pro Gly Leu Val Lys Pro Ser Glu
 1               5                  10                  15

Thr Leu Ser Leu Thr Cys Thr Val Ser Gly Ser Ser Ile Ser Ser Asp
             20                  25                  30

Tyr Trp Gly Trp Ile Arg Gln Pro Pro Gly Lys Gly Leu Glu Trp Met
            35                  40                  45

Gly Phe Ile Thr Tyr Ser Gly Ser Thr Ser Tyr Asn Pro Ser Leu Lys
     50                  55                  60

Ser Arg Ile Thr Ile Ser Val Asp Thr Ser Lys Asn Gln Phe Ser Leu
 65                  70                  75                  80

Lys Leu His Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
            115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 17

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Asp
             20                  25                  30

Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 18

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 19

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 20

Glu Val Gln Leu Gln Glu Ser Gly Pro Gly Leu Val Lys Pro Ser Glu
1               5                   10                  15

Thr Leu Ser Leu Thr Cys Ala Val Ser Gly Ser Ser Ile Ser Ser Asp
            20                  25                  30

Tyr Trp Gly Trp Ile Arg Gln Pro Pro Gly Lys Gly Leu Glu Trp Met
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 21

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu His Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 22

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu His Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 23

Glu Val Gln Leu Gln Glu Ser Gly Pro Gly Leu Val Lys Pro Ser Glu
1               5                   10                  15

Thr Leu Ser Leu Thr Cys Ala Val Ser Gly Ser Ser Ile Ser Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu His Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 24

Glu Val Gln Leu Gln Glu Ser Gly Pro Gly Leu Val Lys Pro Ser Glu
1               5                   10                  15

Thr Leu Ser Leu Thr Cys Ala Val Ser Gly Ser Ser Ile Ser Ser Asp
            20                  25                  30

Tyr Trp Gly Trp Ile Arg Gln Pro Pro Gly Lys Gly Leu Glu Trp Met

```
                35                  40                  45
Gly Phe Ile Thr Tyr Ser Gly Ser Thr Ser Tyr Asn Pro Ser Leu Lys
     50                  55                  60

Ser Arg Ile Thr Ile Ser Arg Asp Thr Ser Lys Asn Gln Phe Ser Leu
 65                  70                  75                  80

Lys Leu His Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125
```

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 25

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Ile His Lys Asn
             20                  25                  30

Leu Ala Trp Tyr Gln Gln Lys Pro Gly Lys Ala Pro Lys Leu Leu Ile
         35                  40                  45

Tyr Tyr Ala Asn Ser Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Gly Trp Thr
                 85                  90                  95

Phe Gly Gly Gly Thr Lys Val Glu Ile Lys
            100                 105
```

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Ile His Lys Asn
             20                  25                  30

Leu Ala Trp Tyr Gln Gln Lys Pro Gly Lys Ala Pro Lys Phe Leu Ile
         35                  40                  45

Tyr Tyr Ala Asn Ser Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Gly Trp Thr
                 85                  90                  95

Phe Gly Gly Gly Thr Lys Val Glu Ile Lys
```

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Ala Pro Lys Phe Leu Ile
        35                  40                  45

Tyr Tyr Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Gly Trp Thr
                85                  90                  95

Phe Gly Gly Gly Thr Lys Val Glu Ile Lys
            100                 105

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Val Pro Lys Leu Leu Ile
        35                  40                  45

Tyr Tyr Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ser Gly Trp Thr
                85                  90                  95

Phe Gly Gly Gly Thr Lys Val Glu Ile Lys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Val Pro Lys Phe Leu Ile
        35                  40                  45

Tyr Tyr Ala Asn Ser Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Tyr Ser Gly Trp Thr
                85                  90                  95

Phe Gly Gly Gly Thr Lys Val Glu Ile Lys
            100                 105

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Val Pro Lys Phe Leu Ile
        35                  40                  45

Tyr Tyr Ala Asn Ser Leu Gln Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Tyr Ser Gly Trp Thr
                85                  90                  95

Phe Gly Gly Gly Thr Lys Val Glu Ile Lys
            100                 105

<210> SEQ ID NO 31
<211> LENGTH: 244
<212> TYPE: PRT
<213> ORGANISM: Homo sapiens

<400> SEQUENCE: 31

Met Arg Trp Cys Leu Leu Leu Ile Trp Ala Gln Gly Leu Arg Gln Ala
 1               5                  10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
 50                  55                  60

Leu Leu Ala Ile Cys Asn Ala Asp Leu Gly Trp His Ile Ser Pro Ser
 65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

```
Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
                180                 185                 190

Ala Pro Ser Pro Pro Gly Ser Cys Val Gln Ala Glu Ala Ala Pro Ala
                195                 200                 205

Gly Leu Cys Gly Glu Gln Arg Gly Glu Asp Cys Ala Glu Leu His Asp
                210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 32
<211> LENGTH: 245
<212> TYPE: PRT
<213> ORGANISM: Macaca fascicularis

<400> SEQUENCE: 32

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
                20                  25                  30

Ile Ser Ala Lys Lys Gly Gly Ser Val Ile Leu Gln Cys His Leu Ser
                35                  40                  45

Ser Thr Met Ala Gln Val Thr Gln Val Asn Trp Glu Gln His Asp His
50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
                100                 105                 110

Thr Tyr Pro Asp Gly Thr Tyr Arg Gly Arg Ile Phe Leu Glu Val Leu
            115                 120                 125

Glu Ser Ser Val Ala Glu His Ser Ala Arg Phe Gln Ile Pro Leu Leu
130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Glu Gln Ile Pro
                180                 185                 190

Ser Ala Pro Ser Pro Pro Gly Ser Cys Val Gln Ala Glu Ala Ala Pro
                195                 200                 205

Ala Gly Leu Cys Gly Glu Gln Gln Gly Asp Asp Cys Ala Glu Leu His
                210                 215                 220

Asp Tyr Phe Asn Val Leu Ser Tyr Arg Ser Leu Gly Ser Cys Ser Phe
225                 230                 235                 240
```

Phe Thr Glu Thr Gly
            245

<210> SEQ ID NO 33
<211> LENGTH: 447
<212> TYPE: PRT
<213> ORGANISM: Artificial Sequence
<220> FEATURE:
<223> OTHER INFORMATION: Description of Artificial Sequence: Synthetic
      Antibody chain polypeptide

<400> SEQUENCE: 33

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro

```
                340             345             350
Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 34
<211> LENGTH: 218
<212> TYPE: PRT
<213> ORGANISM: Artificial Sequence
<220> FEATURE:
<223> OTHER INFORMATION: Description of Artificial Sequence: Synthetic
      Antibody chain polypeptide

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 35
<211> LENGTH: 440
<212> TYPE: PRT
<213> ORGANISM: Artificial Sequence
<220> FEATURE:
```

<223> OTHER INFORMATION: Description of Artificial Sequence: Synthetic
Antibody chain polypeptide

<400> SEQUENCE: 35

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      Antibody chain polypeptide

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 129
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 37

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ala Ser Asp
            20                  25                  30
```

```
Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser Ala
            115                 120                 125

Ser

<210> SEQ ID NO 38
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 38

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ala Ser Asp
            20                  25                  30

Tyr Trp Gly Trp Ile Arg Gln Pro Pro Gly Lys Gly Leu Glu Trp Ile
            35                  40                  45

Gly Phe Ile Thr Tyr Ser Gly Ser Thr Ser Tyr Asn Pro Ser Leu Lys
        50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
            115                 120                 125

<210> SEQ ID NO 39
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 39

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ala Ser Asp
            20                  25                  30

Tyr Trp Gly Trp Ile Arg Lys Pro Pro Gly Lys Gly Leu Glu Trp Ile
            35                  40                  45

Gly Phe Ile Thr Tyr Ser Gly Ser Thr Ser Tyr Asn Pro Ser Leu Lys
        50                  55                  60
```

```
Ser Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125
```

<210> SEQ ID NO 40
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 40

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Ser Ser Ile Ala Ser Asp
                 20                  25                  30

Tyr Trp Gly Trp Ile Arg Gln Pro Pro Gly Lys Lys Leu Glu Trp Ile
             35                  40                  45

Gly Phe Ile Thr Tyr Ser Gly Ser Thr Ser Tyr Asn Pro Ser Leu Lys
     50                  55                  60

Ser Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125
```

<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 41

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Ser Ser Ile Ala Ser Asp
                 20                  25                  30

Tyr Trp Gly Trp Ile Arg Gln Pro Pro Gly Lys Gly Met Glu Trp Ile
             35                  40                  45

Gly Phe Ile Thr Tyr Ser Gly Ser Thr Ser Tyr Asn Pro Ser Leu Lys
     50                  55                  60

Ser Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Met Pro Ser Phe Ile Thr Leu Ala Ser Leu Ser Thr Trp Glu Gly
            100                 105                 110
```

Tyr Phe Asp Phe Trp Gly Gln Gly Thr Met Val Thr Val Ser Ser
            115                 120                 125

<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 42

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ala Ser Asp
            20                  25                  30

Tyr Trp Gly Trp Ile Arg Lys Pro Pro Gly Lys Lys Met Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
            115                 120                 125

<210> SEQ ID NO 43
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 43

Glu Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ala Ser Asp
            20                  25                  30

Tyr Trp Gly Trp Ile Arg Gln Phe Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Asp Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
            115                 120                 125

<210> SEQ ID NO 44
<211> LENGTH: 127
<212> TYPE: PRT
<213> ORGANISM: Artificial Sequence
<220> FEATURE:

<223> OTHER INFORMATION: Description of Artificial Sequence: Synthetic
      Humanized antibody chain polypeptide

<400> SEQUENCE: 44

Glu Val Gln Leu Gln Glu Ser Gly Pro Gly Leu Val Lys Pro Ser Glu
1               5                   10                  15

Thr Leu Ser Leu Thr Cys Thr Val Gly Ser Ser Ile Ala Ser Asp
            20                  25                  30

Tyr Trp Gly Trp Ile Arg Lys Pro Pro Gly Lys Lys Met Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 45
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 45

Glu Val Gln Leu Gln Glu Ser Gly Pro Gly Leu Val Lys Pro Ser Glu
1               5                   10                  15

Thr Leu Ser Leu Thr Cys Ser Val Thr Gly Ser Ser Ile Ala Ser Asp
            20                  25                  30

Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Gln Gly Thr Met Val Thr Val Ser Ser
        115                 120                 125

<210> SEQ ID NO 46
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 46

Glu Val Gln Leu Gln Gln Ser Gly Ala Gly Leu Leu Lys Pro Ser Glu
1               5                   10                  15

Thr Leu Ser Leu Thr Cys Ser Val Thr Gly Ser Ser Ile Ala Ser Asp

```
            20                  25                  30
Tyr Trp Gly Trp Ile Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
                100                 105                 110

Tyr Phe Asp Phe Trp Gly Gln Gly Thr Met Val Thr Val Ser Ser
            115                 120                 125

<210> SEQ ID NO 47
<211> LENGTH: 127
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 47

Glu Val Gln Leu Gln Glu Ser Gly Pro Gly Leu Val Lys Pro Pro Gly
1               5                   10                  15

Thr Leu Ser Leu Thr Cys Ser Val Thr Gly Ser Ser Ile Ala Ser Asp
            20                  25                  30

Tyr Trp Gly Trp Val Arg Gln Pro Pro Gly Lys Gly Leu Glu Trp Ile
        35                  40                  45

Gly Phe Ile Thr Tyr Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Met Pro Ser Phe Ile Thr Leu Ala Ser Leu Ser Thr Trp Glu Gly
                100                 105                 110

Tyr Phe Asp Phe Trp Gly Gln Gly Thr Met Val Thr Val Ser Ser
            115                 120                 125

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Ala Pro Lys Leu Leu Ile
        35                  40                  45

Tyr Tyr Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
```

```
              65                  70                  75                  80
Glu Asp Phe Ala Thr Tyr Tyr Cys Gln Gln Tyr Tyr Ser Gly Trp Thr
                    85                  90                  95

Phe Gly Gly Gly Thr Lys Val Glu Ile Lys
                100                 105
```

<210> SEQ ID NO 49
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
                20                  25                  30

Leu Ala Trp Tyr Gln Gln Lys Pro Gly Lys Ala Pro Lys Phe Leu Ile
            35                  40                  45

Tyr Tyr Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Gly Trp Thr
                    85                  90                  95

Phe Gly Gly Gly Thr Lys Val Glu Ile Lys
                100                 105
```

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
                20                  25                  30

Leu Ala Trp Tyr Gln Gln Lys Pro Gly Lys Ala Pro Lys Leu Leu Ile
            35                  40                  45

Tyr Tyr Ala Asn Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Tyr Ser Gly Trp Thr
                    85                  90                  95

Phe Gly Gly Gly Thr Lys Val Glu Ile Lys
                100                 105
```

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic Humanized antibody chain polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Ala Pro Lys Phe Leu Ile
        35                  40                  45

Tyr Tyr Ala Asn Ser Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Tyr Ser Gly Trp Thr
                85                  90                  95

Phe Gly Gly Gly Thr Lys Val Glu Ile Lys
            100                 105

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Ala Pro Lys Leu Leu Ile
        35                  40                  45

Tyr Tyr Ala Asn Ser Leu Gln Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Gly Trp Thr
                85                  90                  95

Phe Gly Gly Gly Thr Lys Val Glu Ile Lys
            100                 105

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      Leader sequence heavy chains peptide

<400> SEQUENCE: 53

Met Glu Trp Ser Trp Val Phe Leu Phe Phe Leu Ser Val Thr Thr Gly
1               5                   10                  15

Val His Ser

<210> SEQ ID NO 54
<211> LENGTH: 20
<212> TYPE: PRT
<213> ORGANISM: Artificial Sequence
<220> FEATURE:

-continued

<223> OTHER INFORMATION: Description of Artificial Sequence: Synthetic
     Leader sequence light chains peptide

<400> SEQUENCE: 54

Met Ser Val Pro Thr Gln Val Leu Gly Leu Leu Leu Leu Trp Leu Thr
1               5                   10                  15

Asp Ala Arg Cys
            20

<210> SEQ ID NO 55
<211> LENGTH: 325
<212> TYPE: PRT
<213> ORGANISM: Artificial Sequence
<220> FEATURE:
<223> OTHER INFORMATION: Description of Artificial Sequence: Synthetic
     Heavy chain constant domain-IgG4 S228P polypeptide

<400> SEQUENCE: 55

Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Lys Thr Tyr Thr
65                  70                  75                  80

Cys Asn Val Asp His Lys Pro Ser Asn Thr Lys Val Asp Lys Arg Val
                85                  90                  95

Glu Ser Lys Tyr Gly Pro Pro Cys Pro Pro Cys Pro Ala Pro Glu Phe
            100                 105                 110

Leu Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Gln Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300

```
Val Met His Glu Ala Leu His Asn His Tyr Thr Gln Lys Ser Leu Ser
305                 310                 315                 320

Leu Ser Leu Gly Lys
            325

<210> SEQ ID NO 56
<211> LENGTH: 105
<212> TYPE: PRT
<213> ORGANISM: Artificial Sequence
<220> FEATURE:
<223> OTHER INFORMATION: Description of Artificial Sequence: Synthetic
      Kappa light chain constant domain polypeptide

<400> SEQUENCE: 56

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 57

Gly Tyr Ser Ile Thr Ser Asp Tyr Ala Trp Asn
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 58

Tyr Ile Ser Asn Ser Gly Ser Ala Ser Tyr Asn Pro Ser Leu Lys Ser
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 59

Leu Ile Tyr Tyr Asp Tyr Gly Gly Ala Met Asn Phe
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 60

Lys Ala Ser Gln Gly Val Ser Thr Thr Val Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 61

Ser Ala Ser Tyr Arg Tyr Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 62

Gln His Tyr Tyr Ser Thr Pro Trp Thr
1               5

<210> SEQ ID NO 63
<211> LENGTH: 121
<212> TYPE: PRT
<213> ORGANISM: Mus musculus

<400> SEQUENCE: 63

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Asn Ser Gly Ser Ala Ser Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Thr Leu Ile Tyr Tyr Asp Tyr Gly Gly Ala Met Asn Phe Trp Gly
            100                 105                 110

Gln Gly Thr Ser Val Thr Val Ser Ser
        115                 120

<210> SEQ ID NO 64
<211> LENGTH: 107
<212> TYPE: PRT

<213> ORGANISM: Mus musculus

<400> SEQUENCE: 64

Asp Ile Val Met Thr Gln Ser His Lys Phe Met Ser Thr Ser Val Gly
1               5                   10                  15

Asp Arg Val Ser Ile Thr Cys Lys Ala Ser Gln Gly Val Ser Thr Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ser
65                  70                  75                  80

Glu Asp Leu Ala Val Tyr Tyr Cys Gln His Tyr Tyr Ser Thr Pro Trp
                85                  90                  95

Thr Phe Gly Gly Gly Thr Lys Leu Glu Ile Lys
            100                 105

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 65

Tyr Ala Ser Asn Leu Gln Thr
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 66

Tyr Ala Ser Ser Leu Gln Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 67

Tyr Ala Ser Thr Leu Gln Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 68

Tyr Ala Thr Thr Leu Gln Thr

```
<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 69

Tyr Ala Ser Tyr Leu Gln Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 70

Tyr Ala Asn Gln Leu Gln Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 71

Tyr Ala Gly Ser Leu Gln Thr
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 72

Tyr Ala Ser Gln Leu Gln Thr
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 73

Tyr Ala Asp Ser Leu Gln Thr
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued

CDR peptide

<400> SEQUENCE: 74

Gln Gln Tyr Tyr Ser Gly Phe Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 75

Gln Gln Tyr Tyr Ser Gly Tyr Thr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 76

Gln Gln Tyr Tyr Ser Gly Ile Thr
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 77

Gln Gln Tyr Tyr Ser Gly Val Thr
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 78

Gln Gln Tyr Tyr Ser Gly Leu Thr
1               5

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 79

Met Pro Ser Phe Ile Thr Leu Ala Ser Leu Ser Thr Phe Glu Gly Tyr
1               5                   10                  15

Phe Asp Phe

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 80

Met Pro Ser Phe Ile Thr Leu Ala Ser Leu Ser Thr Tyr Glu Gly Tyr
1               5                   10                  15

Phe Asp Phe

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 81

Met Pro Ser Phe Ile Thr Leu Ala Ser Leu Ser Thr Ile Glu Gly Tyr
1               5                   10                  15

Phe Asp Phe

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 82

Met Pro Ser Phe Ile Thr Leu Ala Ser Leu Ser Thr Val Glu Gly Tyr
1               5                   10                  15

Phe Asp Phe

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 83

Met Pro Ser Phe Ile Thr Leu Ala Ser Leu Ser Thr Leu Glu Gly Tyr
1               5                   10                  15

Phe Asp Phe

<210> SEQ ID NO 84
<211> LENGTH: 363
<212> TYPE: DNA
<213> ORGANISM: Mus musculus

<400> SEQUENCE: 84
gatgtgcagc ttcaggagtc gggacctggc ctggtgaaac cttctcagtc tctgtccctc      60
acctgcactg tcactggcta ctcaatcacc agtgattatg cctggaactg gatccgacag     120
tttccaggaa acaaactgga gtggatgggc tacataagca acagtggtag cgctagctac     180
aacccatctc tcaaaagtcg catctctatc actcgagaca catccaagaa ccagttcttc     240

```
ctgcagttga attctgtgac tactgaggac acagccacat attactgtgc aaccctgatc    300
tactatgatt acgggggggc tatgaacttc tggggtcaag gaacctcagt caccgtctcc    360
tca                                                                  363
```

<210> SEQ ID NO 85
<211> LENGTH: 321
<212> TYPE: DNA
<213> ORGANISM: Mus musculus

<400> SEQUENCE: 85

```
gacattgtga tgacccagtc tcacaaattc atgtccacat cagtaggaga cagggtcagc     60
atcacctgca aggccagtca gggtgtgagt actactgtgg cctggtatca acagaaacca    120
ggacaatctc ctaaactact gatttactcg gcatcctacc ggtacactgg agtccctgat    180
cgcttcactg gcagtggatc tgggacggat ttcactttca ccatcagcag tgtgcagtct    240
gaagacctgg cagtttatta ctgtcagcat tattatagta ctccgtggac gttcggtgga    300
ggcaccaagc tggaaatcaa a                                              321
```

<210> SEQ ID NO 86
<211> LENGTH: 330
<212> TYPE: PRT
<213> ORGANISM: Homo sapiens

<400> SEQUENCE: 86

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 87
<211> LENGTH: 133
<212> TYPE: PRT
<213> ORGANISM: Artificial Sequence
<220> FEATURE:
<223> OTHER INFORMATION: Description of Artificial Sequence: Synthetic
      Fusion protein polypeptide

<400> SEQUENCE: 87

Gly Thr Ile Glu Thr Thr Gly Asn Ile Ser Ala Glu Lys Gly Gly Ser
1               5                   10                  15

Ile Ile Leu Gln Cys His Leu Ser Ser Thr Thr Ala Gln Val Thr Gln
            20                  25                  30

Val Asn Trp Glu Gln Gln Asp Gln Leu Leu Ala Ile Cys Asn Ala Asp
            35                  40                  45

Leu Gly Trp His Ile Ser Pro Ser Phe Lys Asp Arg Val Ala Pro Gly
    50                  55                  60

Pro Gly Leu Gly Leu Thr Leu Gln Ser Leu Thr Val Asn Asp Thr Gly
65                  70                  75                  80

Glu Tyr Phe Cys Ile Tyr His Thr Tyr Pro Asp Gly Thr Tyr Thr Gly
                85                  90                  95

Arg Ile Phe Leu Glu Val Leu Glu Ser Ser Val Ala Glu His Gly Ala
            100                 105                 110

Arg Phe Gln Ile Pro Leu Leu Gly Ala His His His His His His His
            115                 120                 125

His His Gly Gly Gln
    130

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 88

Ser Tyr Val Met His
1               5

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide
```

-continued

<400> SEQUENCE: 89

Tyr Ile Asp Pro Tyr Asn Asp Gly Ala Lys Tyr Asn Glu Lys Phe Lys
1               5                   10                  15

Gly

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 90

Gly Gly Pro Tyr Gly Trp Tyr Phe Asp Val
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 91

Arg Ala Ser Glu His Ile Tyr Ser Tyr Leu Ser
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 92

Asn Ala Lys Thr Leu Ala Glu
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 93

Gln His His Phe Gly Ser Pro Leu Thr
1               5

<210> SEQ ID NO 94
<211> LENGTH: 119
<212> TYPE: PRT
<213> ORGANISM: Mus musculus

<400> SEQUENCE: 94

Glu Val Gln Leu Gln Gln Ser Gly Pro Glu Leu Val Lys Pro Gly Ser
1               5                   10                  15

Ser Val Lys Met Ser Cys Lys Ala Ser Gly Tyr Thr Phe Ser Ser Tyr
                20                  25                  30

Val Met His Trp Val Lys Gln Lys Pro Gly Gln Gly Leu Glu Trp Ile

```
                35                  40                  45
Gly Tyr Ile Asp Pro Tyr Asn Asp Gly Ala Lys Tyr Asn Glu Lys Phe
 50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Gly Gly Pro Tyr Gly Trp Tyr Phe Asp Val Trp Gly Ala Gly
                100                 105                 110

Thr Thr Val Thr Val Ser Ser
            115

<210> SEQ ID NO 95
<211> LENGTH: 107
<212> TYPE: PRT
<213> ORGANISM: Mus musculus

<400> SEQUENCE: 95

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu His Ile Tyr Ser Tyr
                 20                  25                  30

Leu Ser Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Thr Tyr Tyr Cys Gln His His Phe Gly Ser Pro Leu
                 85                  90                  95

Thr Phe Gly Ala Gly Thr Thr Leu Glu Leu Lys
            100                 105

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 96

Tyr Ile Asp Pro Tyr Asn Arg Gly Ala Lys Tyr Asn Glu Lys Phe Gly
 1               5                  10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 97

Tyr Ile Asp Pro Tyr Asn Leu Gly Ala Lys Tyr Asn Glu Lys Gly Phe
 1               5                  10                  15

<210> SEQ ID NO 98
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      CDR peptide

<400> SEQUENCE: 98

Tyr Ile Asp Pro Tyr Asn Lys Gly Ala Lys Tyr Asn Glu Lys Phe Gly
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 99

Tyr Ile Asp Pro Tyr Asn Phe Gly Ala Lys Tyr Asn Glu Lys Phe Gly
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 100

Tyr Ile Asp Pro Tyr Asn Ser Gly Ala Lys Tyr Asn Glu Lys Phe Gly
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 101

Tyr Ile Asp Pro Tyr Asn Tyr Gly Ala Lys Tyr Asn Glu Lys Phe Gly
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 102

Tyr Ile Asp Pro Tyr Asn Val Gly Ala Lys Tyr Asn Glu Lys Phe Gly
1               5                   10                  15

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 103

Tyr Ile Asp Pro Tyr Asn Asp Arg Ala Lys Tyr Asn Glu Lys Phe Lys
1               5                   10                  15
```

Gly

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 104

Tyr Ile Asp Pro Tyr Asn Asp Asn Ala Lys Tyr Asn Glu Lys Phe Lys
1               5                   10                  15

Gly

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 105

Tyr Ile Asp Pro Tyr Asn Asp Gln Ala Lys Tyr Asn Glu Lys Phe Lys
1               5                   10                  15

Gly

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 106

Tyr Ile Asp Pro Tyr Asn Asp Glu Ala Lys Tyr Asn Glu Lys Phe Lys
1               5                   10                  15

Gly

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 107

Tyr Ile Asp Pro Tyr Asn Asp Leu Ala Lys Tyr Asn Glu Lys Phe Lys
1               5                   10                  15

Gly

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 108

Tyr Ile Asp Pro Tyr Asn Asp Lys Ala Lys Tyr Asn Glu Lys Phe Lys
1               5                   10                  15

```
<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 109

Tyr Ile Asp Pro Tyr Asn Asp Ser Ala Lys Tyr Asn Glu Lys Phe Lys
1               5                   10                  15

Gly

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 110

Tyr Ile Asp Pro Tyr Asn Asp Tyr Ala Lys Tyr Asn Glu Lys Phe Lys
1               5                   10                  15

Gly

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 111

Tyr Ile Asp Pro Tyr Asn Asp Val Ala Lys Tyr Asn Glu Lys Phe Lys
1               5                   10                  15

Gly

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 112

Ala Ala Lys Thr Leu Ala Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 113

Tyr Ala Lys Thr Leu Ala Glu
1               5
```

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 114

Trp Ala Lys Thr Leu Ala Glu
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 115

Ser Ala Lys Thr Leu Ala Glu
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 116

Thr Ala Lys Thr Leu Ala Glu
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 117

Ile Ala Lys Thr Leu Ala Glu
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 118

Val Ala Lys Thr Leu Ala Glu
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 119

Asn Asn Lys Thr Leu Ala Glu
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 120

Asn Ile Lys Thr Leu Ala Glu
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 121

Asn Leu Leu Thr Leu Ala Glu
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 122

Asn Thr Lys Thr Leu Ala Glu
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 123

Asn Val Lys Thr Leu Ala Glu
1               5

<210> SEQ ID NO 124
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 124

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
                20                  25                  30

Val Met His Trp Val Arg Gln Ala Pro Gly Gln Arg Leu Glu Trp Ile

```
                35                  40                  45
Gly Tyr Ile Asp Pro Tyr Asn Asp Gly Ala Lys Tyr Ser Gln Lys Phe
         50                  55                  60

Gln Gly Arg Val Thr Leu Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Pro Tyr Gly Trp Tyr Phe Asp Val Trp Gly Gln Gly
            100                 105                 110

Thr Thr Val Thr Val Ser Ser
        115

<210> SEQ ID NO 125
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 125

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Tyr
             20                  25                  30

Val Met His Trp Val Arg Gln Ala Pro Gly Gln Arg Leu Glu Trp Ile
         35                  40                  45

Gly Tyr Ile Asp Pro Tyr Asn Asp Gly Ala Lys Tyr Ser Gln Lys Phe
         50                  55                  60

Gln Gly Arg Val Thr Leu Thr Ser Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Pro Tyr Gly Trp Tyr Phe Asp Val Trp Gly Gln Gly
            100                 105                 110

Thr Thr Val Thr Val Ser Ser
        115

<210> SEQ ID NO 126
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 126

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Tyr
             20                  25                  30

Val Met His Trp Val Arg Gln Ala Pro Gly Gln Gly Leu Glu Trp Ile
         35                  40                  45

Gly Tyr Ile Asp Pro Tyr Asn Asp Gly Ala Lys Tyr Ala Gln Lys Phe
         50                  55                  60

Gln Gly Arg Val Thr Leu Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
```

85                  90                  95

Ala Arg Gly Gly Pro Tyr Gly Trp Tyr Phe Asp Val Trp Gly Gln Gly
                100                 105                 110

Thr Thr Val Thr Val Ser Ser
        115

<210> SEQ ID NO 127
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 127

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
                20                  25                  30

Val Met His Trp Val Arg Gln Ala Pro Gly Gln Gly Leu Glu Trp Ile
            35                  40                  45

Gly Tyr Ile Asp Pro Tyr Asn Asp Gly Ala Lys Tyr Ala Gln Lys Phe
    50                  55                  60

Gln Gly Arg Val Thr Leu Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Tyr Gly Trp Tyr Phe Asp Val Trp Gly Gln Gly
                100                 105                 110

Thr Thr Val Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 128

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Val Met His Trp Val Arg Gln Ala Pro Gly Gln Gly Leu Glu Trp Ile
            35                  40                  45

Gly Tyr Ile Asp Pro Tyr Asn Asp Gly Ala Lys Tyr Ala Gln Lys Phe
    50                  55                  60

Gln Gly Arg Val Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Tyr Gly Trp Tyr Phe Asp Val Trp Gly Gln Gly
                100                 105                 110

Thr Thr Val Thr Val Ser Ser
        115

-continued

```
<210> SEQ ID NO 129
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 129

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Val Met His Trp Val Arg Gln Ala Pro Gly Gln Gly Leu Glu Trp Ile
        35                  40                  45

Gly Tyr Ile Asp Pro Tyr Asn Asp Gly Ala Lys Tyr Ala Gln Lys Phe
    50                  55                  60

Gln Gly Arg Val Thr Leu Thr Ser Asp Lys Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Gly Pro Tyr Gly Tyr Tyr Phe Asp Val Trp Gly Gln Gly
            100                 105                 110

Thr Thr Val Thr Val Ser Ser
        115

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Tyr Ser Tyr
            20                  25                  30

Leu Ser Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Phe Gly Ser Pro Leu
                85                  90                  95

Thr Phe Gly Gln Gly Thr Arg Leu Glu Ile Lys
            100                 105

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 131

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Glu His Ile Tyr Ser Tyr
            20                  25                  30

Leu Ser Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His His Phe Gly Ser Pro Leu
                85                  90                  95

Thr Phe Gly Gln Gly Thr Arg Leu Glu Ile Lys
            100                 105

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Tyr Ser Tyr
            20                  25                  30

Leu Ser Trp Tyr Gln Gln Lys Pro Gly Lys Val Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His His Phe Gly Ser Pro Leu
                85                  90                  95

Thr Phe Gly Gln Gly Thr Arg Leu Glu Ile Lys
            100                 105

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized antibody chain polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Tyr Ser Tyr
            20                  25                  30

Leu Ser Trp Tyr Gln Gln Lys Pro Gly Lys Val Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Val Ala Thr Tyr Tyr Cys Gln His His Phe Gly Ser Pro Leu
                85                  90                  95

Thr Phe Gly Gln Gly Thr Arg Leu Glu Ile Lys
            100                 105

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 134

Tyr Ile Asp Pro Tyr Asn Asp Gly Ala Lys Tyr Ala Gln Lys Phe Gln
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 135

Tyr Ile Asp Pro Tyr Asn Asp Gly Ala Lys Tyr Ser Gln Lys Phe Gln
1               5                   10                  15

Gly

<210> SEQ ID NO 136
<211> LENGTH: 116
<212> TYPE: PRT
<213> ORGANISM: Artificial Sequence
<220> FEATURE:
<223> OTHER INFORMATION: Description of Artificial Sequence: Synthetic
      VH sequence polypeptide

<400> SEQUENCE: 136

Gln Val Gln Leu Met Glu Ser Gly Pro Gly Leu Val Gln Pro Ser Gln
1               5                   10                  15

Thr Leu Ser Leu Thr Cys Thr Val Ser Gly Phe Pro Leu Thr Ser Tyr
            20                  25                  30

Thr Val His Trp Val Arg Gln Pro Pro Gly Lys Gly Leu Glu Trp Ile
        35                  40                  45

Gly Ala Ile Trp Ser Ser Gly Ser Thr Asp Tyr Asn Ser Ala Leu Lys
    50                  55                  60

Ser Arg Leu Asn Ile Asn Arg Asp Ser Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Lys Ser Gly Trp Ala Phe Phe Asp Tyr Trp Gly Gln Gly Val Met Val
            100                 105                 110

Thr Val Ser Ser
        115

<210> SEQ ID NO 137
<211> LENGTH: 106
<212> TYPE: PRT
<213> ORGANISM: Artificial Sequence
<220> FEATURE:
<223> OTHER INFORMATION: Description of Artificial Sequence: Synthetic
      VL sequence polypeptide

```
<400> SEQUENCE: 137

Asp Ile Gln Met Thr Gln Ser Pro Ser Leu Leu Ser Ala Ser Val Gly
1               5                   10                  15

Asp Arg Val Thr Leu Asn Cys Ile Ala Ser Gln Asn Ile Tyr Lys Ser
            20                  25                  30

Leu Ala Trp Tyr Gln Leu Lys Leu Gly Glu Ala Pro Lys Leu Leu Ile
        35                  40                  45

Tyr Asn Ala Asn Ser Leu Gln Ala Gly Ile Pro Ser Arg Phe Ser Gly
50                  55                  60

Ser Gly Ser Gly Thr Asp Phe Ala Leu Thr Ile Ser Gly Leu Gln Pro
65                  70                  75                  80

Glu Asp Val Ala Thr Tyr Phe Cys Gln Gln Tyr Ser Gly Gly Tyr Thr
                85                  90                  95

Phe Gly Ala Gly Thr Lys Leu Glu Leu Lys
            100                 105

<210> SEQ ID NO 138
<211> LENGTH: 119
<212> TYPE: PRT
<213> ORGANISM: Artificial Sequence
<220> FEATURE:
<223> OTHER INFORMATION: Description of Artificial Sequence: Synthetic
      VH sequence polypeptide

<400> SEQUENCE: 138

Glu Val Gln Leu Val Glu Ser Gly Gly Asp Leu Val Gln Pro Gly Arg
1               5                   10                  15

Ser Leu Lys Ile Ser Cys Val Ala Ser Gly Phe Thr Phe Ser Asp Tyr
            20                  25                  30

Tyr Met Ala Trp Val Arg Leu Ala Pro Gln Lys Gly Leu Glu Trp Val
        35                  40                  45

Ala Ser Ile Ser Tyr Glu Gly Ser Arg Thr His Tyr Gly Asp Ser Val
50                  55                  60

Arg Gly Arg Phe Ile Ile Ser Arg Asp Asn Pro Lys Asn Ile Leu Tyr
65                  70                  75                  80

Leu Gln Met Asn Ser Leu Gly Ser Glu Asp Thr Ala Thr Tyr Phe Cys
                85                  90                  95

Ala Arg His Thr Gly Thr Leu Asp Trp Leu Val Tyr Trp Gly Gln Gly
            100                 105                 110

Thr Leu Val Ile Val Ser Ser
        115

<210> SEQ ID NO 139
<211> LENGTH: 106
<212> TYPE: PRT
<213> ORGANISM: Artificial Sequence
<220> FEATURE:
<223> OTHER INFORMATION: Description of Artificial Sequence: Synthetic
      VL sequence polypeptide

<400> SEQUENCE: 139

Asn Ile Val Met Ala Gln Ser Pro Lys Ser Met Ser Ile Ser Ala Gly
1               5                   10                  15

Asp Arg Val Thr Met Asn Cys Lys Ala Ser Gln Asn Val Asp Asn Asn
            20                  25                  30

Ile Ala Trp Tyr Gln Gln Lys Pro Gly Gln Ser Pro Lys Leu Leu Ile
        35                  40                  45
```

-continued

```
Phe Tyr Ala Ser Asn Arg Tyr Ser Gly Val Pro Asp Arg Phe Thr Gly
    50                  55                  60

Gly Gly Tyr Gly Thr Asp Phe Thr Leu Thr Ile Lys Ser Val Gln Ala
65                  70                  75                  80

Glu Asp Ala Ala Phe Tyr Tyr Cys Gln Arg Ile Tyr Asn Phe Pro Thr
                85                  90                  95

Phe Gly Ser Gly Thr Lys Leu Glu Ile Lys
            100                 105

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      CDR peptide
<220> FEATURE:
<221> NAME/KEY: MOD_RES
<222> LOCATION: (13)..(13)
<223> OTHER INFORMATION: Trp, Phe, Tyr, Ile, Val or Leu

<400> SEQUENCE: 140

Met Pro Ser Phe Ile Thr Leu Ala Ser Leu Ser Thr Xaa Glu Gly Tyr
1               5                   10                  15

Phe Asp Phe

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR peptide
<220> FEATURE:
<221> NAME/KEY: MOD_RES
<222> LOCATION: (3)..(3)
<223> OTHER INFORMATION: Asn, Ser, Thr, Gly or Asp
<220> FEATURE:
<221> NAME/KEY: MOD_RES
<222> LOCATION: (4)..(4)
<223> OTHER INFORMATION: Ser, Asn, Ser, Thr, Tyr or Gln

<400> SEQUENCE: 141

Tyr Ala Xaa Xaa Leu Gln Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      CDR peptide
<220> FEATURE:
<221> NAME/KEY: MOD_RES
<222> LOCATION: (7)..(7)
<223> OTHER INFORMATION: Trp, Phe, Tyr, Ile, Val or Leu

<400> SEQUENCE: 142

Gln Gln Tyr Tyr Ser Gly Xaa Thr
1               5

<210> SEQ ID NO 143
<211> LENGTH: 127
<212> TYPE: PRT
<213> ORGANISM: Artificial Sequence
<220> FEATURE:
<223> OTHER INFORMATION: Description of Artificial Sequence: Synthetic
```

```
      consensus polypeptide
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (12)..(12)
<223> OTHER INFORMATION: Val or Leu
<220> FEATURE:
<221> NAME/KEY: MOD_RES
<222> LOCATION: (15)..(15)
<223> OTHER INFORMATION: Ser or Pro
<220> FEATURE:
<221> NAME/KEY: MOD_RES
<222> LOCATION: (16)..(16)
<223> OTHER INFORMATION: Gln, Glu or Gly
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (23)..(23)
<223> OTHER INFORMATION: Ser, Thr or Ala
<220> FEATURE:
<221> NAME/KEY: MOD_RES
<222> LOCATION: (25)..(25)
<223> OTHER INFORMATION: Thr or Ser
<220> FEATURE:
<221> NAME/KEY: MOD_RES
<222> LOCATION: (27)..(27)
<223> OTHER INFORMATION: Ile or Val
<220> FEATURE:
<221> NAME/KEY: MOD_RES
<222> LOCATION: (30)..(30)
<223> OTHER INFORMATION: Lys or Gln
<220> FEATURE:
<221> NAME/KEY: MOD_RES
<222> LOCATION: (37)..(37)
<223> OTHER INFORMATION: Pro or Phe
<220> FEATURE:
<221> NAME/KEY: MOD_RES
<222> LOCATION: (39)..(39)
<223> OTHER INFORMATION: Asn or Lys
<220> FEATURE:
<221> NAME/KEY: MOD_RES
<222> LOCATION: (40)..(40)
<223> OTHER INFORMATION: Lys or Gly
<220> FEATURE:
<221> NAME/KEY: MOD_RES
<222> LOCATION: (43)..(43)
<223> OTHER INFORMATION: Met or Leu
<220> FEATURE:
<221> NAME/KEY: MOD_RES
<222> LOCATION: (44)..(44)
<223> OTHER INFORMATION: Met or Ile
<220> FEATURE:
<221> NAME/KEY: MOD_RES
<222> LOCATION: (45)..(45)
<223> OTHER INFORMATION: Ile or Val
<220> FEATURE:
<221> NAME/KEY: MOD_RES
<222> LOCATION: (48)..(48)
<223> OTHER INFORMATION: Ser or Thr
<220> FEATURE:
<221> NAME/KEY: MOD_RES
<222> LOCATION: (67)..(67)
<223> OTHER INFORMATION: Thr or Ser
<220> FEATURE:
<221> NAME/KEY: MOD_RES
<222> LOCATION: (68)..(68)
<223> OTHER INFORMATION: Arg or Val
<220> FEATURE:
<221> NAME/KEY: MOD_RES
```

```
<222> LOCATION: (70)..(70)
<223> OTHER INFORMATION: Phe or Ser
<220> FEATURE:
<221> NAME/KEY: MOD_RES
<222> LOCATION: (71)..(71)
<223> OTHER INFORMATION: Gln or Lys
<220> FEATURE:
<221> NAME/KEY: MOD_RES
<222> LOCATION: (79)..(79)
<223> OTHER INFORMATION: His or Ser
<220> FEATURE:
<221> NAME/KEY: MOD_RES
<222> LOCATION: (81)..(81)
<223> OTHER INFORMATION: Thr or Ala
<220> FEATURE:
<221> NAME/KEY: MOD_RES
<222> LOCATION: (83)..(83)
<223> OTHER INFORMATION: Asp or Ala
<220> FEATURE:
<221> NAME/KEY: MOD_RES
<222> LOCATION: (87)..(87)
<223> OTHER INFORMATION: Thr or Val
<220> FEATURE:
<221> NAME/KEY: MOD_RES
<222> LOCATION: (88)..(88)
<223> OTHER INFORMATION: Ser or Tyr
<220> FEATURE:
<221> NAME/KEY: MOD_RES
<222> LOCATION: (92)..(92)
<223> OTHER INFORMATION: Trp, Phe, Tyr, Ile or Val
<220> FEATURE:
<221> NAME/KEY: MOD_RES
<222> LOCATION: (94)..(94)
<223> OTHER INFORMATION: Met, Val, Leu, Ala, Arg, Asn, Pro, Gln, Glu,
      Gly, Ile His, Lys, Phe, Ser, Thr, Trp or Tyr
<220> FEATURE:
<221> NAME/KEY: MOD_RES
<222> LOCATION: (110)..(110)
<223> OTHER INFORMATION: Val, Thr or Leu
<220> FEATURE:
<221> NAME/KEY: MOD_RES
<222> LOCATION: (119)..(119)
<223> OTHER INFORMATION: Ser, Gly or Tyr
<220> FEATURE:
<221> NAME/KEY: MOD_RES
<222> LOCATION: (122)..(122)
<223> OTHER INFORMATION: Ala or Ser
<220> FEATURE:
<221> NAME/KEY: MOD_RES
<222> LOCATION: (123)..(123)
<223> OTHER INFORMATION: Pro or Gln

<400> SEQUENCE: 143

Glu Val Gln Leu Gln Xaa Ser Gly Xaa Gly Leu Xaa Lys Pro Xaa Xaa
1               5                   10                  15

Xaa Leu Ser Leu Thr Cys Xaa Val Xaa Gly Xaa Ser Ile Xaa Ser Asp
            20                  25                  30

Tyr Trp Gly Trp Xaa Arg Xaa Xaa Pro Gly Xaa Xaa Xaa Glu Trp Xaa
        35                  40                  45

Gly Phe Ile Thr Tyr Ser Gly Ser Thr Ser Tyr Asn Pro Ser Leu Lys
    50                  55                  60

Ser Arg Xaa Xaa Ile Xaa Xaa Asp Thr Ser Lys Asn Gln Phe Xaa Leu
65                  70                  75                  80

Xaa Leu Xaa Ser Val Thr Xaa Xaa Asp Thr Ala Xaa Tyr Xaa Cys Ala
                85                  90                  95

Arg Met Pro Ser Phe Ile Thr Leu Ala Ser Leu Ser Thr Xaa Glu Gly
            100                 105                 110

Tyr Phe Asp Phe Trp Gly Xaa Gly Thr Xaa Xaa Thr Val Ser Ser
        115                 120                 125
```

```
<210> SEQ ID NO 144
<211> LENGTH: 127
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (12)..(12)
<223> OTHER INFORMATION: Val or Leu
<220> FEATURE:
<221> NAME/KEY: MOD_RES
<222> LOCATION: (15)..(15)
<223> OTHER INFORMATION: Ser or Pro
<220> FEATURE:
<221> NAME/KEY: MOD_RES
<222> LOCATION: (16)..(16)
<223> OTHER INFORMATION: Glu or Gly
<220> FEATURE:
<221> NAME/KEY: MOD_RES
<222> LOCATION: (23)..(23)
<223> OTHER INFORMATION: Thr, Ala or Ser
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (27)..(27)
<223> OTHER INFORMATION: Gly, Ser or Tyr
<220> FEATURE:
<221> NAME/KEY: MOD_RES
<222> LOCATION: (30)..(30)
<223> OTHER INFORMATION: Ser or Ala
<220> FEATURE:
<221> NAME/KEY: MOD_RES
<222> LOCATION: (37)..(37)
<223> OTHER INFORMATION: Ile or Val
<220> FEATURE:
<221> NAME/KEY: MOD_RES
<222> LOCATION: (39)..(39)
<223> OTHER INFORMATION: Gln or Lys
<220> FEATURE:
<221> NAME/KEY: MOD_RES
<222> LOCATION: (40)..(40)
<223> OTHER INFORMATION: Pro or Phe
<220> FEATURE:
<221> NAME/KEY: MOD_RES
<222> LOCATION: (44)..(44)
<223> OTHER INFORMATION: Gly or Lys
<220> FEATURE:
<221> NAME/KEY: MOD_RES
<222> LOCATION: (45)..(45)
<223> OTHER INFORMATION: Leu or Met
<220> FEATURE:
<221> NAME/KEY: MOD_RES
<222> LOCATION: (48)..(48)
<223> OTHER INFORMATION: Ile or Met
<220> FEATURE:
<221> NAME/KEY: MOD_RES
<222> LOCATION: (67)..(67)
<223> OTHER INFORMATION: Val or Ile
<220> FEATURE:
<221> NAME/KEY: MOD_RES
<222> LOCATION: (71)..(71)
<223> OTHER INFORMATION: Val or Arg
<220> FEATURE:
<221> NAME/KEY: MOD_RES
<222> LOCATION: (83)..(83)
<223> OTHER INFORMATION: Ser or His
```

```
<220> FEATURE:
<221> NAME/KEY: MOD_RES
<222> LOCATION: (88)..(88)
<223> OTHER INFORMATION: Ala or Asp
<220> FEATURE:
<221> NAME/KEY: MOD_RES
<222> LOCATION: (110)..(110)
<223> OTHER INFORMATION: Trp, Phe, Tyr, Ile, Val or Leu
<220> FEATURE:
<221> NAME/KEY: MOD_RES
<222> LOCATION: (122)..(122)
<223> OTHER INFORMATION: Met, Val, Leu, Ala, Arg, Asn, Pro, Gln, Glu,
      Gly, Ile, His, Lys, Phe, Ser, Thr, Trp or Tyr
<220> FEATURE:
<221> NAME/KEY: MOD_RES
<222> LOCATION: (123)..(123)
<223> OTHER INFORMATION: Val, Thr or Leu

<400> SEQUENCE: 144

Glu Val Gln Leu Gln Xaa Ser Gly Xaa Gly Leu Xaa Lys Pro Xaa Xaa
1               5                   10                  15

Thr Leu Ser Leu Thr Cys Xaa Val Xaa Gly Xaa Ser Ile Xaa Ser Asp
            20                  25                  30

Tyr Trp Gly Trp Xaa Arg Xaa Xaa Pro Gly Lys Xaa Xaa Glu Trp Xaa
        35                  40                  45

Gly Phe Ile Thr Tyr Ser Gly Ser Thr Ser Tyr Asn Pro Ser Leu Lys
    50                  55                  60

Ser Arg Xaa Thr Ile Ser Xaa Asp Thr Ser Lys Asn Gln Phe Ser Leu
65                  70                  75                  80

Lys Leu Xaa Ser Val Thr Ala Xaa Asp Thr Ala Val Tyr Tyr Cys Ala
                85                  90                  95

Arg Met Pro Ser Phe Ile Thr Leu Ala Ser Leu Ser Thr Xaa Glu Gly
            100                 105                 110

Tyr Phe Asp Phe Trp Gly Gln Gly Thr Xaa Xaa Thr Val Ser Ser
        115                 120                 125

<210> SEQ ID NO 145
<211> LENGTH: 106
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (10)..(10)
<223> OTHER INFORMATION: Leu or Ser
<220> FEATURE:
<221> NAME/KEY: MOD_RES
<222> LOCATION: (21)..(21)
<223> OTHER INFORMATION: Leu or Ile
<220> FEATURE:
<221> NAME/KEY: MOD_RES
<222> LOCATION: (22)..(22)
<223> OTHER INFORMATION: Asn or Thr
<220> FEATURE:
<221> NAME/KEY: MOD_RES
<222> LOCATION: (40)..(40)
<223> OTHER INFORMATION: Leu or Pro
<220> FEATURE:
<221> NAME/KEY: MOD_RES
<222> LOCATION: (42)..(42)
<223> OTHER INFORMATION: Glu or Lys
<220> FEATURE:
<221> NAME/KEY: MOD_RES
<222> LOCATION: (43)..(43)
<223> OTHER INFORMATION: Phe or Leu
<220> FEATURE:
<221> NAME/KEY: MOD_RES
<222> LOCATION: (46)..(46)
```

-continued

```
<223> OTHER INFORMATION: Asn, Ser, Thr, Gly or Asp
<220> FEATURE:
<221> NAME/KEY: MOD_RES
<222> LOCATION: (52)..(52)
<223> OTHER INFORMATION: Ser, Asn, Thr, Tyr or Gln
<220> FEATURE:
<221> NAME/KEY: MOD_RES
<222> LOCATION: (53)..(53)
<223> OTHER INFORMATION: Ile or Val
<220> FEATURE:
<221> NAME/KEY: MOD_RES
<222> LOCATION: (58)..(58)
<223> OTHER INFORMATION: Gly or Ser
<220> FEATURE:
<221> NAME/KEY: MOD_RES
<222> LOCATION: (77)..(77)
<223> OTHER INFORMATION: Val or Phe
<220> FEATURE:
<221> NAME/KEY: MOD_RES
<222> LOCATION: (83)..(83)
<223> OTHER INFORMATION: Phe or Tyr
<220> FEATURE:
<221> NAME/KEY: MOD_RES
<222> LOCATION: (87)..(87)
<223> OTHER INFORMATION: Trp, Phe, Tyr, Ile, Val or Leu
<220> FEATURE:
<221> NAME/KEY: MOD_RES
<222> LOCATION: (95)..(95)
<223> OTHER INFORMATION: Leu or Ile
<220> FEATURE:
<221> NAME/KEY: MOD_RES
<222> LOCATION: (105)..(105)
<223> OTHER INFORMATION: Ala or Val

<400> SEQUENCE: 145

Asp Ile Gln Met Thr Gln Ser Pro Ser Xaa Leu Ser Ala Ser Val Gly
1               5                   10                  15

Asp Arg Val Thr Xaa Xaa Cys Lys Ala Ser Gln Ser Ile His Lys Asn
            20                  25                  30

Leu Ala Trp Tyr Gln Gln Lys Xaa Gly Xaa Xaa Pro Lys Xaa Leu Ile
        35                  40                  45

Tyr Tyr Ala Xaa Xaa Leu Gln Thr Gly Xaa Pro Ser Arg Phe Ser Gly
50                  55                  60

Ser Gly Ser Gly Thr Asp Phe Thr Leu Thr Ile Ser Xaa Leu Gln Pro
65                  70                  75                  80

Glu Asp Xaa Ala Thr Tyr Xaa Cys Gln Gln Tyr Tyr Ser Gly Xaa Thr
                85                  90                  95

Phe Gly Gly Gly Thr Lys Val Glu Xaa Lys
                100                 105

<210> SEQ ID NO 146
<211> LENGTH: 106
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (43)..(43)
<223> OTHER INFORMATION: Leu or Phe
<220> FEATURE:
<221> NAME/KEY: MOD_RES
<222> LOCATION: (46)..(46)
<223> OTHER INFORMATION: Asn, Ser, Thr, Gly or Asp
<220> FEATURE:
<221> NAME/KEY: MOD_RES
<222> LOCATION: (52)..(52)
<223> OTHER INFORMATION: Ser, Asn, Thr, Tyr or Gln
<220> FEATURE:
<221> NAME/KEY: MOD_RES
```

```
<222> LOCATION: (53)..(53)
<223> OTHER INFORMATION: Val or Ile
<220> FEATURE:
<221> NAME/KEY: MOD_RES
<222> LOCATION: (58)..(58)
<223> OTHER INFORMATION: Trp, Phe, Tyr, Ile, Val or Leu
<220> FEATURE:
<221> NAME/KEY: MOD_RES
<222> LOCATION: (83)..(83)
<223> OTHER INFORMATION: Ala or Val
<220> FEATURE:
<221> NAME/KEY: MOD_RES
<222> LOCATION: (95)..(95)
<223> OTHER INFORMATION: Phe or Val

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Ile His Lys Asn
            20                  25                  30

Leu Ala Trp Tyr Gln Gln Lys Pro Gly Lys Xaa Pro Lys Xaa Leu Ile
        35                  40                  45

Tyr Tyr Ala Xaa Xaa Leu Gln Thr Gly Xaa Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Xaa Ala Thr Tyr Tyr Cys Gln Gln Tyr Tyr Ser Gly Xaa Thr
                85                  90                  95

Phe Gly Gly Gly Thr Lys Val Glu Ile Lys
            100                 105

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (7)..(7)
<223> OTHER INFORMATION: Asp, Arg, Leu, Lys, Phe, Ser, Tyr or Val
<220> FEATURE:
<221> NAME/KEY: MOD_RES
<222> LOCATION: (8)..(8)
<223> OTHER INFORMATION: Gly, Arg, Asn, Gln, Glu, Leu, Lys, Ser, Tyr or
      Val
<220> FEATURE:
<221> NAME/KEY: MOD_RES
<222> LOCATION: (12)..(12)
<223> OTHER INFORMATION: Asn, Ala or Ser
<220> FEATURE:
<221> NAME/KEY: MOD_RES
<222> LOCATION: (13)..(13)
<223> OTHER INFORMATION: Glu or Gln
<220> FEATURE:
<221> NAME/KEY: MOD_RES
<222> LOCATION: (16)..(16)
<223> OTHER INFORMATION: Lys or Gln

<400> SEQUENCE: 147

Tyr Ile Asp Pro Tyr Asn Xaa Xaa Ala Lys Tyr Xaa Xaa Lys Phe Xaa
1               5                   10                  15

Gly

<210> SEQ ID NO 148
<211> LENGTH: 7
<212> TYPE: PRT
```

<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Asn, Ala, Val, Trp, Ser, Thr, Arg, His, Gly,
      Ile or Val
<220> FEATURE:
<221> NAME/KEY: MOD_RES
<222> LOCATION: (2)..(2)
<223> OTHER INFORMATION: Ala, Asn, Ile, Leu, Thr or Val

<400> SEQUENCE: 148

Xaa Xaa Lys Thr Leu Ala Glu
1               5

<210> SEQ ID NO 149
<211> LENGTH: 119
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (5)..(5)
<223> OTHER INFORMATION: Gln or Val
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (12)..(12)
<223> OTHER INFORMATION: Val or Lys
<220> FEATURE:
<221> NAME/KEY: MOD_RES
<222> LOCATION: (16)..(16)
<223> OTHER INFORMATION: Ser or Ala
<220> FEATURE:
<221> NAME/KEY: MOD_RES
<222> LOCATION: (20)..(20)
<223> OTHER INFORMATION: Met or Val
<220> FEATURE:
<221> NAME/KEY: MOD_RES
<222> LOCATION: (38)..(38)
<223> OTHER INFORMATION: Lys or Arg
<220> FEATURE:
<221> NAME/KEY: MOD_RES
<222> LOCATION: (40)..(40)
<223> OTHER INFORMATION: Lys or Ala
<220> FEATURE:
<221> NAME/KEY: MOD_RES
<222> LOCATION: (44)..(44)
<223> OTHER INFORMATION: Gly or Arg
<220> FEATURE:
<221> NAME/KEY: MOD_RES
<222> LOCATION: (56)..(56)
<223> OTHER INFORMATION: Asp, Arg, Leu, Lys, Phe, Ser, Tyr or Val
<220> FEATURE:
<221> NAME/KEY: MOD_RES
<222> LOCATION: (57)..(57)
<223> OTHER INFORMATION: Gly, Arg, Asn, Gln, Glu, Leu, Lys, Ser, Tyr or
      Val
<220> FEATURE:
<221> NAME/KEY: MOD_RES
<222> LOCATION: (61)..(61)
<223> OTHER INFORMATION: Asn, Ala or Ser
<220> FEATURE:
<221> NAME/KEY: MOD_RES
<222> LOCATION: (62)..(62)

```
<223> OTHER INFORMATION: Glu or Gln
<220> FEATURE:
<221> NAME/KEY: MOD_RES
<222> LOCATION: (65)..(65)
<223> OTHER INFORMATION: Lys or Gln
<220> FEATURE:
<221> NAME/KEY: MOD_RES
<222> LOCATION: (67)..(67)
<223> OTHER INFORMATION: Arg or Lys
<220> FEATURE:
<221> NAME/KEY: MOD_RES
<222> LOCATION: (68)..(68)
<223> OTHER INFORMATION: Ala or Val
<220> FEATURE:
<221> NAME/KEY: MOD_RES
<222> LOCATION: (72)..(72)
<223> OTHER INFORMATION: Ser or Arg
<220> FEATURE:
<221> NAME/KEY: MOD_RES
<222> LOCATION: (74)..(74)
<223> OTHER INFORMATION: Lys or Thr
<220> FEATURE:
<221> NAME/KEY: MOD_RES
<222> LOCATION: (76)..(76)
<223> OTHER INFORMATION: Ser, Ile, Ala or Thr
<220> FEATURE:
<221> NAME/KEY: MOD_RES
<222> LOCATION: (79)..(79)
<223> OTHER INFORMATION: Ala or Val
<220> FEATURE:
<221> NAME/KEY: MOD_RES
<222> LOCATION: (85)..(85)
<223> OTHER INFORMATION: Arg or Ser
<220> FEATURE:
<221> NAME/KEY: MOD_RES
<222> LOCATION: (87)..(87)
<223> OTHER INFORMATION: Thr or Arg
<220> FEATURE:
<221> NAME/KEY: MOD_RES
<222> LOCATION: (89)..(89)
<223> OTHER INFORMATION: Asp or Glu
<220> FEATURE:
<221> NAME/KEY: MOD_RES
<222> LOCATION: (91)..(91)
<223> OTHER INFORMATION: Ser or Thr
<220> FEATURE:
<221> NAME/KEY: MOD_RES
<222> LOCATION: (92)..(92)
<223> OTHER INFORMATION: Ala or Val
<220> FEATURE:
<221> NAME/KEY: MOD_RES
<222> LOCATION: (104)..(104)
<223> OTHER INFORMATION: Trp, Ala, Asp, Gly, Phe, Gly, Ile, Lys, Asn,
      Gln, Arg, Ser, Thr Val or Tyr
<220> FEATURE:
<221> NAME/KEY: MOD_RES
<222> LOCATION: (111)..(111)
<223> OTHER INFORMATION: Ala or Gln

<400> SEQUENCE: 149

Glu Val Gln Leu Xaa Gln Ser Gly Xaa Glu Xaa Xaa Lys Pro Gly Xaa
1               5                   10                  15

Ser Val Lys Xaa Ser Cys Lys Ala Ser Gly Tyr Thr Phe Ser Tyr
            20                  25                  30

Val Met His Trp Val Xaa Gln Xaa Pro Gly Gln Xaa Leu Glu Trp Ile
            35                  40                  45

Gly Tyr Ile Asp Pro Tyr Asn Xaa Xaa Ala Lys Tyr Xaa Xaa Lys Phe
        50                  55                  60

Xaa Gly Xaa Xaa Thr Leu Thr Xaa Asp Xaa Ser Xaa Ser Thr Xaa Tyr
65                  70                  75                  80

Met Glu Leu Ser Xaa Leu Xaa Ser Xaa Asp Xaa Xaa Val Tyr Tyr Cys
                85                  90                  95
```

-continued

Ala Arg Gly Gly Pro Tyr Gly Xaa Tyr Phe Asp Val Trp Gly Xaa Gly
            100                 105                 110

Thr Thr Val Thr Val Ser Ser
        115

<210> SEQ ID NO 150
<211> LENGTH: 119
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (16)..(16)
<223> OTHER INFORMATION: Ala or Ser
<220> FEATURE:
<221> NAME/KEY: MOD_RES
<222> LOCATION: (44)..(44)
<223> OTHER INFORMATION: Arg or Gly
<220> FEATURE:
<221> NAME/KEY: MOD_RES
<222> LOCATION: (56)..(56)
<223> OTHER INFORMATION: Asp, Arg, Leu, Lys, Phe, Ser, Tyr or Val
<220> FEATURE:
<221> NAME/KEY: MOD_RES
<222> LOCATION: (57)..(57)
<223> OTHER INFORMATION: Gly, Arg, Asn, Gln, Glu, Leu, Lys, Ser, Tyr or
      Val
<220> FEATURE:
<221> NAME/KEY: MOD_RES
<222> LOCATION: (61)..(61)
<223> OTHER INFORMATION: Asn, Ala or Ser
<220> FEATURE:
<221> NAME/KEY: MOD_RES
<222> LOCATION: (62)..(62)
<223> OTHER INFORMATION: Glu or Gln
<220> FEATURE:
<221> NAME/KEY: MOD_RES
<222> LOCATION: (65)..(65)
<223> OTHER INFORMATION: Lys or Gln
<220> FEATURE:
<221> NAME/KEY: MOD_RES
<222> LOCATION: (72)..(72)
<223> OTHER INFORMATION: Arg or Ser
<220> FEATURE:
<221> NAME/KEY: MOD_RES
<222> LOCATION: (74)..(74)
<223> OTHER INFORMATION: Thr or Lys
<220> FEATURE:
<221> NAME/KEY: MOD_RES
<222> LOCATION: (76)..(76)
<223> OTHER INFORMATION: Ala, Thr or Ile
<220> FEATURE:
<221> NAME/KEY: MOD_RES
<222> LOCATION: (79)..(79)
<223> OTHER INFORMATION: Arg or Val
<220> FEATURE:
<221> NAME/KEY: MOD_RES
<222> LOCATION: (85)..(85)
<223> OTHER INFORMATION: Ser or Arg
<220> FEATURE:
<221> NAME/KEY: MOD_RES
<222> LOCATION: (89)..(89)
<223> OTHER INFORMATION: Glu or Asp
<220> FEATURE:
<221> NAME/KEY: MOD_RES
<222> LOCATION: (92)..(92)
<223> OTHER INFORMATION: Ala or Val
<220> FEATURE:
<221> NAME/KEY: MOD_RES
<222> LOCATION: (104)..(104)
<223> OTHER INFORMATION: Trp, Ala, Asp, Gly, Phe, Gly, Ile, Lys, Asn,
      Ser, Thr, Val or Tyr

<400> SEQUENCE: 150

```
Glu Val Gln Leu Val Gln Ser Gly Ala Glu Val Lys Lys Pro Gly Xaa
1               5                   10                  15

Ser Val Lys Val Ser Cys Lys Ala Ser Gly Tyr Thr Phe Ser Ser Tyr
            20                  25                  30

Val Met His Trp Val Arg Gln Ala Pro Gly Gln Xaa Leu Glu Trp Ile
            35                  40                  45

Gly Tyr Ile Asp Pro Tyr Asn Xaa Xaa Ala Lys Tyr Xaa Xaa Lys Phe
            50                  55                  60

Xaa Gly Arg Val Thr Leu Thr Xaa Asp Xaa Ser Xaa Ser Thr Xaa Tyr
65                  70                  75                  80

Met Glu Leu Ser Xaa Leu Arg Ser Xaa Asp Thr Xaa Val Tyr Tyr Cys
                85                  90                  95

Ala Arg Gly Gly Pro Tyr Gly Xaa Tyr Phe Asp Val Trp Gly Gln Gly
            100                 105                 110

Thr Thr Val Thr Val Ser Ser
        115
```

<210> SEQ ID NO 151
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (18)..(18)
<223> OTHER INFORMATION: Thr or Arg
<220> FEATURE:
<221> NAME/KEY: MOD_RES
<222> LOCATION: (40)..(40)
<223> OTHER INFORMATION: Gln or Pro
<220> FEATURE:
<221> NAME/KEY: MOD_RES
<222> LOCATION: (43)..(43)
<223> OTHER INFORMATION: Ser, Ala or Val
<220> FEATURE:
<221> NAME/KEY: MOD_RES
<222> LOCATION: (45)..(45)
<223> OTHER INFORMATION: Gln or Lys
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (50)..(50)
<223> OTHER INFORMATION: Asn, Ala, Tyr, Trp, Ser, Thr, Ile or Val
<220> FEATURE:
<221> NAME/KEY: MOD_RES
<222> LOCATION: (51)..(51)
<223> OTHER INFORMATION: Ala, Asn, Ile, Leu, Thr or Val
<220> FEATURE:
<221> NAME/KEY: MOD_RES
<222> LOCATION: (70)..(70)
<223> OTHER INFORMATION: Gln or Asp
<220> FEATURE:
<221> NAME/KEY: MOD_RES
<222> LOCATION: (72)..(72)
<223> OTHER INFORMATION: Ser or Thr
<220> FEATURE:
<221> NAME/KEY: MOD_RES
<222> LOCATION: (74)..(74)

<223> OTHER INFORMATION: Lys or Thr
<220> FEATURE:
<221> NAME/KEY: MOD_RES
<222> LOCATION: (76)..(76)
<223> OTHER INFORMATION: Asn or Ser
<220> FEATURE:
<221> NAME/KEY: MOD_RES
<222> LOCATION: (83)..(83)
<223> OTHER INFORMATION: Phe or Val
<220> FEATURE:
<221> NAME/KEY: MOD_RES
<222> LOCATION: (84)..(84)
<223> OTHER INFORMATION: Gly or Ala
<220> FEATURE:
<221> NAME/KEY: MOD_RES
<222> LOCATION: (100)..(100)
<223> OTHER INFORMATION: Ala or Gln
<220> FEATURE:
<221> NAME/KEY: MOD_RES
<222> LOCATION: (103)..(103)
<223> OTHER INFORMATION: Thr or Arg
<220> FEATURE:
<221> NAME/KEY: MOD_RES
<222> LOCATION: (106)..(106)
<223> OTHER INFORMATION: Leu or Ile

<400> SEQUENCE: 151

Asp Ile Gln Met Thr Gln Ser Pro Xaa Ser Leu Ser Ala Ser Val Gly
1               5                   10                  15

Xaa Xaa Val Thr Ile Thr Cys Arg Ala Ser Glu His Ile Tyr Ser Tyr
            20                  25                  30

Leu Ser Trp Tyr Gln Gln Lys Xaa Gly Lys Xaa Pro Xaa Leu Leu Xaa
        35                  40                  45

Tyr Xaa Xaa Lys Thr Leu Ala Glu Gly Val Pro Ser Arg Phe Ser Gly
50                  55                  60

Ser Gly Ser Gly Thr Xaa Phe Xaa Leu Xaa Ile Xaa Ser Leu Gln Pro
65                  70                  75                  80

Glu Asp Xaa Xaa Thr Tyr Tyr Cys Gln His His Phe Gly Ser Pro Leu
                85                  90                  95

Thr Phe Gly Xaa Gly Thr Xaa Leu Glu Xaa Lys
            100                 105

<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (43)..(43)
<223> OTHER INFORMATION: Ala or Val
<220> FEATURE:
<221> NAME/KEY: MOD_RES
<222> LOCATION: (50)..(50)
<223> OTHER INFORMATION: Asn, Ala, Tyr, Trp, Ser, Thr, Ile or Val
<220> FEATURE:
<221> NAME/KEY: MOD_RES
<222> LOCATION: (51)..(51)
<223> OTHER INFORMATION: Ala, Asn, Ile, Leu, Thr or Val
<220> FEATURE:
<221> NAME/KEY: MOD_RES
<222> LOCATION: (70)..(70)
<223> OTHER INFORMATION: Asp or Gln
<220> FEATURE:
<221> NAME/KEY: MOD_RES
<222> LOCATION: (83)..(83)
<223> OTHER INFORMATION: Phe or Val

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Tyr Ser Tyr
            20                  25                  30

Leu Ser Trp Tyr Gln Gln Lys Pro Gly Lys Xaa Pro Lys Leu Leu Ile
                35                  40                  45

Tyr Xaa Xaa Lys Thr Leu Ala Glu Gly Val Pro Ser Arg Phe Ser Gly
    50                  55                  60

Ser Gly Ser Gly Thr Xaa Phe Thr Leu Thr Ile Ser Ser Leu Gln Pro
65              70                  75                  80

Glu Asp Xaa Ala Thr Tyr Tyr Cys Gln His Phe Gly Ser Pro Leu
            85                  90                  95

Thr Phe Gly Gln Gly Thr Arg Leu Glu Ile Lys
            100                 105
```

```
<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide
<220> FEATURE:
<221> NAME/KEY: MOD_RES
<222> LOCATION: (6)..(6)
<223> OTHER INFORMATION: Trp, Ala, Asp, Glu, Phe, Gly, Ile, Lys, Asn,
      Gln, Arg, Ser, Thr, Val or Tyr

<400> SEQUENCE: 153

Gly Gly Pro Tyr Gly Xaa Tyr Phe Asp Val
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 154

Gly Gly Pro Tyr Gly Ala Tyr Phe Asp Val
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 155

Gly Gly Pro Tyr Gly Asp Tyr Phe Asp Val
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 156
```

```
Gly Gly Pro Tyr Gly Glu Tyr Phe Asp Val
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 157

Gly Gly Pro Tyr Gly Phe Tyr Phe Asp Val
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 158

Gly Gly Pro Tyr Gly Gly Tyr Phe Asp Val
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 159

Gly Gly Pro Tyr Gly Ile Tyr Phe Asp Val
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 160

Gly Gly Pro Tyr Gly Lys Tyr Phe Asp Val
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 161

Gly Gly Pro Tyr Gly Asn Tyr Phe Asp Val
1               5                   10

<210> SEQ ID NO 162
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      CDR peptide

<400> SEQUENCE: 162

Gly Gly Pro Tyr Gly Gln Tyr Phe Asp Val
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 163

Gly Gly Pro Tyr Gly Arg Tyr Phe Asp Val
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 164

Gly Gly Pro Tyr Gly Ser Tyr Phe Asp Val
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 165

Gly Gly Pro Tyr Gly Thr Tyr Phe Asp Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 166

Gly Gly Pro Tyr Gly Val Tyr Phe Asp Val
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR peptide

<400> SEQUENCE: 167

Gly Gly Pro Tyr Gly Tyr Tyr Phe Asp Val
1               5                   10
```

ANTI-TIGIT ANTIBODIES

CROSS-REFERENCE TO RELATED APPLICATIONS

This application is a continuation of U.S. patent application Ser. No. 15/121,624, which application is a § 371 National Phase Application of International Application No. PCT/US2015/045447, filed Aug. 17, 2015, which claims priority from U.S. provisional application 62/126,733 filed Mar. 2, 2015 and U.S. provisional application 62/038,912 filed Aug. 19, 2014.

REFERENCE TO SEQUENCE LISTING SUBMITTED ELECTRONICALLY

The sequence listing of the present application is submitted electronically via EFS-Web as an ASCII formatted sequence listing with a file name "23808USPCT-SEQTXT-17AUG2016.txt", creation date of Aug. 17, 2016, and a size of 132 KB. This sequence listing submitted via EFS-Web is part of the specification and is herein incorporated by reference in its entirety.

FIELD OF THE INVENTION

The present invention relates to anti-TIGIT antibodies, as well as use of these antibodies in the treatment of diseases such as cancer and infectious disease.

BACKGROUND OF THE INVENTION

A key factor for enabling tumor immunotherapy emerged from discoveries that inhibitory immune modulatory receptors (IMRs), that generally function as immune checkpoints to maintain self-tolerance, are central to the ability of tumor microenvironments to evade immunity. Blockade of inhibitory IMRs appears to unleash potent tumor-specific immune responses more effectively than direct stimulation of tumor-immunity with activating cytokines or tumor vaccines, and this approach has the potential to transform human cancer therapy. An important implication and opportunity now arises for the potential to develop new antibody antagonists for other IMRs and to combine antagonist antibodies to more than one IMR in order to increase the proportion of responders in oncology clinical trials, as well as, expand upon oncology indications in which tumor immunotherapy treatments are effective.

Significantly, inhibitory IMRs and ligands that regulate cellular immunity are commonly overexpressed on tumor cells and tumor associated macrophages (TAMs). Notably, overexpression of PD-L1 in tumors is associated with tumor specific T cell exhaustion and a poor prognosis. Blockade of PD-1/PD-L1 ligation in clinical trials resulted in durable tumor regression responses in a substantial proportion of patients. A recent report demonstrated that co-expression of PD-1 and another inhibitory IMR (TIM-3) in melanoma patient derived tumor-specific CD8+ T cells was associated with more dysfunctional T cell exhaustion phenotypes compared to cells expressing either IMR alone. Moreover, several reports using pre-clinical tumor models demonstrated blockade of multiple IMRs, including PD-1, TIM-3, LAG-3 and CTLA-4 more effectively induced anti-tumor responses than antagonizing PD-1 alone. These results underscore the importance of further investigating IMR pathways.

TIGIT (T cell immunoreceptor with Ig and ITIM domains) is an immunomodulatory receptor expressed primarily on activated T cells and NK cells. TIGIT is also known as VSIG9; VSTM3; and WUCAM. Its structure shows one extracellular immunoglobulin domain, a type 1 transmembrane region and two ITIM motifs. TIGIT forms part of a co-stimulatory network that consists of positive (CD226) and negative (TIGIT) immunomodulatory receptors on T cells, and ligands expressed on APCs (CD155 and CD112).

An important feature in the structure of TIGIT is the presence of an immunoreceptor tyrosine-based inhibition motif (ITIM) in its cytoplasmic tail domain. As with PD-1 and CTLA-4, the ITIM domain in the cytoplasmic region of TIGIT is predicted to recruit tyrosine phosphatases, such as SHP-1 and SHP-2, and subsequent de-phosphorylation of tyrosine residues with in the immunoreceptor tyrosine-base activation motifs (ITAM) on T cell receptor (TCR) subunits. Hence, ligation of TIGIT by receptor-ligands CD155 and CD112 expressed by tumor cells or TAMS may contribute to the suppression of TCR-signaling and T cell activation, which is essential for mounting effective anti-tumor immunity. Thus, an antagonist antibody specific for TIGIT could inhibit the CD155 and CD112 induced suppression of T cell responses and enhance anti-tumor immunity. It is an object of the present invention to obtain an anti-TIGIT antibody that can be used for the treatment of cancer, either alone or in combination with other reagents.

SUMMARY OF THE INVENTION

The invention provides anti-TIGIT antibodies and antigen binding fragments thereof comprising the structural and functional features specified below.

In one embodiment, the invention provides an antibody or antigen binding fragment thereof that binds to human TIGIT, comprising: a heavy chain variable region CDR3 comprising the amino acid sequence of SEQ ID NO: 3, 79, 80, 81, 82, 83, 59, 90, 140, 153, 154, 155, 156, 157, 158, 159, 160, 161, 162, 163, 164, 165, 166 or 167. In one embodiment, the antibody or antigen binding fragment thereof optionally has at least one of the following characteristics: (i) binds to human TIGIT with a KD value of about $1 \times 10^{-9}$ M to about $1 \times 10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment thereof that binds to human TIGIT, comprising: a light chain variable region CDR3 comprising the amino acid sequence of SEQ ID NO: 6, 62, 74, 75, 76, 77, 78 or 93. In one embodiment, the antibody optionally has at least one of the following characteristics: (i) binds to human TIGIT with a KD value of about $1 \times 10^{-9}$ M to about $1 \times 10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment thereof that binds to human TIGIT comprising: (i) a heavy chain variable region CDR1 comprising the amino acid sequence of SEQ ID NO: 1; (ii) a heavy chain variable region CDR2 comprising the amino acid sequence of SEQ ID NO: 2; and (iii) a heavy chain variable region CDR3 comprising the amino acid sequence of SEQ ID NO: 140. In one embodiment, the antibody or antigen binding fragment comprises: (i) a heavy chain variable region CDR1 comprising the amino acid sequence of SEQ ID NO: 1; (ii) a heavy chain variable region CDR2 comprising the amino acid sequence of SEQ ID NO: 2; and (iii) a heavy chain variable region CDR3 comprising the amino acid sequence of SEQ ID NO: 3, 79, 80, 81, 82 or 83. In one embodiment, the antibody or antigen binding fragment thereof comprises: (i) a heavy chain variable region CDR1 comprising the amino acid sequence of SEQ ID NO: 1; (ii) a heavy chain variable region CDR2 comprising the amino acid sequence of SEQ ID NO: 2; and (iii) a heavy chain variable region CDR3 comprising the amino acid sequence of SEQ ID NO: 3. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a heavy chain variable region CDR1 comprising the amino acid sequence of SEQ ID NO: 57; (ii) a heavy chain variable region CDR2 comprising the amino acid sequence of SEQ ID NO: 58; and (iii) a heavy chain variable region CDR3 comprising the amino acid sequence of SEQ ID NO: 59. In one embodiment, the antibody or antigen binding fragment thereof optionally has at least one of the following characteristics: (i) binds to human TIGIT with a KD value of about $1\times10^{-9}$M to about $1\times10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a heavy chain variable region CDR1 comprising the amino acid sequence of SEQ ID NO: 88; (ii) a heavy chain variable region CDR2 comprising the amino acid sequence of SEQ ID NO: 147; and (iii) a heavy chain variable region CDR3 comprising the amino acid sequence of SEQ ID NO: 153. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134 or 135; and (iii) a heavy chain variable region CDR3 comprising the amino acid sequence of SEQ ID NO: 90, 154, 155, 156, 157, 158, 159, 160, 161, 162, 163, 164, 165, 166 or 167. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; and (iii) a heavy chain variable region CDR3 comprising the amino acid sequence of SEQ ID NO: 90. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 90. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 154. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 155. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 156. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 157. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 158. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 159. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 160. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 161. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 162. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 163. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 164. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 165. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 166. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; and (iii) a heavy chain variable region CDR3 comprising the amino acid sequence of SEQ ID NO: 167. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a light chain variable region CDR1 comprising the amino acid sequence of SEQ ID NO: 4; (ii) a light chain variable region CDR2 comprising the amino acid sequence of SEQ ID NO: 141; and (iii) a light chain variable region CDR3 comprising the amino acid sequence of SEQ ID NO: 142. In one embodiment, the antibody or antigen binding fragment thereof comprises: (i) a light chain variable region CDR1 comprising the amino acid sequence of SEQ ID NO: 4; (ii) a light chain variable region CDR2 comprising the amino acid sequence of SEQ ID NO: 5, 65, 66, 67, 68, 69, 70, 71, 72 or; and (iii) a light chain variable region CDR3 comprising the amino acid sequence of SEQ ID NO: 6, 74, 75, 76, 77 or 78. In one embodiment, the antibody or antigen binding fragment thereof comprises: (i) a light chain variable region CDR1 comprising the amino acid sequence of SEQ ID NO: 4; (ii) a light chain variable region CDR2 comprising the amino acid sequence of SEQ ID NO: 5; and (iii) a light chain variable region CDR3 comprising the amino acid sequence of SEQ ID NO: 6. In one embodiment, the antibody or antigen binding fragment thereof optionally has at least one of the following characteristics: (i) binds to human TIGIT with a KD value of about $1\times10^{-9}$M to about $1\times10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a light chain variable region CDR1 comprising the amino acid sequence of SEQ ID NO: 60; (ii) a light chain variable region CDR2 comprising the amino acid sequence of SEQ ID NO: 61; and (iii) a light chain variable region CDR3 comprising the amino acid sequence of SEQ ID NO: 62. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a light chain variable region CDR1 comprising the amino acid sequence of SEQ ID NO: 91; (ii) a light chain variable region CDR2 comprising the amino acid sequence of SEQ ID NO: 148; and (iii) a light chain variable region CDR3 comprising the amino acid sequence of SEQ ID NO: 93. In one embodiment, the antibody or antigen binding fragment thereof comprises: (i) a light chain variable region CDR1 comprising the amino acid sequence of SEQ ID NO: 91; (ii) a light chain variable region CDR2 comprising the amino acid sequence of SEQ ID NO: 92, 112, 113, 114, 115, 116, 117, 118, 119, 120, 121 or 122; and (iii) a light chain variable region CDR3 comprising the amino acid sequence of SEQ ID NO: 93. In one embodiment, the antibody or antigen binding fragment thereof comprises: (i) a light chain variable region CDR1 comprising the amino acid sequence of SEQ ID NO: 91; (ii) a light chain variable region CDR2 comprising the amino acid sequence of SEQ ID NO: 92; and (iii) a light chain variable region CDR3 comprising the amino acid sequence of SEQ ID NO: 93. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET); (iii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 140; (iv) a light chain variable region CDR1 comprising the amino acid sequence of SEQ ID NO: 4; (v) a light chain variable region CDR2 comprising the amino acid sequence of SEQ ID NO: 141; and (vi) a light chain variable region CDR3 comprising the amino acid sequence of SEQ ID NO: 142. In one embodiment, the antibody or antigen binding fragment comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82 or 83; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72 or 73; and (vi) a light chain variable region CDR3 comprising the amino acid sequence of SEQ ID NO: 6, 74, 75, 76, 77 or 78. In one embodiment, the antibody or antigen binding fragment thereof comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In one embodiment, the antibody or antigen binding fragment thereof is humanized. In one embodiment, the antibody or antigen binding fragment thereof comprises a heavy chain variable region selected from the group consisting of SEQ ID NOs:9-24, 37-47, 143 and 144; and a light chain variable region selected from the group consisting of SEQ ID NOs: 25-30, 48-52, 146 and 147. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e.g. KinExa or OCTET); (ii) cross-reacts with cynomolgus and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention provides an antibody or antigen binding fragment that binds to human TIGIT comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82 or 83; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72 or 73; and (vi) a light chain variable region CDR3 comprising the amino acid sequence of SEQ ID NO: 6, 74, 75, 76, 77 or 78; wherein the antibody or antigen binding fragment thereof comprises a heavy chain variable region comprising at least 90%, 95%, 96%, 97%, 98% or 99% identity to a heavy chain variable region selected from the group consisting of SEQ ID NOs: 9-24 or 37-47 and a light chain variable region comprising at least 90%, 95%, 96%, 97%, 98% or 99% identity to a heavy chain variable region selected from the group consisting of SEQ ID NOs: 25-30 or 48-52. In this aforementioned embodiment, the sequence variations occur in the framework regions. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention also provides an antibody or antigen binding fragment thereof that binds to human TIGIT comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In one embodiment, the antibody or antigen binding fragment thereof comprises 1, 2 or 3 amino acid substitutions in the heavy chain CDRs (SEQ ID NOs: 1-3) or in the light chain CDRs (SEQ ID NOs: 3-6). In one embodiment, the antibody comprises one amino acid substitution in the heavy chain CDR of SEQ ID NO: 3, wherein the substitution is made at position 13W, and wherein residue 13W is substituted to: F, Y, I, V or L. In one embodiment, the antibody comprises two amino acid substitutions in the light chain CDR of SEQ ID NO: 5, wherein the substitutions are made at position 3-4, and wherein residues 3N and 4S are substituted to: SN, SS, ST, TT, SY, NQ, GS, SQ and DS. In one embodiment, the antibody comprises one amino acid substitution in the light chain CDR of SEQ ID NO: 6, wherein the substitution is made at position 7, and wherein residue 7W is substituted to: F, Y, I, V or L. The VH sequences of SEQ ID NOs: 9-24 and 37-47 have the CDRs of SEQ ID NOs:1-3; and VL sequences of SEQ ID NOs:25-30 and 48-52 have the CDRs of SEQ ID NOs: 4-6. In some embodiments, the CDR substitutions described above can be made in the corresponding CDRs of the VH sequences of SEQ ID NOs: 9-24 and 37-37, and in the CDRs of the VL sequences of SEQ ID NOs: 25-30 and 48-52. In one embodiment, the antibody binds to human TIGIT with a KD value of about $1\times10^{-9}$ M to about $1\times10^{-12}$ M as determined by surface plasmon resonance (e.g., BIACORE) or a similar technique (e g KinExa or OCTET).

In another embodiment, the invention provides an antibody or antigen binding fragment that binds to human TIGIT comprising: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v)

a light chain variable region CDR2 comprising the amino acid sequence of SEQ ID NO: 61; and (vi) a light chain variable region CDR3 comprising the amino acid sequence of SEQ ID NO: 62. In one embodiment, the antibody or antigen binding fragment thereof is humanized. In one embodiment, the antibody or antigen binding fragment thereof comprises 1, 2 or 3 amino acid substitutions in the heavy chain CDRs (SEQ ID NOs: 57-59) or in the light chain CDRs (SEQ ID NOs: 60-62), and retains one or more of its functional characteristics. In one embodiment, the antibody or antigen binding fragment thereof optionally has at least one of the following functional characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET), (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention also provides an antibody or antigen binding fragment thereof that binds to human TIGIT comprising: (i) a heavy chain variable region CDR1 comprising the amino acid sequence of SEQ ID NO: 88; (ii) a heavy chain variable region CDR2 comprising the amino acid sequence of SEQ ID NO: 147; (iii) a heavy chain variable region CDR3 comprising the amino acid sequence of SEQ ID NO: 153; (iv) a light chain variable region CDR1 comprising the amino acid sequence of SEQ ID NO: 91; (v) a light chain variable region CDR2 comprising the amino acid sequence of SEQ ID NO: 148; and (vi) a light chain variable region CDR3 comprising the amino acid sequence of SEQ ID NO: 93. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134 or 135; (iii) a heavy chain variable region CDR3 comprising the amino acid sequence of SEQ ID NO: 90, 154, 155, 156, 157, 158, 159, 160, 161, 162, 163, 164, 165, 166 or 167; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121 or 122; and (vi) a light chain variable region CDR3 comprising the amino acid sequence of SEQ ID NO: 93. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 154; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 155; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 156; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 157; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 158; (iv) a light chain variable region CDR1 comprising the amino acid sequence of SEQ ID NO: 91; (v)

a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 159; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 160; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 161; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 162; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 163; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 164; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 165; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 166; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 167; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody or antigen binding fragment thereof is humanized. In one embodiment, the antibody or antigen binding fragment thereof optionally has at least one of the following characteristics: (i) binds to human TIGIT with a KD value of about $1 \times 10^{-9}$ M to about $1 \times 10^{-12}$ M as determined by surface plasmon resonance (e.g., BIACORE) or a similar technique (e.g. KinExa or OCTET), (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In one embodiment, the antibody or antigen binding fragment thereof binds to human TIGIT and comprises: (i) a heavy chain variable region CDR1 comprising the amino acid sequence of SEQ ID NO: 88; (ii) a heavy chain variable region CDR2 comprising the amino acid sequence of SEQ ID NO: 89; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the antibody comprises one amino acid substitution in the heavy chain CDR2 of SEQ ID NO: 89, wherein the substitution is made at position 7, and wherein residue D is substituted with: R, L, K, F, S, Y or V. In another embodiment, the antibody comprises one amino acid substitution in the heavy chain CDR2 of SEQ ID NO: 89, wherein the substitution is made at position 8, and wherein residue G is substituted with: R, N, Q, E, L K, S, Y or V. In another embodiment, the antibody comprises one amino acid substitution in the heavy chain CDR2 of SEQ ID NO: 89, wherein the substitution is made at position 12, wherein the N is substituted with: A or S. In another embodiment, the antibody comprises one amino acid substitution in the heavy chain CDR2 of SEQ ID NO: 89, wherein the substitution is made at position 13, wherein E is substituted with Q. In another embodiment, the antibody comprises one amino acid substitution in the heavy chain CDR2 of SEQ ID NO: 89, wherein the substitution is made at position 16, wherein K is substituted with Q. In another embodiment, the antibody comprises three amino acid substitution in the heavy chain CDR2 of SEQ ID NO: 89, wherein amino acid residue 12 is substituted with: A or S, amino acid residue 13 is substituted with Q and amino acid residue 16 is substituted with Q. In one embodiment, the antibody comprises one amino acid substitution in the heavy chain CDR3 of SEQ ID NO:90, wherein amino acid residue 6 is substituted with: A, D, E, F, G, I, K, N, Q, R, S, T, V or Y. In another embodiment, the antibody comprises one amino acid substitution in the light chain CDR of SEQ ID NO: 92, wherein the substitution is made at position 1, and wherein residue N is substituted with A, Y, W, S, T, R, H, G, I or V. In another embodiment, the antibody comprises one amino acid substitution in the light chain CDR of SEQ ID NO: 92, wherein the substitution is made at position 2, and wherein residue A is substituted with N, I, L, T, V. In one embodiment, the antibody or antigen binding fragment thereof is humanized. In one embodiment, the antibody or antigen binding fragment thereof optionally has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e g KinExa or OCTET), (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In another embodiment, the invention also provides an antibody or antigen binding fragment thereof that binds to human TIGIT comprising: a heavy chain variable region comprising the CDR1, CDR2 and CDR3 of any of SEQ ID NOs: 124-129 and/or a light chain variable region comprising the CDR1, CDR2 and CDR3 of any of SEQ ID NOs: 130-133. In one embodiment, the invention also provides an isolated antibody or antigen binding fragment thereof that binds to human TIGIT comprising: a heavy chain variable region selected from the group consisting of: SEQ ID NOs: 124-129 and/or a light chain variable region selected from the group consisting of: SEQ ID NOs: 130-133. In one embodiment, the D residue at position 56 of any one of SEQ ID NOs: 124-129 can be substituted with R, L, K, F, S, Y or V. In another embodiment, the G residue at position 57 of any one of SEQ ID NOs: 124-129 can be substituted with R, N, Q, E, L K, S, Y or V. In one embodiment, the W residue at position 104 of any one of SEQ ID NOs: 124-129 can be substituted with: A, D, E, F, G, I, K, N, Q, R, S, T, V or Y. In another embodiment, the N residue at position 50 of any one of SEQ ID NOs: 130-133 can be substituted with A, Y, W, S, T, I or V. In another embodiment, the A residue at position 51 of any of SEQ ID NOs: 130-133 is substituted with N, I, L, T or V. In one embodiment, the invention provides an isolated antibody or antigen binding fragment thereof that binds to human TIGIT comprising: a heavy chain variable region comprising SEQ ID NO:128 or a light chain variable region comprising SEQ ID NO:132. In another embodiment, the invention provides an isolated antibody or antigen binding fragment thereof that binds to human TIGIT comprising: a heavy chain variable region comprising SEQ ID NO:128 or a light chain variable region comprising SEQ ID NO:133. In another embodiment, the invention also provides an isolated antibody or antigen binding fragment thereof that binds to human TIGIT comprising: a heavy chain variable region comprising SEQ ID NO:127 or a light chain variable region comprising SEQ ID NO:130. In one embodiment, the invention provides an isolated antibody or antigen binding fragment thereof that binds to human TIGIT comprising: a heavy chain variable region comprising SEQ ID NO:128 and a light chain variable region comprising SEQ ID NO:132. In another embodiment, the invention also provides an isolated antibody or antigen binding fragment thereof that binds to human TIGIT comprising: a heavy chain variable region comprising SEQ ID NO:128 and a light chain variable region comprising SEQ ID NO:133. In another embodiment, the invention also provides an isolated antibody or antigen binding fragment thereof that binds to human TIGIT comprising: a heavy chain variable region comprising SEQ ID NO:126 and a light chain variable region comprising SEQ ID NO:131. In another embodiment, the invention also provides an isolated antibody or antigen binding fragment thereof that binds to human TIGIT comprising: a heavy chain variable region comprising SEQ ID NO:128 and a light chain variable region comprising SEQ ID NO:131. In another embodiment, the invention also provides an isolated antibody or antigen binding fragment thereof that binds to human TIGIT comprising: a heavy chain variable region comprising SEQ ID NO:125 and a light chain variable region comprising SEQ ID NO:133. In another embodiment, the invention also provides an isolated antibody or antigen binding fragment thereof that binds to human TIGIT comprising: a heavy chain variable region comprising SEQ ID NO:126 and a light chain variable region comprising SEQ ID NO:130. In another embodiment, the invention also provides an isolated antibody or antigen binding fragment thereof that binds to human TIGIT comprising: a heavy chain variable region comprising SEQ ID NO:125 and a light chain variable region comprising SEQ ID NO:132. In another embodiment, the invention also provides an isolated antibody or antigen binding fragment thereof that binds to human TIGIT comprising: a heavy chain variable region comprising SEQ ID NO:127 and a light chain variable region comprising SEQ ID NO:130. In some embodiments, the antibody or antigen binding fragment thereof binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention also provides an antibody or antigen binding fragment thereof that binds to human TIGIT comprising: (i) a heavy chain variable region comprising the CDR1, CDR2 and CDR3 of any one of SEQ ID NOs: 124-129, wherein the heavy chain variable region comprises at least 90%, 95%, 96%, 97%, 98% or 99% identity to any of one SEQ ID NOs: 124-129 and/or (ii) a light chain variable region comprising the CDR1, CDR2 and CDR3 of any one of SEQ ID NOs: 130-133, wherein the light chain variable region comprises at least 90%, 95%, 96%, 97%, 98% or 99% identity to any one of SEQ ID NOs: 130-133. In another embodiment, the invention also provides an antibody or antigen binding fragment thereof that binds to human TIGIT comprising: (i) a heavy chain variable region comprising the CDR1, CDR2 and CDR3 of SEQ ID NOs: 128, wherein the heavy chain variable region comprises 90%, 95%, 96%, 97%, 98% or 99% identity to SEQ ID NOs: 128 and/or (ii) a light chain variable region comprising the CDR1, CDR2 and CDR3 of SEQ ID NOs: 132, wherein the light chain variable region comprises at least 90%, 95%, 96%, 97%, 98% or 99% identity to SEQ ID NOs: 132. In another embodiment, the invention also provides an antibody or antigen binding fragment thereof that binds to human TIGIT comprising: (i) a heavy chain variable region comprising the CDR1, CDR2 and CDR3 of SEQ ID NOs: 128, wherein the heavy chain variable region comprises at least 90%, 95%, 96%, 97%, 98% or 99% identity to SEQ ID NOs: 128 and/or (ii) a light chain variable region comprising the CDR1, CDR2 and CDR3 of SEQ ID NOs: 133, wherein the light chain variable region comprises at least 90%, 95%, 96%, 97%, 98% or 99% identity to SEQ ID NOs: 133. In another embodiment, the invention also provides an antibody or antigen binding fragment thereof that binds to human TIGIT comprising: (i) a heavy chain variable region comprising the CDR1, CDR2 and CDR3 of SEQ ID NOs: 127, wherein the heavy chain variable region comprises at least 90%, 95%, 96%, 97%, 98% or 99% identity to SEQ ID NOs: 127 and/or (ii) a light chain variable region comprising the CDR1, CDR2 and CDR3 of SEQ ID NOs: 130, wherein the light chain variable region comprises at least 90%, 95%, 96%, 97%, 98% or 99% identity to SEQ ID NOs: 130. In these embodiments, the allowed sequence variations occur in the framework regions of the variable chains. In some embodiments, the antibody or antigen binding fragment thereof binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof, comprising: a variable heavy chain comprising the amino acid sequence of SEQ ID NO: 7 and/or a variable light chain selected comprising the amino acid sequence of SEQ ID NO: 8, wherein the antibody or antigen binding fragment thereof binds to human TIGIT. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof, comprising: a variable heavy chain comprising the amino acid sequence of SEQ ID NO: 143 and/or a variable light chain selected comprising the amino acid sequence of SEQ ID NO: 145, wherein the antibody or antigen binding fragment thereof binds to human TIGIT. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof, comprising: a variable heavy chain comprising the amino acid sequence of SEQ ID NO: 144 and/or a variable light chain selected comprising the amino acid sequence of SEQ ID NO: 146, wherein the antibody or antigen binding fragment thereof binds to human TIGIT. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof, comprising: a variable heavy chain comprising the amino acid sequence of SEQ ID NO: 63 and/or a variable light chain selected comprising the amino acid sequence of SEQ ID NO: 64, wherein the antibody or antigen binding fragment thereof binds to human TIGIT. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof, comprising: a variable heavy chain comprising the amino acid sequence of SEQ ID NO: 94 and/or a variable light chain selected comprising the amino acid sequence of SEQ ID NO: 95, wherein the antibody or antigen binding fragment thereof binds to human TIGIT. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In one embodiment, the invention also provides an isolated antibody or antigen binding fragment thereof that binds to human TIGIT comprising: a heavy chain variable region comprising SEQ ID NO:149 and/or a light chain variable region comprising SEQ ID NO:151. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In one embodiment, the invention also provides an isolated antibody or antigen binding fragment thereof that binds to human TIGIT comprising: a heavy chain variable region comprising SEQ ID NO:150 and/or a light chain variable region comprising SEQ ID NO:152. In one embodiment, the antibody binds to human TIGIT with a KD value of about $1\times10^{-9}$ M to about $1\times10^{-12}$ M as determined by surface plasmon resonance (e.g., BIACORE) or a similar technique (e.g. KinExa or OCTET).

In another embodiment, the invention provides an antibody or antigen binding fragment thereof that binds to the same epitope of human TIGIT as an antibody comprising the variable heavy chain of SEQ ID NO: 7 and the variable light chain of SEQ ID NO: 8, wherein the antibody or antigen binding fragment thereof has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e.g. KinExa or OCTET), (ii) blocks binding of human TIGIT to human CD155 and human CD112; (iii) increases T cell activation; (iv) stimulates antigen-specific T-cell production of IL-2 and IFNγ; (v) blocks induction of T cell suppression of activation induced by TIGIT ligation with cognate ligands CD155 and CD112. In one embodiment, the antibody comprises at least 80%, 85%, 90%, 95%, 96%, 97%, 98% or 99% sequence identity with the variable heavy chain and/or the variable light chain of any one of SEQ ID NOs: 7-30 or 37-52. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chain of any one of SEQ ID NOs: 7, 9-24 and 37-47 and/or the variable light chains of any one of SEQ ID NOs: 8, 25-30 and 48-52.

In one embodiment, the invention provides an antibody or antigen binding fragment thereof that binds to an epitope of human TIGIT that comprises at least one of the following regions: residues 54-57 of SEQ ID NO: 31, residues 68-70 of SEQ ID NO:31 and residues 76-81 of SEQ ID NO: 31. In one embodiment, the invention provides an antibody or antigen binding fragment thereof that binds to an epitope of human TIGIT comprising residues: 54-57, 68-70 and 76-81 of SEQ ID NO:31.

In another embodiment, the invention provides an antibody or antigen binding fragment thereof that binds to the same epitope of human TIGIT as an antibody comprising the variable heavy chain of SEQ ID NO: 63 and the variable light chain of SEQ ID NO: 64, wherein the antibody or antigen binding fragment thereof has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112. In one embodiment, the antibody or antigen binding fragment thereof comprises at least 80%, 85%, 90%, 95%, 96%, 97%, 98% or 99% sequence identity with the variable heavy chain of SEQ ID NO:63 and/or the variable light chain of SEQ ID NO: 64. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chain of SEQ ID NO:63 and/or the variable light chain of SEQ ID NO: 64. In another embodiment, the antibody or antigen binding fragment thereof comprises 1, 2 or 3 amino acid substitutions in the heavy chain CDRs (SEQ ID NOs: 57-59) or in the light chain CDRs (SEQ ID NOs: 60-62).

In another embodiment, the invention provides an antibody or antigen binding fragment thereof that binds to the same epitope of human TIGIT as an antibody comprising the variable heavy chain of SEQ ID NO: 94 and the variable light chain of SEQ ID NO:95, wherein the antibody or antigen binding fragment thereof has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112. In one embodiment, the antibody or antigen binding fragment thereof comprises at least 80%, 85%, 90%, 95%, 96%, 97%, 98% or 99% sequence with the variable heavy chain of any one of SEQ ID NOs:94 or 124-129, and/or the variable light chain of any one of SEQ ID NO: 95 or 130-133. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chain of any one of SEQ ID NOs:94 or 124-129, and/or the variable light chain of any one of SEQ ID NO: 95 or 130-133. In another embodiment, the antibody or antigen binding fragment thereof comprises 1, 2 or 3 amino acid substitutions in the heavy chain CDRs (SEQ ID NOs: 88-90) and/or in the light chain CDRs (SEQ ID NOs: 91-93). In another embodiment, the antibody or antigen binding fragment thereof comprises heavy chain CDRs of SEQ ID NOs: 88, 134 and 90 and/or the light chain CDRs of SEQ ID NOs: 91, 92 and 93.

In one embodiment, the invention provides an antibody or antigen binding fragment thereof that binds to an epitope of human TIGIT that comprises at least one of the following regions: residues 53-57, residues 60-65, residues 68-70, residues 72-81, residues 94-95, and residues 109-119 of SEQ ID NO:31. In one embodiment, the invention provides an antibody or antigen binding fragment thereof that binds to an epitope of human TIGIT comprising residues: 53-57, 60-65, 68-70, 72-81, 94-95, and 109-119 of SEQ ID NO:31.

In another embodiment, the invention provides an antibody or antigen binding fragment thereof that cross-blocks the binding of (or competes with) an antibody comprising the variable heavy chain of SEQ ID NO: 7 and the variable light chain of SEQ ID NO: 8 to human TIGIT, wherein the antibody or antigen binding fragment thereof has at least one of the following characteristics: (i) binds to human TIGIT with a KD value of about $1\times10^{-9}$ M to about $1\times10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112. In one embodiment, the antibody or antigen binding fragment thereof comprises at least 80%, 85%, 90%, 95%, 96%, 97%, 98% or 99% sequence identity with the variable heavy chain or variable light chains of SEQ ID NOs: 7-30 or 37-52. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chains of SEQ ID NOs:7, 9-24 and 37-47 or the variable light chains of SEQ ID NOs: 8, 25-30 and 48-52. In another embodiment, the antibody or antigen binding fragment thereof comprises 1, 2 or 3 amino acid substitutions in the heavy chain CDRs (SEQ ID NOs: 1-3) or in the light chain CDRs (SEQ ID NOs: 3-6).

In another embodiment, the invention provides an antibody or antigen binding fragment thereof that cross-blocks the binding of (or competes with) an antibody comprising the variable heavy chain of SEQ ID NO: 63 and the variable light chain of SEQ ID NO: 64 to human TIGIT, wherein the antibody or antigen binding fragment thereof has at least one of the following functional characteristics: (i) binds to human TIGIT with a KD value of about $1 \times 10^{-9}$ M to about $1 \times 10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ (vi) blocks induction of T cell suppression of activation induced by TIGIT ligation with cognate ligands CD155 and CD112. In one embodiment, the antibody comprises at least 80%, 85%, 90%, 95%, 96%, 97%, 98% or 99% sequence identity with the variable heavy chain of SEQ ID NO:63 or the variable light chains of SEQ ID NO: 64. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chain of SEQ ID NO: 63 or the variable light chain of SEQ ID NO: 64. In another embodiment, the antibody or antigen binding fragment thereof comprises 1, 2 or 3 amino acid substitutions in the heavy chain CDRs (SEQ ID NOs: 57-59) or in the light chain CDRs (SEQ ID NOs: 60-62).

In another embodiment, the invention provides an antibody or antigen binding fragment thereof that cross-blocks the binding of (or competes with) an antibody comprising the variable heavy chain of SEQ ID NO: 94 and the variable light chain of SEQ ID NO: 95 to human TIGIT, wherein the antibody or antigen binding fragment thereof has at least one of the following characteristics: (i) binds to human TIGIT with a KD value of about $1 \times 10^{-9}$ M to about $1 \times 10^{-12}$ M as determined by surface plasmon resonance (e.g., BIACORE) or a similar technique (e.g. KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ (vi) blocks induction of T cell suppression of activation induced by TIGIT ligation with cognate ligands CD155 and CD112. In one embodiment, the antibody comprises at least 80%, 85%, 90%, 95%, 96%, 97%, 98% or 99% sequence identity with the variable heavy chain of SEQ ID NO: 94 or the variable light chains of SEQ ID NO: 95. In another embodiment, the antibody or antigen binding fragment thereof comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions in the variable heavy light chain of any one of SEQ ID NOs: 94 or 124-129, or the variable light chain of any one of SEQ ID NOs: 95 or 130-133. In another embodiment, the antibody or antigen binding fragment thereof comprises 1, 2 or 3 amino acid substitutions in the heavy chain CDRs (SEQ ID NOs: 88-90) or in the light chain CDRs (SEQ ID NOs: 91-93). In one embodiment, the antibody or antigen binding fragment thereof comprises: a heavy chain variable region comprising SEQ ID NO:128 and a light chain variable region comprising SEQ ID NO:132. In another embodiment, antibody or antigen binding fragment thereof comprises: a heavy chain variable region comprising SEQ ID NO:127 and a light chain variable region comprising SEQ ID NO:130. In another embodiment, antibody or antigen binding fragment thereof comprises: a heavy chain variable region comprising SEQ ID NO:128 and a light chain variable region comprising SEQ ID NO:133.

In another embodiment, the invention provides an antibody or antigen binding fragment thereof that binds to human TIGIT comprising a variable heavy chain selected from the group consisting of any one of SEQ ID NOs: 9-24 and 37-47, and/or a variable light chain selected from the group consisting of any one of SEQ ID NOs: 25-30 and 48-52. In one embodiment, the antibody comprises an amino acid substitution in FR4 of the heavy chain, wherein the substitution is made at position 122 of SEQ ID NOs: 9-24 and 37-47, wherein the residue is substituted from M to: V, L, A, R, N, P, Q, E, G, I, H, K, F, S, T, W or Y. In one embodiment, the antibody comprises two amino acid substitutions in FR4 of the heavy chain, wherein the substitutions are made at positions 122 and 123 of SEQ ID NOs: 9-24 and 37-47, wherein the residues are substituted from M and V to T and L, respectively.

In another embodiment, the invention provides an antibody or antigen binding fragment thereof that binds to human TIGIT comprising a variable heavy chain selected from the group consisting of any one of SEQ ID NOs: 9-24 and 37-47, and/or a variable light chain selected from the group consisting of any one of SEQ ID NOs: 25-30 and 48-52. In one embodiment, the antibody comprises an amino acid substitution in FR4 of the heavy chain, wherein the substitution is made at position 122 of SEQ ID NOs: 9-24 and 37-47, wherein the residue is substituted from M to: V, L, A, R, N, P, Q, E, G, I, H, K, F, S, T, W or Y. In one embodiment, the antibody comprises two amino acid substitutions in FR4 of the heavy chain, wherein the substitutions are made at positions 122 and 123 of SEQ ID NOs: 9-24 and 37-47, wherein the residues are substituted from M and V to T and L, respectively.

In one embodiment, the invention relates to an isolated antibody or antigen binding fragment that binds to human TIGIT comprising: a heavy chain comprising the amino acid sequence of SEQ ID NO: 7 or variant thereof comprising up to 30 amino acid substitutions, and/or a light chain comprising the amino acid sequence of SEQ ID NO: 8 comprising up to 12 amino acid substitutions. In one embodiment, the heavy chain comprises the amino acid sequence of SEQ ID NO: 7 comprising amino acid substitutions at one or more positions selected from the group consisting of: 6, 9, 12, 15, 16, 17, 23, 25, 37, 39, 40, 43, 44, 45, 48, 67, 68, 70, 71, 79, 81, 83, 87, 88, 92, 94, 119, 122 and 123. In one embodiment, the heavy chain comprises the amino acid sequence of SEQ ID NO:7 comprising amino acid substitutions at one or more positions selected from the group consisting of: 6, 9, 12, 15, 16, 17, 23, 25, 37, 39, 40, 43, 44, 45, 48, 67, 68, 70, 71, 79, 81, 83, 87, 88, 92, 94, 110, 119, 122 and 123, wherein: the amino acid at position 6 can be E or Q, the amino acid at position 9 can be P or A, the amino acid at position 12 can be V or L, the amino acid at position 15 can be S or P, the amino acid at position 16 can be Q or E or G, the amino acid at position 17 can be S or T, the amino acid at position 23 can be S or T, the amino acid at position 25 can be T or S, the amino acid at position 37 can be I or V, the amino acid at position 39 can be K or Q, the amino acid at position 40 can be F or P, the amino acid at position 43 can be N or K, the amino acid at position 44 can be K or G, the amino acid at position 45 can be M or L, the amino acid at position 48 can be M or I, the amino acid at position 67 can be I or V, the amino acid at position 68 can be S or T, the amino acid at position 70 can be T or S, the amino acid at position 71 can be R or V, the amino acid at position 79 can be F or S, the amino acid at position 81 can be Q or K, the amino acid at position 83 can be H or S, the amino acid at position 87 can be T or A, the amino acid at position 88 can be D or A, the amino acid at position 92 can be T or V, the amino acid at position 94 can be S or Y, the amino acid at position 110 can be W, F, Y, I, V or L, the amino acid at position 119 can be P or Q, the amino acid at position 122 can be M, V, L, A, R, N, P, Q, E, G, I, H, K, F, S, T, W or Y, and the amino acid at position 123 can be V, T or L. In one embodiment, the light chain comprises the amino acid sequence of SEQ ID NO: 8 comprising amino acid substitutions at one or more positions selected from the group consisting of: 10, 21, 22, 40, 42, 46, 52, 53, 58, 77, 83, 87, 95 and 106. In one embodiment, the light chain comprises the amino acid sequence of SEQ ID NO: 8 comprising amino acid substitutions at one or more positions selected from the group consisting of: 10, 21, 22, 40, 42, 46, 52, 53, 58, 77, 83, 87, 95 and 106 wherein: the amino acid at position 10 can be L or S, the amino acid at position 21 can be L or I, the amino acid at position 22 can be N or T, the amino acid at position 40 can be L or P, the amino acid at position 42 can be E or K, the amino acid at position 46 can be F or L, the amino acid at position 52 can be N, S, T, G or D, the amino acid at position 53 can be S, N, T, Y or Q, the amino acid at position 58 can be I or V, the amino acid at position 77 can be G or S, the amino acid at position 83 can be V or F, the amino acid at position 87 can be F or Y, the amino acid at position 95 can be W, F, Y, I, V or L, and the amino acid at position 105 can be L or I.

In another embodiment, the invention relates to an antibody or antigen binding fragment that binds to human TIGIT comprising: a heavy chain comprising the amino acid sequence of SEQ ID NO: 9 and/or a light chain comprising the amino acid sequence of SEQ ID NO: 25, wherein each of the variable chains can comprise 1, 2, 3, 4, 5, 6, 7 or 8 amino acid substitutions. In one embodiment, the antibody can comprise mutations at positions 27, 48, 67, 71, 83, 110, 122 and 123 of SEQ ID NO: 9. For example, with respect to SEQ ID NO: 9: the amino acid at position 27 can be G or S; the amino acid at position 48 can be I or M; the amino acid at position 67 can be V or I; the amino acid at position 71 can be V or R; the amino acid at position 83 can be S or H; the amino acid at position 110 can be W, F, Y, I, V or L; the amino acid position 122 can be M, V, L, A, R, N, P, Q, E, G, I, H, K, F, S, T, W or Y; and the amino acid at position 123 can be V, T or L. In another embodiment, the antibody can comprise mutations at positions 46, 52, 53, 58 and 95 of SEQ ID NO: 25. For example, with respect to SEQ ID NO: 25, the amino acid at position 46 can be L or F; the amino acid at position 52 can be N, S, T, G or D, the amino acid at position 53 can be S, N, T, Y or Q; the amino acid at position 58 can be I or V; the amino acid at position 58 can be V or I; and the amino acid at position 95 can be W, F, Y, I, V or L.

In one embodiment, the invention relates to an antibody or antigen binding fragment that binds to human TIGIT comprising: a heavy chain comprising the amino acid sequence of SEQ ID NO: 94 or variant thereof comprising up to 30 amino acid substitutions, and a light chain comprising the amino acid sequence of SEQ ID NO: 95 or a variant thereof comprising up to 18 amino acid substitutions. In one embodiment, the heavy chain comprises a variant of the amino acid sequence of SEQ ID NO: 94 comprising amino acid substitutions at one or more positions selected from the group consisting of: 5, 9, 11, 12, 16, 20, 38, 40, 44, 56, 57, 61, 62, 65, 67, 68, 72, 74, 76, 79, 85, 87, 89, 91, 92, 104 and 111. In one embodiment, the heavy chain comprises a variant of the amino acid sequence of SEQ ID NO: 94 comprising amino acid substitutions at one or more positions selected from the group consisting of: 5, 9, 11, 12, 16, 20, 38, 40, 44, 56, 57, 61, 62, 65, 67, 68, 72, 74, 76, 79, 85, 87, 89, 91, 92, 104 and 111, wherein: the amino acid at position 5 can be Q or V, the amino acid at position 9 can be P or A, the amino acid at position 11 can be V or L, the amino acid at position 12 can be V or K, the amino acid at position 16 can be S or A, the amino acid at position 20 can be M or V, the amino acid at position 38 can be K or R, the amino acid at position 40 can be K or A, the amino acid at position 44 can be G or R, the amino acid at position 56 can be D, R, L, K, F, S, Y or V, the amino acid at position 57 can be G, R, N, Q, E, L K, S, Y or V, the amino acid at position 61 can be N, A or S, the amino acid at position 62 can be E or Q, the amino acid at position 65 can be K or Q, the amino acid at position 67 can be R or K, the amino acid at position 68 can be A or V, the amino acid at position 72 can be S or R, the amino acid at position 74 can be K or T, the amino acid at position 76 can be S, I, A or T, the amino acid at position 79 can be A or V, the amino acid at position 85 can be R or S, the amino acid at position 87 can be T or R, the amino acid at position 89 can be D or E, the amino acid at position 91 can be S or T, the amino acid at position 92 can be A or V, the amino acid at position 104 can be W, A, D, E, F, G, I, K, N, Q, R, S, T, V or Y, and the amino acid at position 111 can be A or Q. In one embodiment, the light chain comprises a variant of the amino acid sequence of SEQ ID NO: 95 comprising amino acid substitutions at one or more positions selected from the group consisting of: 9, 17, 18, 40, 43, 45, 48, 50, 51, 70, 72, 74, 76, 83, 84, 100, 103 and 106. In one embodiment, the light chain comprises a variant of the amino acid sequence of SEQ ID NO: 95 comprising amino acid substitutions at one or more positions selected from the group consisting of: 9, 17, 18, 40, 43, 45, 48, 50, 51, 70, 72, 74, 76, 83, 84, 100, 103 and 106, wherein the amino acid at position 9 can be A or S, the amino acid at position 17 can be E or D, the amino acid at position 18 can be T or R, the amino acid at position 40 can be Q or P, the amino acid at position 43 can be S, A or V, the amino acid at position 45 can be Q or K, the amino acid at position 48 can be V or I, the amino acid at position 50 can be N, A, Y, W, S, T, I or V, the amino acid at position 51 can be A, N, I, L, T or V, the amino acid at position 70 can be Q or D, the amino acid at position 72 can be S or T, the amino acid at position 74 can be K or T, the amino acid at position 76 can be N or S, the amino acid at position 83 can be F or V, the amino acid at position 84 can be G or A, the amino acid at position 100 can be A or Q, the amino acid at position 103 can be T or R and the amino acid at position at position 106 can be L or I.

In one embodiment, the invention relates to an antibody or antigen binding fragment that binds to human TIGIT comprising: a heavy chain comprising the amino acid sequence of SEQ ID NO: 124 or variant thereof comprising up to 10 amino acid substitutions, and/or a light chain comprising the amino acid sequence of SEQ ID NO: 130 or a variant thereof comprising up to 5 amino acid substitutions. In another embodiment, the invention provides an antibody or antigen binding fragment thereof that binds to human TIGIT comprising a variable heavy chain of SEQ ID NO: 124 or a variant thereof, wherein the variant comprises substitutions at one or more positions selected from the group consisting of: 16, 44, 56, 57, 61, 72, 74, 76, 79, 85, 89, 92 and 104. In another embodiment, the invention provides an antibody or antigen binding fragment thereof that binds to human TIGIT comprising a variable heavy chain of SEQ ID NO: 124 or a variant thereof, wherein the variant comprises substitutions at one or more positions selected from the group consisting of: 16, 44, 56, 57, 61, 72, 74, 76, 79, 85, 89, 92 and 104, wherein the amino acid at position 16 can be A or S, the amino acid at position 44 can be R or G, the amino acid at position 56 can be D, R, L, K, F, S, Y or V, the amino acid at position 57 can be G, R, N, Q, E, L K, S, Y or V, the amino acid at position 61 can be S or A, the amino acid at position 72 can be R or S, the amino acid at position 74 can be T or K, the amino acid at position 76 can be A or T or I, the amino acid at position 79 can be A or V, the amino acid at position 85 can be S or R, the amino acid at position 89 can be E or D, the amino acid at position 92 can be A or V and the amino acid at position 104 can be W, A, D, E, F, G, I, K, N, Q, R, S, T, V or Y. In another embodiment, the invention provides an antibody or antigen binding fragment thereof that binds to human TIGIT comprising a variable light chain of SEQ ID NO: 130 or a variant thereof comprising substitutions at one or more positions selected from the group consisting of: 43, 50, 51, 70 and 83. In another embodiment, the invention provides an antibody or antigen binding fragment thereof that binds to human TIGIT comprising a variable light chain of SEQ ID NO: 130 or a variant thereof comprising substitutions at one or more positions selected from the group consisting of: 43, 50, 51, 70 and 83, wherein the amino acid at position 43 can be S, A or V, the amino acid at position 50 can be N, A, Y, W, S, T, I or V, the amino acid at position 51 can be A, N, I, L, T or V, the amino acid at position 70 can be Q or D, and the amino acid at position 83 can be F or V.

In any of the above embodiments, the antibody or antigen binding fragment thereof is isolated.

In any of the above embodiments, the antibody or antigen binding fragment thereof is a recombinant antibody.

In any of the above embodiments, the antibody or antigen binding fragment thereof is a full-length antibody.

In any of the above embodiments, the antibody or antigen binding fragment thereof is a humanized antibody.

In any of the above embodiments, the antibody or antigen binding fragment thereof is a humanized antibody comprising two heavy chains and two light chains. In one embodiment, the heavy chains are of the IgG1 isotype and the light chains are kappa light chains.

In any of the above mentioned embodiments, the antibody or antigen binding fragment thereof of the invention can comprise a variable heavy region consisting of: (a) any of the variable heavy chains described above and (b) a leader peptide (for example, the leader peptide of SEQ ID NO: 53). In any of the above mentioned embodiments, the antibody or antigen binding fragment thereof of the invention can comprise a light heavy region consisting of: (a) any of the light heavy chains described above and (b) a leader peptide (for example, the leader peptide of SEQ ID NO: 54).

In any of the above mentioned embodiments, the antibody or antigen binding fragment thereof of the invention is an antibody comprising any of the variable heavy chains described above and any human heavy chain constant domain. In one embodiment, the antibody or antigen binding fragment thereof of the invention is of the IgG isotype, and comprises a human IgG1, IgG2, IgG3 or IgG4 human heavy chain constant domain. In one embodiment, the antibody or antigen binding fragment thereof of the invention comprises a human heavy chain IgG1 constant domain (SEQ ID NO: 86) or a variant thereof, wherein the variant comprises up to 20 modified amino acid substitutions. In one embodiment, the antibody or antigen binding fragment thereof of the invention is an antibody comprising a human heavy chain IgG1 constant domain comprising the amino acid sequence of SEQ ID NO: 86. In one embodiment, the antibody or antigen binding fragment thereof of the invention comprises a human heavy chain IgG1 constant domain wherein the IgG1 constant domain is afucosylated. In one embodiment, the antibody or antigen binding fragment thereof of the invention comprises a human heavy chain IgG4 constant domain or a variant thereof, wherein the variant comprises up to 20 modified amino acid substitutions. In another embodiment, the antibody or antigen binding fragment thereof of the invention comprises a human heavy chain IgG4 constant domain, wherein the amino acid at position 228 (using EU numbering scheme) has been substituted from Ser to Pro. In one embodiment, the antibody or antigen binding fragment thereof of the invention comprises a human heavy chain IgG4 constant domain comprising the amino acid sequence of SEQ ID NO: 55.

In any of the above mentioned embodiments, the antibody or antigen binding fragment thereof of the invention can comprise any of the variable light chains described above and human light chain constant domain. In one embodiment, the antibody or antigen binding fragment thereof of the invention comprises a human kappa light chain constant domain or a variant thereof, wherein the variant comprises up to 20 modified amino acid substitutions. In another embodiment, the antibody or antigen binding fragment thereof of the invention comprises a human lambda light chain constant domain or a variant thereof, wherein the variant comprises up to 20 modified amino acid substitutions. In one embodiment, the antibody or antigen binding fragment thereof of the invention comprises a human kappa light chain constant domain comprising the amino acid sequence of SEQ ID NO: 56.

In one embodiment, the anti-TIGIT antibody of the invention comprises a full tetrameric structure having two light chains and two heavy chains, wherein each light chain comprises: a variable region comprising SEQ ID NO:132 and a human kappa light chain (SEQ ID NO:56); and each heavy chain comprises: a variable region comprising SEQ ID NO:128, a human IgG1 constant region (SEQ ID NO:86).

In one embodiment, the anti-TIGIT antibody of the invention comprises a full tetrameric structure having two light chains and two heavy chains, wherein each light chain comprises: a variable region comprising SEQ ID NO:130 and a human kappa light chain (SEQ ID NO:56); and each heavy chain comprises: a variable region comprising SEQ ID NO:127, a human IgG1 constant region (SEQ ID NO:86).

In one embodiment, the anti-TIGIT antibody of the invention comprises a full tetrameric structure having two light chains and two heavy chains, wherein each light chain comprises: a variable region comprising SEQ ID NO:133 and a human kappa light chain (SEQ ID NO:56); and each heavy chain comprises: a variable region comprising SEQ ID NO:128, a human IgG1 constant region (SEQ ID NO:86).

In any of the above mentioned embodiments, the anti-TIGIT antibody or antigen binding fragment thereof of the invention can be conjugated to at least one therapeutic agent. In one embodiment, the wherein the therapeutic agent comprises a second antibody or fragment thereof, an immunomodulator, a hormone, a cytotoxic agent, an enzyme, a radionuclide, a second antibody conjugated to at least one immunomodulator, enzyme, radioactive label, hormone, antisense oligonucleotide, or cytotoxic agent, or a combination thereof.

The invention also provides isolated polypeptides comprising the amino acid sequence of any one of SEQ ID NOs: 1-30, 37-52, 57-83 or 88-151, or a fragment of any said sequences.

The invention also provides isolated nucleic acids encoding anyone of the anti-TIGIT antibodies or antigen binding fragments of the invention. In one embodiment, the invention provides isolated nucleic acids encoding anyone of the polypeptides of SEQ ID NOs: 1-30, 37-52, 57-64 or 88-133, wherein said polypeptides can optionally comprise a leader sequence. The invention also provides expression vectors comprising a nucleic acid encoding anyone of the polypeptides of SEQ ID NOs: 1-30, 37-52, 57-83 or 88-167 (wherein said polypeptides can optionally comprise a leader sequence). These isolated nucleic acids and the expression vectors comprising them may be used to express the antibodies of the invention or antigen binding fragments thereof in recombinant host cells. Thus, the invention also provides host cells comprising isolated nucleic acids encoding anyone of the polypeptides of SEQ ID NOs: 1-30, 37-52, 57-83 or 88-151 (wherein said polypeptides can optionally comprise a leader sequence). In one embodiment, the host cell is Chinese hamster ovary cell. In one embodiment, the host cell is a yeast cell, for example a *Pichia* cell or a *Pichia pastoris* host cell.

The invention also provides pharmaceutical compositions comprising an antibody or antigen binding fragment of the invention and a pharmaceutically acceptable carrier or diluent. In one embodiment, the composition comprises a further therapeutic agent. In one embodiment, the further therapeutic agent is selected from the group consisting of: an anti-PD1 antibody or an antigen binding fragment thereof; an anti-LAG3 antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD27 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-SIRPa antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; and an anti-ILT5 antibody or an antigen binding fragment thereof; an anti 4-1BB antibody or an antigen binding fragment thereof. In one embodiment, the anti-PD1 antibody or an antigen binding fragment thereof; is selected from the group consisting of: pembrolizumab or an antigen binding fragment thereof and nivolumab or an antigen binding fragment thereof. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

In one embodiment, the invention provides a composition comprising: (i) an anti-TIGIT antibody or antigen binding fragment of the invention; and (ii) an anti-PD1 antibody comprising the heavy chain sequence of SEQ ID NO: 33 and the light chain variable sequence of SEQ ID NO: 34. In another embodiment, the invention provides a composition comprising: (a) an anti-TIGIT antibody or antigen binding fragment of the invention; and (b) an anti-PD1 antibody comprising the heavy chain sequence of SEQ ID NO: 35 and the light chain variable sequence of SEQ ID NO: 36. In one embodiment, the anti-PD1 antibody is administered prior to the administration of an anti-TIGIT antibody. In one embodiment, the anti-PD1 antibody is administered 4-10 days prior to the administration of the anti-TIGIT antibody. In one embodiment, pretreatment treatment with anti-PD1 antibody may modulate immune cells resulting in enhanced Fc-mediated function of the anti-TIGIT antibodies. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also comprises a combination comprising an anti-TIGIT antibody or antigen binding fragment of the invention, in combination with one, two or more therapeutic agents; wherein the second therapeutic agent is selected from the group consisting of: an anti-PD1 antibody or an antigen binding fragment thereof; an anti-LAG3 antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD27 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-SIRPa antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; an anti-ILT5 antibody or an antigen binding fragment thereof; and an anti 4-1BB antibody or an antigen binding fragment thereof. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a vessel or injection device comprising anyone of the anti-TIGIT antibodies or antigen binding fragments of the invention. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a method of producing an anti-TIGIT antibody or antigen binding fragment of the invention comprising: culturing a host cell comprising a polynucleotide encoding a heavy chain and/or light chain of an antibody of the invention (or an antigen binding fragment thereof) under conditions favorable to expression of the polynucleotide; and optionally, recovering the antibody or antigen binding fragment from the host cell and/or culture medium. In one embodiment, the polynucleotide encoding the heavy chain and the polynucleotide encoding the light chain are in a single vector. In another embodiment, the polynucleotide encoding the heavy chain and the polynucleotide encoding the light chain are in different vectors. In one embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO:4; (v) a light chain variable region CDR2 comprising the amino acid sequence of SEQ ID NO:5, 65, 66, 67, 68, 69, 70, 71, 72, 73 or 141; and (vi) a light chain variable region CDR3 comprising the amino acid sequence of SEQ ID NO:6, 74, 75, 76, 77, 78 or 142. In another embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO:88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In another embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO:62. In another embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In another embodiment, the polynucleotide encoding the heavy chain and the polynucleotide encoding the light chain encode an antibody or antigen binding fragment comprising: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In another embodiment, the polynucleotide encoding the heavy chain and the polynucleotide encoding the light chain encode an antibody or antigen binding fragment comprising: a heavy chain variable region comprising SEQ ID NO:128 and a light chain variable region comprising SEQ ID NO:132. In another embodiment, the polynucleotide encoding the heavy chain and the polynucleotide encoding the light chain encode an antibody or antigen binding fragment comprising: a heavy chain variable region comprising SEQ ID NO:127 and a light chain variable region comprising SEQ ID NO:130. In another embodiment, the polynucleotide encoding the heavy chain and the polynucleotide encoding the light chain encode an antibody or antigen binding fragment comprising: a heavy chain variable region comprising SEQ ID NO:128 and a light chain variable region comprising SEQ ID NO:133.

The invention also provides a method of treating cancer in a subject in need thereof, comprising administering to the subject an effective amount of an anti-TIGIT antibody or antigen binding fragment of the invention, optionally in association with a further therapeutic agent or therapeutic procedure. In one embodiment, the subject been treated is a human subject. In one embodiment, the further therapeutic agent is selected from the group consisting of: an anti-PD1 antibody or an antigen binding fragment thereof; an anti-LAG3 antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD27 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-SIRPa antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; an anti-ILT5 antibody or an antigen binding fragment thereof; and an anti-4-1BB antibody or an antigen binding fragment thereof. In one embodiment, the anti-PD1 antibody or an antigen binding fragment thereof is selected from the group consisting of: pembrolizumab or an antigen binding fragment thereof and nivolumab or an antigen binding fragment thereof. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO:4; (v) a light chain variable region CDR2 comprising the amino acid sequence of SEQ ID NO:5, 65, 66, 67, 68, 69, 70, 71, 72, 73 or 141; and (vi) a light chain variable region CDR3 comprising the amino acid sequence of SEQ ID NO:6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO:88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a method of treating cancer in a subject in need thereof, comprising administering to the subject an effective amount of an anti-TIGIT antibody or antigen binding fragment of the invention, and further administering an anti-PD1 antibody or an antigen binding fragment thereof. In one embodiment, the anti-PD1 antibody or an antigen binding fragment thereof is selected from the group consisting of: pembrolizumab or an antigen binding fragment thereof and nivolumab or an antigen binding fragment thereof. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO:4; (v) a light chain variable region CDR2 comprising the amino acid sequence of SEQ ID NO:5, 65, 66, 67, 68, 69, 70, 71, 72, 73 or 141; and (vi) a light chain variable region CDR3 comprising the amino acid sequence of SEQ ID NO:6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6.

In another embodiment, the anti-TIGIT How antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a method of treating an infection or infectious disease in a subject, comprising administering to the subject an effective amount of an antibody or antigen binding fragment of the invention, optionally in association with a further therapeutic agent or therapeutic procedure. In one embodiment, the subject been treated is a human subject. In one embodiment, the further therapeutic agent is selected from the group consisting of: an anti-PD1 antibody or an antigen binding fragment thereof; an anti-LAG3 antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD27 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-SIRPa antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; an anti-ILT5 antibody or an antigen binding fragment thereof; and an anti-4-1BB antibody or an antigen binding fragment thereof. In one embodiment, the anti-PD1 antibody or an antigen binding fragment thereof; is selected from the group consisting of: pembrolizumab or an antigen binding fragment thereof and nivolumab or an antigen binding fragment thereof. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO:4; (v) a light chain variable region CDR2 comprising the amino acid sequence of SEQ ID NO:5, 65, 66, 67, 68, 69, 70, 71, 72, 73 or 141; and (vi) a light chain variable region CDR3 comprising the amino acid sequence of SEQ ID NO:6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO:88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO:59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO:88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a vaccine comprising an antibody or antigen binding fragment of the invention. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 1401; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO:6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the vaccine further comprises an antigen.

The invention also provides a method for detecting the presence of a TIGIT peptide or a fragment thereof in a sample comprising contacting the sample with an antibody or antigen binding fragment thereof of the invention and detecting the presence of a complex between the antibody or fragment and the peptide; wherein detection of the complex indicates the presence of the TIGIT peptide. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO:4; (v) a light chain variable region CDR2 comprising the amino acid sequence of SEQ ID NO:5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 153; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v)

a light chain variable region CDR2 comprising the amino acid sequence of SEQ ID NO: 5; and (vi) a light chain variable region CDR3 comprising the amino acid sequence of SEQ ID NO: 6. In another embodiment, the antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a method of increasing the activity of an immune cell, comprising contacting the immune cell with any one of the antibodies or antigen binding fragments of the invention. In one embodiment, the invention provides a method of increasing the activity of an immune cell, comprising administering to a subject in need thereof an effective amount of an antibody or antigen binding fragments of the invention. In one embodiment, the method is used for: the treatment of cancer, the treatment of an infection or infectious disease, or as a vaccine adjuvant. In one embodiment, the increase in activity of an immune cell can be detected by measuring the proliferation of the immune cell. For example, an increase in activity of a T cell can be detected by measuring the proliferation of the T cell. In one embodiment, the increase in activity of an immune cell can be detected by measuring T cell activation ex vivo in a sample derived from the subject. In one embodiment, the increase in T cell activity is determined by: (i) measuring mixed lymphocyte reactions or direct anti-CD3 mAb stimulation of T cell receptor (TCR) signaling to induce production of a cytokine selected from the group consisting of: IL-2, TNFα, IL-17, IFNγ, IL-1β, GM-CSF, RANTES, IL-6, IL-8, IL-5 and IL-13; (ii) measuring SEB induced production of one or more cytokines selected from the group consisting of: IL-2, TNFα, IL-17, IFNγ, GM-CSF, RANTES, IL-6, IL-8, IL-5 and IL-13; or (iii) measuring TT induced production of a cytokine selected from the group consisting of: IL-2, TNFα, IL-17, IFNγ, GM-CSF, RANTES, IL-6, IL-8, IL-5 and IL-13. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3, 79, 80, 81, 82, 83 or 140; (iv) a light chain variable region CDR1 comprising the amino acid sequence of SEQ ID NO: 4; (v) a light chain variable region CDR2 comprising the amino acid sequence of SEQ ID NO: 5, 65, 66, 67, 68, 69, 70, 71, 72, 73 or 141; and (vi) a light chain variable region CDR3 comprising the amino acid sequence of SEQ ID NO: 6, 74, 75, 76, 77, 78 or 142. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 96, 97, 98, 99, 100, 101, 102, 103, 104, 105, 106, 107, 108, 109, 110, 111, 134, 135 or 147; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92, 112, 113, 114, 115, 116, 117, 118, 119, 120, 121, 122 or 148; and (vi) a light chain variable region CDR3 comprising the amino acid sequence of SEQ ID NO: 93. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In another embodiment, the anti-TIGIT antibody or antigen binding fragment of the invention comprises: (i) a heavy chain variable region CDR1 comprising the amino acid sequence of SEQ ID NO: 57; (ii) a heavy chain variable region CDR2 comprising the amino acid sequence of SEQ ID NO: 58; (iii) a heavy chain variable region CDR3 comprising the amino acid sequence of SEQ ID NO: 59; (iv) a light chain variable region CDR1 comprising the amino acid sequence of SEQ ID NO: 60; (v) a light chain variable region CDR2 comprising the amino acid sequence of SEQ ID NO: 61; and (vi) a light chain variable region CDR3 comprising the amino acid sequence of SEQ ID NO: 62. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also comprises a method of treating cancer or infectious disease in a subject, comprising administering to the subject an effective amount of an antagonist anti-TIGIT antibody and an antagonist anti-PD1 antibody, wherein the anti-TIGIT antibody has increased effector function when compared to a parental antibody. As used herein, a "parental anti-antibody" refers to antibody having a wild-type Fc region and/or wild type glycosylation (i.e., glycosylation pattern resulting from expression of the polypeptide in a non-engineered mammalian host cell). The effector function of a parental antibody can be increased by mutating its Fc region or by altering its glycosylation (as discussed in further detail below). In one embodiment, the anti-PD1 antibody is administered prior to the administration of a parental antibody. In one embodiment, the anti-PD1 antibody is administered 4-10 days prior to the administration of the anti-TIGIT antibody. In one embodiment, pretreatment treatment with anti-PD1 antibody may modulate immune cells resulting in enhanced Fc-mediated function of the anti-TIGIT antibodies. In one embodiment, the anti-TIGIT antibody comprises a human IgG1 constant domain. In one embodiment, treatment with the anti-TIGIT and anti-PD1 antibodies does not result in depletion of Tregs. In one embodiment, the anti-PD1 antibody or an antigen binding fragment thereof; is selected from the group consisting of: pembrolizumab and nivolumab. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3 (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In one embodiment, the anti-TIGIT antibody or antigen binding fragment of the invention comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90 (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also comprises a method of treating cancer or infectious disease in a subject, comprising administering to the subject an effective amount of an antagonist anti-TIGIT antibody and an antagonist anti-PD1 antibody, wherein the anti-TIGIT antibody is afucosylated. In one embodiment, the anti-TIGIT antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3 (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In one embodiment, the anti-TIGIT antibody or antigen binding fragment of the invention comprises: (i) a heavy chain variable region CDR1 comprising the amino acid sequence of SEQ ID NO: 88; (ii) a heavy chain variable region CDR2 comprising the amino acid sequence of SEQ ID NO: 89, 134 or 135; (iii) a heavy chain variable region CDR3 comprising the amino acid sequence of SEQ ID NO: 90 (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93. In one embodiment, the anti-TIGIT antibody or antigen binding fragment thereof comprises: (i) a heavy chain variable region CDR1 comprising the amino acid sequence of SEQ ID NO: 88; (ii) a heavy chain variable region CDR2 comprising the amino acid sequence of SEQ ID NO: 134; (iii) a heavy chain variable region CDR3 comprising the amino acid sequence of SEQ ID NO: 90; (iv) a light chain variable region CDR1 comprising the amino acid sequence of SEQ ID NO: 91; (v) a light chain variable region CDR2 comprising the amino acid sequence of SEQ ID NO: 92; and (vi) a light chain variable region CDR3 comprising the amino acid sequence of SEQ ID NO: 93.

The invention also provides a method of increasing the anti-tumor activity of an anti-TIGIT antibody comprising: obtaining a parental anti-TIGIT antibody and increasing the effector function of the parental anti-TIGIT antibody; wherein the activity of the resulting anti-TIGIT antibody is increased as compared to the parental anti-TIGIT antibody. As used herein, a "parental anti-antibody" refers to antibody having a wild-type Fc region and/or wild type glycosylation (i.e., glycosylation pattern resulting from expression of the polypeptide in a non-engineered mammalian host cell). The effector function of a parental antibody can be increased by mutating its Fc region or by altering its glycosylation, for example by making the antibody afucosylated (as discussed in further detail below). In one embodiment, the effector function of a parental anti-TIGIT antibody is increased by making mutations in the Fc region of the parental anti-TIGIT antibody. In another embodiment, the effector function of a parental anti-TIGIT antibody is increased by removing the fucose residues from the antibody, or expressing the antibody in a host cell that has been genetically engineered to remove the activity of the enzyme that adds fucose to glycoproteins.

BRIEF DESCRIPTION OF THE FIGURES

FIG. 4 shows binding of antibody 31C6 to human and rhesus TIGIT (expressed in CHO-K1 cells), and also shows that antibody 31C6 blocks hCD155 interaction with hTIGIT.

FIG. 6 shows the activity of antibodies 14A6 and 31C6 in vitro T cell assay.

FIGS. 9A-9D show the effect of concurrent administration of a rat anti-mouse TIGIT antibody (GIGD7) and an anti-mouse PD-1 antibody compared to the monotherapy treatment arms on the anti-tumor response of mice implanted with the CT26 cell line (n=10/group). Treatment was commenced when tumors reached 75 mm3-115 mm3.

FIGS. 13A-13C show the effect of Fc isotype on the anti-tumor activity of an anti-TIGIT antibody (11A11) in combination with an anti-PD-1 antibody in an animal tumor model.

DETAILED DESCRIPTION

Abbreviations

Figure 1:
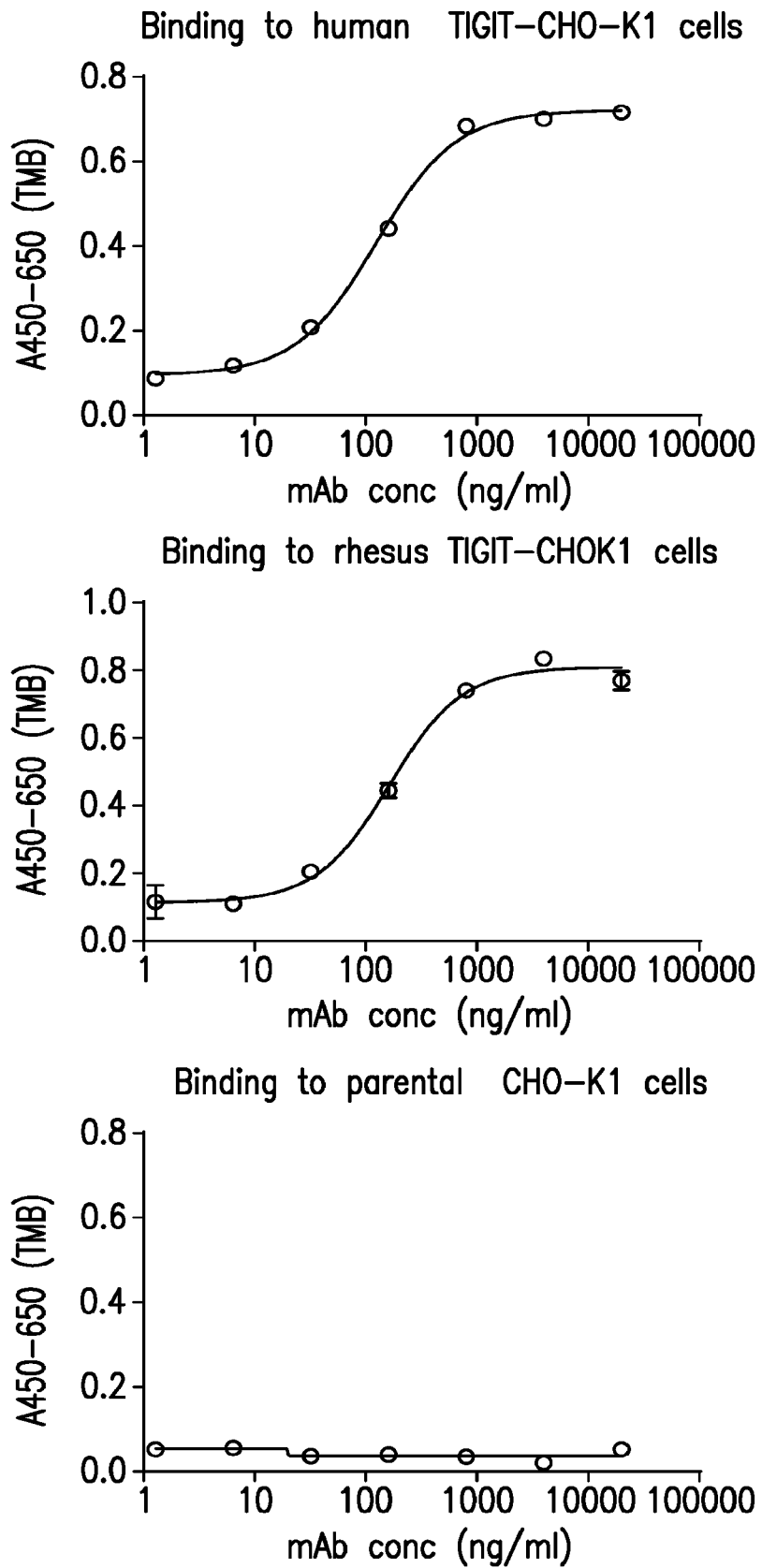
FIG. 1 shows binding of antibody 14A6 to human and rhesus TIGIT (expressed in CHO-K1 cells).

Throughout the detailed description and examples of the invention the following abbreviations will be used:

ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

TIGIT

The term TIGIT includes human TIGIT, cynomolgous monkey TIGIT and rhesus TIGIT as well as fragments thereof such as the mature fragment thereof lacking the signal peptide. In an embodiment of the invention, the amino acid sequence of human TIGIT comprises the amino acid sequence disclosed in amino acid residues 25-244 of Genbank Accession Number NP_776160.2 (SEQ ID NO: 31). (Amino acid residues 1-24 of SEQ ID NO:31 correspond to a leader peptide.)

In an embodiment of the invention, the amino acid sequence of cynomolgous monkey, e.g., *Macaca fascicularis* TIGIT comprises the amino acid sequence disclosed in (SEQ ID NO: 32); see also Genbank Accession no. XP 005548157. The amino acid sequence of rhesus monkey TIGIT is identical to the amino acid sequence of cynomolgous monkey TIGIT. (Amino acid residues 1-24 of SEQ ID NO:32 correspond to a leader peptide.)

Anti-TIGIT Antibodies and Antigen-Binding Fragments Thereof

The present invention provides antibodies or antigen-binding fragments thereof that bind human TIGIT and uses of such antibodies or fragments. In some embodiments, the anti-TIGIT antibodies are isolated.

As used herein, an anti-TIGIT antibody or antigen-binding fragment thereof refers to an antibody or antigen-binding fragment thereof that specifically binds to human TIGIT. An antibody or antigen-binding fragment thereof that "specifically binds to human TIGIT" is an antibody or antigen-binding fragment thereof that binds to human TIGIT with a KD of about 1 nM or a higher affinity (e.g., 1 nM-2 pM, 1 nM, 100 pM, 10 pM or 2 pM), but does not bind to other proteins lacking this sequence. For example, an antibody that "specifically binds" human TIGIT does not bind to human CD226, human CD155 and human CD112. As a further example, an antibody or antigen-binding fragment that specifically binds to human TIGIT may bind to a FLAG®-tagged form of human TIGIT but will not bind to other FLAG®-tagged proteins that lack human TIGIT epitopes. In one embodiment, the antibody of the invention which specifically binds to human TIGIT is also cross-reactive with cynomolgus and rhesus TIGIT. As used herein "cross-reactivity" refers to the ability of an antibody to react with a homologous protein from other species. Whether an antibody specifically binds to human TIGIT can be determined using any assay known in the art. Examples of assays known in the art to determining binding affinity include surface plasmon resonance (e.g., BIACORE) or a similar technique (e.g. KinExa or OCTET).

The present invention includes anti-TIGIT antibodies and methods of use thereof. As used herein, the term "antibody" refers to any form of antibody that exhibits the desired biological activity. Thus, it is used in the broadest sense and specifically covers, but is not limited to, monoclonal antibodies (including full length monoclonal antibodies comprising two light chains and two heavy chains), polyclonal antibodies, multispecific antibodies (e.g., bispecific antibodies), humanized antibodies, fully human antibodies, chimeric antibodies and camelized single domain antibodies.

The present invention includes non-human parental (e.g. mouse and rodent) anti-TIGIT antibodies and antigen-binding fragments thereof and methods of use thereof. These antibodies may be modified for an intended use, such as humanization of an antibody for use as a human therapeutic antibody or fragment.

The present invention includes anti-TIGIT antigen-binding fragments and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

The present invention includes anti-TIGIT Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-TIGIT antibodies and antigen-binding fragments thereof which comprise an Fc region and methods of use thereof. An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

The present invention includes anti-TIGIT Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

The present invention includes anti-TIGIT F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The present invention includes anti-TIGIT Fv fragments and methods of use thereof. The "Fv region" comprises the variable regions from both the heavy and light chains, but lacks the constant regions.

The present invention includes anti-TIGIT scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

The present invention includes anti-TIGIT domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-TIGIT bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-TIGIT camelized single domain antibodies and methods of use thereof. In certain embodiments, antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

The present invention includes anti-TIGIT diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, an antibody or antigen-binding fragment of the invention which is modified in some way retains at least 10% of its binding activity (when compared to the parental antibody) when that activity is expressed on a molar basis. Preferably, an antibody or antigen-binding fragment of the invention retains at least 20%, 50%, 70%, 80%, 90%, 95% or 100% or more of the TIGIT binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-TIGIT antibodies and antigen-binding fragments thereof and methods of use thereof. "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention includes monoclonal anti-TIGIT antibodies and antigen-binding fragments thereof as well as monoclonal compositions comprising a plurality of isolated monoclonal antibodies. The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

The present invention includes anti-TIGIT chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) Proc. Natl. Acad. Sci. USA 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

The present invention includes anti-TIGIT humanized antibodies and antigen-binding fragments thereof (e.g., rat or mouse antibodies that have been humanized) and methods of use thereof. The invention includes any humanized version of the 14A6 antibody (comprising SEQ ID NOs:7 and 8), the 28H5 antibody (comprising SEQ ID NOs:63 and 64) and the 31C6 antibody (comprising SEQ ID NOs: 94-95). As used herein, the term "humanized antibody" refers to forms of antibodies that contain sequences from both human and non-human (e.g., mouse or rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); *Kabat* (1978) *Adv. Prot. Chem.* 32:1-75; Kabat, et al., (1977)*J. Biol. Chem.* 252: 6609-6616; Chothia, et al., (1987) *J Mol. Biol.* 196:901-917 or Chothia, et al., (1989) *Nature* 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

Physical and Functional Properties of the Exemplary Anti-TIGIT Antibodies

The present invention provides anti-TIGIT antibodies and antigen-binding fragments thereof having specified structural and functional features, and methods of use of the antibodies or antigen-binding fragments thereof in the treatment or prevention of disease (e.g., cancer or infectious disease).

An "anti-TIGIT antibody or antigen-binding fragment thereof of the present invention" includes: any antibody or antigen-binding fragment thereof that is discussed herein (e.g., 14A6, 28H5, 31C6 or humanized versions of the these antibodies disclosed in Table 4) or a variant thereof (e.g., sequence variant or functional variant); any antibody or antigen-binding fragment comprising any one or more of the CDRs set forth in Table 4; any antibody or antigen-binding fragment that binds to the same epitope in human TIGIT as the antibodies discussed herein (e.g., 14A6, 28H5 or 31C6); and any antibody or antigen-binding fragment that cross-blocks (partially or fully) or is cross-blocked (partially or fully) by an antibody discussed herein (e.g., 14A6, 28H5 or 31C6) for TIGIT binding.

Cross-blocking antibodies and antigen-binding fragments thereof can be identified based on their ability to cross-compete with an antibody of the invention in standard binding assays (e.g., BIACore, ELISA, flow cytometry). For example, standard ELISA assays can be used in which a recombinant TIGIT (e.g., human TIGIT) protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of another antibody (for example, antibody 14A6 or 28H5 or 31C6) to TIGIT (e.g., human TIGIT) demonstrates that the test antibody can compete with another antibody (e.g., 14A6 or 28H5 or 31C6) for binding to TIGIT (e.g., human TIGIT) and thus, may, in some cases, bind to the same epitope on TIGIT (e.g., human TIGIT) as antibody 14A6 or 28H5 or 31C6 or to an overlapping epitope.

As stated above, antibodies and fragments that bind to the same epitope as any of the anti-TIGIT antibodies or antigen-binding fragments thereof of the present invention also form part of the present invention. Further, antibodies that bind to an epitope that overlaps with the epitope bound by any of the anti-TIGIT antibodies of the invention also form part of the present invention. There are several methods available for mapping antibody epitopes on target antigens, including: H/D-Ex Mass spec, X-ray crystallography, pepscan analysis and site directed mutagenesis. For example, HDX (Hydrogen Deuterium Exchange) coupled with proteolysis and mass spectrometry can be used to determine the epitope of an antibody on a specific antigen Y. HDX-MS relies on the accurate measurement and comparison of the degree of deuterium incorporation by an antigen when incubated in $D_2O$ on its own and in presence of its antibody at various time intervals. Deuterium is exchanged with hydrogen on the amide backbone of the proteins in exposed areas whereas regions of the antigen bound to the antibody will be protected and will show less or no exchange after analysis by LC-MS/MS of proteolytic fragments. Example 9 exemplifies the use of HDX to map the epitope bound by antibody 14A6.

Examples of the immunoglobulin chains of anti-TIGIT antibodies of the invention as well as their CDRs include, but are not limited those disclosed in Table 4 (SEQ ID NOs: 1-30, 37-52, 57-83 or 88-167). The present invention includes any polypeptide comprising or consisting of the amino acid sequences of SEQ ID NOs: 1-30, 37-52, 57-83 or 88-167, and recombinant nucleotides encoding such polypeptides.

The scope of the present invention includes isolated anti-TIGIT antibodies and antigen-binding fragments thereof (e.g., humanized antibodies), comprising a variant of an immunoglobulin chain set forth herein, e.g., any of SEQ ID NOs: 7-30, 37-52, 63-64, 94-95 or 124-133; wherein the variant exhibits one or more of the following properties: (i) binds human TIGIT; (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

In other embodiments, the invention provides antibodies or antigen-binding fragment thereof that binds human TIGIT (e.g., humanized antibodies) and has $V_L$ domains and $V_H$ domains with at least 80%, 85%, 90%, 95%, 96%, 97%, 98% or 99% sequence identity with SEQ ID NOs: 7-30, 37-52, 63-64, 94-95 or 124-133; wherein the variant exhibits the desired binding and properties, e.g., (i) binds human TIGIT with a KD value of about $1 \times 10^{-9}$ M to about $1 \times 10^{-12}$ M as determined by surface plasmon resonance (e.g., BIACORE) or a similar technique (e g KinExa or OCTET); (ii) cross-reacts with cynomolgous and rhesus TIGIT; (iii) blocks binding of human TIGIT to human CD155 and human CD112; (iv) increases T cell activation; (v) stimulates antigen-specific T-cell production of IL-2 and IFNγ; (vi) blocks induction of T cell suppression of activation induced by TIGIT ligation with cognate ligands CD155 and CD112.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1.

TABLE 1

| Exemplary Conservative Amino Acid Substitutions | |
|---|---|
| Original residue | Conservative substitution |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 1. Also provided are isolated polypeptides comprising the $V_L$ domains of the anti-TIGIT antibodies of the invention (e.g., SEQ ID NOs: 8, 25-30 and 48-52), and isolated polypeptides comprising the $V_H$ domains (e.g., SEQ ID NOs: 7, 9-24 and 37-47) of the anti-TIGIT antibodies of the invention having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions. Also provided are isolated polypeptides comprising the $V_L$ domains of the anti-TIGIT antibodies of the invention (e.g., SEQ ID NO:64) and isolated polypeptides comprising the $V_H$ domains (e.g., SEQ ID NO:63) of the anti-TIGIT antibodies of the invention having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions. Also provided are isolated polypeptides comprising the $V_L$ domains of the anti-TIGIT antibodies of the invention (e.g., SEQ ID NOs: 95 and 130-133) and isolated polypeptides comprising the $V_H$ domains (e.g., SEQ ID NOs: 94 and 124-129) of the anti-TIGIT antibodies of the invention having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions.

In another embodiment, provided is an antibody or antigen-binding fragment thereof that binds TIGIT and has $V_L$ domains and $V_H$ domains with at least 99% 98%, 97%, 96%, 95%, 90%, 85%, 80% or 75% sequence identity to one or more of the $V_L$ domains or $V_H$ domains described herein, and exhibits specific binding to TIGIT. In another embodiment the binding antibody or antigen-binding fragment thereof of the present invention comprises $V_L$ and $V_H$ domains (with and without signal sequence) having up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions, and exhibits specific binding to TIGIT.

Polynucleotides and Polypeptides

The present invention further comprises the polynucleotides encoding any of the polypeptides or immunoglobulin chains of anti-TIGIT antibodies and antigen-binding fragments thereof of the invention. For example, the present invention includes the polynucleotides encoding the amino acids described in SEQ ID NOs: 1-30, 37-52, 57-83 and 88-167, as well as polynucleotides which hybridize thereto and, also, any polypeptide encoded by such a hybridizing polynucleotide. In one embodiment, the invention comprises a nucleic acid sequence comprising or consisting essentially of SEQ ID NO:84 or SEQ ID NO:85.

In general, the polynucleotides hybridize under low, moderate or high stringency conditions, and encode antibodies or antigen-binding fragments thereof that maintain the ability to bind to TIGIT (human, rhesus and/or cynomolgous monkey, e.g., *Macaca fascicularis*). A first polynucleotide molecule is "hybridizable" to a second polynucleotide molecule when a single stranded form of the first polynucleotide molecule can anneal to the second polynucleotide molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two polynucleotide contain complementary sequences, although, depending on the stringency of the hybridization, mismatches between bases are possible. The appropriate stringency for hybridizing polynucleotides depends on the length of the polynucleotides and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter polynucleotides, e.g., oligonucleotides, the position of mismatches becomes more important, and the length of the oligonucleotide determines its specificity (see Sambrook, et al., supra, 11.7-11.8).

In another embodiment, an isolated polynucleotide, for example DNA, encoding the polypeptide chains of the isolated antibodies or antigen-binding fragments set forth herein is provided. In one embodiment, the isolated polynucleotide encodes an antibody or antigen-binding fragment thereof comprising at least one mature immunoglobulin light chain variable ($V_L$) domain according to the invention and/or at least one mature immunoglobulin heavy chain variable ($V_H$) domain according to the invention. In some embodiments the isolated polynucleotide encodes both a light chain and a heavy chain on a single polynucleotide molecule, and in other embodiments the light and heavy chains are encoded on separate polynucleotide molecules. In another embodiment the polynucleotides further encodes a signal sequence.

In one embodiment, the invention comprises an isolated polynucleotide encoding an antibody heavy variable ($V_H$) domain or an antigen-binding fragment thereof comprising CDR-H1 (SEQ ID NO:1), CDR-H2 (SEQ ID NO:2) and CDR-H3 (SEQ ID NO:3 or 79 or 80 or 81 or 82, 83 or 140).

In one embodiment, the invention comprises an isolated polynucleotide encoding an antibody light chain variable ($V_L$) domain or an antigen-binding fragment thereof comprising CDR-L1 (SEQ ID NO:4), CDR-L2 (SEQ ID NO:5 or 65 or 66 or 67 or 68 or 69 or 70 or 71 or 72 or 73 or 141) and CDR-L3 (SEQ ID NO:6 or 74 or 75 or 76 or 77 or 78).

In one embodiment, the invention comprises an isolated polynucleotide encoding the immunoglobulin heavy chain variable ($V_H$) domain of SEQ ID NO: 7.

In one embodiment, the invention comprises an isolated polynucleotide encoding the immunoglobulin heavy chain variable ($V_L$) domain of SEQ ID NO: 8.

In one embodiment, the invention comprises an isolated polynucleotide encoding the immunoglobulin heavy chain variable ($V_H$) domain of any one of SEQ ID NOs: 9-24 or 37-47.

In one embodiment, the invention comprises an isolated polynucleotide encoding the immunoglobulin heavy chain variable ($V_L$) domain of any one of SEQ ID NOs: 25-30 or 48-52

In one embodiment, the invention comprises an isolated polynucleotide encoding an antibody heavy variable ($V_H$) domain or an antigen-binding fragment thereof comprising CDR-H1 (SEQ ID NO:57), CDR-H2 (SEQ ID NO:58) and CDR-H3 (SEQ ID NO:59).

In one embodiment, the invention comprises an isolated polynucleotide encoding an antibody light chain variable ($V_L$) domain or an antigen-binding fragment thereof comprising CDR-L1 (SEQ ID NO:60), CDR-L2 (SEQ ID NO:61) and CDR-L3 (SEQ ID NO:62).

In one embodiment, the invention comprises an isolated polynucleotide encoding the immunoglobulin heavy chain variable ($V_H$) domain of SEQ ID NO: 63.

In one embodiment, the invention comprises an isolated polynucleotide encoding the immunoglobulin heavy chain variable ($V_L$) domain of SEQ ID NO: 64.

In one embodiment, the invention comprises an isolated polynucleotide encoding an antibody heavy variable ($V_H$) domain or an antigen-binding fragment thereof comprising CDR-H1 (SEQ ID NO: 88), CDR-H2 (SEQ ID NO: 89, 96, 97, 98, 99, 100, 101, 102, 103, 104, 105, 106, 107, 108, 109, 110, 111, 134 or 135) and CDR-H3 (SEQ ID NO: 90).

In one embodiment, the invention comprises an isolated polynucleotide encoding an antibody light chain variable ($V_L$) domain or an antigen-binding fragment thereof comprising CDR-L1 (SEQ ID NO: 91), CDR-L2 (SEQ ID NO: 92, 112, 113, 114, 115, 116, 117, 118, 119, 120, 121, 122 or 123) and CDR-L3 (SEQ ID NO: 93).

In one embodiment, the invention comprises an isolated polynucleotide encoding the immunoglobulin heavy chain variable ($V_H$) domain of SEQ ID NO: 94.

In one embodiment, the invention comprises an isolated polynucleotide encoding the immunoglobulin heavy chain variable ($V_L$) domain of SEQ ID NO: 95.

In one embodiment, the invention comprises an isolated polynucleotide encoding the immunoglobulin heavy chain variable ($V_H$) domain of any one of SEQ ID NOs: 124-129.

In one embodiment, the invention comprises an isolated polynucleotide encoding the immunoglobulin heavy chain variable ($V_L$) domain of any one of SEQ ID NOs: 130-133.

In one embodiment, the invention comprises an isolated polynucleotide encoding the immunoglobulin heavy chain variable ($V_H$) domain of SEQ ID NO: 127.

In one embodiment, the invention comprises an isolated polynucleotide encoding the immunoglobulin heavy chain variable ($V_H$) domain of SEQ ID NO: 128.

In one embodiment, the invention comprises an isolated polynucleotide encoding the immunoglobulin heavy chain variable ($V_L$) domain of SEQ ID NO: 130.

In one embodiment, the invention comprises an isolated polynucleotide encoding the immunoglobulin heavy chain variable ($V_L$) domain of SEQ ID NO: 132.

In one embodiment, the invention comprises an isolated polynucleotide encoding the immunoglobulin heavy chain variable ($V_L$) domain of SEQ ID NO: 133.

This present invention also provides vectors, e.g., expression vectors, such as plasmids, comprising the isolated polynucleotides of the invention, wherein the polynucleotide is operably linked to control sequences that are recognized by a host cell when the host cell is transfected with the vector. Also provided are host cells comprising a vector of the present invention and methods for producing the antibody or antigen-binding fragment thereof or polypeptide disclosed herein comprising culturing a host cell harboring an expression vector or a nucleic acid encoding the immunoglobulin chains of the antibody or antigen-binding fragment thereof in culture medium, and isolating the antigen or antigen-binding fragment thereof from the host cell or culture medium.

Also included in the present invention are polypeptides, e.g., immunoglobulin polypeptides, comprising amino acid sequences that are at least about 75% identical, 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences (e.g. expect threshold: 10; word size: 3; max matches in a query range: 0; BLOSUM 62 matrix; gap costs: existence 11, extension 1; conditional compositional score matrix adjustment).

Sequence identity refers to the degree to which the amino acids of two polypeptides are the same at equivalent positions when the two sequences are optimally aligned.

The following references relate to BLAST algorithms often used for sequence analysis: BLAST ALGORITHMS: Altschul et al. (2005) *FEBS J.* 272(20): 5101-5109; Altschul, S. F., et al., (1990) *J. Mol. Biol.* 215:403-410; Gish, W., et al., (1993) *Nature Genet.* 3:266-272; Madden, T. L., et al., (1996) *Meth. Enzymol.* 266:131-141; Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock, J. M. et al., (1994) *Comput. Appl. Biosci.* 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) *J. Mol. Biol.* 219:555-565; States, D. J., et al., (1991) *Methods* 3:66-70; Henikoff, S., et al., (1992) *Proc. Natl. Acad. Sci. USA* 89:10915-10919; Altschul, S. F., et al., (1993) *J. Mol. Evol.* 36:290-300; ALIGNMENT STATISTICS: Karlin, S., et al., (1990) *Proc. Natl. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Binding Affinity

By way of example, and not limitation, the antibodies and antigen-binding fragments disclosed herein may bind human TIGIT with a $K_D$ value of at least about $1\times10^{-9}$M (i.e., a $K_D$ value of $1\times10^{-9}$M or lower) as determined by surface plasmon resonance (e.g., BIACORE) or a similar technique (e.g. KinExa or OCTET). In one embodiment, the antibodies and antigen-binding fragments disclosed herein may bind human TIGIT with a $K_D$ value of at least about $1\times10^{-9}$M to about $1\times10^{-12}$M as determined by surface plasmon resonance (e.g., BIACORE) or a similar technique (e.g. KinExa or OCTET). In one embodiment, the antibodies and antigen-binding fragments disclosed herein may bind human TIGIT with a $K_D$ value of at about $1\times10^{-9}$ M to about $1\times10^{-12}$M as determined by surface plasmon resonance (e.g., BIACORE) or a similar technique (e.g. KinExa or OCTET). In one embodiment, the antibodies and antigen-binding fragments disclosed herein may bind human TIGIT with a $K_D$ value of at least about 50 pM (i.e, a $K_D$ value of about 50 pM or lower) as determined by BIACORE or a similar technique. In one embodiment, the antibodies and antigen-binding fragments disclosed herein may bind human TIGIT with a $K_D$ value of at least about 10 pM (i.e, a $K_D$ value of about 10 pm lower) as determined by BIACORE or a similar technique. In one embodiment, the antibodies and antigen-binding fragments of the invention may bind to human TIGIT with a $K_D$ of about 50 pM to about 1 pM as determined by BIACORE or a similar technique.

Immune Cell Activation

In some embodiments, the antibodies or antigen binding fragments of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject. In one embodiment, the increase in T cell activity is determined by: (i) measuring SEB (*Staphylococcus* Enterotoxin B) induced production of one or more pro-inflammatory cytokines selected from the group consisting of: IL-2, TNFα, IL-17, IFNγ, IL-1β, GM-CSF, RANTES, IL-6, IL-8, IL-5 and IL-13; or (ii) measuring mixed lymphocyte reactions or direct anti-CD3 mAb stimulation of T cell receptor (TCR) signaling to induce production of a cytokine selected from the group consisting of: IL-2, TNFα, IL-17, IFNγ, IL-1β, GM-CSF, RANTES, IL-6, IL-8, IL-5 and IL-13. In certain embodiments, the anti-TIGIT antibody or antigen binding fragment thereof of the present invention will stimulates antigen-specific T-cell production of IL-2 and/or IFNγ by at least 1.5 fold.

The present invention includes antagonist anti-TIGIT antibodies and antigen-binding fragments thereof and methods of use thereof, e.g., humanized, antagonist anti-TIGIT antibodies and fragments. An antagonist anti-TIGIT antibody or antigen-binding fragment thereof antagonizes an activity of human TIGIT such as by inhibiting TIGIT binding to CD155 and CD112, and inhibiting functional ITIM signal transduction by TIGIT upon binding to CD155 and CD112. Measurement of anti-TIGIT antagonist activity can be assessed by demonstrating blocking of T cell suppression following TCR activation induced by TIGIT ligation with cognate ligands CD155 and CD112. Hence, in one embodiment of increased responses, treating with antagonist anti-TIGIT antibodies are able to rescue IL-2 responses to levels observed in T cells that are not repressed by CD155 or CD112 induction of TIGIT. In a more preferred level of activation, responses, following treatment with an anti-TIGIT antagonist antibody may increase responses to a level higher than T cell responses not repressed by CD155 or CD112.

Ability of Anti-hTIGIT Antibodies to Block Binding to hCD155 and hCD112

In some embodiments, the anti-TIGIT antibodies or antigen binding fragments of the invention are able to block binding of human TIGIT to human CD155 and human CD112. The ability to block binding of human TIGIT to human CD155 and human CD112 can be determined using any method known in the art. In one embodiment, the ability of the antibodies to block binding of human TIGIT to human CD155 and human CD112 is determined using an ELISA assay as described in Example 2.

Methods of Making Antibodies and Antigen-Binding Fragments Thereof

Hybridoma cells that produce parental (e.g., rat or mouse) monoclonal anti-TIGIT antibodies or antigen-binding fragments thereof discussed herein may be produced by methods which are commonly known in the art. Such isolated hybridomas are part of the present invention. These methods include, but are not limited to, the hybridoma technique originally developed by Kohler, et al., (1975) (Nature 256: 495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), the EBV-hybridoma technique (Cole, et al., in *Monoclonal Antibodies and Cancer Therapy*, Alan R. Liss, Inc., pp. 77-96, 1985), and electric field based electrofusion using a Cyto Pulse large chamber cull fusion electroporator (Cyto Pulse Sciences, Inc., Glen Burnie, Md.). Preferably, mouse splenocytes are isolated and fused with PEG or by electrofusion to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately $2 \times 10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for anti-TIGIT monoclonal IgG antibodies. Once extensive hybridoma growth occurs, medium can be observed usually after 10-14 days. The antibody secreting hybridomas may be replated, screened again, and if still positive for human IgG, anti-TIGIT monoclonal antibodies, can be subcloned at least twice by limiting dilution. The stable subclones may then be cultured in vitro to generate small amounts of antibody in tissue culture medium for characterization.

Thus, the present invention includes methods for making an anti-TIGIT antibody or antigen-binding fragment thereof of the present invention comprising culturing a hybridoma cell that expresses the antibody or fragment under condition favorable to such expression and, optionally, isolating the antibody or fragment from the hybridoma and/or the growth medium (e.g. cell culture medium).

The anti-TIGIT antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., $V_H$ or $V_L$) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-TIGIT antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-TIGIT antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa. Pichia sp.*, any *Saccharomyces sp., Hansenula polymorpha*, any *Kluyveromyces sp., Candida albicans*, any *Aspergillus sp., Trichoderma reesei, Chrysosporium lucknowense*, any *Fusarium sp., Yarrowia lipolytica*, and *Neurospora crassa*. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

Antibodies and antigen-binding fragments thereof and immunoglobulin chains can be recovered from the culture medium using standard protein purification methods. Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-TIGIT antibody or antigen-binding fragment thereof of the present invention comprising introducing a sample comprising the antibody or fragment to a purification medium (e.g., cation exchange medium, anion exchange medium, hydrophobic exchange medium, affinity purification medium (e.g., protein-A, protein-G, protein-A/G, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

The present invention includes polyclonal anti-TIGIT antibodies and antigen-binding fragments thereof, e.g., a composition comprising a plurality of anti-TIGIT antibodies and fragments, which include one or more of the anti-TIGIT antibodies or antigen-binding fragments thereof of the present invention, and methods of use thereof. A polyclonal antibody is an antibody which was produced among or in the presence of one or more other, non-identical antibodies. In general, polyclonal antibodies are produced from collections of different B-lymphocytes, e.g., the B-lymphocyte of an animal treated with an immunogen of interest, which produces a population of different antibodies but which are all directed to the immunogen. Usually, polyclonal antibodies are obtained directly from an immunized animal, e.g., spleen, serum or ascites fluid.

The present invention includes bispecific and bifunctional antibodies and antigen-binding fragments having a binding specificity for TIGIT and another antigen such as, for example, PD-1 or PD-L1 or LAG-3, and methods of use thereof. In an embodiment of the invention, the anti-TIGIT chains comprise any one of the VH/VL sequences described in Table 4, and the PD1 chains comprise the amino acid sequence of SEQ ID NOs: 33 and 34 or of SEQ ID NOs: 35 and 36 (or an antigen binding fragment of any of said sequences). A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

The present invention further includes anti-TIGIT antigen-binding fragments of the anti-TIGIT antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG1, IgG2, IgG3 and IgG4; IgA1 and IgA2. The invention comprises antibodies and antigen-binding fragments of any of these classes or subclasses of antibodies.

In one embodiment, the antibody or antigen-binding fragment comprises a heavy chain constant region, e.g. a human constant region, such as γ1, γ2, γ3, or γ4 human heavy chain constant region or a variant thereof. In another embodiment, the antibody or antigen-binding fragment comprises a light chain constant region, e.g. a human light chain constant region, such as lambda or kappa human light chain region or variant thereof. By way of example, and not limitation the human heavy chain constant region can be γ4 and the human light chain constant region can be kappa. In an alternative embodiment, the Fc region of the antibody is γ4 with a Ser228Pro mutation (Schuurman, J et. al., Mol. Immunol. 38: 1-8, 2001).

In one embodiment, the antibody or antigen-binding fragment comprises a heavy chain constant region of the IgG1 subtype.

In some embodiments, different constant domains may be appended to humanized V$_L$ and V$_H$ regions derived from the CDRs provided herein. For example, if a particular intended use of an antibody (or fragment) of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. The present invention includes anti-TIGIT antibodies and antigen-binding fragments thereof which comprise an IgG4 constant domain, e.g., antagonist, humanized anti-TIGIT antibodies and fragments, and methods of use thereof. In one embodiment, the IgG4 constant domain can differ from the native human IgG4 constant domain (Swiss-Prot Accession No. P01861.1) at a position corresponding to position 228 in the EU system and position 241 in the KABAT system, where the native Ser108 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) Mol. Imunol. 30:105. In other instances, a modified IgG1 constant domain which has been modified to increase half-life or reduce effector function can be used.

Antibody Engineering

Further included are embodiments in which the anti-TIGIT antibodies and antigen-binding fragments thereof are engineered antibodies to include modifications to framework residues within the variable domains of a parental (e.g., mouse or rat) monoclonal antibody, e.g. to improve the properties of the antibody or fragment. Typically, such framework modifications are made to decrease the immunogenicity of the antibody or fragment. This is usually accomplished by replacing non-CDR residues in the variable domains (i.e. framework residues) in a parental (e.g. rodent) antibody or fragment with analogous residues from the immune repertoire of the species in which the antibody is to be used, e.g. human residues in the case of human therapeutics. Such an antibody or fragment is referred to as a "humanized" antibody or fragment. In some cases it is desirable to increase the affinity, or alter the specificity of an engineered (e.g. humanized) antibody. One approach is to "backmutate" one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. Nos. 5,693,762, 5,585,089 and 5,530,101.)

In certain embodiments, the anti-TIGIT antibodies and antigen-binding fragments thereof are engineered (e.g. humanized) to include modifications to in the framework and/or CDRs to improve their properties. Such engineered changes can be based on molecular modelling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) *Sequences of Proteins of Immunological Interest*, Kabat, et al.; National Institutes of Health, Bethesda, Md.; 5$^{th}$ ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J Mol. Biol.* 196:901-917 or Chothia, et al., (1989) *Nature* 342:878-883. There are variations between regions classified as "CDRs" and "hypervariable loops". Later studies (Raghunathan et al, (2012) *J. Mol Recog.* 25, 3, 103-113) analyzed several antibody—antigen crystal complexes and observed that the antigen binding regions in antibodies do not necessarily conform strictly to the "CDR" residues or "hypervarible" loops. The molecular model for the variable region of the non-human antibody can be used to guide the selection of regions that can potentially bind to the antigen. In practice the potential antigen binding regions based on model differ from the conventional "CDR"s or "hyper variable" loops. Commercial scientific software such as MOE (Chemical Computing Group) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for TIGIT, or other desired biological activity to unacceptable levels.

TABLE 2

Exemplary stabilizing CDR variants

| CDR Residue | Stabilizing Variant Sequence |
| --- | --- |
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

In some embodiments of the instant invention, the CDR3 of SEQ ID NO:3 can be modified at position 110W to reduce or remove potential oxidation (wherein the numbering is according to Kabat). Thus, for example SEQ ID NO:3 (MPSFITLASLSTWEGYFDF) can be modified to any of the following sequences: MPSFITLASLSTFEGYFDF (SEQ ID NO:79), MPSFITLASLSTYEGYFDF (SEQ ID NO:80), MPSFITLASLSTIEGYFDF (SEQ ID NO:81), MPSFITLASLSTVEGYFDF (SEQ ID NO:82) or MPSFITLASLSTLEGYFDF (SEQ ID NO:83). Therefore, in some embodiments of the instant invention, the anti-TIGIT antibody of the invention comprises a heavy chain variable region comprising the CDR1 of SEQ ID NO:1, the CDR2 of SEQ ID NO:2 and the CDR3 of SEQ ID NO: 3, 79, 80, 81, 82 or 83.

In some embodiments of the instant invention, the CDR2 of SEQ ID NO:5 can be modified at positions 52N and 53S to reduce or remove potential deamidation sites (wherein the numbering is according to Kabat). Thus, for example SEQ ID NO:5 (YANSLQT) can be modified to any of the following sequences: YASNLQT (SEQ ID NO:65), YASSLQT (SEQ ID NO:66), YASTLQT (SEQ ID NO:67), YATTLQT (SEQ ID NO:68), YASYLQT (SEQ ID NO:69), YANQLQT (SEQ ID NO:70), YAGSLQT (SEQ ID NO:71), YASQLQT (SEQ ID NO:72), YADSLQT (SEQ ID NO:73). Therefore, in some embodiments of the instant invention, the anti-TIGIT antibody of the invention comprises a light chain variable region comprising the CDR1 of SEQ ID NO:4, the CDR2 of SEQ ID NO:5, SEQ ID NO:66, SEQ ID NO:67, SEQ ID NO:68, SEQ ID NO:69, SEQ ID NO:70, SEQ ID NO:72, SEQ ID NO:72 or SEQ ID NO:73, and the CDR3 of SEQ ID NO:6.

In some embodiments of the instant invention, the CDR3 of SEQ ID NO:6 can be modified at position 95W to reduce or remove potential oxidation (wherein the numbering is according to Kabat). Thus, for example SEQ ID NO:6 (QQYYSGWT) can be modified to any of the following sequences: QQYYSGFT (SEQ ID NO:74), QQYYSGYT (SEQ ID NO:75), QQYYSGIT (SEQ ID NO: 76), QQYYSGVT (SEQ ID NO:77), QQYYSGLT (SEQ ID NO:78). Therefore, in some embodiments of the instant invention, the anti-TIGIT antibody of the invention comprises a light chain variable region comprising the CDR1 of SEQ ID NO:4, the CDR2 of SEQ ID NO:5 and the CDR3 of SEQ ID NO:6, SEQ ID NO:74, SEQ ID NO:75, SEQ ID NO:76, SEQ ID NO:77 or SEQ ID NO:78.

In some embodiments of the instant invention, the anti-TIGIT antibody of the invention comprises a light chain variable region comprising the CDR1 of SEQ ID NO:4, the CDR2 of SEQ ID NO:5, SEQ ID NO:66, SEQ ID NO:67, SEQ ID NO:68, SEQ ID NO:69, SEQ ID NO:70, SEQ ID NO:72, SEQ ID NO:72 or SEQ ID NO:73, and the CDR3 of SEQ ID NO:6, SEQ ID NO:74, SEQ ID NO:75, SEQ ID NO:76, SEQ ID NO:77 or SEQ ID NO:78.

In another embodiment of the instant invention, the anti-TIGIT antibody of the invention comprises a heavy chain FR4 region which comprises the amino acid sequence of any one of SEQ ID NOs: 7, 9-24 or 38-47, wherein the M at position 122 is substituted with V, L, A, R, N, P Q, E, G, I, H, K, F, S, T, W, or L to avoid potential oxidation.

In another embodiment of the instant invention, the anti-TIGIT antibody of the invention comprises a heavy chain FR4 region which comprises the amino acid sequence of any one of SEQ ID NOs: 7, 9-24 or 38-47, wherein the M at position 122 and the V at position 123 are substituted with T and L respectively to avoid potential oxidation.

In some embodiments of the instant invention, the CDR3 of SEQ ID NO:90 can be modified at position 6 to reduce or remove potential oxidation. Thus, for example SEQ ID NO:90 (GGPYGWYFDV) be modified to any of the following sequences: SEQ ID NOs: 154-167.

Antibody Engineering of the Fc Region

The antibodies (e.g., humanized antibodies) and antigen-binding fragments thereof disclosed herein (e.g., 14A6, 28H5, 31C6 and humanized versions thereof) can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein (e.g., 14A6, 28H5, 31C6 and humanized versions thereof) can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein (e.g., 14A6, 28H5, 31C6 and humanized versions thereof) also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) *J. Allergy Clin. Immunol.* 116: 731 at 734-35.

In one embodiment, the antibody or antigen-binding fragment of the invention (e.g., 14A6, 28H5, 31C6 or humanized versions thereof) is an IgG4 isotype antibody or fragment comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment of the invention (e.g., 14A6, 28H5 or 31C6 or humanized versions thereof) is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment of the invention (e.g., 14A6 or 28H5 or a humanized version thereof) is modified to increase its biological half-life. Various approaches are possible. For example, one or more of the following mutations can be introduced: T252L, T254S, T256F, as described in U.S. Pat. No. 6,277, 375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to decrease the ability of the antibody or antigen-binding fragment of the invention (e.g., 14A6 or 28H5 or a humanized version thereof) to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604).

In one embodiment of the invention, the Fc region is modified to decrease the ability of the antibody of the invention (e.g., 14A6, 28H5, 31C6 and humanized versions thereof) to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

Effector Function Enhancement

In some embodiments, the Fc region of an anti-TIGIT antibody is modified to increase the ability of the antibody or antigen-binding fragment to mediate effector function and/or to increase their binding to the Fcgamma receptors (FcγRs).

The term "Effector Function" as used herein is meant to refer to one or more of Antibody Dependant Cell mediated Cytotoxic activity (ADCC), Complement-dependant cytotoxic activity (CDC) mediated responses, Fc-mediated phagocytosis or antibody dependant cellular phagocytosis (ADCP) and antibody recycling via the FcRn receptor.

The interaction between the constant region of an antigen binding protein and various Fc receptors (FCR) including FcgammaRI (CD64), FcgammaRII (CD32) and FcgammaRIII (CD16) is believed to mediate the effector functions, such as ADCC and CDC, of the antigen binding protein. The Fc receptor is also important for antibody cross-linking, which can be important for anti-tumor immunity.

Effector function can be measured in a number of ways including for example via binding of the FcgammaRIII to Natural Killer cells or via FcgammaRI to monocytes/macrophages to measure for ADCC effector function. For example an antigen binding protein of the present invention can be assessed for ADCC effector function in a Natural Killer cell assay. Examples of such assays can be found in Shields et al, 2001 *J. Biol. Chem.*, Vol. 276, p 6591-6604; Chappel et al, 1993 *J. Biol. Chem.*, Vol 268, p 25124-25131; Lazar et al, 2006 PNAS, 103; 4005-4010.

The ADCC or CDC properties of antibodies of the present invention, or their cross-linking properties, may be enhanced in a number of ways.

Human IgG1 constant regions containing specific mutations or altered glycosylation on residue Asn297 have been shown to enhance binding to Fc receptors. In some cases these mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment, the antigen binding protein of the invention herein described is mutated at positions 239 and 332, for example S239D and I332E or in a further embodiment it is mutated at three or more positions selected from 239 and 332 and 330, for example S239D and I332E and A330L. (EU index numbering).

In an alternative embodiment of the present invention, there is provided an antibody comprising a heavy chain constant region with an altered glycosylation profile such that the antigen binding protein has enhanced effector function. For example, wherein the antibody has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125.

In a further aspect, the present invention provides "non-fucosylated" or "afucosylated" antibodies. Non-fucosylated antibodies harbour a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcgammaRIIIa binding capacity.

The present invention also provides a method for the production of an antibody according to the invention comprising the steps of: a) culturing a recombinant host cell comprising an expression vector comprising the isolated nucleic acid as described herein, wherein the recombinant host cell does not comprise an alpha-1,6-fucosyltransferase; and b) recovering the antigen binding protein. The recombinant host cell may be not normally contain a gene encoding an alpha-1,6-fucosyltransferase (for example yeast host cells such as *Pichia* sp.) or may have been genetically modified to inactive an alpha-1,6-fucosyltransferase. Recombinant host cells which have been genetically modified to inactivate the FUT8 gene encoding an alpha-1,6-fucosyltransferase are available. See, e.g., the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. Nos. 7,214,775, 6,946,292, WO0061739 and WO0231240. Those of ordinary skill in the art will also recognize other appropriate systems.

It will be apparent to those skilled in the art that such modifications may not only be used alone but may be used in combination with each other in order to further enhance effector function.

Production of Antibodies with Modified Glycosylation

In still another embodiment, the antibodies or antigen-binding fragments of the invention (e.g., 14A6, 28H5, 31C6 and humanized versions thereof) comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a TIGIT antigen. Such modifications can be accomplished by, for example, altering one or more of the glycosylation sites within the antibody or fragment sequence. For example, one or more amino acid substitutions can be made that result removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Antibodies and antigen-binding fragments disclosed herein (e.g., 14A6, 28H5, 31C6 and humanized versions thereof) may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443; Nett et al., *Yeast* 28(3):237-52 (2011); Hamilton et al., *Curr Opin Biotechnol.* October; 18(5):387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein (e.g., 14A6, 28H5, 31C6 and humanized versions thereof) further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein (e.g., 14A6, 28H5, 31C6 and humanized versions thereof) may comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein (e.g., 14A6, 28H5, 31C6 and humanized versions thereof) comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans in comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc_{1-2})Man_3GlcNAc_2$, $NANAGal_2GlcNAc_2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects, the antibodies (e.g., humanized antibodies) or antigen-binding fragments thereof comprise high mannose N-glycans, including but not limited to, $Man_8GlcNAc_2$, $Man_7GlcNAc_2$, $Man_6GlcNAc_2$, $Man_5GlcNAc_2$, $Man_4GlcNAc_2$, or N-glycans that consist of the $Man_3GlcNAc_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The antibodies and antigen-binding fragments thereof disclosed herein (e.g., 14A6, 28H5, 31C6 and humanized versions thereof) may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence.

Each antibody or antigen-binding fragment (e.g., 14A6, 28H5, 31C6 or humanized versions thereof) will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment (e.g., 14A6, 28H5, 31C6 or humanized versions thereof) will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, antibodies and antigen-binding fragments thereof (e.g., 14A6, 28H5, 31C6 and humanized versions thereof) are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies (e.g., 14A6, 28H5, 31C6 and humanized versions thereof) and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

Antibody Conjugates

The anti-TIGIT antibodies and antigen-binding fragments thereof disclosed herein (e.g., 14A6, 28H5, 31C6 and humanized versions thereof) may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein (e.g., 14A6, 28H5, 31C6 and humanized versions thereof) may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antibodies and antigen-binding fragments disclosed herein (e.g., 14A6, 28H5, 31C6 and humanized versions thereof) may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein (e.g., 14A6, 28H5, 31C6 and humanized versions thereof) may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention (e.g., 14A6, 28H5, 31C6 and humanized versions thereof) may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention (e.g., 14A6, 28H5, 31C6 and humanized versions thereof) to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies and fragments are conventional and very well known in the art.

Therapeutic Uses of Anti-TIGIT Antibodies

Further provided are methods for treating subjects, including human subjects, in need of treatment with the isolated antibodies or antigen-binding fragments thereof disclosed herein (e.g., 14A6, 28H5, 31C6 and humanized versions thereof). In one embodiment of the invention, such subject suffers from an infection or an infectious disease. In another embodiment of the invention, such subject suffers from cancer. In one embodiment, the cancer is a solid tumor which is infiltrated by tumor-infiltrating lymphocytes which express TIGIT. In one embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating subjects using an anti-TIGIT antibody or antigen-binding fragment thereof of the invention (e.g., 14A6, 28H5, 31C6 and humanized versions thereof), wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an anti-TIGIT antibody or antigen-binding fragment thereof of the invention, wherein the subject suffers from a bacterial infection. In one embodiment, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using an anti-TIGIT antibody or antigen-binding fragment thereof of the invention, wherein the subject suffers from a fungal infection. In one embodiment, the fungal infection is infection with a fungus selected from the group consisting of *Candida (albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

In an embodiment, the invention provides methods for treating subjects using an anti-TIGIT antibody or antigen-binding fragment thereof of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

In addition, the present invention provides a method for preventing or inhibiting TIGIT binding to MHC class II, enhancing antigen-specific T-cell activation or stimulating T-cell production of interleukin-2 in a subject (e.g., human), for example, wherein the subject suffers from cancer or infectious disease (e.g., as discussed herein) comprising administering an effective amount of anti-TIGIT antibody or antigen-binding fragment thereof (e.g., 14A6, 28A5, 31C6 and humanized versions thereof), optionally in association with a further chemotherapeutic agent.

A "subject" may be a mammal such as a human, dog, cat, horse, cow, mouse, rat, monkey (e.g., cynomolgus monkey, e.g., *Macaca fascicularis*) or rabbit. In preferred embodiments of the invention, the subject is a human subject.

In particular embodiments, the antibodies or antigen-binding fragments thereof disclosed herein (e.g., 14A6, 28H5, 31C6 and humanized versions thereof) may be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also part of the present invention.

In particular embodiments, the antibodies or antigen-binding fragments thereof disclosed herein (e.g., 14A6, 28H5, 31C6 and humanized versions thereof) may be used alone, or in association with tumor vaccines.

In particular embodiments, the antibodies or antigen-binding fragments thereof disclosed herein (e.g., 14A6, 28H5, 31C6 and humanized versions thereof) may be used alone, or in association with chemotherapeutic agents.

In particular embodiments, the antibodies or antigen-binding fragments thereof disclosed herein (e.g., 14A6, 28H5, 31C6 and humanized versions thereof) may be used alone, or in association with radiation therapy.

In particular embodiments, the antibodies or antigen-binding fragments thereof disclosed herein (e.g., 14A6, 28H5, 31C6 and humanized versions thereof) may be used alone, or in association with targeted therapies. Examples of targeted therapies include: hormone therapies, signal transduction inhibitors (e.g., EGFR inhibitors, such as cetuximab (ERBITUX) and erlotinib (TARCEVA)); HER2 inhibitors (e.g., trastuzumab (HERCEPTIN) and pertuzumab (PERJETA)); BCR-ABL inhibitors (such as imatinib (GLEEVEC) and dasatinib (SPRYCEL)); ALK inhibitors (such as crizotinib (XALKORI) and ceritinib (ZYKADIA)); BRAF inhibitors (such as vemurafenib (ZELBORAF) and dabrafenib (TAFINLAR)), gene expression modulators, apoptosis inducers (e.g., bortezomib (VELCADE) and carfilzomib (KYPROLIS)), angiogenesis inhibitors (e.g., bevacizumab (AVASTIN) and ramucirumab (CYRAMZA), monoclonal antibodies attached to toxins (e.g., brentuximab vedotin (ADCETRIS) and ado-trastuzumab emtansine (KADCYLA)).

In particular embodiments, the anti-TIGIT antibodies or antigen-binding fragments thereof of the invention (e.g., 14A6, 28H5, 31C6 and humanized versions thereof) may be used in combination with an anti-cancer therapeutic agent or immunomodulatory drug such as an immunomodulatory receptor inhibitor, e.g., an antibody or antigen-binding fragment thereof that specifically binds to the receptor.

Thus, the present invention includes compositions comprising an anti-TIGIT antibody or antigen-binding fragment thereof of the present invention (e.g., 14A6, 28H5, 31C6 and humanized versions thereof) in association with pembrolizumab; as well as methods for treating or preventing cancer in a subject comprising administering an effective amount of the anti-TIGIT antibody or antigen-binding fragment thereof and pembrolizumab to the subject. Optionally, the subject is also administered a further therapeutic agent.

In an embodiment of the invention, an anti-TIGIT antibody or antigen-binding fragment thereof of the present invention (e.g., 14A6, 28H5, 31C6 and humanized versions thereof) is in association with an isolated antibody comprising an immunoglobulin heavy chain comprising the amino acid sequence of SEQ ID NO:33 and an immunoglobulin light chain comprising the amino acid sequence of SEQ ID NO:34. SEQ ID NOs: 33 and 34 encode the heavy and light chain of pembrolizumab.

In an embodiment of the invention, an anti-TIGIT antibody) or antigen-binding fragment thereof of the present invention (e.g., 14A6, 28H5, 31C6 and humanized versions thereof) is in association with an isolated antibody comprising an immunoglobulin heavy chain comprising the amino acid sequence of SEQ ID NO:35 and an immunoglobulin light chain comprising the amino acid sequence of SEQ ID NO:36. SEQ ID NOs: 35 and 36 encode the heavy and light chain of nivolumab.

In an embodiment of the invention, an anti-TIGIT antibody or antigen-binding fragment thereof of the invention (e.g., 14A6, 28H5, 31C6 and humanized versions thereof) is in association with one or more of: anti-PD1 antibody (e.g., pembrolizumab, nivolumab, pidilizumab (CT-011)), anti-PDLL antibody, anti-CTLA4 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD-L1 antibody (e.g., BMS-936559, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-SIRPa, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, IL-10 or PEGylated IL-10, or any small organic molecule inhibitor of such targets.

In an embodiment of the invention, an anti-TIGIT antibody or antigen-binding fragment thereof of the invention (e.g., 14A6, 28H5, 31C6 or humanized versions thereof) is in association with an anti-PD1 antibody.

In an embodiment of the invention, an anti-TIGIT antibody or antigen-binding fragment thereof of the invention (e.g., 14A6, 28H5, 31C6 or humanized versions thereof) is in association with an anti-PDLL antibody (e.g., BMS-936559, MSB0010718C or MPDL3280A).

In an embodiment of the invention, an anti-TIGIT antibody or antigen-binding fragment thereof of the invention (e.g., 14A6, 28H5, 31C6 or humanized versions thereof) is in association with an anti-CTLA4 antibody.

In an embodiment of the invention, an anti-TIGIT antibody or antigen-binding fragment thereof of the invention (e.g., 14A6, 28H5, 31C6 or humanized versions thereof) is in association with an anti-CS1 antibody.

In an embodiment of the invention, an anti-TIGIT antibody or antigen-binding fragment thereof of the invention (e.g., 14A6, 28H5, 31C6 or humanized versions thereof) is in association with an anti-KIR2DL1/2/3 antibody.

In an embodiment of the invention, an anti-TIGIT antibody or antigen-binding fragment thereof of the invention (e.g., 14A6, 28H5, 31C6 or humanized versions thereof) is in association with an anti-CD137 (e.g., urelumab) antibody.

In an embodiment of the invention, an anti-TIGIT antibody or antigen-binding fragment thereof of the invention (e.g., 14A6, 28H5, 31C6 or humanized versions thereof) is in association with an anti-GITR (e.g., TRX518) antibody.

In an embodiment of the invention, an anti-TIGIT antibody or antigen-binding fragment thereof of the invention (e.g., 14A6, 28H5, 31C6 or humanized versions thereof) is in association with an anti-PD-L2 antibody.

In an embodiment of the invention, an anti-TIGIT antibody or antigen-binding fragment thereof of the invention (e.g., 14A6, 28H5, 31C6 or humanized versions thereof) is in association with an anti-ITL1 antibody.

In an embodiment of the invention, an anti-TIGIT antibody or antigen-binding fragment thereof of the invention (e.g., 14A6, 28H5, 31C6 or humanized versions thereof) is in association with an anti-ITL2 antibody.

In an embodiment of the invention, an anti-TIGIT antibody or antigen-binding fragment thereof of the invention (e.g., 14A6, 28H5, 31C6 or humanized versions thereof) is in association with an anti-ITL3 antibody.

In an embodiment of the invention, an anti-TIGIT antibody or antigen-binding fragment thereof of the invention (e.g., 14A6, 28H5, 31C6 or humanized versions thereof) is in association with an anti-ITL4 antibody.

In an embodiment of the invention, an anti-TIGIT antibody or antigen-binding fragment thereof of the invention (e.g., 14A6, 28H5, 31C6 or humanized versions thereof) is in association with an anti-ITL5 antibody.

In an embodiment of the invention, an anti-TIGIT antibody or antigen-binding fragment thereof of the invention (e.g., 14A6, 28H5, 31C6 or humanized versions thereof) is in association with an anti-ITL6 antibody.

In an embodiment of the invention, an anti-TIGIT antibody or antigen-binding fragment thereof of the invention (e.g., 14A6, 28H5, 31C6 or humanized versions thereof) is in association with an anti-ITL7 antibody.

In an embodiment of the invention, an anti-TIGIT antibody or antigen-binding fragment thereof of the invention (e.g., 14A6, 28H5, 31C6 or humanized versions thereof) is in association with an anti-ITL8 antibody.

In an embodiment of the invention, an anti-TIGIT antibody or antigen-binding fragment thereof of the invention (e.g., 14A6, 28H5, 31C6 or humanized versions thereof) is in association with an anti-CD40 antibody.

In an embodiment of the invention, an anti-TIGIT antibody or antigen-binding fragment thereof of the invention (e.g., 14A6, 28H5, 31C6 or humanized versions thereof) is in association with an anti-OX40 antibody.

In an embodiment of the invention, an anti-TIGIT antibody or antigen-binding fragment thereof of the invention (e.g., 14A6, 28H5, 31C6 or humanized versions thereof) is in association with an anti-KIR2DL1 antibody.

In an embodiment of the invention, an anti-TIGIT antibody or antigen-binding fragment thereof of the invention (e.g., 14A6, 28H5, 31C6 or humanized versions thereof) is in association with an anti-KIR2DL2/3 antibody.

In an embodiment of the invention, an anti-TIGIT antibody or antigen-binding fragment thereof of the invention (e.g., 14A6, 28H5, 31C6 or humanized versions thereof) is in association with an anti-KIR2DL4 antibody.

In an embodiment of the invention, an anti-TIGIT antibody or antigen-binding fragment thereof of the invention (e.g., 14A6, 28H5, 31C6 or humanized versions thereof) is in association with an anti-KIR2DL5A antibody.

In an embodiment of the invention, an anti-TIGIT antibody or antigen-binding fragment thereof of the invention (e.g., 14A6, 28H5, 31C6 or humanized versions thereof) is in association with an anti-KIR2DL5B antibody.

In an embodiment of the invention, an anti-TIGIT antibody or antigen-binding fragment thereof of the invention (e.g., 14A6, 28H5, 31C6 or humanized versions thereof) is in association with an anti-KIR3DL1 antibody.

In an embodiment of the invention, an anti-TIGIT antibody or antigen-binding fragment thereof of the invention (e.g., 14A6, 28H5, 31C6 or humanized versions thereof) is in association with an anti-KIR3DL2 antibody.

In an embodiment of the invention, an anti-TIGIT antibody or antigen-binding fragment thereof of the invention (e.g., 14A6, 28H5, 31C6 or humanized versions thereof) is in association with an anti-KIR3DL3 antibody.

In an embodiment of the invention, an anti-TIGIT antibody or antigen-binding fragment thereof of the invention (e.g., 14A6, 28H5, 31C6 or humanized versions thereof) is in association with an anti-NKG2A antibody.

In an embodiment of the invention, an anti-TIGIT antibody or antigen-binding fragment thereof of the invention (e.g., 14A6, 28H5, 31C6 or humanized versions thereof) is in association with an anti-NKG2C antibody.

In an embodiment of the invention, an anti-TIGIT antibody or antigen-binding fragment thereof of the invention (e.g., 14A6, 28H5, 31C6 or humanized versions thereof) is in association with an anti-ICOS antibody.

In an embodiment of the invention, an anti-TIGIT antibody or antigen-binding fragment thereof of the invention (e.g., 14A6, 28H5, 31C6 or humanized versions thereof) is in association with an anti-SIRPa antibody.

In an embodiment of the invention, an anti-TIGIT antibody or antigen-binding fragment thereof of the invention (e.g., 14A6, 28H5, 31C6 or humanized versions thereof) is in association with an anti-4-1BB antibody.

In an embodiment of the invention, an anti-TIGIT antibody or antigen-binding fragment thereof of the invention (e.g., 14A6, 28H5, 31C6 or humanized versions thereof) is in association with an anti-IL-10 antibody.

In an embodiment of the invention, an anti-TIGIT antibody or antigen-binding fragment thereof of the invention (e.g., 14A6, 28H5, 31C6 or humanized versions thereof) is in association with an anti-TSLP antibody.

In an embodiment of the invention, an anti-TIGIT antibody or antigen-binding fragment thereof of the invention (e.g., 14A6, 28H5, 31C6 or humanized versions thereof) is in association with IL-10 or PEGylated IL-10.

In an embodiment of the invention, an anti-TIGIT antibody or antigen-binding fragment thereof of the invention (e.g., 14A6, 28H5, 31C6 or humanized versions thereof) is in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, an anti-TIGIT antibody or antigen-binding fragment thereof of the invention (e.g., 14A6, 28H5, 31C6 or humanized versions thereof) is in association with any one or more of: 13-cis-retinoic acid, 3-[5-(methylsulfonylpiperadinemethyl)-indolyl]-quinolone, 4-hydroxytamoxifen, 5-deoxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, Bacillus Calmette-Guerin (BCG) vaccine, batabulin, BC-210, besodutox, bevacizumab, bicalutamide, Bio111, BIO140, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, Cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD121974, endostatin, enzalutamide, enzastaurin, epirubicin, epithilone B, ERA-923, Erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, INO1001, interferon, interleukin-12, ipilimumab, irinotecan, JNJ-16241199, ketoconazole, KRX-0402, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, Neratinib, neuradiab, nilotinib, nilutimide, nolatrexed, NVP-BEZ235, oblimersen, octreotide, ofatumumab, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, ticilimumab, tipifarnib, tivozanib, TKI-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, ZSTK474.

In an embodiment of the invention, an anti-TIGIT antibody or antigen-binding fragment thereof of the invention (e.g., 14A6, 28H5, 31C6 or humanized versions thereof) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co.; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an anti-TIGIT antibody or antigen-binding fragment thereof (e.g., 14A6, 28H5, 31C6 or humanized versions thereof) is in association with an agent which treats or prevents such a deficiency, such as, e.g., filgrastim, PEG-filgrastim, erythropoietin, epoetin alfa or darbepoetin alfa.

In an embodiment of the invention, an anti-TIGIT antibody or antigen-binding fragment thereof of the invention (e.g., 14A6, 28H5, 31C6 or humanized versions thereof) is administered in association with anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures. In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with an anti-TIGIT antibody or antigen-binding fragment thereof (e.g., 14A6, 28H5, 31C6 or humanized versions thereof) is surgical tumorectomy.

The term "in association with" indicates that the components administered in a method of the present invention (e.g., an anti-TIGIT antibody (e.g., humanized antibody) or antigen-binding fragment thereof (e.g., 14A6, 28H5, 31C6 or humanized versions thereof) along with pembrolizumab) can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Experimental and Diagnostic Uses

The anti-TIGIT antibodies and antigen-binding fragments thereof disclosed herein (e.g., 14A6, 28H5, 31C6 and humanized versions thereof) may be used as affinity purification agents. In this process, the anti-TIGIT antibodies and antigen-binding fragments thereof are immobilized on a solid phase such a Sephadex, glass or agarose resin or filter paper, using methods well known in the art. The immobilized antibody or fragment is contacted with a sample containing the TIGIT protein (or a fragment thereof) to be purified, and thereafter the support is washed with a suitable solvent that will remove substantially all the material in the sample except the TIGIT protein, which is bound to the immobilized antibody or fragment. Finally, the support is washed with a solvent which elutes the bound TIGIT (e.g., protein A). Such immobilized antibodies and fragments form part of the present invention.

Further provided are antigens for generating secondary antibodies which are useful for example for performing Western blots and other immunoassays discussed herein. In particular, polypeptides are disclosed which comprise the variable regions and/or CDR sequences of a therapeutic antibody disclosed herein (e.g., 14A6, 28H5 or 31C6) and which may be used to generate anti-idiotypic antibodies for use in specifically detecting the presence of the antibody, e.g., in a therapeutic context.

Anti-TIGIT antibodies (e.g., humanized antibodies) and antigen-binding fragments thereof may also be useful in diagnostic assays for TIGIT protein, e.g., detecting its expression in specific cells, tissues, or serum, e.g., tumor cells such as melanoma cells. Such diagnostic methods may be useful in various disease diagnoses.

The present invention includes ELISA assays (enzyme-linked immunosorbent assay) incorporating the use of an anti-TIGIT antibody or antigen-binding fragment thereof disclosed herein (e.g., 14A6 or a humanized version thereof).

For example, such a method comprises the following steps:
(a) coat a substrate (e.g., surface of a microtiter plate well, e.g., a plastic plate) with anti-TIGIT antibody or antigen-binding fragment thereof;
(b) apply a sample to be tested for the presence of TIGIT to the substrate;
(c) wash the plate, so that unbound material in the sample is removed;
(d) apply detectably labeled antibodies (e.g., enzyme-linked antibodies) which are also specific to the TIGIT antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.

Detection of the label associated with the substrate indicates the presence of the TIGIT protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3$H) which can be detected by scintillation counter in the presence of a scintillant.

An anti-TIGIT antibody or antigen-binding fragment thereof of the invention (e.g., 14A6, 28H5, 31C6 or humanized versions thereof) may be used in a Western blot or immune-protein blot procedure. Such a procedure forms part of the present invention and includes e.g.: (1) optionally transferring proteins from a sample to be tested for the presence of TIGIT (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound TIGIT or a fragment thereof with an anti-TIGIT antibody or antigen-binding fragment thereof of the invention.

Such a membrane may take the form of a nitrocellulose or vinyl-based (e.g., polyvinylidene fluoride (PVDF)) membrane to which the proteins to be tested for the presence of TIGIT in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-TIGIT antibody or fragment, the membrane is optionally blocked, e.g., with non-fat dry milk or the like so as to bind non-specific protein binding sites on the membrane.

(2) washing the membrane one or more times to remove unbound anti-TIGIT antibody or fragment and other unbound substances; and (3) detecting the bound anti-TIGIT antibody or fragment.

Detection of the bound antibody or fragment indicates that the TIGIT protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-TIGIT antibodies and antigen-binding fragments thereof disclosed herein (e.g., 14A6, 28H5, 31C6 and humanized versions thereof) may also be used for immunohistochemistry. Such a method forms part of the present invention and comprises, e.g., (1) contacting a cell (e.g., a tumor cell such as a melanoma cell) to be tested for the presence of TIGIT protein with an anti-TIGIT antibody or antigen-binding fragment thereof of the invention; and (2) detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-TIGIT antibodies and antigen-binding fragments thereof disclosed herein (e.g., 14A6, 28H5, 31C6 and humanized versions thereof) may also be used for in vivo tumor imaging. Such a method may include injection of a radiolabeled anti-TIGIT antibody or antigen-binding fragment thereof into the body of a patient to be tested for the presence of a tumor associated with TIGIT expression (e.g., which expresses TIGIT, for example, on the tumor cell surface) followed by nuclear imaging of the body of the patient to detect the presence of the labeled antibody or fragment e.g., at loci comprising a high concentration of the antibody or fragment which are bound to the tumor. The detection of the loci indicates the presence of the TIGIT+ tumor and tumor cells.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-TIGIT antibodies and antigen-binding fragments of the invention (e.g., 14A6, 28H5, 31C6 and humanized versions thereof), the antibody or antigen-binding fragment thereof is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms*: Parenteral Medications, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-TIGIT antibody or antigen-binding fragment thereof of the invention (e.g., 14A6, 28H5, 31C6) in accordance with the *Physicians' Desk Reference* 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-TIGIT antibodies or antigen-binding fragments thereof of the invention (e.g., 14A6, 28H5, 31C6 and humanized versions thereof) can be administered by an invasive route such as by injection. In further embodiments of the invention, an anti-TIGIT antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention (e.g., 14A6, 28H5, 31C6 and humanized versions thereof) or a pharmaceutical composition thereof. The present invention also provides an injection device comprising any of the antibodies or antigen-binding fragments of the invention (e.g., 14A6, 28H5, 31C6 and humanized versions thereof) or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-TIGIT antibody or antigen-binding fragment of the invention (e.g., 14A6, 28H5, 31C6 or humanized versions thereof) in a local rather than systemic manner, for example, via injection of the antibody or fragment directly into a tumor, e.g., a $TIGIT^+$ tumor. Furthermore, one may administer the antibody or fragment in a targeted drug delivery system, for example, in a liposome coated with a tissue-specific antibody, targeting, for example, a tumor e.g., a $TIGIT^+$ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein (e.g., 14A6, 28H5, 31C6 and humanized versions thereof) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al.

(1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-TIGIT antibody in the subject's serum, such as 0.1, 0.3, 1, 3, 10, 30, 100, 300 µg/ml or more. In other embodiments, An anti-TIGIT antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-TIGIT or antigen-binding fragment thereof of the invention (e.g., humanized 14A6 or humanized 28H5) that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-TIGIT antibody or antigen-binding fragment, as discussed herein (e.g., humanized 14A6 or humanized 28H5 or humanized 31C6) in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-TIGIT antibody or antigen-binding fragment thereof of the invention (e.g., humanized 14A6 or humanized 28H5 or humanized 31C6) or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an anti-TIGIT antibody or antigen-binding fragment thereof of the invention (e.g., humanized 14A6 or humanized 28H5 or humanized 31C6) along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Therapeutic Kits

As a matter of convenience, an anti-TIGIT antibody or antigen-binding fragment thereof of the invention (e.g., 14A6, 28H5, 31C6 or humanized versions thereof) can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-TIGIT antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-TIGIT antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-TIGIT antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-TIGIT antibody or fragment. In certain embodiments, an anti-TIGIT antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-

243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Example 1

Generation of Rat and Mouse Anti-hTIGIT Antibodies

To generate antibodies to human TIGIT, Lewis rats were immunized with his-tagged human TIGIT recombinant protein from Sino Biologicals Cat#10917-H08H) using RIBI adjuvant and footpad injection on a biweekly schedule. Alternatively, Balb/C mice were immunized with human Fc-tagged human TIGIT recombinant protein using RIBI adjuvant and footpad injection on a biweekly schedule. Immunized animals were bled and serum titers determined for binding to human TIGIT transfected CHOK1 cells using a cell-based ELISA (described below). The animals with the highest titers were given a final boost with recombinant protein and draining popliteal lymph nodes isolated four days later. Hybridomas were generated by electrofusion of isolated lymphocytes with the myeloma fusion partner P3X63-AG8.653 using the Cytopulse Hybrimmune electrofusion system. Fused cells were plated in 96-well plates in DMEM/F12, 15% BCS, HAT, IL-6, OPI supplement, and gentamycin.

Hybridoma supernatants were assayed for binding to human TIGIT expressing CHOK1 cells and cross-reactivity to rhesus TIGIT expressing CHO cells using a cell-based ELISA format. Human TIGIT and rhesus TIGIT expressing CHO-K1 cells were plated in 96-well tissue-culture plates in 50 µl of DMEM/F12, 10% BCS and gentamycin (CHO-K1 media). Cells were plated at either $2 \times 10^4$ cells/well two days prior to the assay or $4 \times 10^4$ cells/well one day prior to the assay. Media was removed from the wells prior to the assay and 50 µl of hybridoma supernatant added. Hybridoma supernatants were incubated for 30-60 minutes at room temperature and washed 3 times with PBS/0.05% TWEEN® 20 (polysorbate 20) using a cell ELISA washing protocol on the Biotek EL405x Select CW plate washer. Fifty microliters of the detection antibody (HRP-conjugated goat anti-rat IgG (Southern Biotech cat#3030-05) or HRP-conjugated goat anti-mouse IgG (Southern Biotech cat#1043-05)), was added at a 1:2000 dilution in CHO-K1 media and incubated at room temperature for 30-60 minutes. Assay plates were washed as above and developed with TMB and stopped with TMB stop solution (KPL cat#50-85-06) or 0.1N phosphoric acid. The absorbance at 450 nm-620 nm was determined.

Positive clones were reactive to both human TIGIT and rhesus TIGIT transfected CHO-K1 cells, and were negative for binding to parental CHO-K1 cells. In these assays, if an antibody showed binding to parental (untransfected) CHO-K1 cells; we discarded that antibody in screening as not specific to TIGIT.

Positive hybridomas were subcloned by limiting dilution or subcloned by plating hybridomas in semi-solid media and clones picked on the ClonePix® (Genetix). Two rounds of subcloning were performed on the parental hybridomas. Final subclones were grown in small-scale cultures in serum-free hybridoma production medium and purified to generate purified antibody for further characterization.

Using these methods, about 819 hybridomas were generated.

Example 2

Characterization of Anti-hTIGIT Antibodies

Supernatants from positive clones were tested for their ability to block recombinant human CD155-huFc protein binding to hTIGIT CHOK1 cells in a cell-based ELISA format. Human TIGIT-CHO-K1 cells were plated in 96-well plates as described above. Media was removed from the plates and 50 µl of hybridoma supernatant was incubated with the human TIGIT CHO-K1 cells at 4° C. for 30 minutes. Fifty microliters of human CD155-huFc was added to the plate for a final concentration of 0.5 µg/ml of human CD155-huFc and incubated for 30 minutes at 4° C. Assay plates were washed 3 times with PBS/0.05% TWEEN® 20 (polysorbate 20) as above. Binding of human CD155-huFc to the hTIGIT-CHOK1 cells was detected using an HRP-conjugate F(ab)'2 goat anti-human IgG secondary antibody (Jackson 109-036-098) at 1:2000 dilution in CHO-K1 media. Plates were developed using TMB and stopped using TMB Stop Solution as described above and the A450-620 nm determined.

Figure 3:
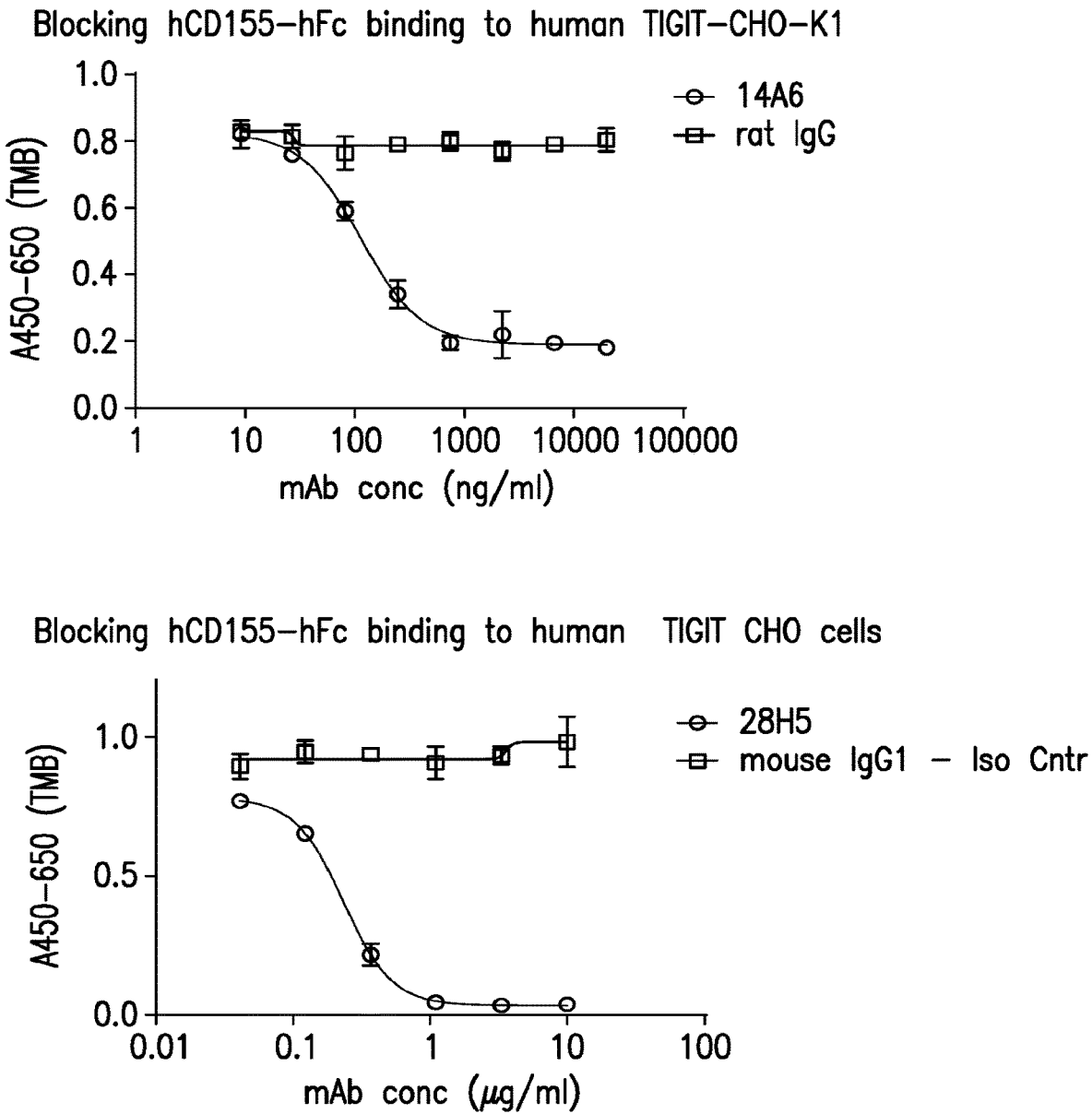
FIG. 3 shows that antibodies 14A6 and 28H5 block hCD155 interaction with hTIGIT as determined by a cell-based ELISA blocking assay.

A rat antibody generated according to the above described method is referred to as 14A6, and was derived from clone LB155.14A6.G2.A8. This rat antibody (14A6) is of the IgG2/kappa isotype and comprises the heavy chain variable region of SEQ ID NO:7 and the light chain variable region of SEQ ID NO:8. Purified 14A6 antibody binds to human TIGIT and rhesus TIGIT as determined by cell-based ELISA binding to human TIGIT and rhesus TIGIT-CHOK1 cells (FIG. 1) using the methods described above. (An isotype control antibody did not show any binding (data not shown.) Purified 14A6 antibody can also block the hTIGIT and hCD155 interaction using a cell-based ELISA blocking assay (FIG. 3) using the method described above.

Figure 2:
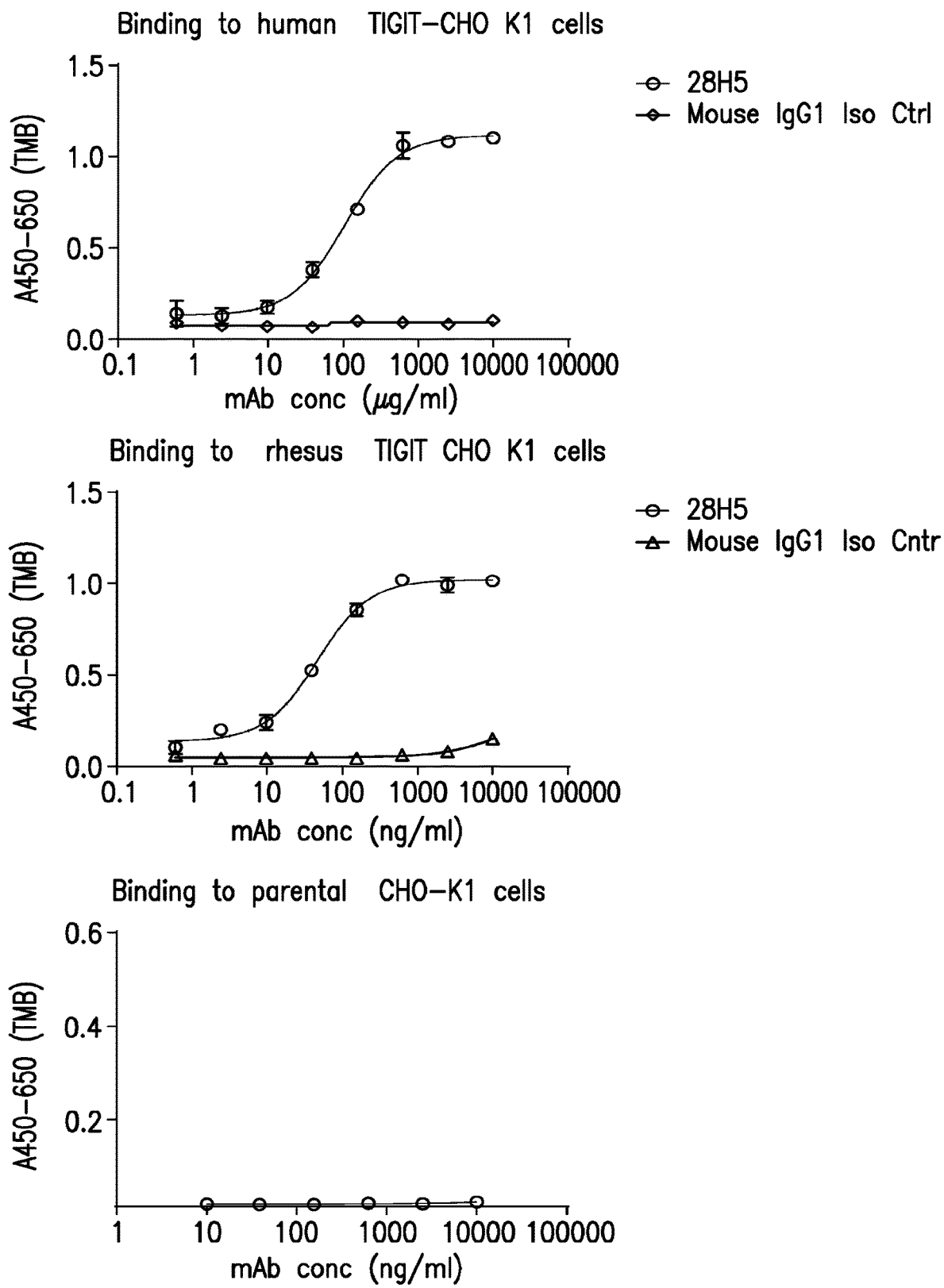
FIG. 2 shows binding of antibody 28H5 to human and rhesus TIGIT (expressed in CHO-K1 cells).

A mouse antibody generated according to the above described method is referred to as 28H5, and was derived from clone TC167.28H5.H5. This mouse antibody (28H5) is of the IgG1/kappa isotype and comprises the heavy chain variable region of SEQ ID NO:63 and the light chain variable region of SEQ ID NO:64. Purified 28H5 antibody also binds to human TIGIT and rhesus TIGIT as determined by cell-based ELISA binding to human TIGIT and rhesus TIGIT-CHOK1 cells (FIG. 2) using the methods described above. Purified 28H5 antibody also block the hTIGIT and hCD155 interaction using a cell-based ELISA blocking assay (FIG. 3) using the method described above.

Another mouse antibody generated according to the above described method is referred to as 31C6, and was derived from clone MEB125.31C6.A1.205. This mouse antibody (31C6) is of the IgG1/kappa isotype and comprises the heavy chain variable region of SEQ ID NO:94 and the light chain variable region of SEQ ID NO:95. Purified 31C6 antibody also binds to human TIGIT and rhesus TIGIT as determined by cell-based ELISA binding to human TIGIT and rhesus TIGIT-CHOK1 cells (FIG. 4) using the methods described above. Purified 31C6 antibody also block the hTIGIT and hCD155 interaction using a cell-based ELISA blocking assay (FIG. 4) using the method described above.

Affinity Determination for Binding of Parental (Non-Human) Anti-TIGIT Antibodies to Human TIGIT Recombinant Protein:

The kinetic binding activity of anti-human TIGIT antibodies 14A6 and 31C6 (made as described in Example 1) and of commercial antibody MBSA43 was measured by surface plasmon resonance using a Biacore T200 system (Biacore, GE Healthcare, Piscataway, N.J.). Approximately 5000 RU of Anti-mouse IgG, GE Healthcare Catalog Number BR-1008-38, or approximately 13,000 RU of Goat Anti-Rat IgG Fc gamma, Fragment Specific, Jackson ImmunoResearch Catalog Number 112-006-071, was immobilized via amine coupling chemistry onto a Series S CM5 sensor chip, catalog number BR-1005-30. Mouse anti-human TIGIT clones, 31C6 and MBSA43, were each injected over the immobilized anti-mouse surfaces at 1 ug/mL for a capture level of 40 RU. Rat anti-human TIGIT clone 14A6 was injected over the immobilized anti-rat surfaces at 1 ug/mL for a capture level of 40 RU. HBS-EP+ buffer (BR-1006-69) was used as the running buffer with a flow rate of 304/min. Varying concentrations of human TIGIT-His protein or TIGIT-Fc protein, ranging from 0.29 nM to 40 nM, at a flow rate of 454/min were injected over the antibody surfaces. Following each Mouse anti-human TIGIT injection cycle for clones 31C6 and MBSA43, the Series S CM5 chip surface was regenerated using one three-minute injection of 10 mM Glycine pH 1.7 at a flow rate of 10 µL/min. Following each Rat anti-human TIGIT injection cycle, the Series S CM5 chip surface was regenerated using one 20-second injection of 10 mM Glycine pH 1.5 followed by two 10-second injections of 12.5 mM NaOH at a flow rate of 604/min.

Background subtraction binding sensorgrams were used for analyzing the rate constant of association ($k_a$) and dissociation ($k_d$), and the equilibrium dissociation constant $K_D$. The resulting data sets were fitted with a 1:1 Langmuir Binding Model using the Biacore T200 evaluation software (version 2.0). Table 3 summarizes the affinities for the anti-human TIGIT antibodies to human TIGIT-His protein and TIGIT-Fc protein.

TABLE 3

Measurement of Affinity for anti-Human TIGIT Antibodies to human TIGIT-His protein and TIGIT-Fc protein using BIAcore.

| Clone | BIAcore KD (human TIGIT-his) (pM) | BIAcore KD (human TIGIT-Fc) (pM) |
| --- | --- | --- |
| 14A6 (rIgG2a/K) | 3.09 | 3.12 |
| 31C6 (mIgG1/K) | 34.4 | 10.9 |
| Comparator MBSA43 (mIgG1) | 36.3 | 16.5 |

Example 3

In Vitro T-Cell Activity Assay for Antagonistic Anti-hTIGIT Antibodies

Of the antibodies tested, approximately 352 monoclonal antibodies shown to block binding of CD155-Fc to CHO cells expressing hTIGIT were screened for their capacity enhance T cell activity in vitro using cell-based functional assays.

One assay we developed to characterize the functional consequence of blocking human TIGIT receptor utilized Jurkat cells, an immortalized line of human T lymphocyte cells (clone, E6-1; ATCC TIB-152), engineered to over-express human TIGIT (hTIGIT-Jurkat) which were co-cultured with THP-1 cells, a human monocytic cell line in the presence or absence of one of the TIGIT ligands, CD155 and CD112. hTIGIT-Jurkat cells co-cultured with THP-1 cells and stimulated with plate-bound anti-CD3 mAb produce IL-2, but when TIGIT ligand (CD155 or CD112) is added to the co-culture, IL-2 levels were reduced in a ligand-dependent manner. Treatment with antibodies that blocked the CD155- or CD112-TIGIT interaction, such as a commercially available anti-hTIGIT Ab, clone MBSA43 (eBioscience Cat#12-9500-42), rescues IL-2 production in this assay in a dose-dependent fashion (FIG. 5).

96-well flat-bottom plates were coated with mouse anti-human CD3 antibody (1 ug/ml in PBS; Clone HIT3a; BD Pharmingen Cat#555336) overnight at 4° C. The next day, hTIGIT-Jurkat cells (50,000) were plated in the pre-coated plates and pre-incubated for 30-60 minutes with mAb at varying concentrations. THP-1 cells (50,000) were added to the culture followed by either CD155-Fc (ECD of human CD155 fused to human Fc; 1.0 µg/ml) or CD112-Fc (ECD of human CD112 fused to human Fc; 0.5 µg/ml). After incubation for 18-24 h at 37° C. and 5.0% $CO_2$, IL-2 levels were assessed in culture supernatants by Meso Scale (Human IL-2 Tissue Culture MESO Kit: Cat#K151AHB-2). Treatment with MBSA43 (10 µg/ml) rescues IL-2 to a level equal to when activated hTIGIT Jurkat cells are cultured with THP-1 in the absence of CD155 or CD112.

Figure 5:
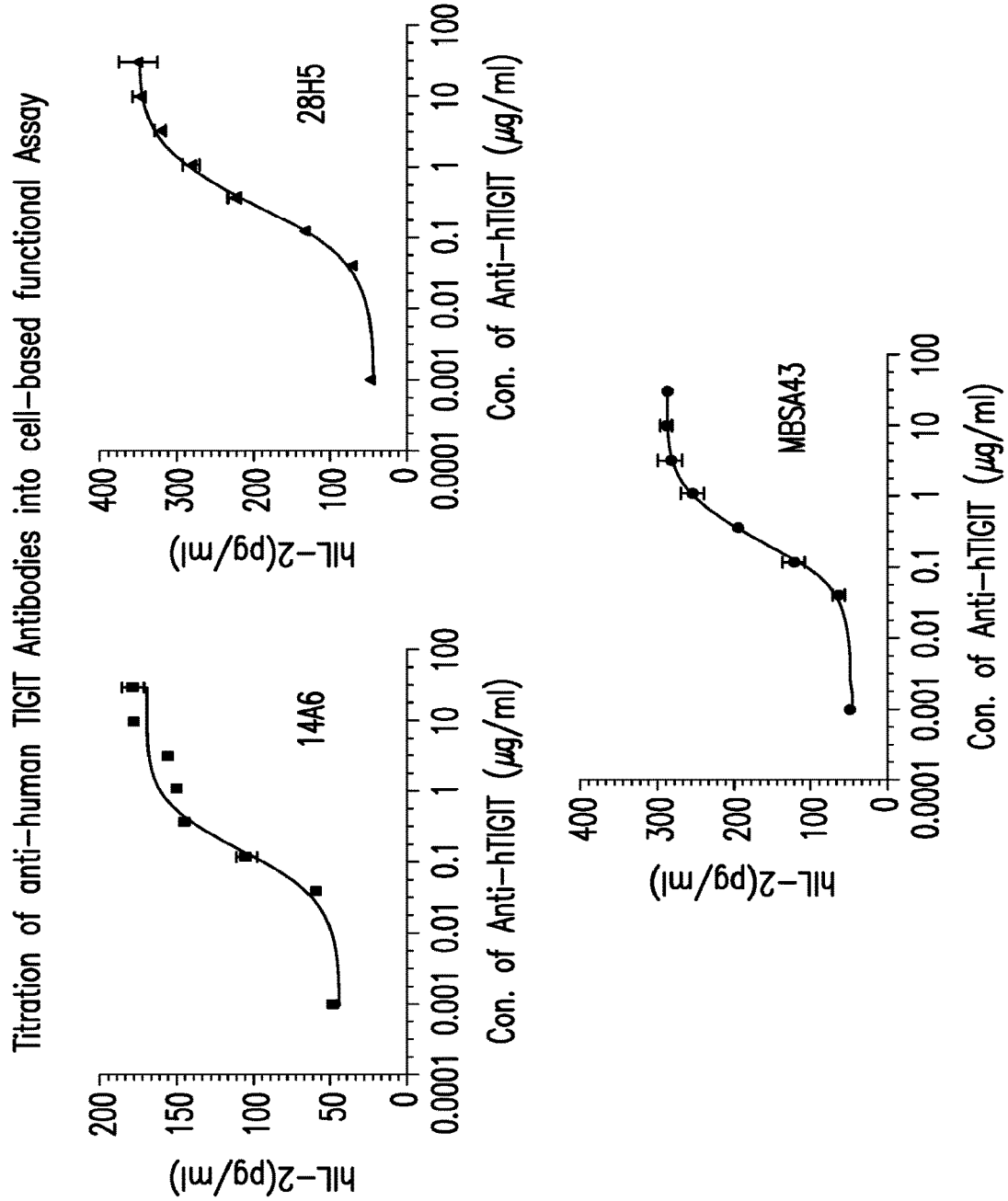
FIG. 5 shows the activity of antibodies 14A6 and 28H5 in an in vitro T cell assay.

As shown in FIG. 5, a titration of the anti-hTIGIT clone 14A6 from 30 µg/ml down to 0.04 µg/ml gave an EC50 of 0.190 µg/ml as compared to MBSA43 at 0.24 µg/ml using this assay. Clone 14A6 (30 µg/ml) rescued IL-2 to 82% of MBSA43 (10 µg/ml).

Also shown in FIG. 5, a titration of the anti-hTIGIT clone 28H5 from 30 µg/ml down to 0.04 µg/ml gave an EC50 of 0.24 µg/ml as compared to MBSA43 at 0.24 µg/ml using this assay.

Also shown in FIG. 6, a titration of the anti-hTIGIT clone 31C6 from 30 µg/ml down to 0.04 µg/ml gave an EC50 of 0.14 µg/ml as compared to MBSA43 at 0.24 µg/ml using this assay. Clone 31C6 (30 µg/ml) rescued IL-2 to 118% of MBSA43 (10 µg/ml).

Of the 352 monoclonal antibodies tested, approximately 113 were able to enhance T cell activity in vitro using cell-based functional assays.

Example 4

In Vitro T-Cell Activity Assay for Antagonistic Anti-hTIGIT Antibodies

Figure 7:
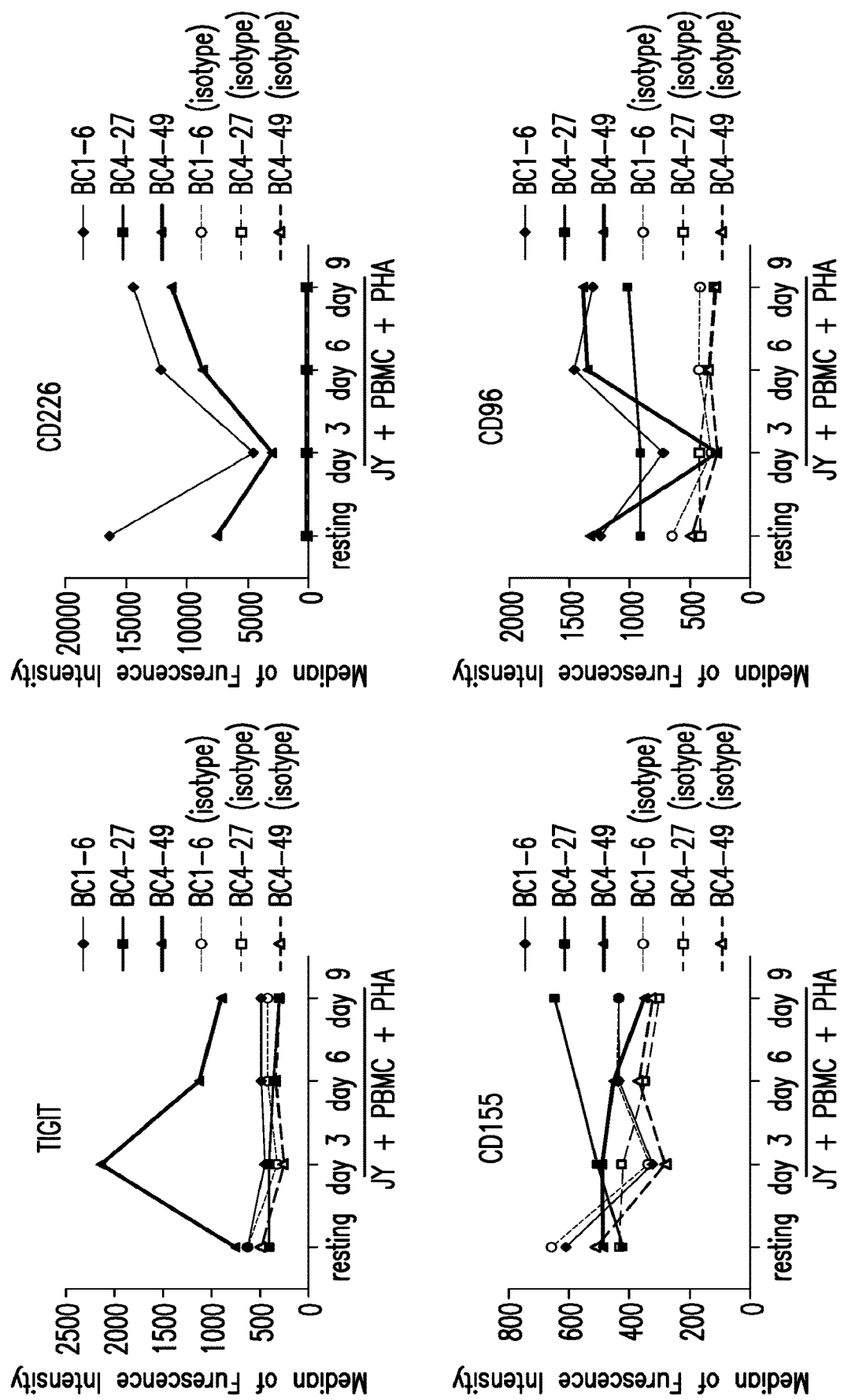
FIG. 7 shows expression of TIGIT, CD226, CD155 and CD96 in primary human T cell lines. At day 3, clone BC4-49 shows highest up-regulation of TIGIT (negative) ad down-regulation of CD226 (positive)

We further analyzed the relative functional antagonism of TIGIT and rescue of T cell activation and effector function using a primary human T cell line expressing endogenous TIGIT upon T cell receptor (TCR) activation. The BC4-clone 49 human T cell line is an allo-antigen specific human CD4+ T cell clone expressing a TCR specific for HLA-class II MHC molecules expressed on the EBV transformed cell line, JY (HLA-DR1,4). The BC4-clone 49 human T cell line requires re-stimulation with allo antigen every two weeks, using irradiated (5000 Rads) JY stimulator cells, irradiated PBMC (4000 Rads) isolated from two buffy coats and PHA-P (2.5 µg/ml; Sigma), as well as 10 ng/ml human IL-2 (R&D) supplement every 3-4 day following restimulation and expansion. Numerous T cell clones (BC1-6, BC4-27, BC4-49) were analyzed by PCR and then by flow cytometry for relative expression of TIGIT following restimulation and BC4-clone 49 was selected as it had the highest expression of TIGIT compared to other clones. The relative expression and kinetics of TIGIT, CD226, CD96 and CD155 were monitored following re-stimulation with irradiated (5000 Rads) JY stimulator cells, irradiated PBMC and PHA-P to assess the best time to assay antagonist mAbs for relative TIGIT-antagonist activity. Peak expression of TIGIT was observed at 3-4 days post restimulation, while expression of CD226 and CD96 decreased over the same time period. Expression of TIGIT then decreased, while expression of CD226 and CD96 increased again by day 6 post-restimulation (FIG. 7). Accordingly, candidate TIGIT antagonist mAbs were assessed at 3-4 days post-restimulation. Transfectant JY overexpressing human CD155 were generated using pMX→huTIGIT retroviral vectors as a means to suppress BC4-clone 47 T cell responses in the primary T cell bioassay and to assess the relative capacity of anti-TIGIT mAbs to antagonize CD155 activation of TIGIT and rescue T cell proliferation and IFNγ three days later.

The primary T cell assay for relative anti-hTIGIT antagonist mAbs was set up as follows. Human CD4+ T cell line BC4-clone 49 was co-cultured with CD155-Fc blocking mAbs specific for hTIGIT at various concentrations (33, 11, 3.7, 1.2, 0.4 and 0.1 µg/ml) for 30 minutes and then plated in round-bottom 96-well plates ($2 \times 10^4$ c/well). JY-hCD155 transfectants, expressing the allo-antigen and high levels of hCD155, were irradiated (5000 Rads), washed and then added to the wells containing the anti-TIGIT mAb treated BC4-clone 49 T cells for a final concentration of $1 \times 10^4$ (2:1 T cell: target cell ratio) or $5 \times 10^3$ (1:4 T cell: target cell ratio) in a total volume of 200 µl/well. Controls included no mAb treatment, co-culture with isotype mAb treated T cells, T cell only and JY-CD155 cells only. After three or four days of co-culture, supernatants were harvested for interferon-gamma (IFNγ) cytokine quantification, and the T cells were pulsed 6 hours with tritiated-thymidine to assess relative proliferation.

Figure 8A:
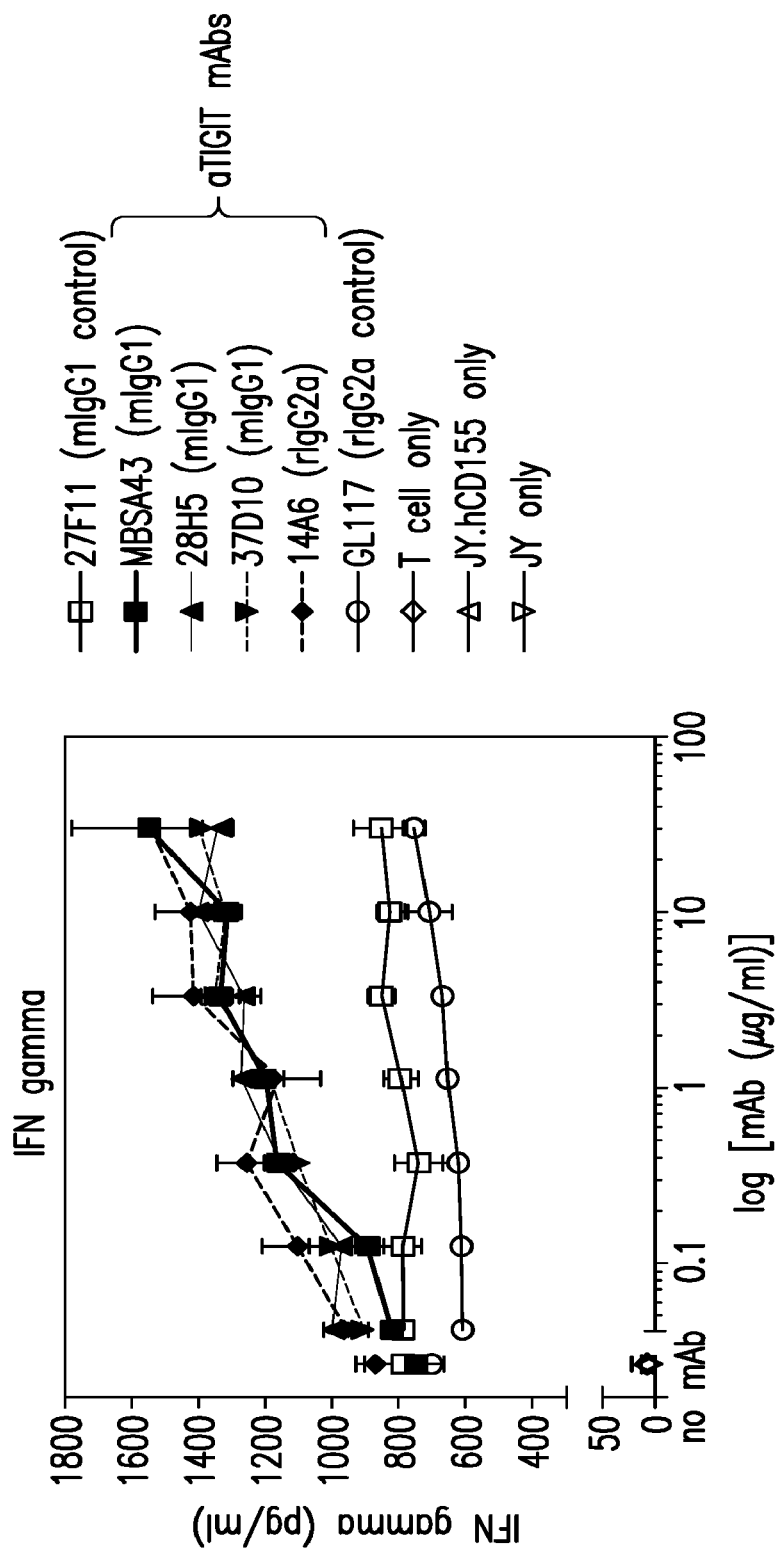
FIGS. 8A and 8B show the activity of various anti-TIGIT antibodies in an in vitro T cell assay. It shows that MBS43 and 14A6, 37D10 and 28H5 anti-TIGIT antibodies rescue IFNγ responses in primary human T cells.
Figure 8B:
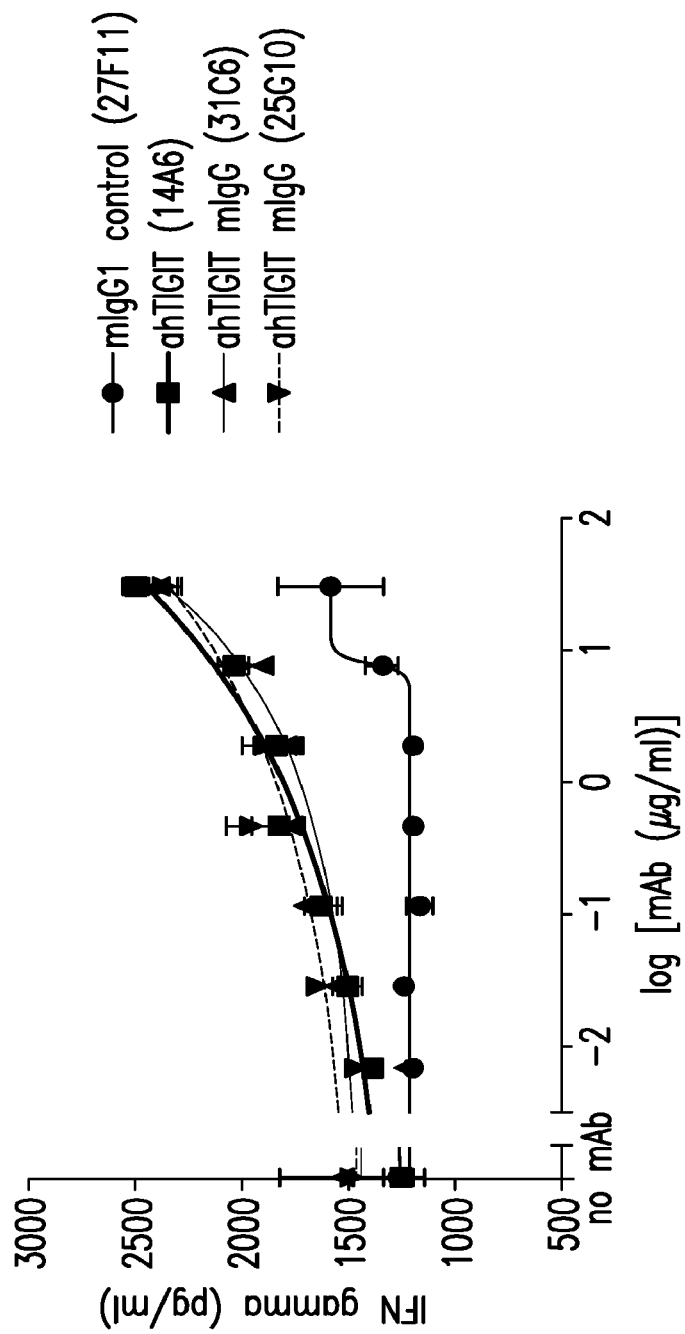

As shown in FIGS. 8A and 8B, anti-hTIGIT mAb 14A6, 28H5 and 31C6 treatment of BC4-clone 49 T cells resulted in rescue of IFNγ and proliferative responses as assessed by increased responses compared to isotype and untreated T cells. Commercial antibody MBSA43 and antibodies 37D10 and 25G10 (anti-TIGIT antibodies produced as described in Example 1) also show activity in this assay. The increase in IFNγ production after treatment with 14A6, 28H5 and 31C6 was on about 2 fold on average.

Example 5

Anti-Tumor Activity of Anti-TIGIT and Anti-PD1 Antibodies in Animal Tumor Model

Mice:

Approximately seven to eight week old female BALB/cAnN mice with an average body weight of 20 grams were obtained from Taconic Laboratory (Germantown, N.Y.). Conventional animal chow and water were provided ad libitum.

Antibody Reagents:

A monoclonal antibody of murine isotype IgG1 against murine PD-1 and isotype controls were obtained from internal sources as frozen (−80° C.) stocks. The rat anti-mouse TIGIT (GIGD7) antibody was obtained from eBioscience as a 4° C. stock. The IgG1 isotype control was a mouse monoclonal antibody specific for adenoviral hexon 25. The IgG2a isotype control was a rat monoclonal antibody specific for beta-galactosidase. Murine isotype IgG1 is the murine counterpart isotype to human isotype IgG4.

Formulations of Antibody Reagents:

The formulation buffers were specific for each antibody to stabilize proteins and prevent precipitation. The formulations were as follows: mIgG1:75 mM NaCl, 10 mM sodium phosphate, 3% sucrose, pH7.3; anti-PD-1: 20 mM sodium acetate, 7% sucrose, pH5.5; rat IgG2a: 20 mM sodium acetate, 9% sucrose pH 5.5; and anti-TIGIT (GIGD7): PBS pH 7.0.

Tumor Cell Line Preparation and Implant:

CT26 colon carcinoma cells were cultured in RPMI medium supplemented with 10% heat-inactivated fetal bovine serum. $3 \times 10^5$ log-phase and sub-confluent CT26 cells were injected subcutaneously (SC) in a 100 μL volume of serum-free RPMI in the right lower dorsal flank of each mouse. Mice were first shaved with electronic clippers in the area that would be used for the implant.

CT-26 is a murine colorectal adenocarcinoma cell line syngeneic to the BALB/c mouse strain. CT-26 is a relevant model system for evaluating the mechanism of action for an anti-PD-1 antibody because of the translatable molecular profile of this tumor post-anti-PD-1 therapy.

Tumor Measurements and Body Weights:

Tumors were measured the day before the first dose and twice a week thereafter. Tumor length and width were measured using electronic calipers and tumor volume determined using the formula Volume $(mm^3) = 0.5 \times Length \times Width$ where length is the longer dimension. Mice were weighed periodically to monitor general health but also to estimate actual mg/kg dose delivery per mouse where needed. Before treatment, mice were weighed and tumors from individual mice were measured. To prevent bias, any outliers by weight or tumor volume were removed and the remaining mice randomized into various treatment groups with equivalent mean tumor size. When the mean tumor volume in the CT26 tumor-bearing mice reached ~100 mm$^3$, around 7 days post implant, animals were randomized into treatment groups of 10 mice per group and dosing was started. Animals were administered at the dosing concentrations specified below.

Dosing Solution Preparation, Administration, and Analyses:

Frozen stocks of the antibodies to be tested in the animal model were thawed and transferred to wet ice. To avoid repeated freeze thaw, each vial of stock was thawed once and aliquots made in volumes sufficient for one time use. Polypropylene, low adhesion tubes were used for this purpose. The aliquots were snap frozen in dry ice and stored at −80° C. Before each dosing, one aliquot was thawed and diluted to nominal concentration in the appropriate diluent and dosed immediately. Aliquots of dosing solutions were snap frozen in dry ice and stored at −80° C. until analyses. Dosing solutions were assessed using the Meso Scale Discovery (MSD®, Rockville, Md.) platform which is based on multiarray technology; a combination of electrochemiluminescence detection and patterned arrays.

Dosing Anti-TIGIT/Anti-PD1 Treatment Results:

CT26 tumor-bearing BALB/cAnN mice were administered rat anti-mouse TIGIT (GIGD7) at a 20 mg/kg dose, IP, every 4 days for each of 5 cycles. An anti-mouse PD-1 (described above) was administered at a 10 mg/kg dose, IP, every 4 days for each of 5 cycles. Post dosing, animals continued to be monitored and tumor volumes were measured out to 36 days. Treatment was started once the tumor size averaged 100 mm$^3$ (75 mm$^3$-115 mm$^3$). Tumors were measured twice weekly. As demonstrated by the results, which are shown in FIG. 9, the mean anti-tumor response of combination therapy with the PD-1 antagonist and TIGIT antagonist was greater than the anti-tumor response observed with either anti-PD1 single agent ($p<0.05$) or anti-TIGIT single agent ($p<0.005$) treatment. For single agent anti-TIGIT treatment, 21% tumor growth inhibition (TGI) was observed at day 14. For single agent anti-PD1 treatment, 52% TGI was observed at day 14. Combination treatment resulted in 85% TGI at day 14 and demonstrated 40% complete regressions (CR) such that no measurable tumor remained in 4 out of 10 mice by day 36. The anti-tumor efficacy with either antibody delivered as monotherapy was 0-10% CR.

Example 6

Humanization of Antibodies

The rat 14A6 and the mouse 31C6 antibody were humanized using methods described in the specification. From the rat antibody 14A6, the following humanized variable heavy chains were constructed: SEQ ID NOs: 9-24 and SEQ ID NOs: 37-47; and the following humanized variable light chains were constructed: SEQ ID NOs: 25-30 and SEQ ID NOs: 48-52. From mouse antibody 31C6, the following humanized variable heavy chains were constructed: SEQ ID NOs: 124-129; and the following humanized variable light chains were constructed: SEQ ID Nos: 130-133.

Example 7

Effect of Fc Isotype on the Anti-Tumor Activity of Anti-TIGIT Antibodies in Animal Tumor Model Mice:

Approximately seven to eight week old female BALB/cAnN mice with an average body weight of 20 grams were obtained from Taconic Laboratory (Germantown, N.Y.). Conventional animal chow and water were provided ad libitum.

Antibody Reagents:

Murine anti-mouse PD1 antibody—IgG1 subtype

Rat anti-mouse TIGIT antibody (18G10)—rat IgG1 subtype. This antibody is described in the Figures as 18G10 parental. The 18G10 antibody has the VH sequence of SEQ ID NO:136 and the VL sequence of SEQ ID NO:137.

Chimeric rat anti-mouse TIGIT antibody (18G10)—comprising a mouse Fc region of mIgG1 subtype. This antibody is described in the Figures as 18G10-G2a. (Murine isotype IgG1 is the murine counterpart isotype to human isotype IgG4.)

Chimeric rat anti-mouse 18G10 TIGIT antibody—comprising a mouse Fc region of mIgG2a subtype. This antibody is described in the Figures as 18G10-G2a. (Murine isotype IgG2a is the murine counterpart isotype to human isotype IgG1.)

Isotype control murine IgG1 antibody (mouse IgG1 isotype-matched control monoclonal antibody specific for adenoviral hexon 25))

Isotype control rat IgG1 antibody (rat IgG1 isotype-matched control monoclonal antibody specific for human IL-4)

Isotype control murine IgG2a antibody (mouse IgG2a isotype-matched control monoclonal antibody specific for adenoviral hexon 25).

Formulations of Antibody Reagents:

The formulations were as follows:

mIgG1:75 mM NaCl, 10 mM sodium phosphate, 3% sucrose, pH7.4;

anti-PD-1: 20 mM sodium acetate, 9% sucrose, pH5.5; mIgG2a: 75 mM NaCl, 10 mM sodium phosphate, 3% sucrose, pH7.3;

rat IgG1: 20 mM sodium acetate, 7% sucrose pH 5.5; 18G10: 20 mM NaAc, 100 mM NaCl, 3% sucrose; 18G10-G1: 20 mM NaAc, 9% sucrose, pH 5.5; 18G10-G2a: 20 mM NaAc, 9% sucrose, pH 5.5.

Tumor Cell Line Preparation and Implant:

CT26 colon carcinoma cells were cultured in RPMI medium supplemented with 10% heat-inactivated fetal bovine serum. $3 \times 10^5$ log-phase and sub-confluent CT26 cells were injected subcutaneously (SC) in a 100 µL, volume of serum-free RPMI in the right lower dorsal flank of each mouse. Mice were first shaved with electronic clippers in the area that would be used for the implant.

CT-26 is a murine colorectal adenocarcinoma cell line syngeneic to the BALB/c mouse strain. CT-26 is a relevant model system for evaluating the mechanism of action for an anti-PD-1 antibody because of the translatable molecular profile of this tumor post-anti-PD-1 therapy.

Tumor Measurements and Body Weights:

Tumors were measured the day before the first dose and twice a week thereafter. Tumor length and width were measured using electronic calipers and tumor volume determined using the formula Volume $(mm^3)=0.5 \times Length \times Width^2$ where length is the longer dimension. Mice were weighed periodically to monitor general health but also to estimate actual mg/kg dose delivery per mouse where needed. Before treatment, mice were weighed and tumors from individual mice were measured. To prevent bias, any outliers by weight or tumor volume were removed and the remaining mice randomized into various treatment groups with equivalent mean tumor size.

Dosing Solution Preparation, Administration, and Analyses:

Frozen stocks of the antibodies to be tested in the animal model were thawed and transferred to wet ice. To avoid repeated freeze thaw, each vial of stock was thawed once and aliquots made in volumes sufficient for one time use. Polypropylene, low adhesion tubes were used for this purpose. The aliquots were snap frozen in dry ice and stored at −80° C. Before each dosing, one aliquot was thawed and diluted to nominal concentration in the appropriate diluent and dosed immediately. Aliquots of dosing solutions were snap frozen in dry ice and stored at −80° C. until analyses. Dosing solutions were assessed using the Meso Scale Discovery (MSD®, Rockville, Md.) platform which is based on multi-array technology; a combination of electrochemiluminescence detection and patterned arrays.

Figure 10:
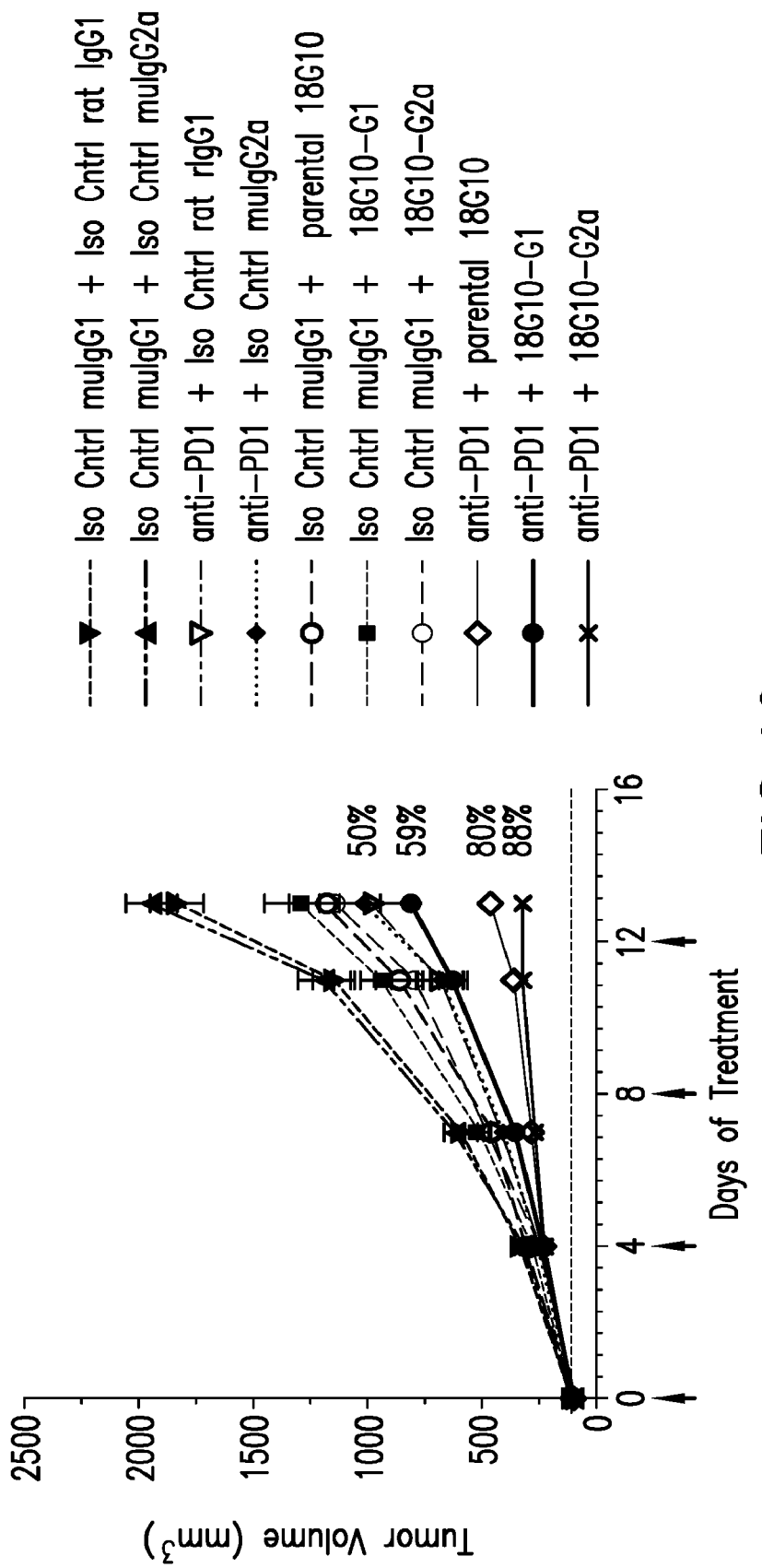
FIG. 10 shows the effect of Fc isotype on the anti-tumor activity of an anti-TIGIT antibody (18G10) in combination with an anti-PD-1 antibody in an animal tumor model.
Figure 11A:
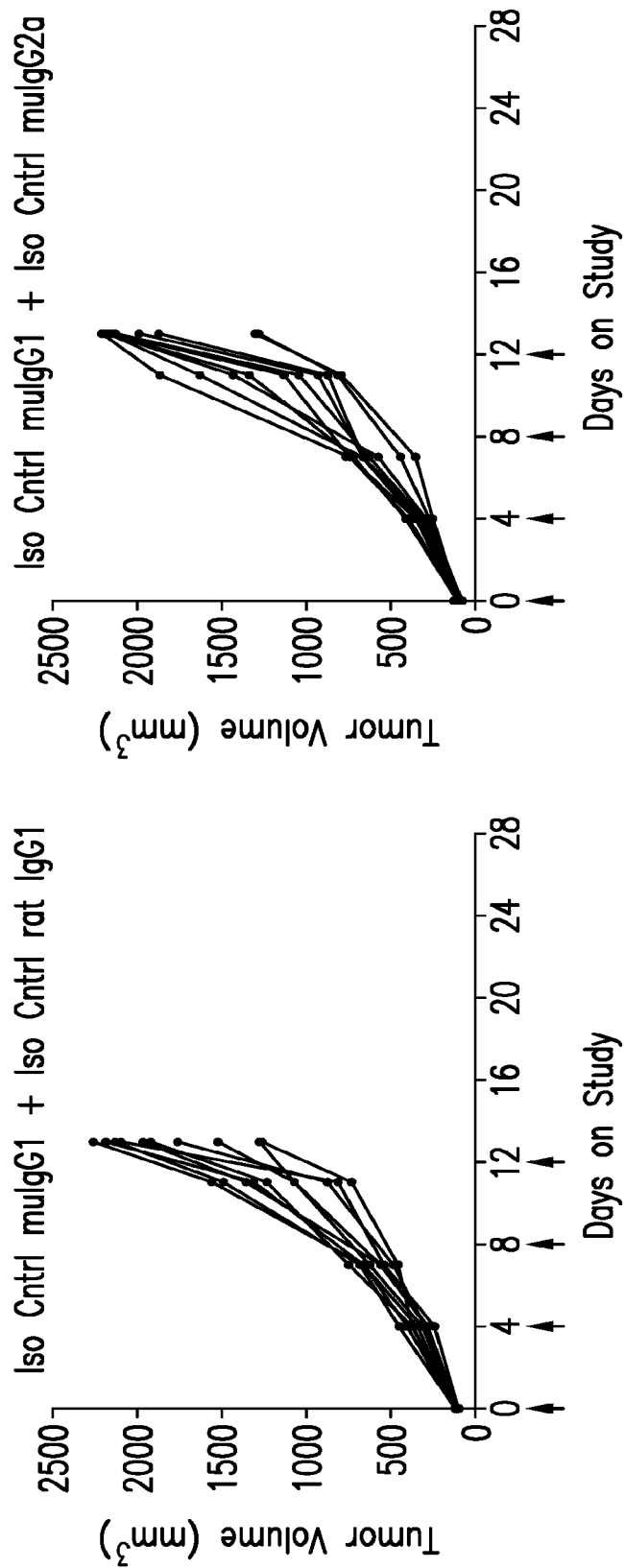
FIGS. 11A-11C show the effect of Fc isotype on the anti-tumor activity of an anti-TIGIT antibody (18G10) in combination with an anti-PD-1 antibody in an animal tumor model.
Figure 11B:
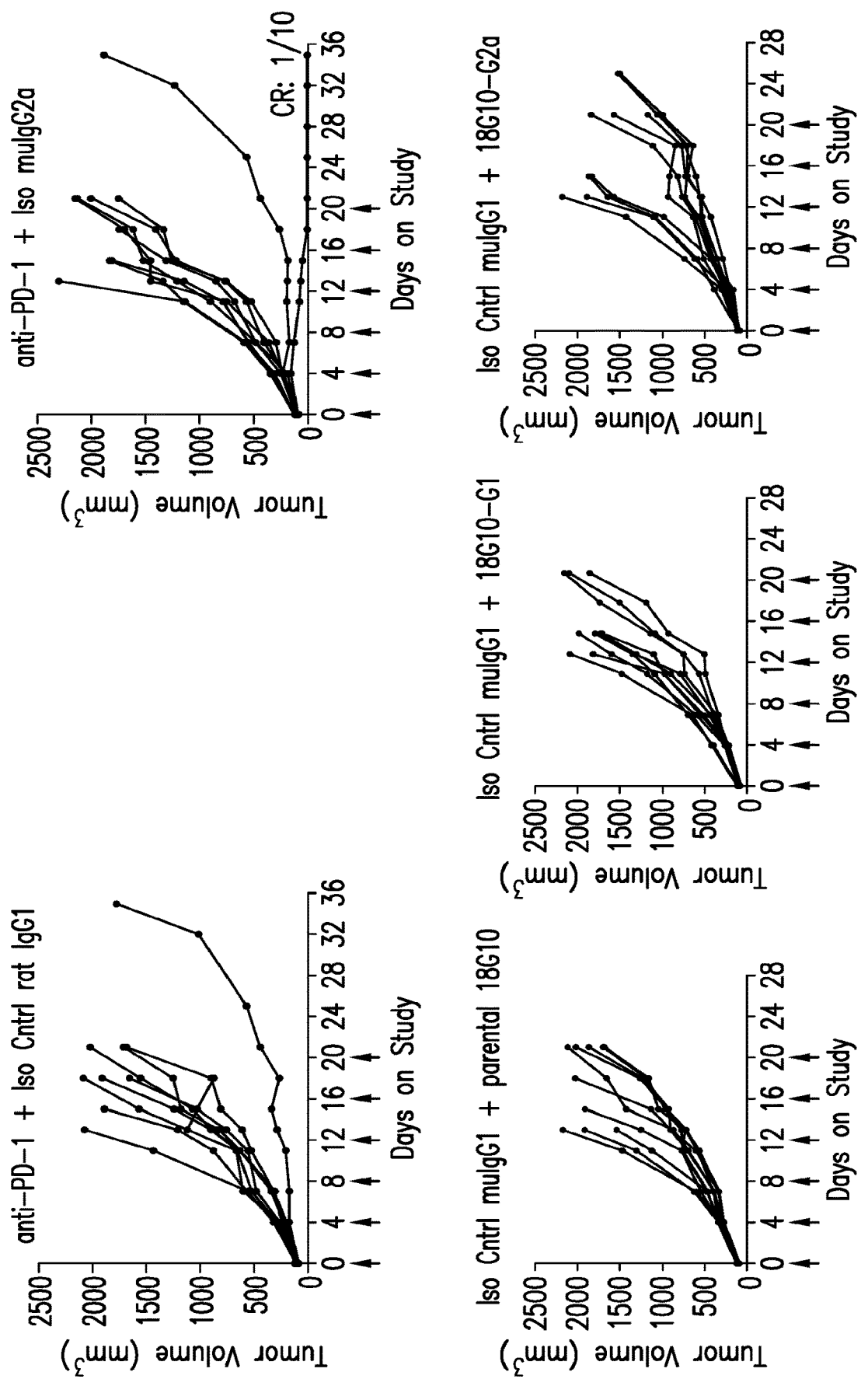
Figure 11C:
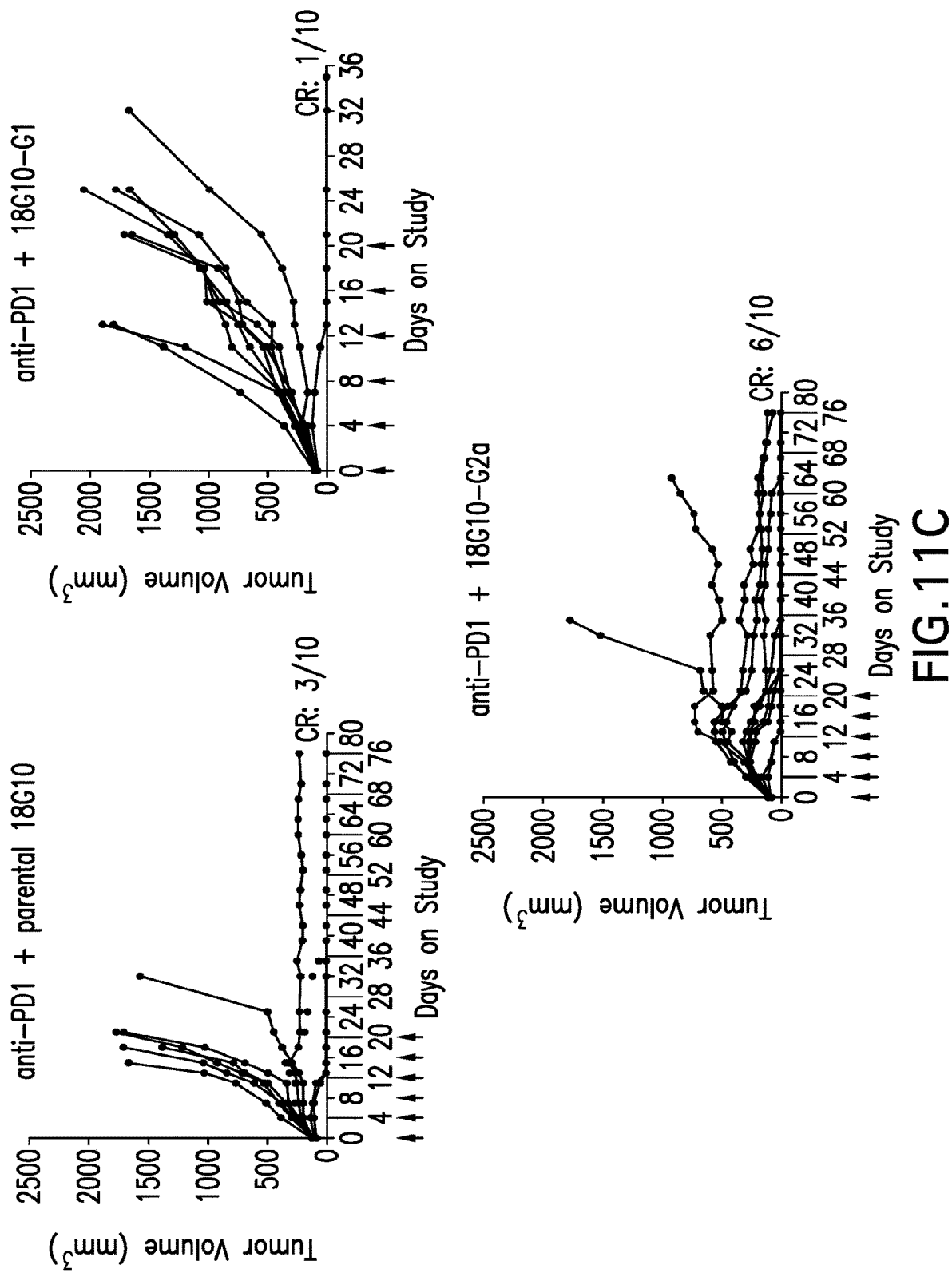

Dosing Anti-TIGIT/Anti-PD1 Treatment Results:

CT26 tumor-bearing BALB/cAnN mice were randomized into 10 treatment groups when the mean tumor volume of these mice reached a tumor size average of 100 mm3 (80 mm3-119 mm3): (1) muIgG1 isotype control+rat IgG1 isotype control; (2) muIgG1 isotype control+muIgG2a isotype control; (3) muDX400+rat IgG1 isotype control; (4) muDX400+muIgG2a isotype control; (5) muIgG1 isotype control+18G10; (6) muIgG1 isotype control+18G10-G1; (7) muIgG1 isotype control+18G10-G2a; (8) muDX400+18G10; (9) muDX400+18G10_G1; (10) muDX400+ 18G10_G2a. Animals were administered rat anti-mouse TIGIT (18G10) or chimeric anti-TIGIT antibodies 18G10-G1 or 18G10-G2a (described above) at a 18 mg/kg dose, IP, every 4 days for each of 6 cycles. An anti-mouse PD-1 (described above) was administered at a 10 mg/kg dose, IP, every 4 days for each of 6 cycles. Post dosing, animals continued to be monitored and tumor volumes were measured out to 76 days for some treatment groups. Tumors were measured twice weekly. The results are shown in FIGS. 10 and 11. Single agent anti-TIGIT treatment using 18G10-G2a showed 44% tumor growth inhibition (TGI) at day 13; while 18G10 parental antibody showed 38% and the 18G10-G1 antibody showed 36%. For single agent anti-PD1 treatment combined with isotype control rIgG1, 51% TGI was observed at day 13. When anti-PD-1 was combined with isotype control muIgG2a, 50% TGI and 10% complete regressions (CR) were observed at day 18, such that 1 complete response out of 10 animals was observed. The combination of anti-PD1 and parental 18G10 showed 80% TGI at day 13 and demonstrated 300% CR by day 39. The combination of anti-PD1 and 18G10-G1 showed 59% TGI at day 13 and demonstrated 10% CR by day 13. The combination of anti-PD1 and 18G10-G2a showed 88% TGI at day 13 and demonstrated 60% CR at day 63. The combination of anti-PD1 and 18G10-G2a showed greater anti-tumor activity and more complete regressions compared to combinations of anti-PD1 with 18G10 parental or 18G10-G1. There was no significant body weight loss associated with administration of single agents or combination therapy indicating that treatments were well tolerated.

Example 8

Effect of Fc Isotype on the Anti-Tumor Activity of Anti-TIGIT Antibodies in Animal Tumor Model The Experiment described in Example 7 was repeated, except that the rat 18G10 antibody was substituted with rat antibody 11A11.

Mice:

Approximately seven to eight week old female BALB/cAnN mice with an average body weight of 20 grams were obtained from Taconic Laboratory (Germantown, N.Y.). Conventional animal chow and water were provided ad libitum.

Antibody Reagents:

Murine anti-mouse PD1 antibody—IgG1 subtype

Rat anti-mouse TIGIT antibody (11A11)—rat IgG1 subtype. This antibody is described in the Figures as 11A11 parental. The 11A11 antibody has the VH sequence of SEQ ID NO:138 and the VL sequence of SEQ ID NO:139.

Chimeric rat anti-mouse TIGIT antibody (11A11)—comprising a mouse Fc region of mIgG1 subtype. This antibody is described in the Figures as 11A11-G2a. (Murine isotype IgG1 is the murine counterpart isotype to human isotype IgG4.)

Chimeric rat anti-mouse 11A11 TIGIT antibody—comprising a mouse Fc region of mIgG2a subtype. This antibody is described in the Figures as 11A11-G2a. (Murine isotype IgG2a is the murine counterpart isotype to human isotype IgG1.)

Isotype control murine IgG1 antibody (mouse IgG1 isotype-matched control monoclonal antibody specific for adenoviral hexon 25))

Isotype control rat IgG1 antibody (rat IgG1 isotype-matched control monoclonal antibody specific for human IL-4)

Isotype control murine IgG2a antibody (mouse IgG2a isotype-matched control monoclonal antibody specific for adenoviral hexon 25).

Formulations of Antibody Reagents:

The formulations were as follows:

mIgG1: 75 mM NaCl, 10 mM sodium phosphate, 3% sucrose, pH7.4;
anti-PD-1: 20 mM sodium acetate, 9% sucrose, pH5.5;
mIgG2a: 75 mM NaCl, 10 mM sodium phosphate, 3% sucrose, pH7.3;
rat IgG1: 20 mM sodium acetate, 7% sucrose pH 5.5;
11A11: 20 mM NaAc, 100 mM NaCl, 3% sucrose pH5.5; 11A11-G1: 20 mM NaAc, 9% sucrose, pH 5.5;
11A11-G2a: 20 mM NaAc, 9% sucrose, pH 5.5.

Tumor Cell Line Preparation and Implant:

CT26 colon carcinoma cells were cultured in RPMI medium supplemented with 10% heat-inactivated fetal bovine serum. $3 \times 10^5$ log-phase and sub-confluent CT26 cells were injected subcutaneously (SC) in a 100 µL, volume of serum-free RPMI in the right lower dorsal flank of each mouse. Mice were first shaved with electronic clippers in the area that would be used for the implant.

CT-26 is a murine colorectal adenocarcinoma cell line syngeneic to the BALB/c mouse strain. CT-26 is a relevant model system for evaluating the mechanism of action for an anti-PD-1 antibody because of the translatable molecular profile of this tumor post-anti-PD-1 therapy.

Tumor Measurements and Body Weights:

Tumors were measured the day before the first dose and twice a week thereafter. Tumor length and width were measured using electronic calipers and tumor volume determined using the formula Volume $(mm^3)=0.5 \times Length \times Width$ where length is the longer dimension. Mice were weighed periodically to monitor general health but also to estimate actual mg/kg dose delivery per mouse where needed. Before treatment, mice were weighed and tumors from individual mice were measured. To prevent bias, any outliers by weight or tumor volume were removed and the remaining mice randomized into various treatment groups with equivalent mean tumor size. When the mean tumor volume in the CT26 tumor-bearing mice reached ~100 $mm^3$, around 7 days post implant, animals were randomized into treatment groups of 10 mice per group and dosing was started. Animals were administered at the dosing concentrations specified below.

Dosing Solution Preparation, Administration, and Analyses:

Frozen stocks of the antibodies to be tested in the animal model were thawed and transferred to wet ice. To avoid repeated freeze thaw, each vial of stock was thawed once and aliquots made in volumes sufficient for one time use. Polypropylene, low adhesion tubes were used for this purpose. The aliquots were snap frozen in dry ice and stored at −80° C. Before each dosing, one aliquot was thawed and diluted to nominal concentration in the appropriate diluent and dosed immediately. Aliquots of dosing solutions were snap frozen in dry ice and stored at −80° C. until analyses. Dosing solutions were assessed using the Meso Scale Discovery (MSD®, Rockville, Md.) platform which is based on multi-array technology; a combination of electrochemiluminescence detection and patterned arrays.

Figure 12:
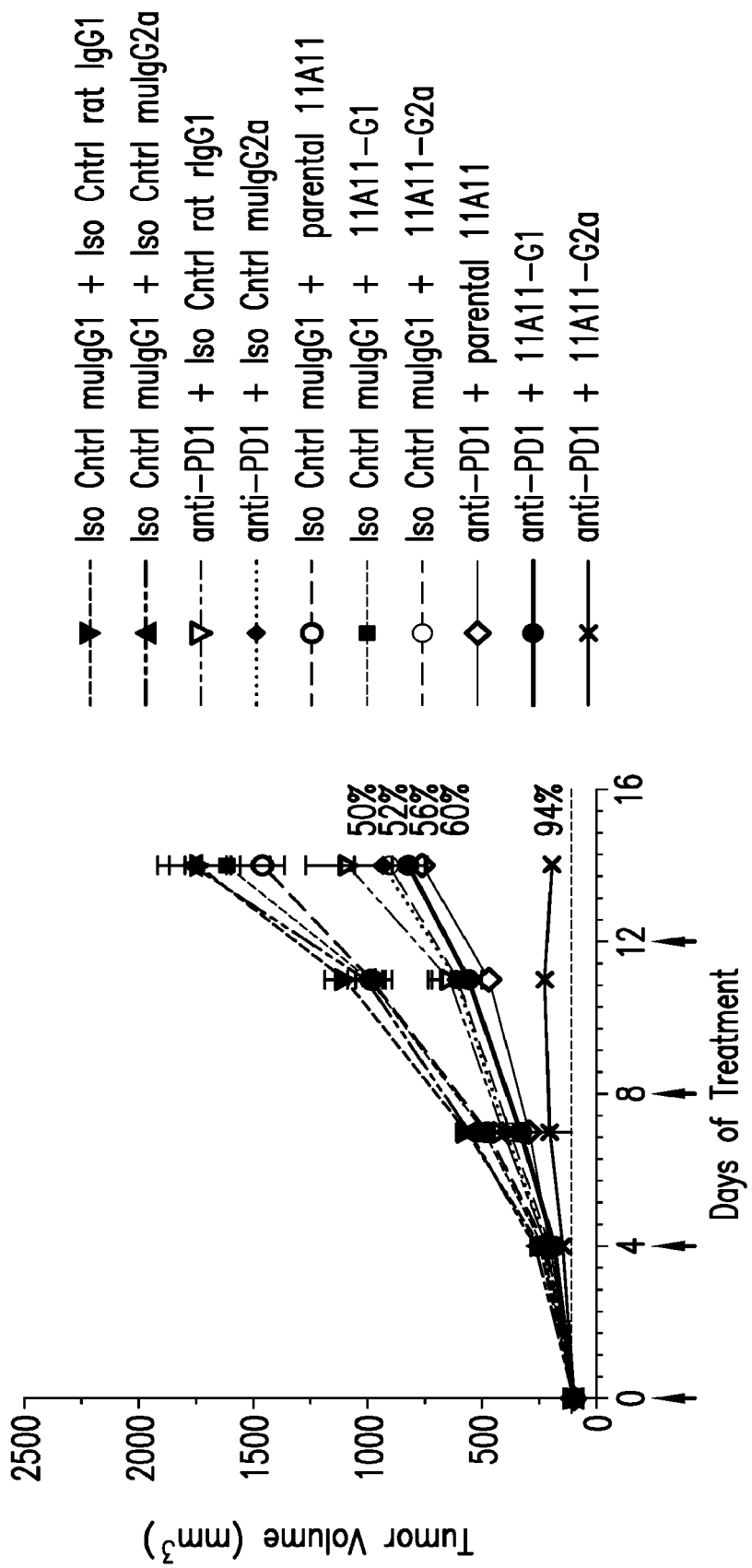
FIG. 12 shows the effect of Fc isotype on the anti-tumor activity of an anti-TIGIT antibody (11A11) in combination with an anti-PD-1 antibody in an animal tumor model.
Figure 13A:
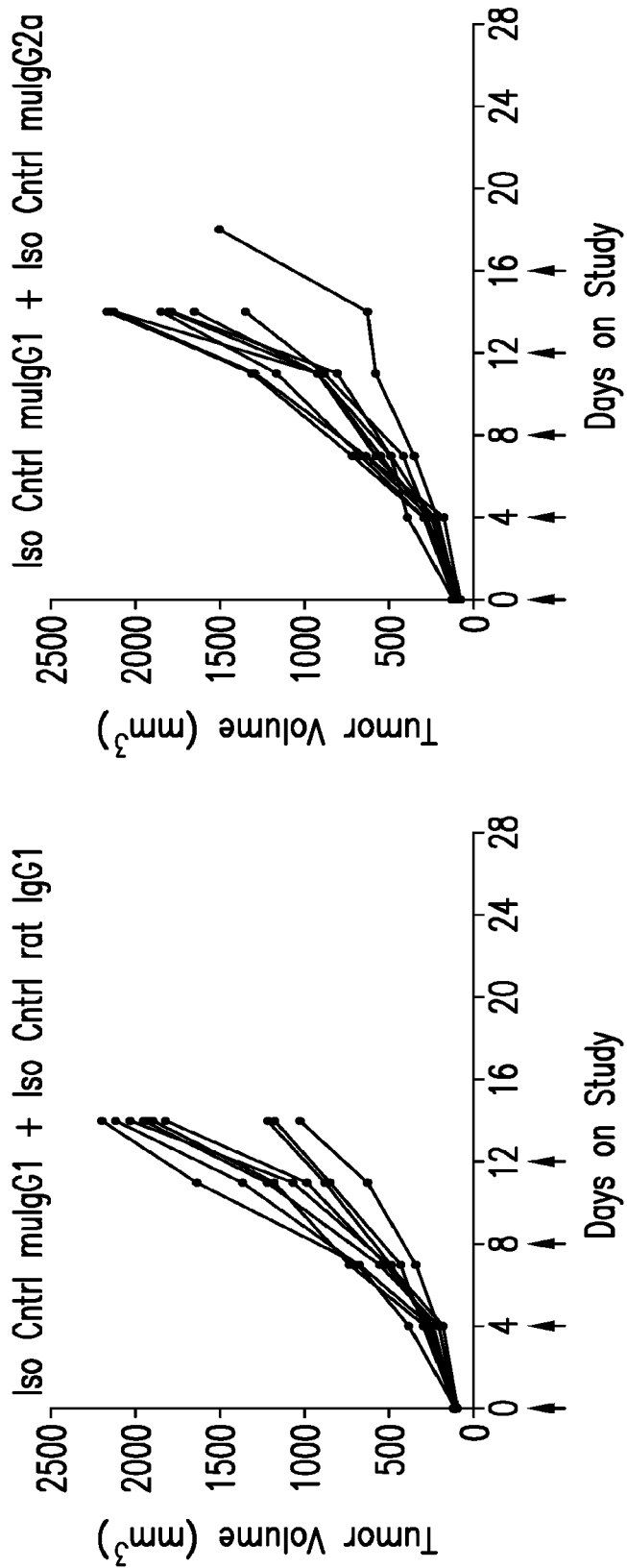
Figure 13C:
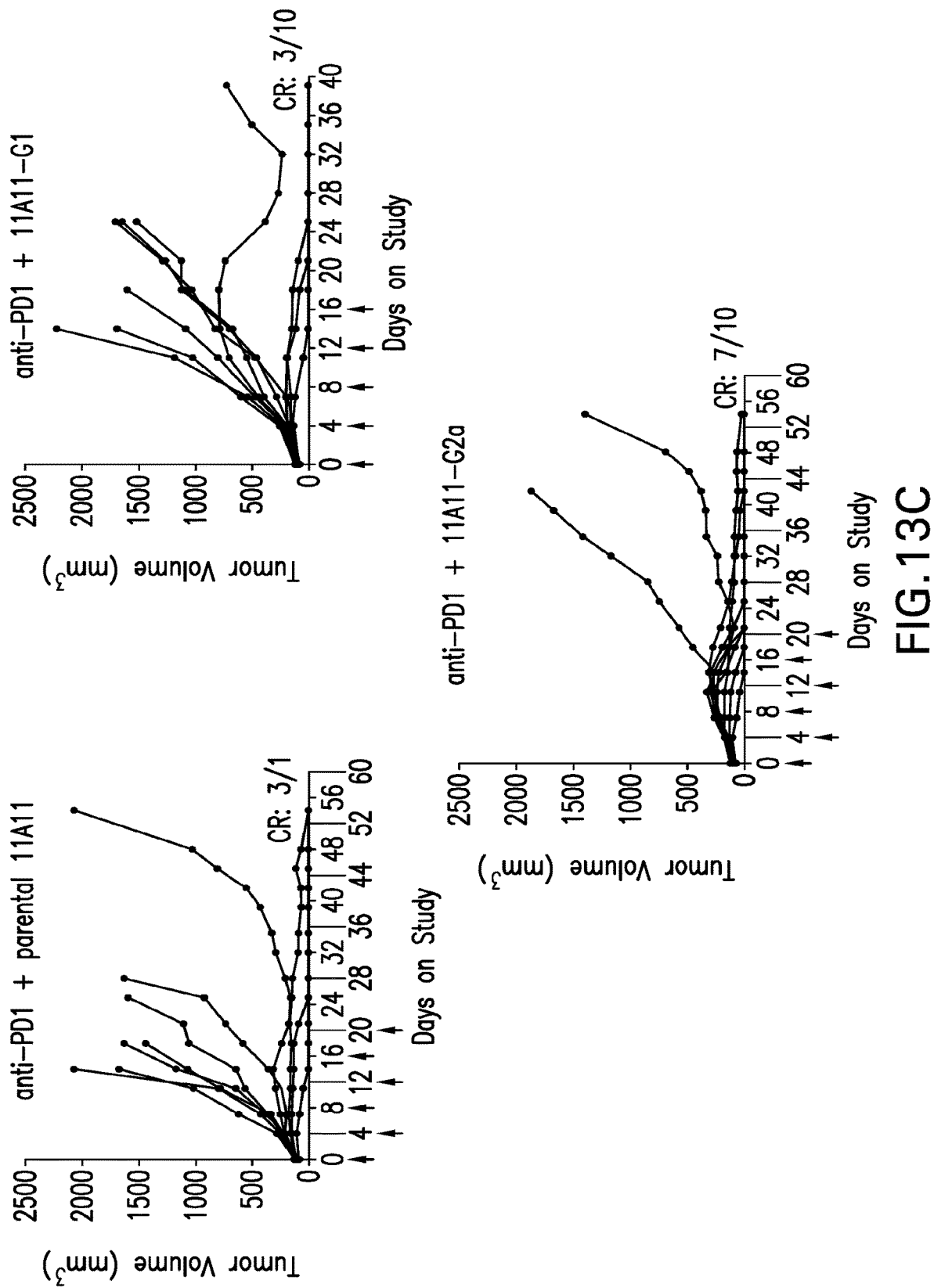

Dosing Anti-TIGIT/Anti-PD1 Treatment Results:

CT26 tumor-bearing BALB/cAnN mice were randomized into 10 treatment groups when the mean tumor volume of these mice reached a tumor size average of 100 $mm^3$ (75 $mm^3$-115 $mm^3$): (1) muIgG1 isotype control+rat IgG1 isotype control; (2) muIgG1 isotype control+muIgG2a isotype control; (3) muDX400+rat IgG1 isotype control; (4) muDX400+muIgG2a isotype control; (5) muIgG1 isotype control+11A11; (6) muIgG1 isotype control+11A11-G1; (7) muIgG1 isotype control+11A11-G2a; (8) muDX400+ 11A11; (9) muDX400+11A11_G1; (10) muDX400+ 11A11_G2a. Animals were administered rat anti-mouse TIGIT (11A11) or chimeric anti-TIGIT antibodies 11A11-G1 or 11A11-G2a (described above) at a 20 mg/kg dose, IP, every 4 days for each of 6 cycles. An anti-mouse PD-1 (described above) was administered at a 10 mg/kg dose, IP, every 4 days for each of 6 cycles. Post dosing, animals continued to be monitored and tumor volumes were measured out to 54 days for some treatment groups. Tumors were measured twice weekly. The results are shown in FIGS. 12 and 13. Single agent anti-TIGIT treatment using 11A11-G2a showed 52% tumor growth inhibition (TGI) at day 14; while little to no activity was observed using the 11A11 parental antibody or the 11A11-G1 antibody. For single agent anti-PD1 treatment, 40-50% TGI was observed at day 14. When combined with isotype control rat IgG1, anti-PD-1 showed 10% complete regressions (CR) by day 28, such that 1 complete response out of 10 animals was observed. The combination of anti-PD1 and parental 11A11 showed 60% TGI at day 14 and demonstrated 30% CR by day 54. The combination of anti-PD1 and 11A11-G1 showed 56% TGI at day 14 and demonstrated 30% CR by day 25. The combination of anti-PD1 and 11A11-G2a showed 94% TGI at day 14 and demonstrated 70% CR at day 42. The combination of anti-PD1 and 11A11-G2a showed greater anti-tumor activity and more complete regressions compared to combinations of anti-PD1 with 11A11 parental or 11A11-G1. There was no significant body weight loss associated with administration of single agents or combination therapy indicating that treatments were well tolerated.

Example 9

Epitope Mapping of hTIGIT 14A6 Antibody by Hydrogen Deuterium Exchange Mass Spectrometry The contact areas between anti-TIGIT antibody 14A6 and human TIGIT were determined by use of hydrogen deuterium exchange mass spectrometry (HDX-MS) analysis. HDX-MS measures the exchange of deuterium with hydrogen into the amide backbone of the protein. The exchange rate is influenced by the hydrogen's exposure to solvent. Comparison of the exchange levels in the antigen when the antibody is bound can identify regions of the protein where the antibody is binding.

Materials

Human TIGIT-His—Comprising the extracellular domain of hTIGIT (residues 25-150 of SEQ ID NO:31) and a histidine tag (SEQ ID NO:87).

Rat anti-hTIGIT 14A6 antibody (comprising the VH/VL sequences of SEQ ID NOs:7/8 (lot#78AGU) and a ratIgG2a Fc region) (Ratx[TIGIT_H] mAb (LB155.14A6.G2.A8)

IgG2a/Kappa (HY)).

Liquid Chromatography-Mass Spectrometry

The mass spectrometer was a Thermo Scientific Orbitrap-Velos. For the measurement of deuterium labeled samples, the mass spectrometer was set to acquire one full scan MS data in the orbitrap at 60,000 resolving power, a target ion count of 1E6, a maximum ion injection time of 500 milliseconds and two microscans. For the acquisition of MS/MS data for peptide identifications, the mass spectrometer was set to acquire one full scan spectrum at 60,000 resolving power followed by ten data-dependent MS/MS spectra in the ion trap.

The liquid chromatography system was a Waters® nano-ACQUITY for the analytical column gradient and a Waters® 515 isocratic pump for the sample digestion and loading. For sample digestion and loading, the buffer used was 2% acetonitrile and 0.05% trifluoroacetic acid at a flow rate of 80 ul/min. For the analytical gradient, the buffers were Buffer A) 0.1% formic acid in water and Buffer B) 0.1% formic acid in acetonitrile.

The gradient was at 40 ul/min from 2% B to 36% B in 10 minutes, followed by a wash of 80% B for 2 minutes and a reequilibration at 2% B for 3 minutes. The column was then washed by cycling the gradient between 2% and 80% B, three times with 1 minute at each step, followed by a final equilibration at 2% B for 5 minutes. The trapping column was a Waters® Vanguard C18 BEH 1.7 um Guard Column and the analytical column was a Waters® C18 BEH300, 1.7 um 1×50 mm column.

Sample handling for the deuterium labeling was done by a Leaptec H/D-X PAL system. The labeling sample tray was set to a temperature of 25° C., the quenching tray was set to 1.5° C. and the trap and analytical column chamber was set to 1.5° C. The immobilized pepsin column (Porosyme Immobilized Pepsin 2.1×30 mmm, Life Technologies) was kept outside the column chamber at room temperature.

Deuterium Labeling hTIGIT-His (30 pmol/μl) was mixed with an equal volume of the antibody (14 pmol/μl) or, in the unbound control, PBS pH 7.6. The antibody bound samples and the unbound control were incubated at room temperature for 1 hour before beginning the labeling experiment.

To deuterium label the samples, 2 μl of sample was mixed with 25 μl of PBS in dueterium oxide pD 7.6. Labeling time points were 30, 300, 1500, 4500 or 9000 seconds. After the set time, 25 μl of the labeling mixture was added to 35 μl of cold quench buffer (8M Urea, 100 mM TCEP). The quenched sample was incubated at 1.5° C. for one minute. 55 μl was then injected into the column cooling chamber where the sample was passed over the pepsin column and the resulting peptides loaded onto the trapping column. After three minutes, a valve switch took the pepsin column out of line and the trap was washed at additional one minute. After that the trap was switched inline with the analytical column and the analytical gradient and the mass spectometer were started.

A fully deuterated sample was generated by incubating 2 μl of hTIGIT with 108 μl of deuterated denaturing buffer (4M Urea, 100 mM TCEP, 0.01% DDM in 99.5% deueterium oxide). The sample was incubated at room temperature overnight. 55 μl was then directly injected into the column chamber and the data acquired as before.

Data Analysis

LC-MS/MS data was acquired of an unlabeled sample and searched before deuterium labeling to verify successful digestion of the proteins and to generate a list of peptides from pepsin digestion. Data was database searched using Proteome Discoverer 1.4 and the SEQUEST HT search algorithm (ThermoFisher Scientific). The protein database used was the human TIGIT-His and anti-hTIGIT antibody sequences concatenated to the yeast *Saccharomyces cerevisiae* uniprot (May 20, 2013) database.

MS data from the deuterium labeling experience was processed by HDExaminer (version 1.3, Sierra Analytics). The mass and retention time selected by the software for each peptide was verified manually.

Results

Figure 14:
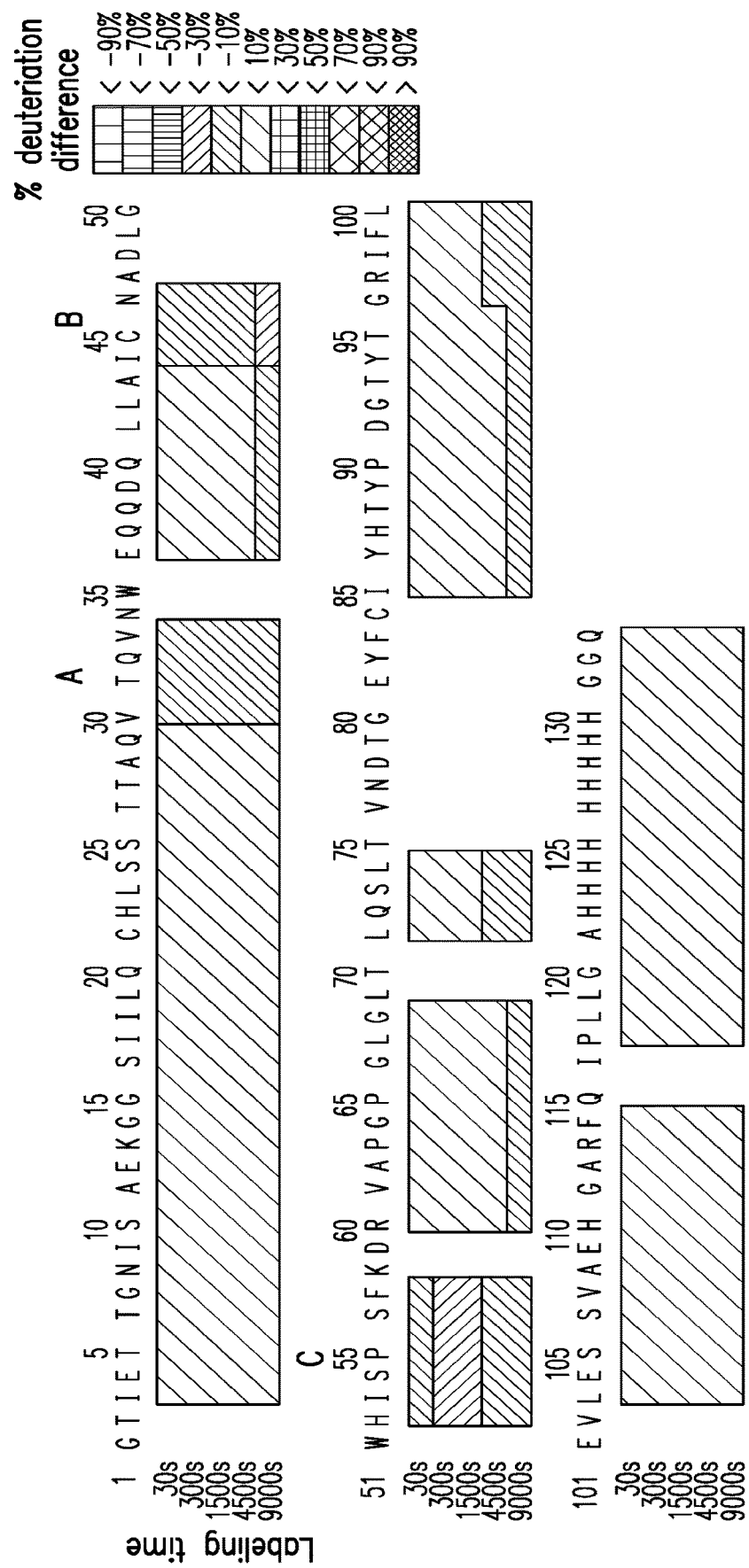
FIG. 14 shows a heat map indicating regions of human TIGIT which are strongly or weakly protected from deuteration by the binding of the 14A6 antibody. The amino acid sequence shown in the heatmap corresponds to SEQ ID NO:87.

The human TIGIT peptides protected by bound 14A6 antibody are illustrated in the heatmap of FIG. 14 and correspond to amino acid residues 54-57, 68-70 and 76-81 of SEQ ID NO:31. (These same amino acids are shown as residues 30-33, 44-46 and 52-57 of SEQ ID NO:87.)

Example 10

Epitope Mapping of hTIGIT 31C6 Antibody by Hydrogen Deuterium Exchange Mass Spectrometry The contact areas between anti-TIGIT antibody 31C6 and human TIGIT were determined by use of hydrogen deuterium exchange mass spectrometry (HDX-MS) analysis. HDX-MS measures the exchange of deuterium with hydrogen into the amide backbone of the protein. One factor influencing the exchange rate is the hydrogen's exposure to solvent. Comparison of the exchange levels in the antigen when the antibody is bound can identify regions of the protein where the antibody is binding.

Materials

Human TIGIT-His—Comprising the extracellular domain of hTIGIT (residues 25-145 of SEQ ID NO:31) and a histidine tag (SEQ ID NO:87).

Mouse anti-hTIGIT 31C6 antibody (lot#41AHK) (Mouse×[TIGIT_H] mAb (MEB125.31C6.A1.205) IgG1/Kappa (HY))

Liquid Chromatography-Mass Spectrometry

The mass spectrometer was a Thermo Scientific Orbitrap-Elite. For the measurement of deuterium labeled samples, the mass spectrometer was set to acquire one full scan MS data in the orbitrap at 120,000 resolving power, a target ion count of 1E6, a maximum ion injection time of 500 milliseconds and two microscans. For the acquisition of MS/MS data for peptide identifications, the mass spectrometer was set to acquire one full scan spectrum at 120,000 resolving power followed by ten data-dependent MS/MS spectra in the ion trap.

The liquid chromatography system was a Waters nano-Acuity for the analytical column gradient and a Waters 515 isocratic pump for the sample digestion and loading. For sample digestion and loading, the buffer used was 2% acetonitrile and 0.05% trifluoroacetic acid at a flow rate of 80 ul/min. For the analytical gradient, the buffers were Buffer A) 0.1% formic acid in water and Buffer B) 0.1% formic acid in acetonitrile.

The gradient was at 40 ul/min from 2% B to 36% B in 10 minutes, followed by a wash of 80% B for 2 minutes and a re-equilibration at 2% B for 3 minutes. The column was then washed by cycling the gradient between 2% and 80% B, three times with 1 minute at each step, followed by a final equilibration at 2% B for 5 minutes. The trapping column was a Waters Vanguard CSH C18 1.7 um Guard Column and the analytical column was a Waters CSH C18, 1.7 um 1×50 mm column.

Sample handling for the deuterium labeling was done by a Leaptec H/D-X PAL system. The labeling sample tray was set to a temperature of 25° C., the quenching tray was set to 1.5° C. and the trap and analytical column chamber was set to 1.5° C. The immobilized pepsin column (Enzymate BEH Pepsin, Waters corporation) was kept outside the column chamber at room temperature.

Deuterium Labeling hTIGIT-His (63 pmol/ul) was mixed with an equal volume of the antibody (32 pmol/ul) or, in the unbound control, PBS pH 7.6. The antibody bound samples and the unbound control were incubated at room temperature for 1 hour before beginning the labeling experiment.

To deuterium label the samples, 2 μl of sample was mixed with 25 μl of PBS in deuterium oxide pH 7.6. Labeling time points were 30, 300, 1500, 4500, 9000 and 13500 seconds. After the set time, 25 μl of the labeling mixture was added to 35 μl of cold quench buffer (8M Urea, 100 mM TCEP). The quenched sample was incubated at 1.5° C. for one minute. 55 μl was then injected into the column cooling chamber where the sample was passed over the pepsin column and the resulting peptides loaded onto the trapping column. After three minutes, a valve switch took the pepsin column out of line and the trap was washed at additional one minute. The trap was then switched in-line with the analytical column and the analytical gradient and the mass spectrometer data acquisition was started. Each time point was acquired in triplicate in randomized order.

A fully deuterated sample was generated by incubating 2 μl of hTIGIT (63 pmol/ul) with 108 μl of deuterated denaturing buffer (4M Urea, 100 mM TCEP, 0.01% DDM in 99.5% deuterium oxide). The sample was incubated at room temperature overnight. 55 μl was then directly injected into the column chamber and the data acquired as before.

Data Analysis

LC-MS/MS data was acquired of an unlabeled sample and database searched to verify successful digestion of the proteins and to generate a list of peptides from the pepsin digestion. Database search was done using Proteome Discoverer 1.4 and the SEQUEST HT search algorithm (ThermoFisher Scientific). The protein database used was the human TIGIT-His and anti-hTIGIT antibody sequences concatenated to the yeast *Saccharomyces cerevisiae* uniprot (May 20, 2013) database.

MS data from the deuterium labeling experience was processed by HDExaminer (version 1.3, Sierra Analytics). The mass and retention time selected by the software for each peptide was verified manually.

Results

Figure 15:
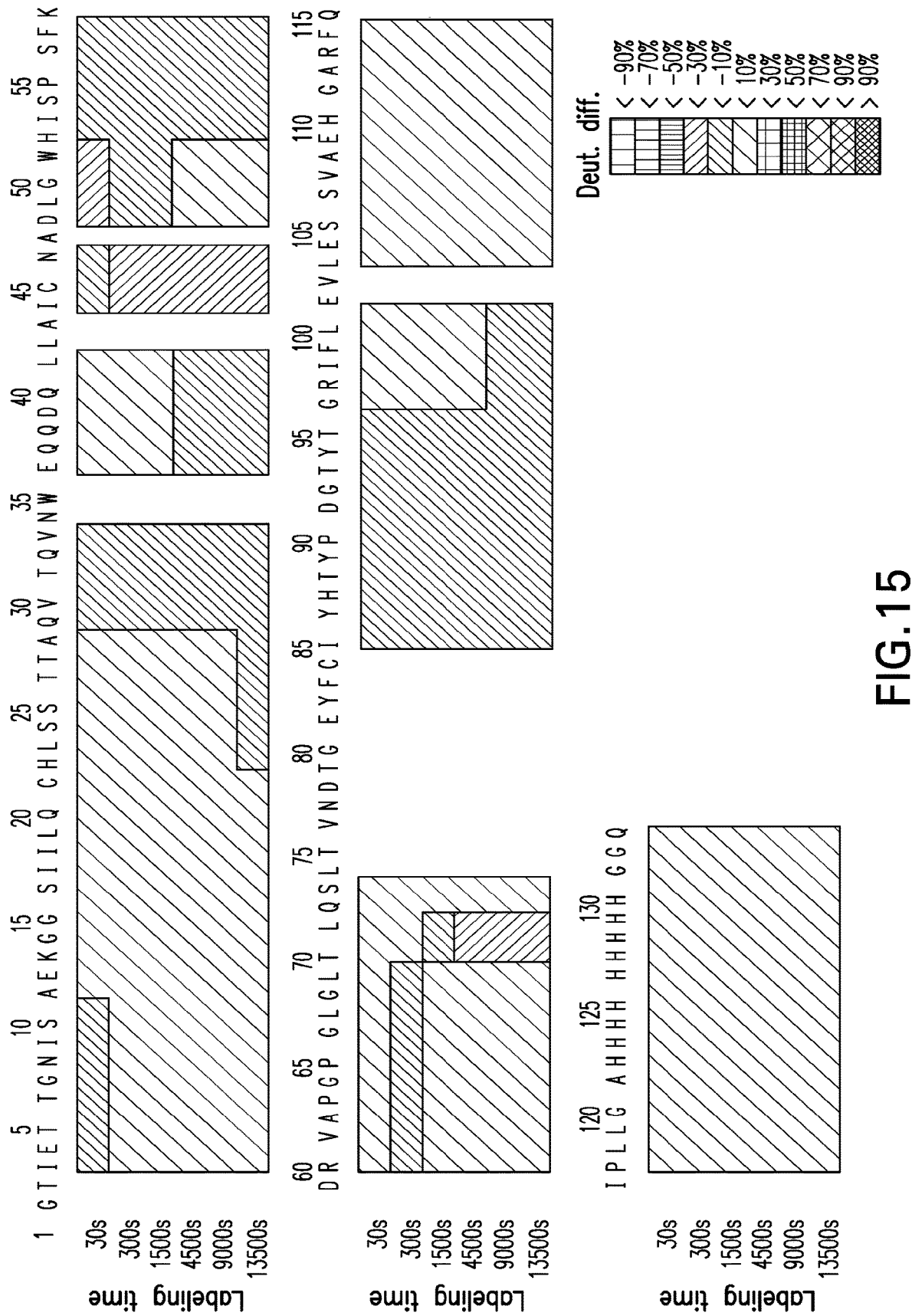
FIG. 15 shows a heat map indicating regions of human TIGIT which are strongly or weakly protected from deuteration by the binding of the 31C6 antibody. The amino acid sequence shown in the heatmap corresponds to SEQ ID NO:87.

The human TIGIT peptides protected by bound 31C6 antibody are illustrated in the heatmap of FIG. 15 and correspond to amino acid residues 53-57, 60-65, 68-70, 72-81, 94-95, 109-119 of SEQ ID NO:31. (These same amino acids are shown as residues 29-33, 36-41, 44-46, 48-57, 70-71, 85-95 of SEQ ID NO:87.)

Example 11

In Vitro T-Cell Activity Assay for Humanized Anti-hTIGIT Antibodies

We further analyzed the activity of various humanized variants of one of the antibodies of the invention (31C6). In one assay we characterized the functional consequence of blocking human TIGIT receptor using hTIGIT-Jurkat cells. In this assay the hTIGIT-Jurkat were co-cultured with JY cells engineered to express human CD155 (hCD155-JY). The JY cell line used is an Epstein-Barr virus (EBV) immortalized B cell lymphoblastoid cell line. As in the assay described above in Example 3, when the hTIGIT Jurkat cells are stimulated with plate bound α-CD3 and co-cultured with parental JY cells (not expressing human CD155), they produce IL-2. However, when the hTIGIT-Jurkat are co-cultured with hCD155-JY, IL-2 levels were reduced in a ligand dependent manner. Treatment with anti-hTIGIT antibodies of the invention rescues IL-2 production in this assay in a dose-dependent fashion.

Figure 16:
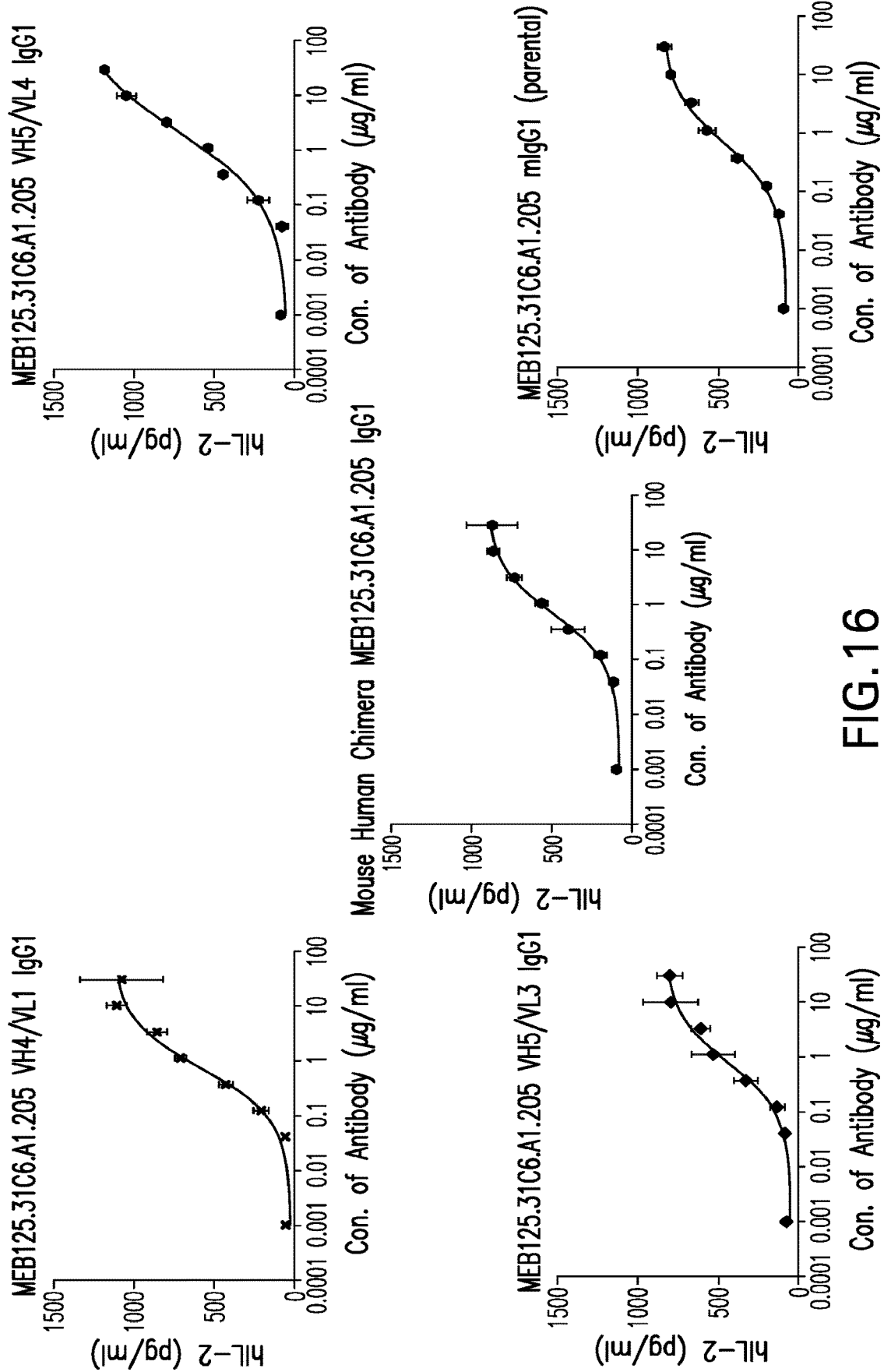
FIG. 16 shows the effect of various humanized clones of 31C6 as compared to chimera and parental antibodies in an engineered T cell functional assay.

In this assay 96-well flat-bottom plates were coated with mouse anti-human CD3 antibody (1m/ml in PBS; Clone HIT3a; BD Pharmingen Cat#555336) overnight at 4° C. The next day, hTIGIT expressing Jurkat cells (50,000) were plated in the pre-coated plates and pre-incubated for 30-60 minutes with mAb at varying concentrations. Human CD155 expressing JY cells (50,000) were added to the culture. After incubation for 18-24 h at 37° C. and 5.0% CO2, IL-2 levels were assessed in culture supernatants by mesoscale (Human IL-2 Tissue Culture MESO Kit: Cat#K151AHB-2). The results are shown in FIG. 16. A titration of the parental mouse anti-hTIGIT clone 31C6 (MEB125.31C6.A1.205 mIgG1) from 30 μg/ml down to 0.04 μg/ml gives an $EC_{50}$ of 0.730 μg/ml, and the same titration of the mouse human 31C6 chimera (Mouse human chimera MEB125.31C6.A1.205 IgG1) gives an EC50 of 0.910 μg/ml. (The mouse human 31C6 chimera comprised the variable regions of the parental 31C6 clone (SEQ ID Nos: 94 and 95) and a human IgG1 region.) Similarly, a titration of the 31C6 humanized variants from 30 μg/ml down to 0.04 μg/ml gives the following $EC_{50}$s:

| Humanized Variant | $EC_{50}$ |
|---|---|
| MEB125.31C6.A1.205 VH4/VL1 (An antibody comprising the VH of SEQ ID NO: 127 and VL of SEQ ID NO: 130, and a human IgG1 Fc region) | 0.620 μg/ml |
| MEB125.31C6.A1.205 VH5/VL4 (An antibody comprising the VH of SEQ ID NO: 128 and VL of SEQ ID NO: 133, and a human IgG1 Fc region) | 1.2 μg/ml |
| MEB125.31C6.A1.205 VH5/VL3 (An antibody comprising the VH of SEQ ID NO: 128 and VL of SEQ ID NO: 132, and a human IgG1 Fc region) | 1.2 μg/ml |

We also used a primary cell-based assay to demonstrate that the humanized anti-hTIGIT antibodies had activity in primary cells. Several lots of human peripheral blood mononuclear cells (PBMCs) were screened for TIGIT expression after stimulation (mixed lymphocyte reaction stimulation and α-CD3 stimulation). PBMCs were then chosen for primary cell-based assays based on their TIGIT expression after stimulation. HuCD155-Fc was coated onto tissue culture plates and PBMCs were stimulated with anti-CD3.

Figure 17:
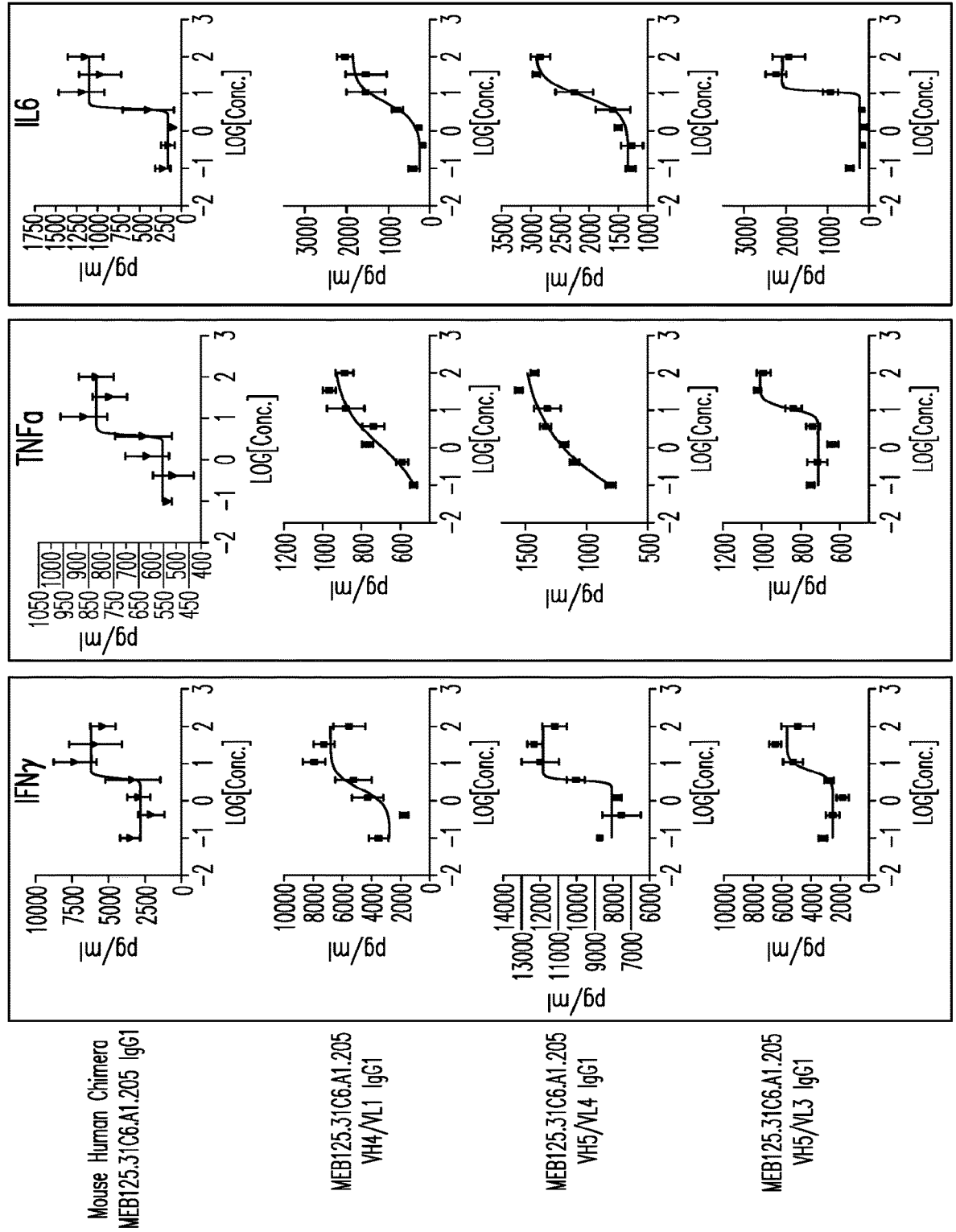
FIG. 17 shows the effect of various humanized clones of 31C6 as compared to chimera antibodies in a primary T cell functional assay.

In this assay 96-well high binding plates (Corning 3361) were coated with human CD155-Fc (in-house generated, 1 ug/ml in PBS) overnight at 4° C. The next day, 50,000 human PBMC (Precision Bioservice Cat#83000C-1.0, lot#12920 in RPMI+10% human serum Bio-world cat#30611043-1, lot#V15022401, RBCs were removed by BD Pharmlyse BD cat#555899) were plated in the pre-coated plates and pre-incubated for 30-60 minutes with anti-TIGIT mAbs at varying concentrations. Anti-CD3 antibody (eBioscience 16-0037-85) at final concentration 1 ug/ml was then added. After incubation for 48 h at 37° C. and 5.0% CO2, Proinflammatory cytokines (IFNγ, IL1β, IL6 and TNFα) were assessed in culture supernatants by mesoscale assay (Human Proinflammatory-4 I tissue culture MESO Kit: Cat#K15009B-4). As shown in FIG. 17, humanized variants of 31C6 were able to stimulate IL-6, TNFα and IFNγ in a dose dependent manner similar to the mouse human 31C6 chimeric antibody.

The labels in FIG. 17 correspond to the following antibodies:
  Mouse human chimera MEB125.31C6.A1.205 IgG1 corresponds to an antibody comprising the variable regions of the parental 31C6 clone (SEQ ID Nos: 94 and 95) and a human IgG1 region.)
  MEB125.31C6.A1.205 VH4/VL1 corresponds to an antibody comprising the VH of SEQ ID NO: 127 and VL of SEQ ID NO:130, and a human IgG1 Fc region)
  MEB125.31C6.A1.205 VH5/VL4 corresponds to an antibody comprising the VH of SEQ ID NO: 128 and VL of SEQ ID NO:133, and a human IgG1 Fc region)
  MEB125.31C6.A1.205 VH5/VL3 corresponds to an antibody comprising the VH of SEQ ID NO: 128 and VL of SEQ ID NO:133, and a human IgG1 Fc region)
All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

TABLE 4

Sequence Information

| Description | SEQ ID NO: | SEQUENCE |
| --- | --- | --- |
| 14A6 H - CDR1 | 1 | SDYWG |
| 14A6 H - CDR2 | 2 | FITYSGSTSYNPSLKS |
| 14A6 H - CDR3 | 3 | MPSFITLASLSTWEGYFDF |
| 14A6 L - CDR1 | 4 | KASQSIHKNLA |
| 14A6 L - CDR2 | 5 | YANSLQT |
| 14A6 L - CDR3 | 6 | QQYYSGWT |
| 14A6 PARENTAL VH | 7 | EVQLQESGPGLVKPSQSLSLTCSVTGSSIA<u>SDYWG</u>WIRKFPGNKMEWMG<u>FI TYSGSTSYNPSLKS</u>RISITRDTSKNQFFLQLHSVTTDDTATYSCAR<u>MPSFI TLASLSTWEGYFDF</u>WGPGTMVTVSS |
| 14A6 PARENTAL VL | 8 | DIQMTQSPSLLSASVGDRVTLNC<u>KASQSIHKNLA</u>WYQQKLGEAPKFLIY<u>YA NSLQT</u>GIPSRFSGSGSGTDFTLTISGLQPEDVATYFC<u>QQYYSGWT</u>FGGGTK VELK |
| Hu14A6VH.1 | 9 | EVQLQESGPGLVKPSETLSLTCTVSGGSIS<u>SDYWG</u>WIRQPPGKGLEWIG<u>FI TYSGSTSYNPSLKS</u>RVTISVDTSKNQFSLKLSSVTAADTAVYYCAR<u>MPSFI TLASLSTWEGYFDF</u>WGQGTMVTVSS |
| Hu14A6VH.1a | 10 | EVQLQESGPGLVKPSETLSLTCTVSGGSIS<u>SDYWG</u>WIRQPPGKGLEWIG<u>FI TYSGSTSYNPSLKS</u>RVTISRDTSKNQFSLKLSSVTAADTAVYYCAR<u>MPSFI TLASLSTWEGYFDF</u>WGQGTMVTVSS |
| Hu14A6VH.1b | 11 | EVQLQESGPGLVKPSETLSLTCTVSGGSIS<u>SDYWG</u>WIRQPPGKGLEWIG<u>FI TYSGSTSYNPSLKS</u>RITISRDTSKNQFSLKLSSVTAADTAVYYCAR<u>MPSFI TLASLSTWEGYFDF</u>WGQGTMVTVSS |
| Hu14A6VH.1c | 12 | EVQLQESGPGLVKPSETLSLTCTVSGGSIS<u>SDYWG</u>WIRQPPGKGLEWMG<u>FI TYSGSTSYNPSLKS</u>RITISRDTSKNQFSLKLSSVTAADTAVYYCAR<u>MPSFI TLASLSTWEGYFDF</u>WGQGTMVTVSS |
| Hu14A6VH.1d | 13 | EVQLQESGPGLVKPSETLSLTCTVSGGSIS<u>SDYWG</u>WIRQPPGKGLEWIG<u>FI TYSGSTSYNPSLKS</u>RVTISRDTSKNQFSLKLHSVTAADTAVYYCAR<u>MPSFI TLASLSTWEGYFDF</u>WGQGTMVTVSS |
| Hu14A6VH.1e | 14 | EVQLQESGPGLVKPSETLSLTCTVSGGSIS<u>SDYWG</u>WIRQPPGKGLEWIG<u>FI TYSGSTSYNPSLKS</u>RITISRDTSKNQFSLKLHSVTAADTAVYYCAR<u>MPSFI TLASLSTWEGYFDF</u>WGQGTMVTVSS |

TABLE 4-continued

Sequence Information

| Description | SEQ ID NO: | SEQUENCE |
|---|---|---|
| Hu14A6VH.1f | 15 | EVQLQESGPGLVKPSETLSLTCTVSGSSISS<u>SDYWG</u>WIRQPPGKGLEWIG<u>FI TYSGSTSYNPSLKS</u>RITISRDTSKNQFSLKLHSVTAADTAVYYCAR<u>MPSFI TLASLSTWEGYFDF</u>WGQGTMVTVSS |
| Hu14A6VH.1g | 16 | EVQLQESGPGLVKPSETLSLTCTVSGSSISS<u>SDYWG</u>WIRQPPGKGLEWMG<u>FI TYSGSTSYNPSLKS</u>RITISVDTSKNQFSLKLHSVTAADTAVYYCAR<u>MPSFI TLASLSTWEGYFDF</u>WGQGTMVTVSS |
| Hu14A6VH.2 | 17 | EVQLQESGPGLVKPSETLSLTCAVSGYSISS<u>SDYWG</u>WIRQPPGKGLEWIG<u>FI TYSGSTSYNPSLKS</u>RVTISVDTSKNQFSLKLSSVTAADTAVYYCAR<u>MPSFI TLASLSTWEGYFDF</u>WGQGTMVTVSS |
| Hu14A6VH.2a | 18 | EVQLQESGPGLVKPSETLSLTCAVSGYSISS<u>SDYWG</u>WIRQPPGKGLEWIG<u>FI TYSGSTSYNPSLKS</u>RVTISRDTSKNQFSLKLSSVTAADTAVYYCAR<u>MPSFI TLASLSTWEGYFDF</u>WGQGTMVTVSS |
| Hu14A6VH.2b | 19 | EVQLQESGPGLVKPSETLSLTCAVSGYSISS<u>SDYWG</u>WIRQPPGKGLEWIG<u>FI TYSGSTSYNPSLKS</u>RITISRDTSKNQFSLKLSSVTAADTAVYYCAR<u>MPSFI TLASLSTWEGYFDF</u>WGQGTMVTVSS |
| Hu14A6VH.2c | 20 | EVQLQESGPGLVKPSETLSLTCAVSGSSISS<u>SDYWG</u>WIRQPPGKGLEWMG<u>FI TYSGSTSYNPSLKS</u>RITISRDTSKNQFSLKLSSVTAADTAVYYCAR<u>MPSFI TLASLSTWEGYFDF</u>WGQGTMVTVSS |
| Hu14A6VH.2d | 21 | EVQLQESGPGLVKPSETLSLTCAVSGYSISS<u>SDYWG</u>WIRQPPGKGLEWIG<u>FI TYSGSTSYNPSLKS</u>RVTISRDTSKNQFSLKLHSVTAADTAVYYCAR<u>MPSFI TLASLSTWEGYFDF</u>WGQGTMVTVSS |
| Hu14A6VH.2e | 22 | EVQLQESGPGLVKPSETLSLTCAVSGYSISS<u>SDYWG</u>WIRQPPGKGLEWIG<u>FI TYSGSTSYNPSLKS</u>RITISRDTSKNQFSLKLHSVTAADTAVYYCAR<u>MPSFI TLASLSTWEGYFDF</u>WGQGTMVTVSS |
| Hu14A6VH.2f | 23 | EVQLQESGPGLVKPSETLSLTCAVSGSSISS<u>SDYWG</u>WIRQPPGKGLEWIG<u>FI TYSGSTSYNPSLKS</u>RITISRDTSKNQFSLKLHSVTAADTAVYYCAR<u>MPSFI TLASLSTWEGYFDF</u>WGQGTMVTVSS |
| Hu14A6VH.2e | 24 | EVQLQESGPGLVKPSETLSLTCAVSGSSISS<u>SDYWG</u>WIRQPPGKGLEWMG<u>FI TYSGSTSYNPSLKS</u>RITISRDTSKNQFSLKLHSVTAADTAVYYCAR<u>MPSFI TLASLSTWEGYFDF</u>WGQGTMVTVSS |
| Hu14A6Vk.1 | 25 | DIQMTQSPSSLSASVGDRVTITC<u>KASQSIHKNLA</u>WYQQKPGKAPKLLIY<u>YA NSLQT</u>GVPSRFSGSGSGTDFTLTISSLQPEDFATYYC<u>QQYYSGWT</u>FGGGTK VEIK |
| Hu14A6Vk.1a | 26 | DIQMTQSPSSLSASVGDRVTITC<u>KASQSIHKNLA</u>WYQQKPGKAPKFLIY<u>YA NSLQT</u>GVPSRFSGSGSGTDFTLTISSLQPEDFATYYC<u>QQYYSGWT</u>FGGGTK VEIK |
| Hu14A6Vk.1b | 27 | DIQMTQSPSSLSASVGDRVTITC<u>KASQSIHKNLA</u>WYQQKPGKAPKFLIY<u>YA NSLQT</u>GIPSRFSGSGSGTDFTLTISSLQPEDFATYYC<u>QQYYSGWT</u>FGGGTK VEIK |
| Hu14A6Vk.2 | 28 | DIQMTQSPSSLSASVGDRVTITC<u>KASQSIHKNLA</u>WYQQKPGKVPKLLIY<u>YA NSLQT</u>GVPSRFSGSGSGTDFTLTISSLQPEDVATYYC<u>QQYYSGWT</u>FGGGTK VEIK |
| Hu14A6Vk.2a | 29 | DIQMTQSPSSLSASVGDRVTITC<u>KASQSIHKNLA</u>WYQQKPGKVPKFLIY<u>YA NSLQT</u>GVPSRFSGSGSGTDFTLTISSLQPEDVATYYC<u>QQYYSGWT</u>FGGGTK VEIK |
| Hu14A6Vk.2b | 30 | DIQMTQSPSSLSASVGDRVTITC<u>KASQSIHKNLA</u>WYQQKPGKVPKFLIY<u>YA NSLQT</u>GIPSRFSGSGSGTDFTLTISSLQPEDVATYYC<u>QQYYSGWT</u>FGGGTK VEIK |
| Human TIGIT | 31 | mrwcllliwa qglrqaplas gmmtgtiett gnisaekggs iilqchlsst taqvtqvnwe qqdqllaicn adlgwhisps fkdrvapgpg lgltlqsltv ndtgeyfciy htypdgtytg riflevless vaehgarfqi pllgamaatl vvictavivv valtrkkkal rihsvegdlr rksagqeews psapsppgsc vqaeaapagl cgegrgedca elhdyfnvls yrslgncsff tetg |
| Cyno / Rhesus TIGIT | 32 | mrwclfliwa qglrqaplas gmmtgtiett gnisakkggs vilqchlsst maqvtqvnwe qhdhsllair naelgwhiyp |

TABLE 4-continued

Sequence Information

| Description | SEQ ID NO: | SEQUENCE |
|---|---|---|
| | | afkdrvapgp glgltlqslt mndtgeyfct yhtypdgtyr<br>griflevles svaehsarfq ipllgamamm lvviciaviv<br>vvvlarkkks lrihsvesgl qrkstgqeeq ipsapsppgs<br>cvqaeaapag lcgeqqgddc aelhdyfnvl syrslgscsf ftetg |
| Pembrolizumab Heavy chain | 33 | QVQLVQSGVEVKKPGASVKVSCKASGYTFTNYYMYWVRQAPGQGLEWMGGI<br>NPSNGGTNFNEKFKNRVTLTTDSSTTTAYMELKSLQFDDTAVYYCARRDYR<br>FDMGFDYWGQGTTVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYS<br>RLTVDKSRWQEGNVFSCSVMHEALHNHYTQKSLSLSLGK |
| Pembrolizumab Light chain | 34 | EIVLTQSPATLSLSPGERATLSCRASKGVSTSGYSYLHWYQQKPGQAPRLL<br>IYLASYLESGVPARFSGSGSGTDFTLTISSLEPEDFAVYYCQHSRDLPLTF<br>GGGTKVEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQG<br>LSSPVTKSFNRGEC |
| Nivolumab heavy chain | 35 | QVQLVESGGGVVQPGRSLRLDCKASGITFSNSGMHWVRQAPGKGLEWVAVI<br>WYDGSKRYYADSVKGRFTISRDNSKNTLFLQMNSLRAEDTAVYYCATNDDY<br>WGQGTLVTVSSASTKGPSVFPLAPCSRSTSESTAALGCLVKDYFPEPVTVS<br>WNSGALTSGVHTFPAVLQSSGLYSLSSVVTVPSSSLGTKTYTCNVDHKPSN<br>TKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDW<br>LNGKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVDKS<br>RWQEGNVFSCSVMHEALHNHYTQKSLSLSLGK |
| Nivolumab light chain | 36 | EIVLTQSPATLSLSPGERATLSCRASQSVSSYLAWYQQKPGQAPRLLIYDA<br>SNRATGIPARFSGSGSGTDFTLTISSLEPEDFAVYYCQQSSNWPRTFGQGT<br>KVEIKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSP<br>VTKSFNRGEC |
| 16AHA_tigit_1<br>4a6_humanized<br>VH1<br>LB155.14A6.G2.<br>A8_VH1 | 37 | EVQLQESGPGLVKPSETLSLTCTVSGSSIA<u>SDYWG</u>WIRQPPGKGLEWIG<u>FI<br>TYSGSTSYNPSLKS</u>RVTISVDTSKNQFSLKLSSVTAADTAVYYCAR<u>MPSFI<br>TLASLSTWEGYFDF</u>WGQGTMVTVSSAS |
| 18AHA_tigit_1<br>4a6_humanized_<br>VH2<br>LB155.14A6.G2.<br>A8_VH2 | 38 | EVQLQESGPGLVKPSETLSLTCTVSGSSIA<u>SDYWG</u>WIRQPPGKGLEWIG<u>FI<br>TYSGSTSYNPSLKS</u>RVTISRDTSKNQFSLKLSSVTAADTAVYYCAR<u>MPSFI<br>TLASLSTWEGYFDF</u>WGQGTMVTVSS |
| 20AHA_tigit_1<br>4a6_humanized<br>VH3<br>LB155.14A6.G2.<br>A8_VH3 | 39 | EVQLQESGPGLVKPSETLSLTCTVSGSSIA<u>SDYWG</u>WIRKPPGKGLEWIG<u>FI<br>TYSGSTSYNPSLKS</u>RVTISRDTSKNQFSLKLSSVTAADTAVYYCAR<u>MPSFI<br>TLASLSTWEGYFDF</u>WGQGTMVTVSS |
| 21AHA_tigit_1<br>4a6_humanized<br>VH4<br>LB155.14A6.G2.<br>A8_VH4 | 40 | EVQLQESGPGLVKPSETLSLTCTVSGSSIA<u>SDYWG</u>WIRQPPGKKLEWIG<u>FI<br>TYSGSTSYNPSLKS</u>RVTISRDTSKNQFSLKLSSVTAADTAVYYCAR<u>MPSFI<br>TLASLSTWEGYFDF</u>WGQGTMVTVSS |
| 19AHA_tigit_1<br>4a6_humanized<br>VH5<br>LB155.14A6.G2.<br>A8_VH5 | 41 | EVQLQESGPGLVKPSETLSLTCTVSGSSIA<u>SDYWG</u>WIRQPPGKGMEWIG<u>FI<br>TYSGSTSYNPSLKS</u>RVTISRDTSKNQFSLKLSSVTAADTAVYYCAR<u>MPSFI<br>TLASLSTWEGYFDF</u>WGQGTMVTVSS |
| 22AHA_tigit_1<br>4a6_humanized<br>VH6<br>LB155.14A6.G2.<br>A8_VH6 | 42 | EVQLQESGPGLVKPSETLSLTCTVSGSSIA<u>SDYWG</u>WIRKPPGKKMEWIG<u>FI<br>TYSGSTSYNPSLKS</u>RVTISRDTSKNQFSLKLSSVTAADTAVYYCAR<u>MPSFI<br>TLASLSTWEGYFDF</u>WGQGTMVTVSS |
| 23AHA_tigit_1 | 43 | EVQLQESGPGLVKPSETLSLTCTVSGSSIA<u>SDYWG</u>WIRQFPGKGLEWIG<u>FI |

TABLE 4-continued

Sequence Information

| Description | SEQ ID NO: | SEQUENCE |
|---|---|---|
| 4a6_humanized VH7 LB155.14A6.G2.A8_VH7 | | TYSGSTSYNPSLKSRVTISRDTSKNQFSLKLSSVTADDTAVYYCARMPSFI TLASLSTWEGYFDFWGQGTMVTVSS |
| 24AHA_tigit_14a6_humanized VH8 LB155.14A6.G2.A8_VH8 | 44 | EVQLQESGPGLVKPSETLSLTCTVSGSSIASDYWGWIRKPPGKKMEWIGFI TYSGSTSYNPSLKSRVTISVDTSKNQFSLKLSSVTAADTAVYYCARMPSFI TLASLSTWEGYFDFWGQGTMVTVSS |
| 25AHA_tigit_14a6_humanized VH9 LB155.14A6.G2.A8_VH9 | 45 | EVQLQESGPGLVKPSETLSLTCSVTGSSIASDYWGWIRQPPGKGLEWIGFI TYSGSTSYNPSLKSRVTISRDTSKNQFSLKLSSVTAADTAVYYCARMPSFI TLASLSTWEGYFDFWGQGTMVTVSS |
| 26AHA_tigit_14a6_humanized VH10 LB155.14A6.G2.A8_VH10 | 46 | EVQLQQSGAGLLKPSETLSLTCSVTGSSIASDYWGWIRQPPGKGLEWIGFI TYSGSTSYNPSLKSRVTISVDTSKNQFSLKLSSVTAADTAVYYCARMPSFI TLASLSTWEGYFDFWGQGTMVTVSS |
| 27AHA_tigit_14a6_humanized VH11 LB155.14A6.G2.A8_VH11 | 47 | EVQLQESGPGLVKPPGTLSLTCSVTGSSIASDYWGWVRQPPGKGLEWIGFI TYSGSTSYNPSLKSRVTISVDTSKNQFSLKLSSVTAADTAVYYCARMPSFI TLASLSTWEGYFDFWGQGTMVTVSS |
| 09AHA_tigit_14a6_humanized VL1 LB155.14A6.G2.A8_VL1 | 48 | DIQMTQSPSSLSASVGDRVTITCKASQSIHKNLAWYQQKPGKAPKLLIYYA NSLQTGVPSRFSGSGSGTDFTLTISSLQPEDFATYYCQQYYSGWTFGGGTK VEIK |
| 11AHA_tigit_14a6_humanized VL2 LB155.14A6.G2.A8_VL2 | 49 | DIQMTQSPSSLSASVGDRVTITCKASQSIHKNLAWYQQKPGKAPKFLIYYA NSLQTGVPSRFSGSGSGTDFTLTISSLQPEDFATYYCQQYYSGWTFGGGTK VEIK |
| 12AHA_tigit_14a6_humanized VL3 LB155.14A6.G2.A8_VL3 | 50 | DIQMTQSPSSLSASVGDRVTITCKASQSIHKNLAWYQQKPGKAPKLLIYYA NSLQTGVPSRFSGSGSGTDFTLTISSLQPEDFATYFCQQYYSGWTFGGGTK VEIK |
| 13AHA_tigit_14a6_humanized VL4 LB155.14A6.G2.A8_VL4 | 51 | DIQMTQSPSSLSASVGDRVTITCKASQSIHKNLAWYQQKPGKAPKFLIYYA NSLQTGVPSRFSGSGSGTDFTLTISSLQPEDFATYFCQQYYSGWTFGGGTK VEIK |
| 15AHA_tigit_14a6_humanized VL5 LB155.14A6.G2.A8_VL5 | 52 | DIQMTQSPSSLSASVGDRVTITCKASQSIHKNLAWYQQKPGKAPKLLIYYA NSLQTGIPSRFSGSGSGTDFTLTISSLQPEDFATYYCQQYYSGWTFGGGTK VEIK |
| Leader sequence heavy chains | 53 | MEWSWVFLFFLSVTTGVHS |
| Leader sequence light chains | 54 | MSVPTQVLGLLLLWLTDARC |
| Heavy chain constant domain-IgG4 S228P | 55 | TKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGP PCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDI AVEWESNGQPENNYKTTPPVLDSDGSFFLYSRLTVDKSRWQEGNVFSCSVM HEALHNHYTQKSLSLSLGK |

TABLE 4-continued

Sequence Information

| Description | SEQ ID NO: | SEQUENCE |
|---|---|---|
| Kappa light chain constant domain | 56 | VAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNR GEC |
| 28H5 H - CDR1 | 57 | GYSITSDYAWN |
| 28H5 H - CDR2 | 58 | YISNSGSASYNPSLKS |
| 28H5 H - CDR3 | 59 | LIYYDYGGAMNF |
| 28H5 L - CDR1 | 60 | KASQGVSTTVA |
| 28H5 L - CDR2 | 61 | SASYRYT |
| 28H5 L - CDR3 | 62 | QHYYSTPWT |
| 28H5 PARENTAL VH | 63 | DVQLQESGPGLVKPSQSLSLTCTVTGYSITSDYAWNWIRQFPGNKLEWMGY ISNSGSASYNPSLKSRISITRDTSKNQFFLQLNSVTTEDTATYYCATLIYY DYGGAMNFWGQGTSVTVSS |
| 28H5 PARENTAL VL | 64 | DIVMTQSHKFMSTSVGDRVSITCKASQGVSTTVAWYQQKPGQSPKLLIYSA SYRYTGVPDRFTGSGSGTDFTFTISSVQSEDLAVYYCQHYYSTPWTFGGGT KLEIK |
| 14H6 L - CDR2 variant | 65 | YASNLQT |
| 14H6 L - CDR2 variant | 65 | YASSLQT |
| 14H6 L - CDR2 variant | 67 | YASTLQT |
| 14H6 L - CDR2 variant | 68 | YATTLQT |
| 14H6 L - CDR2 variant | 69 | YASYLQT |
| 14H6 L - CDR2 variant | 70 | YANQLQT |
| 14H6 L - CDR2 variant | 71 | YAGSLQT |
| 14H6 L - CDR2 variant | 72 | YASQLQT |
| 14H6 L - CDR2 variant | 73 | YADSLQT |
| 14H6 L - CDR3 variant | 74 | QQYYSGFT |
| 14H6 L - CDR3 variant | 75 | QQYYSGYT |
| 14H6 L - CDR3 variant | 76 | QQYYSGIT |
| 14H6 L - CDR3 variant | 77 | QQYYSGVT |
| 14H6 L - CDR3 variant | 78 | QQYYSGLT |
| 14H6 H - CDR3 variant | 79 | MPSFITLASLSTFEGYFDF |
| 14H6 H - CDR3 variant | 80 | MPSFITLASLSTYEGYFDF |

TABLE 4-continued

Sequence Information

| Description | SEQ ID NO: | SEQUENCE |
|---|---|---|
| 14H6 H - CDR3 variant | 81 | MPSFITLASLSTIEGYFDF |
| 14H6 H - CDR3 variant | 82 | MPSFITLASLSTVEGYFDF |
| 14H6 H - CDR3 variant | 83 | MPSFITLASLSTLEGYFDF |
| Nucleic acid encoding 28H5 PARENTAL VH | 84 | GATGTGCAGCTTCAGGAGTCGGGACCTGGCCTGGTGAAACCTTCTCAGTCTCTGTCCCTCAC CTGCACTGTCACTGGCTACTCAATCACCAGTGATTATGCCTGGAACTGGATCCGACAGTTTC CAGGAAACAAACTGGAGTGGATGGGCTACATAAGCAACAGTGGTAGCGCTAGCTACAACCCA TCTCTCAAAAGTCGCATCTCTATCACTCGAGACACATCCAAGAACCAGTTCTTCCTGCAGTT GAATTCTGTGACTACTGAGGACACAGCCACATATTACTGTGCAACCCTGATCTACTATGATT ACGGGGGGGCTATGAACTTCTGGGGTCAAGGAACCTCAGTCACCGTCTCCTCA |
| Nucleic acid encoding 28H5 PARENTAL VL | 85 | GACATTGTGATGACCCAGTCTCACAAATTCATGTCCACATCAGTAGGAGACAGGGTCAGCAT CACCTGCAAGGCCAGTCAGGGTGTGAGTACTACTGTGGCCTGGTATCAACAGAAACCAGGAC AATCTCCTAAACTACTGATTTACTCGGCATCCTACCGGTACACTGGAGTCCCTGATCGCTTC ACTGGCAGTGGATCTGGGACGGATTTCACTTTCACCATCAGCAGTGTGCAGTCTGAAGACCT GGCAGTTTATTACTGTCAGCATTATTATAGTACTCCGTGGACGTTCGGTGGAGGCACCAAGC TGGAAATCAAA |
| Heavy chain constant domain-IgG1 | 86 | ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKSRWQQGNVFSCSV MHEALHNHYTQKSLSLSPGK |
| hTIGIT-HIS | 87 | gtiett gnisaekggs iilqchlsst taqvtqvnwe qqdqllaicn adlgwhisps fkdrvapgpg lgltlqsltv ndtgeyfciy htypdgtytg riflevless vaehgarfqi pllga hhhhhhhhggq |
| 31C6 H -CDR1 | 88 | SYVMH |
| 31C6 H -CDR2 | 89 | YIDPYNDGAKYNEKFKG |
| 31C6 H -CDR3 | 90 | GGPYGWYFDV |
| 31C6 L - CDR1 | 91 | RASEHIYSYLS |
| 31C6 L - CDR2 | 92 | NAKTLAE |
| 31C6 L - CDR3 | 93 | QHHFGSPLT |
| 31C6 PARENTAL VH (with CDRs underlined) | 94 | EVQLQQSGPELVKPGSSVKMSCKASGYTFSSYVMHWVKQKPGQGLEWIGYIDPYNDGAKYNE KFKGKATLTSDKSSSTAYMELSSLTSEDSAVYYCARGGPYGWYFDVWGAGTTVTVSS |
| 31C6 PARENTAL VL (with CDRs underlined) | 95 | DIQMTQSPASLSASVGETVTITCRASEHIYSYLSWYQQKQGKSPQLLVYNAKTLAEGVPSRF SGSGSGTQFSLKINSLQPEDFGTYYCQHHFGSPLTFGAGTTLELK |
| 31C6 H - CDR2 VARIANT (D56R) | 96 | YIDPYNrGAKYNEKFG |
| 31C6 H - CDR2 VARIANT (D56L) | 97 | YIDPYNlGAKYNEKGF |
| 31C6 H - CDR2 VARIANT (D56K) | 98 | YIDPYNkGAKYNEKFG |
| 31C6 H - CDR2 VARIANT (D56F) | 99 | YIDPYNfGAKYNEKFG |
| 31C6 H - CDR2 VARIANT (D56S) | 100 | YIDPYNsGAKYNEKFG |

TABLE 4-continued

Sequence Information

| Description | SEQ ID NO: | SEQUENCE |
|---|---|---|
| 31C6 H - CDR2 VARIANT (D56Y) | 101 | YIDPYNyGAKYNEKFG |
| 31C6 H - CDR2 VARIANT (D56V) | 102 | YIDPYNvGAKYNEKFG |
| 31C6 H - CDR2 VARIANT (G57R) | 103 | YIDPYNDrAKYNEKFKG |
| 31C6 H - CDR2 VARIANT (G57N) | 104 | YIDPYNDnAKYNEKFKG |
| 31C6 H - CDR2 VARIANT (G57Q) | 105 | YIDPYNDqAKYNEKFKG |
| 31C6 H - CDR2 VARIANT (G57E) | 106 | YIDPYNDeAKYNEKFKG |
| 31C6 H - CDR2 VARIANT (G57L) | 107 | YIDPYNDlAKYNEKFKG |
| 31C6 H - CDR2 VARIANT (G57K) | 108 | YIDPYNDkAKYNEKFKG |
| 31C6 H - CDR2 VARIANT (G57S) | 109 | YIDPYNDsAKYNEKFKG |
| 31C6 H - CDR2 VARIANT (G57Y) | 110 | YIDPYNDyAKYNEKFKG |
| 31C6 H - CDR2 VARIANT (G57V) | 111 | YIDPYNDvAKYNEKFKG |
| 31C6 L - CDR2 variant (N50A) | 112 | AAKTLAE |
| 31C6 L - CDR2 variant (N50Y) | 113 | YAKTLAE |
| 31C6 L - CDR2 variant (N50W) | 114 | WAKTLAE |
| 31C6 L - CDR2 variant (N50S) | 115 | SAKTLAE |
| 31C6 L - CDR2 variant (N50T) | 116 | TAKTLAE |
| 31C6 L - CDR2 variant (N50I) | 117 | IAKTLAE |
| 31C6 L - CDR2 variant (N50V) | 118 | VAKTLAE |
| 31C6 L - CDR2 variant | 119 | NNKTLAE |

TABLE 4-continued

Sequence Information

| Description | SEQ ID NO: | SEQUENCE |
|---|---|---|
| (A51N) | | |
| 31C6 L - CDR2 variant (A51I) | 120 | NIKTLAE |
| 31C6 L - CDR2 variant (A51L) | 121 | NLLTLAE |
| 31C6 L - CDR2 variant (A51T) | 122 | NTKTLAE |
| 31C6 L - CDR2 variant (A51V) | 123 | NVKTLAE |
| 31C6_HUMZ_VH1 (with CDRs underlined) | 124 | EVQLVQSGAEVKKPGASVKVSCKASGYTFS<u>SYVMH</u>WVRQAPGQRLEWIG<u>YIDPYNDGAKYSQKFQG</u>RVTLTRDTSASTAYMELSSLRSEDTAVYYCAR<u>GGPYGWYFDV</u>WGQGTTVTVSS |
| 31C6_HUMZ_VH2 (with CDRs underlined) | 125 | EVQLVQSGAEVKKPGASVKVSCKASGYTFS<u>SYVMH</u>WVRQAPGQRLEWIG<u>YIDPYNDGAKYSQKFQG</u>RVTLTSDKSASTAYMELSSLRSEDTAVYYCAR<u>GGPYGWYFDV</u>WGQGTTVTVSS |
| 31C6_HUMZ_VH3 (with CDRs underlined) | 126 | EVQLVQSGAEVKKPGASVKVSCKASGYTFS<u>SYVMH</u>WVRQAPGQGLEWIG<u>YIDPYNDGAKYAQKFQG</u>RVTLTRDTSTSTVYMELSSLRSEDTAVYYCAR<u>GGPYGWYFDV</u>WGQGTTVTVSS |
| 31C6_HUMZ_VH4 (with CDRs underlined) | 127 | EVQLVQSGAEVKKPGASVKVSCKASGYTFS<u>SYVMH</u>WVRQAPGQGLEWIG<u>YIDPYNDGAKYAQKFQG</u>RVTLTSDKSTSTVYMELSSLRSEDTAVYYCAR<u>GGPYGWYFDV</u>WGQGTTVTVSS |
| 31C6_HUMZ_VH5 (with CDRs underlined) | 128 | EVQLVQSGAEVKKPGSSVKVSCKASGYTFS<u>SYVMH</u>WVRQAPGQGLEWIG<u>YIDPYNDGAKYAQKFQG</u>RVTLTSDKSTSTAYMELSSLRSEDTAVYYCAR<u>GGPYGWYFDV</u>WGQGTTVTVSS |
| 31C6_HUMZ_VH6 (with CDRs underlined) | 129 | EVQLVQSGAEVKKPGASVKVSCKASGYTFS<u>SYVMH</u>WVRQAPGQGLEWIG<u>YIDPYNDGAKYAQKFQG</u>RVTLTSDKSISTAYMELSRLSDDTVVYYCAR<u>GGPYGWYFDV</u>WGQGTTVTVSS |
| 31C6_Humz_L1 (with CDRs underlined) | 130 | DIQMTQSPSSLSASVGDRVTITC<u>RASEHIYSYLS</u>WYQQKPGKAPKLLIY<u>NAKTLAE</u>GVPSRFSGSGSGTDFTLTISSLQPEDFATYYC<u>QHHFGSPLT</u>FGQGTRLEIK |
| 31C6_Humz_L2 (with CDRs underlined) | 131 | DIQMTQSPSSLSASVGDRVTITC<u>RASEHIYSYLS</u>WYQQKPGKAPKLLIY<u>NAKTLAE</u>GVPSRFSGSGSGTQFTLTISSLQPEDFATYYC<u>QHHFGSPLT</u>FGQGTRLEIK |
| 31C6_Humz_L3 (with CDRs underlined) | 132 | DIQMTQSPSSLSASVGDRVTITC<u>RASEHIYSYLS</u>WYQQKPGKVPKLLIY<u>NAKTLAE</u>GVPSRFSGSGSGTDFTLTISSLQPEDVATYYC<u>QHHFGSPLT</u>FGQGTRLEIK |
| 31C6_Humz_L4 (with CDRs underlined) | 133 | DIQMTQSPSSLSASVGDRVTITC<u>RASEHIYSYLS</u>WYQQKPGKVPKLLIY<u>NAKTLAE</u>GVPSRFSGSGSGTQFTLTISSLQPEDVATYYC<u>QHHFGSPLT</u>FGQGTRLEIK |
| 31C6 H - CDR2 variant | 134 | YIDPYNDGAKYAQKFQG |
| 31C6 H - CDR2 variant | 135 | YIDPYNDGAKYSQKFQG |
| 18G10 - VH sequence | 136 | QVQLMESGPGLVQPSQTLSLTCTVSGFPLTSYTVHWVRQPPGKGLEWIGAIWSSGSTDYNSALKSRLNINRDSSKSQVFLKMNSLQTEDTAIYFCTKSGWAFFDYWGQGVMVTSS |
| 18G10 - VL sequence | 137 | DIQMTQSPSLLSASVGDRVTLNCIASQNIYKSLAWYQLKLGEAPKLLIYNANSLQAGIPSRFSGSGSGTDFALTISGLQPEDVATYFCQQYSGGYTFGAGTKLELK |
| 11A11 - VH sequence | 138 | EVQLVESGGDLVQPGRSLKISCVASGFTFSDYYMAWVRLAPQKGLEWVASISYEGSRTHYGDSVRGRFIISRDNPKNILYLQMNSLGSEDTATYFCARHTGTLDWLVYWGQGTLVIVSS |
| 11A11 - VL | 139 | NIVMAQSPKSMSISAGDRVTMNCKASQNVDNNIAWYQQKPGQSPKLLIFYASNRYSGVPDRF |

TABLE 4-continued

Sequence Information

| Description | SEQ ID NO: | SEQUENCE |
|---|---|---|
| sequence | | TGGGYGTDFTLTIKSVQAEDAAFYYCQRIYNFPTFGSGTKLEIK |
| 14A6 H - CDR3 CONSENSUS | 140 | MPSFITLASLSTXEGYFDF<br>X = W, F, Y, I, V, L |
| 14A6 L - CDR2 CONSENSUS | 141 | YAX$_1$X$_2$LQT<br>X$_1$ = N, S, T, G, D<br>X$_2$ = S, N, S, T, Y, Q |
| 14A6 L - CDR3 CONSENSUS | 142 | QQYYSGXT<br>X = W, F, Y, I, V, L |
| 14A6 VH PARENTAL CONSENSUS | 143 | EvQLQX$_1$SGX$_2$GLX$_3$KPX$_4$X$_5$X$_6$LSLTCX$_7$VX$_8$GX$_{30}$SIX$_{31}$SDYWGWX$_9$RX$_{10}$X$_{11}$PGX$_{12}$X$_{13}$X$_{14}$EW X$_{15}$GFITYSGSTSYNPSLKSRX$_{16}$X$_{17}$IX$_{18}$X$_{19}$DTSKNQFX$_{20}$LX$_{21}$LX$_{22}$SVTX$_{23}$X$_{24}$DTAX$_{25}$Y X$_{26}$CARMPSFITLASLSTX$_{27}$EGYFDFWGX$_{32}$GTX$_{28}$X$_{29}$TVSS<br>X$_1$ = E or Q<br>X$_2$ = P or A<br>X$_3$ = V or L<br>X$_4$ = S or P<br>X$_5$ = Q or E or G<br>X$_6$ = S or T<br>X$_7$ = S or T or A<br>X$_8$ = T or S<br>X$_9$ = I or V<br>X$_{10}$ = K or Q<br>X$_{11}$ = F or P<br>X$_{12}$ = N or K<br>X$_{13}$ = K or G<br>X$_{14}$ = M or L<br>X$_{15}$ = M or I<br>X$_{16}$ = I or V<br>X$_{17}$ = S or T<br>X$_{18}$ = T or S<br>X$_{19}$ = R or V<br>X$_{20}$ = F or S<br>X$_{21}$ = Q or K<br>X$_{22}$ = H or S<br>X$_{23}$ = T or A<br>X$_{24}$ = D or A<br>X$_{25}$ = T or V<br>X$_{26}$ = S or Y,<br>X$_{27}$ = W, F, Y, I, V or L<br>X$_{28}$ = N, V, L, A, R, N, P, Q, E, G, I, H, K, F, S, T, W or Y<br>X$_{29}$ = V, T or L<br>X$_{30}$ = S or G or Y<br>X$_{31}$ = A or S<br>X$_{31}$ = P or Q |
| 14A6 VH HUMANIZED CONSENSUS | 144 | EVQLQX$_1$SGX$_2$GLX$_3$KPX$_4$X$_5$TLSLTCX$_6$VX$_7$GX$_8$SIX$_9$SDYWGWX$_{10}$RX$_{11}$X$_{12}$PGKX$_{13}$X$_{14}$EWX$_{15}$ GFITYSGSTSYNPSLKSRX$_{16}$TISX$_{17}$DTSKNQFSLKLX$_{18}$SVTAX$_{19}$DTAVYYCARMPSFITLA SLSTX$_{20}$EGYFDFWGQGTX$_{21}$X$_{22}$TVSS<br>X$_1$ = E or Q<br>X$_2$ = P or A<br>X$_3$ = V or L<br>X$_4$ = S or P<br>X$_5$ = E or G<br>X$_6$ = T or A or S<br>X$_7$ = S or T<br>X$_8$ = G or S or Y<br>X$_9$ = S or A<br>X$_{10}$ = I or V<br>X$_{11}$ = Q or K<br>X$_{12}$ = P or F<br>X$_{13}$ = G or K<br>X$_{14}$ = L or M<br>X$_{15}$ = I or M<br>X$_{16}$ = V or I<br>X$_{17}$ = V or R<br>X$_{18}$ = S or H<br>X$_{19}$ = A or D<br>X$_{20}$ = W, F, Y, I, V, L<br>X$_{21}$ = M, V, L, A, R, N, P, Q, E, G, I, H, K, F, S, T, W or Y<br>X$_{22}$ = V, T or L |

TABLE 4-continued

Sequence Information

| Description | SEQ ID NO: | SEQUENCE |
|---|---|---|
| 14A6 VL PARENTAL CONSENSUS | 145 | DIQMTQSPSX$_1$LSASVGDRVTX$_2$X$_3$CKASQSIHKNLAWYQQKX$_4$GX$_5$X$_{15}$PKX$_6$LIYYAX$_7$X$_8$LQTGX$_9$PSRFSGSGSGTDFTLTISX$_{10}$LQPEDX$_{11}$ATYX$_{12}$CQQYYSGX$_{13}$TFGGGTKVEX$_{14}$K<br>X$_1$ = L or S<br>X$_2$ = L or I<br>X$_3$ = N or T<br>X$_4$ = L or P<br>X$_5$ = E or K<br>X$_6$ = F or L<br>X$_7$ = N, S, T, G or D<br>X$_8$ = S, N, T, Y or Q<br>X$_9$ = I or V<br>X$_{10}$ = G or S<br>X$_{11}$ = V or F<br>X$_{12}$ = F or Y<br>X$_{13}$ = W, F, Y, I, V or L<br>X$_{14}$ = L or I<br>X$_{15}$ = A or V |
| 14A6 VL HUMANIZED CONSENSUS | 146 | DIQMTQSPSSLSASVGDRVTITCKASQSIHKNLAWYQQKPGKX$_6$PKX$_1$LIYYAX$_2$X$_3$LQTGX$_4$PSRFSGSGSGTDFTLTISSLQPEDX$_7$ATYYCQQYYSGX$_5$TFGGGTKVEIK<br>X$_1$ = L or F<br>X$_2$ = N, S, T, G or D<br>X$_3$ = S, N, T, Y or Q<br>X$_4$ = V or I<br>X$_5$ = W, F, Y, I, V or L<br>X$_6$ = A or V<br>X$_7$ = F or V |
| 31C6 H -CDR2 CONSENSUS | 147 | YIDPYNX$_1$X$_2$AKYX$_3$X$_4$KFX$_5$G<br>X$_1$ = D, R, L, K, F, S, Y or V<br>X$_2$ = G, R, N, Q, E, L K, S, Y or V<br>X$_3$ = N, A or S<br>X$_4$ = E or Q<br>X$_5$ = K or Q |
| 31C6 L - CDR2 CONSENSUS | 148 | X$_1$X$_2$KTLAE<br>X$_1$ = N, A, V, W, S, T, R, H G, I or V<br>X$_2$ = A, N, I, L, T or V |
| 31C6 VH PARENTAL CONSENSUS | 149 | EVQLX$_1$QSGX$_2$EX$_3$X$_4$KPGX$_5$SVKX$_6$SCKASGYTFSSYVMHWVX$_7$QX$_8$PGQX$_9$LEWIGYIDPYNX$_{10}$X$_{11}$AKYX$_{12}$X$_{13}$KFX$_{14}$GX$_{15}$X$_{16}$TLTX$_{17}$DX$_{18}$SX$_{19}$STX$_{20}$YMELSX$_{21}$LX$_{22}$SX$_{23}$DX$_{24}$X$_{25}$VYYCARGGPYGX$_{26}$YFDVWGX$_{27}$GTTVTVSS<br>X$_1$ = Q or V<br>X$_2$ = P or A<br>X$_3$ = V or L<br>X$_4$ = V or K<br>X$_5$ = S or A<br>X$_6$ = M or V<br>X$_7$ = K or R<br>X$_8$ = K or A<br>X$_9$ = G or R<br>X$_{10}$ = D, R, L, K, F, S, Y or V<br>X$_{11}$ = G, R, N, Q, E, L K, S, Y or V<br>X$_{12}$ = N, A or S<br>X$_{13}$ = E or Q<br>X$_{14}$ = K or Q<br>X$_{15}$ = R or K<br>X$_{16}$ = A or V<br>X$_{17}$ = S or R<br>X$_{18}$ = K or T<br>X$_{19}$ = S, I , A or T<br>X$_{20}$ = A or V<br>X$_{21}$ = R or S<br>X$_{22}$ = T or R<br>X$_{23}$ = D or E<br>X$_{24}$ = S or T<br>X$_{25}$ = A or V<br>X$_{26}$ = W, A, D, E, F, G, I, K, N, Q, R, S, T, V or Y<br>X$_{27}$ = A or Q |
| 31C6 VH HUMANIZED CONSENSUS | 150 | EVQLVQSGAEVKKPGX$_1$SVKVSCKASGYTFSSYVMHWVRQAPGQX$_2$LEWIGYIDPYNX$_3$X$_4$AKYX$_5$X$_6$KFX$_7$GRVTLTX$_8$DX$_9$SX$_{10}$STX$_{11}$YMELSX$_{12}$LRSX$_{13}$DTX$_{14}$VYYCARGGPYGX$_{15}$YFDVWGQGTTVTVSS<br>X$_1$ = A or S |

TABLE 4-continued

Sequence Information

| Description | SEQ ID NO: | SEQUENCE |
|---|---|---|
| | | $X_2$ = R or G<br>$X_3$ = D, R, L, K, F, S, Y or V<br>$X_4$ = G, R, N, Q, E, L K, S, Y or V<br>$X_5$ = N, A or S<br>$X_6$ = E or Q<br>$X_7$ = K or Q<br>$X_8$ = R or S<br>$X_9$ = T or K<br>$X_{10}$ = A, T or I<br>$X_{11}$ = A or V<br>$X_{12}$ = S Or R<br>$X_{13}$ = E or D<br>$X_{14}$ = A or V<br>$X_{15}$ = W, A, D, E, F, G, I, K, N, Q, R, S, T, V or Y |
| 31C6 VL PARENTAL CONSENSUS | 151 | DIQMTQSPX$_1$SLSASVGX$_2$X$_3$VTITC<u>RASEHIYSYLS</u>WYQQKX$_4$GKX$_5$PX$_6$LLX$_7$YX$_8$X$_9$KTLAE GVPSRFSGSGSGTX$_{10}$FX$_{11}$LX$_{12}$IX$_{13}$SLQPEDX$_{14}$X$_{15}$TYYC<u>QHHFGSPLT</u>FGX$_{16}$GTX$_{17}$LEX$_{18}$ K<br>$X_1$ = A or S<br>$X_2$ = E or D<br>$X_3$ = T or R<br>$X_4$ = Q or P<br>$X_5$ = S, A or V<br>$X_6$ = Q or K<br>$X_7$ = V or I<br>$X_8$ = N, A, Y, W, S, T, I or V<br>$X_9$ = A, N, I, L, T or V<br>$X_{10}$ = Q or D<br>$X_{11}$ = S or T<br>$X_{12}$ = K or T<br>$X_{13}$ = N or S<br>$X_{14}$ = F or V<br>$X_{15}$ = G or A<br>$X_{16}$ = A or Q<br>$X_{17}$ = T or R<br>$X_{18}$ = L or I |
| 31C6 L - VL HUMANIZED CONSENSUS | 152 | DIQMTQSPSSLSASVGDRVTITC<u>RASEHIYSYLS</u>WYQQKPGKX$_1$PKLLIY X$_2$X$_3$KTLAEGVPSRFSGSGSGTX$_4$FTLTISSLQPEDX$_5$ATYYC<u>QHHFGSPLT</u>FGQGTR <u>LEIK</u><br>$X_1$ = A or V<br>$X_2$ = N, A, Y, W, W, T, I or V<br>$X_3$ = A, N, I, L, T or V<br>$X_4$ = D or Q<br>$X_5$ = F or V |
| 31C6 H -CDR3 CONSENSUS | 153 | GGPYGXYFDV<br>$X_{15}$ = W, A, D, E, F, G, I, K, N, Q, R, S, T, V or Y |
| 31C6 H -CDR3 VARIANT | 154 | GGPYGAYFDV |
| 31C6 H -CDR3 VARIANT | 155 | GGPYGDYFDV |
| 31C6 H -CDR3 VARIANT | 156 | GGPYGEYFDV |
| 31C6 H -CDR3 VARIANT | 157 | GGPYGFYFDV |
| 31C6 H -CDR3 VARIANT | 158 | GGPYGGYFDV |
| 31C6 H -CDR3 VARIANT | 159 | GGPYGIYFDV |
| 31C6 H -CDR3 VARIANT | 160 | GGPYGKYFDV |
| 31C6 H -CDR3 VARIANT | 161 | GGPYGNYFDV |
| 31C6 H -CDR3 | 162 | GGPYGQYFDV |

TABLE 4-continued

Sequence Information

| Description | SEQ ID NO: | SEQUENCE |
|---|---|---|
| VARIANT | 163 | GGPYGRYFDV |
| 31C6 H -CDR3 | 164 | GGPYGSYFDV |
| VARIANT | 165 | GGPYGTYFDV |
| 31C6 H -CDR3 | 166 | GGPYGVYFDV |
| VARIANT | 167 | GGPYGYYFDV |

The invention claimed is:

1. A monoclonal antibody or antigen binding fragment thereof that binds to mature human TIGIT, wherein the antibody and antigen binding fragment thereof comprise a heavy chain variable region and a light chain variable region, wherein the heavy chain variable region comprises a heavy chain variable region CDR1 comprising the amino acid sequence of SEQ ID NO:88, a heavy chain variable region CDR2 comprising the amino acid sequence of SEQ ID NO:89 and a heavy chain variable region CDR3 comprising the amino acid sequence of SEQ ID NO:90, and wherein the light chain variable region comprises a light chain variable region CDR1 comprising the amino acid sequence of SEQ ID NO:91, a light chain variable region CDR2 comprising the amino acid sequence of SEQ ID NO:92, and a light chain variable region CDR3 comprising the amino acid sequence of SEQ ID NO:93.

2. A monoclonal antibody or antigen binding fragment thereof that binds to mature human TIGIT, wherein the antibody and antigen binding fragment thereof comprise a heavy chain variable region and a light chain variable region, wherein the heavy chain variable region comprises a heavy chain variable region CDR1 comprising the amino acid sequence of SEQ ID NO:88, a heavy chain variable region CDR2 comprising the amino acid sequence of SEQ ID NO: 134, and a heavy chain variable region CDR3 comprising the amino acid sequence of SEQ ID NO:90, and wherein the light chain variable region comprises a light chain variable region CDR1 comprising the amino acid sequence of SEQ ID NO:91, a light chain variable region CDR2 comprising the amino acid sequence of SEQ ID NO:92, and a light chain variable region CDR3 comprising the amino acid sequence of SEQ ID NO:93.

3. The monoclonal antibody or antigen binding fragment thereof of claim 2, wherein the monoclonal antibody and antigen binding fragment thereof comprise:
   a. a heavy chain variable region comprising the amino acid sequence of SEQ ID NO:128 and a light chain variable region comprising the amino acid sequence of SEQ ID NO:132;
   b. a heavy chain variable region comprising the amino acid sequence of SEQ ID NO:127 and a light chain variable region comprising the amino acid sequence of SEQ ID NO:130;
   c. a heavy chain variable region comprising the amino acid sequence of SEQ ID NO:128 and a light chain variable region comprising the amino acid sequence of SEQ ID NO:133;
   d. a heavy chain variable region comprising at least 97% identity to SEQ ID NO:128 and a light chain variable region comprising at least 97% identity to SEQ ID NO: 132, wherein any sequence variations occur in the framework regions of the antibody;
   e. a heavy chain variable region comprising at least 97% identity to SEQ ID NO:127 and a light chain variable region comprising at least 97% identity to SEQ ID NO: 130, wherein any sequence variations occur in the framework regions of the antibody; or
   f. a heavy chain variable region comprising at least 97% identity to SEQ ID NO:128 and a light chain variable region comprising at least 97% identity to SEQ ID NO: 133, wherein any sequence variations occur in the framework regions of the antibody.

4. The monoclonal antibody or antigen binding fragment thereof of claim 1, wherein the monoclonal antibody or antigen binding fragment thereof binds to mature human TIGIT with a KD value of $1 \times 10^{-9}$ M to $1 \times 10^{-12}$ M as determined by surface plasmon resonance.

5. The monoclonal antibody or antigen binding fragment thereof of claim 1, which is a monoclonal antibody comprising two heavy chains and two light chains.

6. The monoclonal antibody or antigen binding fragment thereof of claim 1, which is a monoclonal antibody, wherein the monoclonal antibody comprises a human IgG1 constant domain and a human kappa constant domain.

7. A composition comprising the monoclonal antibody or antigen binding fragment thereof of claim 1 and a pharmaceutically acceptable carrier or diluent.

8. The composition of claim 7, further comprising an anti-PD1 monoclonal antibody or an antigen binding fragment thereof.

9. The composition of claim 7, further comprising an anti-PD1 monoclonal antibody or an antigen binding fragment thereof, wherein the anti-PD1 monoclonal antibody is nivolumab.

10. The composition of claim 7, further comprising an anti-PD1 monoclonal antibody or an antigen binding fragment thereof, wherein the anti-PD1 monoclonal antibody is pembrolizumab.

11. A monoclonal antibody that binds to mature human TIGIT comprising a heavy chain variable region comprising the amino acid sequence of SEQ ID NO:128 and a light chain variable region comprising the amino acid sequence of SEQ ID NO:132.

12. The monoclonal antibody or antigen binding fragment thereof of claim 3 that is a monoclonal antibody comprising a heavy chain variable region comprising at least 97% identity to SEQ ID NO:128 and a light chain variable region comprising at least 97% identity to SEQ ID NO: 132, wherein any sequence variations occur in the framework regions of the antibody.

13. The monoclonal antibody or antigen binding fragment thereof of claim 2, wherein the antibody or antigen binding fragment thereof binds to mature human TIGIT with a KD value of $1 \times 10^{-9}$ M to $1 \times 10^{-12}$ M as determined by surface plasmon resonance.

14. The monoclonal antibody or antigen binding fragment thereof of claim 2, which is a monoclonal antibody comprising two heavy chains and two light chains.

15. The monoclonal antibody or antigen binding fragment thereof of claim 2, which is a monoclonal antibody, wherein the monoclonal antibody comprises a human IgG1 constant domain and a human kappa constant domain.

16. The monoclonal antibody of claim 15, wherein the human IgG1 constant domain comprises SEQ ID NO: 86 and the human kappa constant domain comprises SEQ ID NO: 56.

17. The monoclonal antibody of claim 6, wherein the human IgG1 constant domain comprises SEQ ID NO: 86 and the human kappa constant domain comprises SEQ ID NO: 56.

18. The monoclonal antibody or antigen binding fragment thereof of claim 1, which is a monoclonal antibody, wherein the monoclonal antibody comprises a human IgG4 constant domain and a human kappa constant domain.

19. The monoclonal antibody or antigen binding fragment thereof of claim 2, which is a monoclonal antibody, wherein the monoclonal antibody comprises a human IgG4 constant domain and a human kappa constant domain.

20. The monoclonal antibody of claim 18, wherein the human IgG4 constant domain comprises SEQ ID NO: 55 and the human kappa constant domain comprises SEQ ID NO: 56.

21. The monoclonal antibody of claim 19, wherein the human IgG4 constant domain comprises SEQ ID NO: 55 and the human kappa constant domain comprises SEQ ID NO: 56.

22. A composition comprising the monoclonal antibody or antigen binding fragment thereof of claim 2 and a pharmaceutically acceptable carrier or diluent.

23. The composition of claim 22, further comprising an anti-PD1 monoclonal antibody or an antigen binding fragment thereof.

24. The composition of claim 22 further comprising an anti-PD1 monoclonal antibody or an antigen binding fragment thereof, wherein the anti-PD1 monoclonal antibody is nivolumab.

25. The composition of claim 22, further comprising an anti-PD1 monoclonal antibody or an antigen binding fragment thereof, wherein the anti-PD1 monoclonal antibody is pembrolizumab.

26. A monoclonal antibody which comprises two heavy chains and two light chains, wherein the heavy chains comprise (i) a heavy chain variable region comprising SEQ ID NO: 128 and (ii) an IgG1 constant domain comprising SEQ ID NO: 86, and wherein the light chains comprise (i) a light chain variable region comprising SEQ ID NO: 132 and (ii) a human kappa constant domain comprising SEQ ID NO: 56.

27. A monoclonal antibody which comprises two heavy chains and two light chains, wherein the heavy chains comprise (i) a heavy chain variable region comprising SEQ ID NO: 128 and (ii) an IgG4 constant domain comprising SEQ ID NO: 55, and wherein the light chains comprise (i) a light chain variable region comprising SEQ ID NO: 132 and (ii) a human kappa constant domain comprising SEQ ID NO: 56.

28. A composition comprising (a) a monoclonal antibody which comprises two heavy chains and two light chains, wherein the heavy chains comprise (i) a heavy chain variable region comprising SEQ ID NO: 128 and (ii) an IgG1 constant domain comprising SEQ ID NO: 86, and wherein the light chains comprise (i) a light chain variable region comprising SEQ ID NO: 132 and (ii) a human kappa constant domain comprising SEQ ID NO: 56 and (b) pembrolizumab.

29. A composition comprising (a) a monoclonal antibody which comprises two heavy chains and two light chains, wherein the heavy chains comprise (i) a heavy chain variable region comprising SEQ ID NO: 128 and (ii) an IgG4 constant domain comprising SEQ ID NO: 55, and wherein the light chains comprise (i) a light chain variable region comprising SEQ ID NO: 132 and (ii) a human kappa constant domain comprising SEQ ID NO: 56 and (b) pembrolizumab.

30. The composition of claim 7, further comprising an anti-PDL-1 monoclonal antibody.

31. The composition of claim 30, wherein the anti-PDL-1 monoclonal antibody is MPDL3280A.

32. The monoclonal antibody or antigen binding fragment thereof of claim 1, wherein the monoclonal antibody and antigen binding fragment thereof comprise a heavy chain variable region comprising the amino acid sequence of SEQ ID NO: 94 and a light chain variable region comprising the amino acid sequence of SEQ ID NO: 95.

* * * * *